(12) United States Patent
Thomann et al.

(10) Patent No.: US 11,326,213 B2
(45) Date of Patent: May 10, 2022

(54) NMR METHODS AND SYSTEMS FOR THE RAPID DETECTION OF TICK-BORNE PATHOGENS

(71) Applicant: T2 Biosystems, Inc., Lexington, MA (US)

(72) Inventors: Ulrich Hans Thomann, Stow, MA (US); Lori Anne Neely, Reading, MA (US); Rahul Krishan Dhanda, Dorchester, MA (US); Frédéric Sweeney, Natick, MA (US); Thomas Jay Lowery, Jr., Belmont, MA (US); Jessica Ann Townsend, Boston, MA (US); Jessica Lee Snyder, Arlington, MA (US); Heidi Susanne Giese, Newburyport, MA (US); Cheryl Ann Bandoski-Gralinski, Malden, MA (US); Daniella Lynn Logan, Cotuit, MA (US)

(73) Assignee: T2 Biosystems, Inc., Lexington, MA (US)

( * ) Notice: Subject to any disclaimer, the term of this patent is extended or adjusted under 35 U.S.C. 154(b) by 483 days.

(21) Appl. No.: 15/545,663

(22) PCT Filed: Jan. 21, 2016

(86) PCT No.: PCT/US2016/014348
§ 371 (c)(1),
(2) Date: Jun. 13, 2018

(87) PCT Pub. No.: WO2016/118766
PCT Pub. Date: Jul. 28, 2016

(65) Prior Publication Data
US 2018/0171388 A1 Jun. 21, 2018

Related U.S. Application Data

(60) Provisional application No. 62/106,093, filed on Jan. 21, 2015.

(51) Int. Cl.
*C12Q 1/689* (2018.01)
*C12N 15/10* (2006.01)
*G01N 24/08* (2006.01)

(52) U.S. Cl.
CPC ......... *C12Q 1/689* (2013.01); *C12N 15/1013* (2013.01); *G01N 24/08* (2013.01); *C12Q 2600/112* (2013.01); *C12Q 2600/124* (2013.01); *C12Q 2600/156* (2013.01); *G01N 2333/20* (2013.01); *G01N 2800/26* (2013.01); *Y02A 50/30* (2018.01)

(58) Field of Classification Search
None
See application file for complete search history.

(56) References Cited

U.S. PATENT DOCUMENTS

| 8,409,807 | B2 | 4/2013 | Neely et al. | |
|---|---|---|---|---|
| 8,563,298 | B2 | 10/2013 | Lowery, Jr. et al. | |
| 8,883,423 | B2 | 11/2014 | Neely | |
| 9,046,493 | B2 | 6/2015 | Neely et al. | |
| 9,360,457 | B2 | 6/2016 | Neely et al. | |
| 9,488,648 | B2 | 11/2016 | Neely et al. | |
| 9,702,852 | B2 | 7/2017 | Lowery, Jr. et al. | |
| 9,714,940 | B2 | 7/2017 | Lowery, Jr. et al. | |
| 2010/0136039 | A1* | 6/2010 | Lundberg | C07K 7/06 424/190.1 |
| 2012/0164644 | A1* | 6/2012 | Neely | C12Q 1/6816 435/6.11 |
| 2013/0029345 | A1 | 1/2013 | Neely et al. | |
| 2013/0244238 | A1 | 9/2013 | Neely et al. | |
| 2013/0273522 | A1 | 10/2013 | Lowery, Jr. et al. | |
| 2013/0273523 | A1 | 10/2013 | Neely et al. | |
| 2014/0106442 | A1 | 4/2014 | Lowery, Jr. et al. | |
| 2017/0233798 | A1 | 8/2017 | Neely et al. | |
| 2019/0085381 | A1 | 3/2019 | Neely et al. | |

FOREIGN PATENT DOCUMENTS

| WO | WO-2004/005479 | A2 | 1/2004 | |
| WO | WO-2004005479 | A2 * | 1/2004 | ............. C12Q 1/689 |

OTHER PUBLICATIONS

Ornstein et al. 2002 (Three Major Lyme Borrelia Genospecies (*Borrelia burgdorferi* sensu stricto, *B. afzelii* and *B. garinii*) Identifed by PCR in Cerebrospinal Fluid from Patients with Neuroborreliosis in Sweden; Scand J Infect Dis 34: 341-346) (Year: 2002).*

Eshoo et al, "Direct molecular detection and genotyping of Borrelia burgdorferi from whole blood of patients with early Lyme disease," PLoS One. 7(5):e36825 (2012) (6 pages).

Lebech et al, "Diagnostic Detection and Direct Genotyping of Borrelia burgdorferi by Polymerase Chain Reaction in Cerebrospinal Fluid in Lyme Neuroborreliosis," Mol Diagn. 3(3):131-41 (1998).

Partial Supplementary European Search Report for European Patent Application No. 16740774.1, dated Jul. 3, 2018 (16 pages).

Rauter et al, "Distribution of clinically relevant Borrelia genospecies in ticks assessed by a novel, single-run, real-time PCR," J Clin Microbiol. 40(1):36-43 (2002).

Rudenko et al, "Improved method of detection and molecular typing of Borrelia burgdorferi sensu lato in clinical samples by polymerase chain reaction without DNA purification," Folia Microbiol. 50(1):31-9 (2005).

(Continued)

*Primary Examiner* — Mary Maille Lyons
(74) *Attorney, Agent, or Firm* — Clark & Elbing LLP

(57) ABSTRACT

The invention features methods, systems, and panels for rapid detection of tick-borne pathogens in a sample (including *Borrelia* spp. such as *B. burgdorferi*, *B. afzelii*, and *B. garinii*) and for diagnosis and monitoring of tick-transmitted diseases, including Lyme disease, Rocky Mountain spotted fever, Q-fever, babesiosis, ehrlichiosis, tularemia, and anaplasmosis.

29 Claims, 11 Drawing Sheets
Specification includes a Sequence Listing.

(56) References Cited

OTHER PUBLICATIONS

Snyder et al, "T2 Magnetic Resonance Assay-Based Direct Detection of Three Lyme Disease-Related *Borrelia* Species in Whole-Blood Samples," J Clin Microbiol. 55(8):2453-61 (2017).
Strube et al, "Establishment of a minor groove binder-probe based quantitative real time PCR to detect Borrelia burgdorferi sensu lato and differentiation of Borrelia spielmanii by ospA-specific conventional PCR," Parasit Vectors. 3(69) (2010) (10 pages).
GenBank accession No. CP001370.1, "Borrelia burgdorferi 72a plasmid 72a_lp54, complete sequence," retrieved Jun. 22, 2016 (25 pages).
GenBank accession No. CP009213.1, "Borrelia afzelii Tom3107 plasmid cp26, complete sequence," retrieved Jun. 22, 2016 (13 pages).
International Search Report and Written Opinion for International Application No. PCT/US16/14348, dated Jul. 26, 2016 (23 pages).
International Preliminary Report on Patentability for International Application No. PCT/US16/14348, dated Jul. 25, 2017 (13 pages).
Andre et al., "A Prospective Clinical Evaluation of the T2Lyme® Diagnostic Demonstrated a High Positive Predictive Value for *Borrelia* Infection." Poster presented at the International Conference on Lyme Borreliosis and Other Tick-Borne Diseases (2018) (1 page).

\* cited by examiner

Figure 1

| Pathogen | Analyte | | Panel | Tissue primarily affected by Assay | | | |
|---|---|---|---|---|---|---|---|
| Borrelia burgdorferi | Bbsl | | Lyme | | Blood | | Synovial |
| Borrelia afzelii | | | | | | | |
| Borrelia garinii | | | | | | | |
| Borellia spp. | | pan-Borellia | | | | | |
| Coxiella burnetii | intracellular | | non-Lyme | | Blood | CSF | Synovial |
| Anaplasma phagocytophilum | | | | | Blood | CSF | Synovial |
| Rickettsia rickettsii | | | | | Blood | CSF | Synovial |
| Ehrlichia chaffeensis | | | | | Blood | CSF | Synovial |
| Francisella tularensis subspp. | | | | | Blood | | |
| Babesia microti | | | | | Blood | CSF | Synovial |
| Streptococcus pneumoniae | CSF | | | | Blood | CSF | Synovial |
| Neisseria meningitidis | | | | | Blood | CSF | Synovial |

Figure 7

| | 4/200 | 4.5/200 | 4.5/300 | 4.5/400 | 5/400 | 5/300 |
|---|---|---|---|---|---|---|
| Bb | | | | | | |
| Avg T2 (ms) | 382.0 | 336.8 | 526.0 | 415.3 | 584.8 | 389.9 |
| stdev | 155.3 | 123.1 | 61.8 | 107.8 | 62.1 | 135.5 |
| hitrate | 67% | 100% | 100% | 100% | 100% | 83% |
| Ba | | | | | | |
| Avg T2 (ms) | 342.1 | 368.6 | 207.4 | 415.3 | 213.2 | 312.3 |
| stdev | 35.7 | 74.3 | 27.5 | 107.8 | 10.6 | 59.9 |
| hitrate | 100% | 100% | 100% | 100% | 100% | 100% |
| Bg | | | | | | |
| Avg T2 (ms) | 713.5 | 671.7 | 917.6 | 886.2 | 847.5 | 779.9 |
| stdev | 405.0 | 355.5 | 284.7 | 116.0 | 290.8 | 203.8 |
| hitrate | 67% | 67% | 100% | 100% | 83% | 83% |

SEQUENCE LISTING

```
<160> NUMBER OF SEQ ID NOS: 168

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
agaggacttt taatactggg cattgctg                                    28

<210> SEQ ID NO 2
<211> LENGTH: 29
<212> TYPE: DNA
<213> ORGANISM: Artificial Sequence
<220> FEATURE:
<223> OTHER INFORMATION: Synthetic Construct

<400> SEQUENCE: 2
ggccattatg taggaatctc taatggtgc                                   29

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
ctaaaccaaa agatgatatt gtctttggtg                                  30

<210> SEQ ID NO 4
<211> LENGTH: 26
<212> TYPE: DNA
<213> ORGANISM: Artificial Sequence
<220> FEATURE:
<223> OTHER INFORMATION: Synthetic Construct

<400> SEQUENCE: 4
ggacatttct tacgacaaca cctgct                                      26

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
```

-continued acataatggc cttagaaaat gagcttgatg    30

<210> SEQ ID NO 6
<211> LENGTH: 26
<212> TYPE: DNA
<213> ORGANISM: Artificial Sequence
<220> FEATURE:
<223> OTHER INFORMATION: Synthetic Construct

<400> SEQUENCE: 6
cccgcttgta accatgtttt ctgagc    26

<210> SEQ ID NO 7
<211> LENGTH: 29
<212> TYPE: DNA
<213> ORGANISM: Artificial Sequence
<220> FEATURE:
<223> OTHER INFORMATION: Synthetic Construct

<400> SEQUENCE: 7
aacctattaa catcaaagat aaaaaatgc    29

<210> SEQ ID NO 8
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8
gcttacacac ccaatattta taccc    25

<210> SEQ ID NO 9
<211> LENGTH: 30
<212> TYPE: DNA
<213> ORGANISM: Artificial Sequence
<220> FEATURE:
<223> OTHER INFORMATION: Synthetic Construct

<400> SEQUENCE: 9
ggatattcaa atcctgaggt tgacgaacta    30

<210> SEQ ID NO 10
<211> LENGTH: 26
<212> TYPE: DNA
<213> ORGANISM: Artificial Sequence
<220> FEATURE:
<223> OTHER INFORMATION: Synthetic Construct

<400> SEQUENCE: 10
ctgatagggc aaatctttct gaagca    26

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct

<400> SEQUENCE: 11
ctgagattga agttgacgaa aaaatcag    28

<210> SEQ ID NO 12
<211> LENGTH: 28
<212> TYPE: DNA

```
<213> ORGANISM: Artificial Sequence
<220> FEATURE:
<223> OTHER INFORMATION: Synthetic Construct

<400> SEQUENCE: 12
gatcatccaa taattccaat ctacagcg                                              28

<210> SEQ ID NO 13
<211> LENGTH: 26
<212> TYPE: DNA
<213> ORGANISM: Artificial Sequence
<220> FEATURE:
<223> OTHER INFORMATION: Synthetic Construct

<400> SEQUENCE: 13
ccgtgggcag agtctatgac aatcag                                                26

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gcccaaaaaa ccatcaacac taataagg                                              28

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
tagcagctcc tactcttagc ttgc                                                  24

<210> SEQ ID NO 16
<211> LENGTH: 27
<212> TYPE: DNA
<213> ORGANISM: Artificial Sequence
<220> FEATURE:
<223> OTHER INFORMATION: Synthetic Construct

<400> SEQUENCE: 16
aatattgctt tgtaagcatt ttggttt                                               27

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
caaggtgcaa tgactttgtt tgggca                                                26

<210> SEQ ID NO 18
<211> LENGTH: 31
<212> TYPE: DNA
<213> ORGANISM: Artificial Sequence
<220> FEATURE:
<223> OTHER INFORMATION: Synthetic Construct

<400> SEQUENCE: 18
gcaacttcaa agtgtacagt attggtatcc c                                          31
```

<210> SEQ ID NO 19
<211> LENGTH: 25
<212> TYPE: DNA
<213> ORGANISM: Artificial Sequence
<220> FEATURE:
<223> OTHER INFORMATION: Synthetic Construct

<400> SEQUENCE: 19
ttgtagaaca atctgggctt tttgg                                         25

<210> SEQ ID NO 20
<211> LENGTH: 24
<212> TYPE: DNA
<213> ORGANISM: Artificial Sequence
<220> FEATURE:
<223> OTHER INFORMATION: Synthetic Construct

<400> SEQUENCE: 20
ggagaactca tatcaggagc acaa                                          24

<210> SEQ ID NO 21
<211> LENGTH: 1590
<212> TYPE: DNA
<213> ORGANISM: Borrelia burgdorferi

<400> SEQUENCE: 21
atgataataa aaaaaagagg acttttaata ctgggcattg ctactgtaat ctcgtgctca 60
gcaatgtcta aaccaaaaga tgatattgtc tttggtgttg gaattggaaa cgaaccaaca 120
tcgcttgatc cacaattttg cagcgatagg ctaggtaatt taattataaa cgaactattt 180
gtagggcttt taaggggtga ccccaaaacg ggtggataca ggccaggact tgcaaaaaat 240
tgggacattt cttacgacaa cacctgctat acattccatt taagagacga catttattgg 300
agtgacggca ttaaaataac agcaagcacc attagagatt cctacataat ggccttagaa 360
aatgagcttg atgtgccaca tattaaccta ttaacatcaa agataaaaaa tgcacaagaa 420
ttttacgaaa caaaattaaa tgcagatgaa gttggagtaa aggtaatcaa tgagcaaact 480
ttagaaataa ctctctctcg cccagcaaga tattttcttg acatgcttac acacccaata 540
tttataccca ttcctacgca cattgttaaa aagtttggaa acaaatggac aagctcagaa 600
aacatggtta caagcgggcc tttcaagcta aaaagaagga tcttaaacga agaaatatct 660
cttgaaaaaa atgaaaaatt ctatgatgct aaaaacgttg ctattaatga gctcatattt 720
gttactataa acgacacccg cagaatttac agtatgtacg agcacaacga aatagatgct 780
atttttaata acatcccctt aagccttatt aatgagctta tcttaagaga agatttttat 840
tcagctgaca ttaatcaaat tgggtttttt tcactaaaca caaatgttaa acctcttaac 900
aatgtaaaag taagagaagc attggctctt gcggttgaca gagaaactct aacttacaga 960
gttcttgaca acaactttaa agcaacaaga aaaataagcc ctaatattaa caactataat 1020
tatgggaaaa agcttaagcc atacaacccg cgaaaagcag aaaagctctt agccgaagct 1080
ggatatccag atggtaaaaa ttttccaact cttacaataa aatacaataa aaatgacctt 1140
gaaaaagaag ttgctagttt tattcaaagc caatggaaaa aagttttaaa tattgatgta 1200
gaaattgagc ctgaaacatg ggtcaaccac atatcaaata ttttaaaagg tcaatatgag 1260
atctcagtaa ggtcctggca aggagattat ttagatccca tggcattctt taatatattt 1320
gaaactaaaa actcacattt tgcatcttac ggatattcaa atcctgaact tgatgagctt 1380

```
ataataaaat ccgatcttga agaggatgaa aaactaagat tagaaatatt aaaaaagata    1440
gaagaaataa ttattgaaaa tgattatcca ataattccaa tatacagtgt tgcgggaaac    1500
tatcttttta aaaacgacaa atggctaggg tggaatacaa acaattcaga aagatttgcc    1560
ctatcagaaa taaaacctat agaagaataa                                     1590
```

<210> SEQ ID NO 22
<211> LENGTH: 1587
<212> TYPE: DNA
<213> ORGANISM: Borrelia garinii

<400> SEQUENCE: 22

```
atgataagaa aaaaatatt acttttaaca ctactcatta cagctgcaag ctcatgcaca      60
atttctaaaa caaagagga tcttgtcttt ggagttggaa tcggaaacga accaacatca    120
cttgatccac agttttgcag cgataaatcg ggtaacttaa ttataaacga gctatttata    180
gggcttttac gaggggatcc aaaaacaggt ggttataggc caggacttgc aaaaaattgg    240
gaaatttctc aagacaacac ctcctataca ttccacttaa gagacgacat ttattggagt    300
gacggcgtta aaataacagc agacactatt agaggctcat acataatggc cttagaaact    360
gaggagaatc tcccacatat taaccttta acatcaaaaa taaaaaatgc aaaagaattt    420
cacacaacaa aattaaattc agatgaagtt ggaataaagg taattgatga aaaaactttg    480
gaaataactc ttgaacaacc aacagcatat ttccttgata tgattacaca tccaatattt    540
atacctattc ctactcacgt tgttaaaaag tttggaaata atggacaaa cccagaaaac    600 atggttacaa gcgggccttt caaactaaaa agaagaatat taaacgaaga aatttctctt    660
gaaaaaaata aaaaatttta tgatgctaaa aatgttgata ttaatgagct tacatttgtt    720
actataaacg atgcccgcag aatttacagc atgtatgaac acaacgaaat agatgctatt    780
tttaacaaca ttccgttaaa tcttattaat gagcttattt taagagaaga ttttttattca    840 tctgacatta accaaattgg ttttctttca ttaaacctaa atgttaaacc ccttgacaac    900
ccaaaagtaa gagaagcatt atctctagcg gttgacagag aaacattggc ctacagagtg    960
cttgataaca actttaaagc aacaagaaag gtaagcccta atattaataa ttataattat   1020
ggaaaaaaat taaaccata taacccacga aaggcagaaa acttttagc cgaagctgga   1080 tatcctgatg ggaaaaaatt tccaactatt acaataaaat atgataaaaa tgaacttgga   1140
aaggaagttg ccaattttat tcaaagccaa tggaaaaaag tttaaatat taatgtagaa   1200 gtcgagactg aaacacgagg tagccacata tcaaatattc taaaggaca gtatgagatc   1260 tcagtaagat cctggcaagg agattattta gatcccatga cattctttaa tatatttgaa   1320
actaaaaact cacatctttc agcttacgga tattcaaatc ctgaggttga cgaactatta   1380
aataaatctg agattgaagt tgacgaaaaa atcagattag aactatttaa aaagattgaa   1440
gaataattta ttgaaaatga tcatccaata attccaatct acagcgttgc ggggaactat   1500
cttttcaaaa atgataaatg gacagggtgg aacacaaatg cttcagaaag atttgcccta   1560
tcagaaatta aacctttgga agaataa                                       1587
```

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
tattgtcttt ggtgttggaa ttgga                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
acctgctata cattccattt aagag                                          25

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
atgaacttgg aaaggaagtt gccaa                                          25

<210> SEQ ID NO 26
<211> LENGTH: 28
<212> TYPE: DNA
<213> ORGANISM: Artificial Sequence
<220> FEATURE:
<223> OTHER INFORMATION: Synthetic Construct

<400> SEQUENCE: 26
cctaaatgtt aaacccttg acaaccca                                        28

<210> SEQ ID NO 27
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 27
ctgtcctttt ngantatttg atatgtggct a                                   31

<210> SEQ ID NO 28
<211> LENGTH: 29
<212> TYPE: DNA
<213> ORGANISM: Artificial Sequence
<220> FEATURE:
<223> OTHER INFORMATION: Synthetic Construct

<400> SEQUENCE: 28
tcagaaatga taaatggaca gggtggaac                                      29

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
tctagcggtt gacagagaaa cattg					25

<210> SEQ ID NO 30
<211> LENGTH: 28
<212> TYPE: DNA
<213> ORGANISM: Artificial Sequence
<220> FEATURE:
<223> OTHER INFORMATION: Synthetic Construct

<400> SEQUENCE: 30
aaaaaattaa aaccatataa cccacgaa					28

<210> SEQ ID NO 31
<211> LENGTH: 695
<212> TYPE: DNA
<213> ORGANISM: Borrelia burgdorferi

<400> SEQUENCE: 31
ttaatctaaa taataataaa tagttgaagc aatccttaat atttctttag gataaagctt		60
tgggttgcca agattatat caactagaaa aaatttaaag tattcttgat ttgcatttt		120
aattttatct aatttggaac caaaatgtct cgtaaattct aaagcagaaa gttctgcatt		180
tcttattgaa cctgctagaa tttgaaaatt tgtatcatta attctattta aataatatct		240
taaatctcta ttactgctaa ttggcaagcc ttgattataa aactcaataa tatttttttc		300
tactgttttc atttttttcaa tatcaattgt attggtaatt aaagcaatat acatacatat		360
ttaataaaaa agctttaatc ttagataaat ttaaattatt tgctttaatg ccgtcattaa		420
tcgaatcact attcaagtca taatgcaaat tacaacttac agatgccaaa aggatttctt		480
tttcgcttat gccctagcc ttaatacaat tgccatttt aatgacaatt ccttttactc		540
tgcaagaaat tataattgaa aatgacagaa aaagtattaa aaaaaataaa tcctttcttc		600
caggcatata acaattcctc ctaaaaaaga ataataatt gttaaatcag ctcgtttatt		660
ctaacatatt atataatgtt aatgaatcga aaaat					695

<210> SEQ ID NO 32
<211> LENGTH: 29
<212> TYPE: DNA
<213> ORGANISM: Artificial Sequence
<220> FEATURE:
<223> OTHER INFORMATION: Synthetic Construct

<400> SEQUENCE: 32
gcagaaagtt ctgcatttct tattgaacc					29

<210> SEQ ID NO 33
<211> LENGTH: 31
<212> TYPE: DNA
<213> ORGANISM: Artificial Sequence
<220> FEATURE:
<223> OTHER INFORMATION: Synthetic Construct

<400> SEQUENCE: 33
ggaaccaaaa tgtctcgtaa attctaaagc a					31

<210> SEQ ID NO 34
<211> LENGTH: 25
<212> TYPE: DNA
<213> ORGANISM: Artificial Sequence
<220> FEATURE:
<223> OTHER INFORMATION: Synthetic Construct

```
<400> SEQUENCE: 34
ctttaggata aagctttggg ttgcc                                          25

<210> SEQ ID NO 35
<211> LENGTH: 29
<212> TYPE: DNA
<213> ORGANISM: Artificial Sequence
<220> FEATURE:
<223> OTHER INFORMATION: Synthetic Construct

<400> SEQUENCE: 35
agtgattcga ttaatgacgg cattaaagc                                      29

<210> SEQ ID NO 36
<211> LENGTH: 30
<212> TYPE: DNA
<213> ORGANISM: Artificial Sequence
<220> FEATURE:
<223> OTHER INFORMATION: Synthetic Construct

<400> SEQUENCE: 36
gtgattcgat taatgacggc attaaagcaa                                     30

<210> SEQ ID NO 37
<211> LENGTH: 30
<212> TYPE: DNA
<213> ORGANISM: Artificial Sequence
<220> FEATURE:
<223> OTHER INFORMATION: Synthetic Construct

<400> SEQUENCE: 37
aataatatct taaatctcta ttactgctaa                                     30

<210> SEQ ID NO 38
<211> LENGTH: 28
<212> TYPE: DNA
<213> ORGANISM: Artificial Sequence
<220> FEATURE:
<223> OTHER INFORMATION: Synthetic Construct

<400> SEQUENCE: 38
cagaaagttc tgcatttctt attgaacc                                       28

<210> SEQ ID NO 39
<211> LENGTH: 30
<212> TYPE: DNA
<213> ORGANISM: Artificial Sequence
<220> FEATURE:
<223> OTHER INFORMATION: Synthetic Construct

<400> SEQUENCE: 39
attggtaatt aaagcaatat acatacatat                                     30

<210> SEQ ID NO 40
<211> LENGTH: 32
<212> TYPE: DNA
<213> ORGANISM: Artificial Sequence
<220> FEATURE:
<223> OTHER INFORMATION: Synthetic Construct

<400> SEQUENCE: 40
gtattggtaa ttaaagcaat atacatacat at                                  32

<210> SEQ ID NO 41
```

```
<211> LENGTH: 281
<212> TYPE: DNA
<213> ORGANISM: Borrelia afzelii

<400> SEQUENCE: 41
atgcacaatt tatttgattt tttaaaatta aaacagcata taataaaaat gcatggcaag 60
caaataaatc aattatacaa aaagctctta attaaatttt ttcatcgata tccattaata 120
ttacaaatgg attcaagaaa taaactatct acaccttaca aaaaaggata taattcattc 180
gagaaataca taaaaatgtt taataacata gtaaacgaaa gaaaaatcac aaaaaaattga 240
aaaatttgct aatgaaattg gtttattgca ttatccaata a 281

<210> SEQ ID NO 42
<211> LENGTH: 32
<212> TYPE: DNA
<213> ORGANISM: Artificial Sequence
<220> FEATURE:
<223> OTHER INFORMATION: Synthetic Construct
<400> SEQUENCE: 42
aaattaaaac agcatataat aaaaatgcat gg 32

<210> SEQ ID NO 43
<211> LENGTH: 29
<212> TYPE: DNA
<213> ORGANISM: Artificial Sequence
<220> FEATURE:
<223> OTHER INFORMATION: Synthetic Construct
<400> SEQUENCE: 43
ttggatatgc aataaccaat ttcattagc 29

<210> SEQ ID NO 44
<211> LENGTH: 30
<212> TYPE: DNA
<213> ORGANISM: Artificial Sequence
<220> FEATURE:
<223> OTHER INFORMATION: Synthetic Construct
<400> SEQUENCE: 44
gctcttaatt aaattttttc atcgatatcc 30

<210> SEQ ID NO 45
<211> LENGTH: 33
<212> TYPE: DNA
<213> ORGANISM: Artificial Sequence
<220> FEATURE:
<223> OTHER INFORMATION: Synthetic Construct
<400> SEQUENCE: 45
ggatataatt cattcgagaa atacataaaa atg 33

<210> SEQ ID NO 46
<211> LENGTH: 717
<212> TYPE: DNA
<213> ORGANISM: Borrelia burgdorferi
<400> SEQUENCE: 46
atggtattta gaacatataa acatttggaa ctaataatgc tgcccatgtt aatgctgagt 60
tgcgcttttt ttaagaaacc acaatctgta catcaagaca gcaatactgg caaaccaata 120
agcgatgaaa aattacattt aatatcaggc aaaatttcaa ataaaaaatt gccaatcata 180
aatagtaatc atgacgtaac ttggataaaa acaaaggcaa tgacaatctt aggcgaagat 240
```

```
ggaaaagaaa taccagaatt taaaaacaaa tttggatatt cttatataat atctcctgta 300
aaaatggatg gaaaatatag ttattacgcg tcattattaa tactttttga aacaactaaa 360
aatggagatg atgaatatga aattgaagat gttaaatttg taacagctgg ttccacccta 420
gaacttaaaa attctctttt agctgttgaa aattcacaag aagaaggata tgttactgca 480
tacccatttg gaatattgat gagtgacgag attaaaaatg cttttaaatt aacatataaa 540
aatggtcatt ggaattatat gcttgcagat ttaactgtca aaaataaact tactcaagaa 600
actaaaattt ataaaatttc tcttaattca aaattaatta ttgaattttt aaaagaagtg 660
ctaaaagaaa attctatatt aaaagacata gctggagatt tatttgaaga tatataa 717
```

<210> SEQ ID NO 47
<211> LENGTH: 28
<212> TYPE: DNA
<213> ORGANISM: Artificial Sequence
<220> FEATURE:
<223> OTHER INFORMATION: Synthetic Construct

<400> SEQUENCE: 47

```
acatttggaa ctaataatgc tgcccatg 28
```

<210> SEQ ID NO 48
<211> LENGTH: 32
<212> TYPE: DNA
<213> ORGANISM: Artificial Sequence
<220> FEATURE:
<223> OTHER INFORMATION: Synthetic Construct

<400> SEQUENCE: 48

```
agttgtttca aaaagtatta ataatgacgc gt 32
```

<210> SEQ ID NO 49
<211> LENGTH: 31
<212> TYPE: DNA
<213> ORGANISM: Artificial Sequence
<220> FEATURE:
<223> OTHER INFORMATION: Synthetic Construct

<400> SEQUENCE: 49

```
catgttaatg ctgagttgcg cttttttaa g 31
```

<210> SEQ ID NO 50
<211> LENGTH: 29
<212> TYPE: DNA
<213> ORGANISM: Artificial Sequence
<220> FEATURE:
<223> OTHER INFORMATION: Synthetic Construct

<400> SEQUENCE: 50

```
catgacgtaa cttggataaa aacaaaggc 29
```

<210> SEQ ID NO 51
<211> LENGTH: 735
<212> TYPE: DNA
<213> ORGANISM: Borrelia afzelii

<400> SEQUENCE: 51

```
atgatattta gaacatataa gcatttaaaa ttaatagcaa tacttatgtt aatgttgagt 60
tgcgcttttt ttaaaaagcc acaaactgca caacaaaacg gagctattgg aaacccaata 120
agggatgaat tgcctttaaa cgatggaaaa ttacatttaa tatcaggaaa aattttgaat 180
```

```
aaaaaattgc cagtcgtaaa tgaaaatcat gacgtaactt ggataaaaac aaaggcaatg    240
gcaatcttag ataaagatgg acaagcaatg ccagaattca aaaacaaatt tggatattct    300
tatatactat cccctataaa aatgaatgat gaatatagta gttacacatc gctattaata    360 cttttttgaaa caactgaaaa tggagataaa gaatatgaaa ttgaagatat taaacttata    420
acagctggtt ccaacctaga acttaaacat tctcttctaa ttgctgaaaa atcacaagaa    480
gaaggatatg ttactgcata cccatttgga atcttgatgg acgaagaact tagaaaagct    540
tttcaattaa catatcaaaa tggtcattgg aattatatgc ttgcaaattt aaccgttaaa    600
aacaagatta ctcaaaaaac tgaaatttat acaatttctc ttaattcaaa attaattatt    660
gactttgtaa aagaagtatt aaagaaaat cccatcttaa aagagacaaa tggagatcta    720
tttgaagata tataa                                                    735
```

<210> SEQ ID NO 52
<211> LENGTH: 26
<212> TYPE: DNA
<213> ORGANISM: Artificial Sequence
<220> FEATURE:
<223> OTHER INFORMATION: Synthetic Construct

<400> SEQUENCE: 52
ccacaaactg cacaacaaaa cggagc                                         26

<210> SEQ ID NO 53
<211> LENGTH: 30
<212> TYPE: DNA
<213> ORGANISM: Artificial Sequence
<220> FEATURE:
<223> OTHER INFORMATION: Synthetic Construct

<400> SEQUENCE: 53
ccaatttgtt tttgattctg gtattgcttg                                     30

<210> SEQ ID NO 54
<211> LENGTH: 31
<212> TYPE: DNA
<213> ORGANISM: Artificial Sequence
<220> FEATURE:
<223> OTHER INFORMATION: Synthetic Construct

<400> SEQUENCE: 54
tgaatgatga atatagtagt tacacatcgc t                                   31

<210> SEQ ID NO 55
<211> LENGTH: 25
<212> TYPE: DNA
<213> ORGANISM: Artificial Sequence
<220> FEATURE:
<223> OTHER INFORMATION: Synthetic Construct

<400> SEQUENCE: 55
gaaacccaat aagggatgaa ttgcc                                          25

<210> SEQ ID NO 56
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: n is deoxyinosine

<400> SEQUENCE: 56
ggaaacccaa taagngatga attgcc                                        26

<210> SEQ ID NO 57
<211> LENGTH: 26
<212> TYPE: DNA
<213> ORGANISM: Artificial Sequence
<220> FEATURE:
<223> OTHER INFORMATION: Synthetic Construct

<400> SEQUENCE: 57
gacgtaactt ggataaaaac aaaggc                                        26

<210> SEQ ID NO 58
<211> LENGTH: 24
<212> TYPE: DNA
<213> ORGANISM: Artificial Sequence
<220> FEATURE:
<223> OTHER INFORMATION: Synthetic Construct

<400> SEQUENCE: 58
gatggacaag caatgccaga attc                                          24

<210> SEQ ID NO 59
<211> LENGTH: 649
<212> TYPE: DNA
<213> ORGANISM: Borrelia garinii

<400> SEQUENCE: 59
atgaaaagaa taagtatttt atcaatacta ctgttattat tgttgttttc ttgtaaacag    60
tatggtgatg ttaaatcatt aacagaagtt gctactgatc ttgaggatga caattctttt   120
gcttctggga gtgtagagtc taaagatcaa attatcgaaa aaggaccgt tttaacatca    180 gaggagtttg aaaggttaga ggctttaaaa acctttttaa aagacgcaat gggtgttaat   240
ggtagagaag gcgatacaaa agctgagtat gagaaatcct ataaagaatt ttttgattgg   300
ctttctaagg atgttaacag acagaaagag tttgtaagtt ttttttaacaa tatttgtggc   360 attattacta aagcagtgga tgcaagcaaa aaaaggtata atagtaatcc aaaatcctta   420
ggttttaatg aatatgtttg ttatgatatt aaaaccagga ctggggatga tttaagttta   480
tttttccaaa aagtagctga tgcatttggc actcaagagt acaaaaataa agatgaggat   540
gatgagaaca atcaaaagcc tgaaaaatgc aatgaagaga ttttaagt aattaaaga    600 gtgtttactg aaagcgagaa taataacgaa ttggcaaatt taaaaaatt                649

<210> SEQ ID NO 60
<211> LENGTH: 35
<212> TYPE: DNA
<213> ORGANISM: Artificial Sequence
<220> FEATURE:
<223> OTHER INFORMATION: Synthetic Construct

<400> SEQUENCE: 60
ggtgatgtta aatcgttaac agaagttgct actga                              35

<210> SEQ ID NO 61
<211> LENGTH: 36
<212> TYPE: DNA
<213> ORGANISM: Artificial Sequence
<220> FEATURE:
<223> OTHER INFORMATION: Synthetic Construct

<400> SEQUENCE: 61
ggtgatgtta aatcgttaac agaagttgct actgat                                36

<210> SEQ ID NO 62
<211> LENGTH: 35
<212> TYPE: DNA
<213> ORGANISM: Artificial Sequence
<220> FEATURE:
<223> OTHER INFORMATION: Synthetic Construct

<400> SEQUENCE: 62
ctgattttga ggatggcaat tcttttgttt ctggg                                 35

<210> SEQ ID NO 63
<211> LENGTH: 30
<212> TYPE: DNA
<213> ORGANISM: Artificial Sequence
<220> FEATURE:
<223> OTHER INFORMATION: Synthetic Construct

<400> SEQUENCE: 63
ttgtctgtta acatccttag aaagccaatc                                       30

<210> SEQ ID NO 64
<211> LENGTH: 30
<212> TYPE: DNA
<213> ORGANISM: Artificial Sequence
<220> FEATURE:
<223> OTHER INFORMATION: Synthetic Construct

<400> SEQUENCE: 64
ttgtctgtta mcatccttag aaagccaatc                                       30

<210> SEQ ID NO 65
<211> LENGTH: 34
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: n is deoxyinosine

<400> SEQUENCE: 65 cttttgtct gttancatcc ttagaaagcc aatc                                   34

<210> SEQ ID NO 66
<211> LENGTH: 29
<212> TYPE: DNA
<213> ORGANISM: Artificial Sequence
<220> FEATURE:
<223> OTHER INFORMATION: Synthetic Construct

<400> SEQUENCE: 66
ttgaggatgg caattctttt gtttctggg                                        29

<210> SEQ ID NO 67
<211> LENGTH: 26
<212> TYPE: DNA
<213> ORGANISM: Artificial Sequence
<220> FEATURE:
<223> OTHER INFORMATION: Synthetic Construct

<400> SEQUENCE: 67
aaggacctgt tttaacatca gaggag                                           26

<210> SEQ ID NO 68
<211> LENGTH: 27
<212> TYPE: DNA
<213> ORGANISM: Artificial Sequence
<220> FEATURE:
<223> OTHER INFORMATION: Synthetic Construct

<400> SEQUENCE: 68

```
aagctgagta tgagaaatcc tataaag                                27
```

<210> SEQ ID NO 69
<211> LENGTH: 1248
<212> TYPE: DNA
<213> ORGANISM: Borrelia afzelii

<400> SEQUENCE: 69

```
ttaacgtcta ctaatttctt ttatcaaacc gtttaaaatg cgatttatat aatcataaag    60
ttttttattt ttgccaatat ttttataata aagtttaaaa atttctaaaa gggtatttct   120
aactttaaga attactattc ttttgttttt attctcaaca gaccctaatg cctgtttgaa   180
agatttggtt gatttctcca tttcttttaa aaatctatta acattataat ttagcgttat   240
ttcttctagc tttctcaata tcaacctaga atattctttt ccaagtcttt taaataaatc   300
atcaagattc tcagaatcta attctccgtc taataaaacc ctacaaaatt gtaacgtctc   360
gtcttcttcg tctgttaaat tccgcttcca atttaaatac caatcaagct ctgactttgt   420
agtaagagaa aaattttta attcaagaag ctctttgcta acgctactaa tttgttgatc   480
aactgttttt tcaagagcaa caagaatgtc tgtgtttgaa ccactagcat taattttggt   540
taagtaaaat tgttgacaca aattcatatc taagagagaa atttcatctt ctctatcact   600
tttatcggaa tagttttcaa tcaatcccac taaaatactt attttagaag acaaatctcc   660
ccaacgcttt tgcctatat caatcaagaa ctgattaaca tcttttttcgc tgtacttata   720
ctttactaac acctcatcat tgtttaaaag ccatccacca agagcatatc tattctcatc   780
attttgcaaa gatttcttga aaaactcaaa attttttatcc tcttccaagt ttaaatgggg   840
aatcaaacta tcatcatgag aattttttcag caaagcttta ctgtatcttg atttaccaat   900
actgtgcttt gaagaagttt tttgcaaaga cttataatta tctaaattat tgctagcctg   960
atctaagttt tgcgacattg aatttttaga atttcttaaa gtttgtaaat cccttttaga  1020
atctttaaat tctcttgagt ttacttggct attttttttg cttttaaaat tacttaaatt  1080
gggatcttta ggcttattgt ttttagaatc caaagatttt ttttcattaa tgattaagtt  1140
ttgtttattg ctagaagtgg taattttga atcttcttct aaagatttgc tactgcaatt  1200
aataaacaat agaaaactaa taataaatga aattcctatt ttattcat                1248
```

<210> SEQ ID NO 70
<211> LENGTH: 35
<212> TYPE: DNA
<213> ORGANISM: Artificial Sequence
<220> FEATURE:
<223> OTHER INFORMATION: Synthetic Construct

<400> SEQUENCE: 70

```
cagcaaagct ttactgtatc ttgatttacc aatac                       35
```

<210> SEQ ID NO 71
<211> LENGTH: 35
<212> TYPE: DNA

<213> ORGANISM: Artificial Sequence
<220> FEATURE:
<223> OTHER INFORMATION: Synthetic Construct

<400> SEQUENCE: 71
gctttactgt atcttgattt accaatactg tgctt                          35

<210> SEQ ID NO 72
<211> LENGTH: 40
<212> TYPE: DNA
<213> ORGANISM: Artificial Sequence
<220> FEATURE:
<223> OTHER INFORMATION: Synthetic Construct

<400> SEQUENCE: 72
caaaaattac cacttctagc aataaacaaa acttaatcat                     40

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
tgggatcttt aggcttattg tttttagaat cc                             32

<210> SEQ ID NO 74
<211> LENGTH: 33
<212> TYPE: DNA
<213> ORGANISM: Artificial Sequence
<220> FEATURE:
<223> OTHER INFORMATION: Synthetic Construct

<400> SEQUENCE: 74
tttgcaaaga cttataatta tctaaattat tgc                            33

<210> SEQ ID NO 75
<211> LENGTH: 33
<212> TYPE: DNA
<213> ORGANISM: Artificial Sequence
<220> FEATURE:
<223> OTHER INFORMATION: Synthetic Construct

<400> SEQUENCE: 75
ccttttagaa tctttaaatt ctcttgagtt tac                            33

<210> SEQ ID NO 76
<211> LENGTH: 1194
<212> TYPE: DNA
<213> ORGANISM: Borrelia garinii

<400> SEQUENCE: 76
ttaacgtcta ctaatctctt ttattaagct gtttaaaata cgatttatat aatcataaag    60 tttttttattc ttgccaatat ttttgtaata aagtttaaaa atttccaaaa gagtatttct   120
aaccttagaa atcaacccctt ttctgttttt atttctaata gagactaatg cttgtttgaa   180
agatttgcgt gatttttcca tttcctttaa aaaactatta acatcataat ttaatatgat   240
ttcctctagc tttctcaata tcaacctaga atattccttt ccaagccttt taaacaaatc   300
atcaagattc tcaaaatcta attccccatc taccaaaacc ctgcacaatt gtagtgtttc   360
gtcttcttcg tctgttaaat tgcgcttcca atttaaatgc caatcaagct ctgactttgt   420
agtaagggaa aaattttttta attcaagaag ctctttgcta acactgctaa tttgttgatc   480

```
gattgttttt tcaagagcaa caaaaatgtc tgcatttgaa ccattggcat taatcttggt    540
taaataaaat tgttgacaca aattcatatc taaaagagac atttcatctt ctctatcact    600
tttatcggaa taattttcaa tcaatcgcac taaaatgctc attttagcag acaactctcc    660
ccatcgcttt ttccctatat caatcaaaaa ctgattaaca tcttttttcgc tgtacctata   720 ctttaccaac acttcatcat tgtttaaaag ccatccacca agagcatatc tattctcatc    780
gttttgcaaa gatttcttga aaaactcaaa attttttatcc tcttctgagt ttaaatgggg   840
aatcaaaatc tcatcctgag cattttttcag caaagctttg ctgtgttttg cttattaat    900 attgtgcttt gaagaagttt tttgtaaaga tctagaatta tctaaattat ccaaatcatt    960
gctggtctga ttcgggtcta ttaacattaa attttttagaa ttttttaaag tttgtgaatc   1020 cttttttagaa tcttccaact tattctttt agacgccaaa gatttttttt cattgccgat   1080
taaatttcgt ctattgtggg aagtggtggt ttttaaatct tcttctaaag atttactatt    1140
acaattaaca aaaacagaa agctaatact aaatgcaatt cctattttat tcat           1194
```

<210> SEQ ID NO 77
<211> LENGTH: 27
<212> TYPE: DNA
<213> ORGANISM: Artificial Sequence
<220> FEATURE:
<223> OTHER INFORMATION: Synthetic Construct

<400> SEQUENCE: 77
cagcaaagct ttgctgtgtt ttggctt                                        27

<210> SEQ ID NO 78
<211> LENGTH: 28
<212> TYPE: DNA
<213> ORGANISM: Artificial Sequence
<220> FEATURE:
<223> OTHER INFORMATION: Synthetic Construct

<400> SEQUENCE: 78
ctcatcctga gcattttttca gcaaagct                                      28

<210> SEQ ID NO 79
<211> LENGTH: 32
<212> TYPE: DNA
<213> ORGANISM: Artificial Sequence
<220> FEATURE:
<223> OTHER INFORMATION: Synthetic Construct

<400> SEQUENCE: 79
ccacttccca taatagacga aatttaatcg gc                                  32

<210> SEQ ID NO 80
<211> LENGTH: 28
<212> TYPE: DNA
<213> ORGANISM: Artificial Sequence
<220> FEATURE:
<223> OTHER INFORMATION: Synthetic Construct

<400> SEQUENCE: 80
gaagaagttt aaaactacca cttcccac                                       28

<210> SEQ ID NO 81
<211> LENGTH: 34
<212> TYPE: DNA
<213> ORGANISM: Artificial Sequence
<220> FEATURE:

<223> OTHER INFORMATION: Synthetic Construct

<400> SEQUENCE: 81
gtaaagatct agaattatct aaattatcca aatc                                    34

<210> SEQ ID NO 82
<211> LENGTH: 36
<212> TYPE: DNA
<213> ORGANISM: Artificial Sequence
<220> FEATURE:
<223> OTHER INFORMATION: Synthetic Construct

<400> SEQUENCE: 82
gtttgtgaat cctttttaga atcttccaac ttattc                                  36

<210> SEQ ID NO 83
<211> LENGTH: 28
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (21)..(21)
<223> OTHER INFORMATION: n is deoxyinosine

<400> SEQUENCE: 83
ccaacttatt cttttttggac nccaaaga                                          28

<210> SEQ ID NO 84
<211> LENGTH: 1323
<212> TYPE: DNA
<213> ORGANISM: Borrelia garinii

<400> SEQUENCE: 84

| | | |
|---|---|---|
| atgaattttc aaaattttat tgaaactact ttagttccta ttgctagtaa aattggttca | 60 |
| aatagatatt taattgcttt aagagatggt tttactttt ctatgccctt tttgatagtt | 120 |
| ggttctttta ttttactttt agttaattta cccttttacag attctacaac attattatat | 180 |
| caacagtggt atgttgattt aatggctaaa tataaaggaa atattgttca gccattttat | 240 |
| gtaagtatgg ggattatgtc catatttgtt gtttttggta ttggttataa cttatctaat | 300 |
| cattataaac ttagtggaat tacaggagga ttcctgtctc tttatacatt tttaatttta | 360 |
| gctggacaat cagattggat accttacgga ggagatgctg ctaaatgggg aattcagcct | 420 |
| aattcatggt ttcctgtaat tgatgcaaga tattttagtg ctcaaggagt atttacagct | 480 |
| attatttctg ctatttttgc tgttgaagtt tataaatttt tagttcaaag aaatatggca | 540 |
| attaaacttc cagagtctgt tccgcctgct gtttttaaaat cttttgaagc tttagttcct | 600 |
| gttgttgtac tttccattgt ggctcaaagt gttaatattg ctattcaaag tttagcaggc | 660 |
| agccttttcc ccgaaataat tatgagtatg tttaggcctg ttttacaaat tagcgatact | 720 |
| ttagttggga cttaatgat ttctttttatc gttcatatac tatggttttg tggccttcat | 780 |
| ggtaccaatg ttattgttgc cttgcttaat cccataattc tgacaaatct tgattctaat | 840 |
| attagggctc tttctgacaa tcttccactt cctcatattt tagcgggtgg atttcttgat | 900 |
| tcatttgtat atattggtgg tgctggttca actttaggcc ttgttattgc catgatgctt | 960 |
| agtaaatctc aacatctaaa ggccataggt aaactttcat ttgctcctgg tctttttaat | 1020 |
| attaatgagc ctattatgtt tggggcacca atagttttaa atcctatact aggtattcct | 1080 |
| tttttactta ttcctatgtt taatataatt gtcgcatata ctcttactaa ttttggaatt | 1140 |

```
attgaaagag ttagaacctt aactccatgg acaaccctg ctcctattgc cgcttttttg    1200
tctacagggc ttgatattaa atcttttgtt ctggttttat tattattgat tatttcggta    1260
tttatgtatt tacccttat aaaagcatat gataaggttc tgcttttgca ggaaaaagaa    1320
tag                                                                  1323
```

<210> SEQ ID NO 85
<211> LENGTH: 32
<212> TYPE: DNA
<213> ORGANISM: Artificial Sequence
<220> FEATURE:
<223> OTHER INFORMATION: Synthetic Construct

<400> SEQUENCE: 85

```
cttttagtta atttaccctt tacagattct ac                                    32
```

<210> SEQ ID NO 86
<211> LENGTH: 29
<212> TYPE: DNA
<213> ORGANISM: Artificial Sequence
<220> FEATURE:
<223> OTHER INFORMATION: Synthetic Construct

<400> SEQUENCE: 86

```
gtaaggtatc caatctgatt gtccagcta                                        29
```

<210> SEQ ID NO 87
<211> LENGTH: 30
<212> TYPE: DNA
<213> ORGANISM: Artificial Sequence
<220> FEATURE:
<223> OTHER INFORMATION: Synthetic Construct

<400> SEQUENCE: 87

```
cgtaaggtat ccaatctgat tgtccagcta                                       30
```

<210> SEQ ID NO 88
<211> LENGTH: 27
<212> TYPE: DNA
<213> ORGANISM: Artificial Sequence
<220> FEATURE:
<223> OTHER INFORMATION: Synthetic Construct

<400> SEQUENCE: 88

```
cagcagtggt atgttgattt aatggct                                          27
```

<210> SEQ ID NO 89
<211> LENGTH: 35
<212> TYPE: DNA
<213> ORGANISM: Artificial Sequence
<220> FEATURE:
<223> OTHER INFORMATION: Synthetic Construct

<400> SEQUENCE: 89

```
ggattcctgt ctctttatac attttaatt ttagc                                  35
```

<210> SEQ ID NO 90
<211> LENGTH: 35
<212> TYPE: DNA
<213> ORGANISM: Artificial Sequence
<220> FEATURE:
<223> OTHER INFORMATION: Synthetic Construct

<400> SEQUENCE: 90
cattataaac ttagtggaat tacaggagga ttcct                          35

<210> SEQ ID NO 91
<211> LENGTH: 30
<212> TYPE: DNA
<213> ORGANISM: Artificial Sequence
<220> FEATURE:
<223> OTHER INFORMATION: Synthetic Construct

<400> SEQUENCE: 91
ataaacttag tggaattaca ggaggattcc                                30

<210> SEQ ID NO 92
<211> LENGTH: 22
<212> TYPE: DNA
<213> ORGANISM: Artificial Sequence
<220> FEATURE:
<223> OTHER INFORMATION: Synthetic Construct

<400> SEQUENCE: 92
agcaggcgga acagactctg ga                                        22

<210> SEQ ID NO 93
<211> LENGTH: 32
<212> TYPE: DNA
<213> ORGANISM: Artificial Sequence
<220> FEATURE:
<223> OTHER INFORMATION: Synthetic Construct

<400> SEQUENCE: 93
ctctttatac atttttaatt ttagctgggc aa                             32

<210> SEQ ID NO 94
<211> LENGTH: 28
<212> TYPE: DNA
<213> ORGANISM: Artificial Sequence
<220> FEATURE:
<223> OTHER INFORMATION: Synthetic Construct

<400> SEQUENCE: 94
caaagaaata tggcaattaa acttccag                                  28

<210> SEQ ID NO 95
<211> LENGTH: 29
<212> TYPE: DNA
<213> ORGANISM: Artificial Sequence
<220> FEATURE:
<223> OTHER INFORMATION: Synthetic Construct

<400> SEQUENCE: 95
gggcaatcag attggatgcc ttacggagg                                 29

<210> SEQ ID NO 96
<211> LENGTH: 28
<212> TYPE: DNA
<213> ORGANISM: Artificial Sequence
<220> FEATURE:
<223> OTHER INFORMATION: Synthetic Construct

<400> SEQUENCE: 96
gggcaatcag attggatgcc ttacggag                                  28

<210> SEQ ID NO 97
<211> LENGTH: 31
<212> TYPE: DNA
<213> ORGANISM: Artificial Sequence

```
<220> FEATURE:
<223> OTHER INFORMATION: Synthetic Construct

<400> SEQUENCE: 97
gctgggcaat cagattggat gccttacgga g                                  31

<210> SEQ ID NO 98
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is deoxyinosine

<400> SEQUENCE: 98
taattatttc ggngaaaagg ctgcctgcta                                    30

<210> SEQ ID NO 99
<211> LENGTH: 32
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: n is deoxyinosine

<400> SEQUENCE: 99
cataattatt tcggngaaaa ggctgcctgc ta                                 32

<210> SEQ ID NO 100
<211> LENGTH: 28
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: n is deoxyinosine

<400> SEQUENCE: 100
gggattcagc ctaatncatg gtttcctg                                      28

<210> SEQ ID NO 101
<211> LENGTH: 25
<212> TYPE: DNA
<213> ORGANISM: Artificial Sequence
<220> FEATURE:
<223> OTHER INFORMATION: Synthetic Construct

<400> SEQUENCE: 101
gtactttcca ttgtggctca aggtg                                         25

<210> SEQ ID NO 102
<211> LENGTH: 1212
<212> TYPE: DNA
<213> ORGANISM: Borrelia afzelii

<400> SEQUENCE: 102
ttacggcatt ttaaaaacat cgtgtggatg cgattctttt aatgaagaat ggcttatttt    60
tacaaactta gaatttattt ttaaatcaga tattgtgatt gctcctaaat aacccattcc   120
```

```
agacattaat ccaccttta gttggttcaa aatatctttt aattctccag aatacggtac    180 catacct tca attccttcag ggactaattt tttaggctcg ttgttctcga gttgaaaata    240
tcttgattta gagccccttt tcatagcgga aatagaaccc attccaacgt aagatttgaa    300
tttctttcca ttgtaaatta tttcctctga aggagattct ttcgcgcctg caaagagatt    360
tcctatcatt acgctatcag ctcctgctgc aatggcttta actacatctc ctgaaaaccg    420
gattccaccg tctgctataa tgcaaatatt tgtgttttg caaacttcat aaacgtcgca    480
gattgctgtt atttggggaa cgccaactcc tgcaacgatt cttgttgtgc atatactacc    540
tggacctatt cctacttta aacagtctgc tcctgcattg attaaatcta atgcggcttc    600
tttagttact atattgccag caataaggtc taaatttgga tacttgtttt taattgtttt    660
tacaagttct attattcttg tagaatgccc gtgggcagag tctatgacaa tcagatctac    720
atgtgctttt acaagttctt caactcgttc tatggtatca atatcaatag aaatagcagc    780
tcctactctt agcttgctat ttaaatcttt acatgcatta gaaaaatctt ctttgtgttc    840 tgtatttta tgtatttcgg gttcttctaa atattgcttt gtaagcattt tggtttcttg    900
ttcgtttgta accttattag tgttgatggt tttttgggct ttatatgttt ttactttctc    960
aatttctttt ttttgagcct ctattgacat attttatgt ataatcccta ttccgccttc    1020
tttagcaata gctattgcca tttggctttc tgtaacagta tccatggctg agcttaaaaa    1080
tggtatattt aaggatatgt tttttgtcaa ctgtgttttt aagctaacct cactaggtaa    1140
tatagaggat tttcttggaa ttaaagacac atcatcaaaa gttaaagctt cttttattat    1200
cttgtttgtc at                                                         1212

<210> SEQ ID NO 103
<211> LENGTH: 1626
<212> TYPE: DNA
<213> ORGANISM: Borrelia afzelii

<400> SEQUENCE: 103
atgtcaacat catccgcatc tatatctata tttacaatat acaaaaagt aggaaaagct      60 ttcatgcttc ctatagcact tttaccagca gctggaattt tattgggaat cggaggagca    120
tttaccaacg aaacaatgat tcaggcttat ggattagaag gaatacttgg aaaaggaact    180
gtagcaagct caatacttta ccttatgaaa tatacaggag aagtaatttt tgctaactta    240
cctttaatgt ttgcagcagc aattccaata ggacttgcta agtagaaaaa aggaacagct    300
gctttagcag gagtagttgg ttttttagtt atgcaccaaa ctataaatgg aatcttatat    360
atacaaggaa tcacaccaga aagcgcaagc ttaaaagcac tattagaatt aggaatgcct    420
gaaacagctg caactgcaaa aagtcaggaa tatacaaatg tacttggaat attctctctt    480
caaatgagcg taatgggggg actagtagca ggatttgttg ctgttttttct tcataacaga    540 ttctataata ttcaattacc cacattttta gcattttttg gaggcacaag atttgtacca    600
atcataacca caataaccat gtttgtagta gggatatttt aacatttat ttggcctttc    660 attcaaggtg caatgacttc gtttgggcaa attgtagaac aatctgggct ttttggaaca    720
tttgcatatg gagcaataaa aagatcctta attccatttg gacttcacca tatattttac    780
ttaccatttt ggcaaacagc tgttggtgga acattagaaa taaatggaga actcatatca    840
ggagcacaaa atatattctt caagcaactt ggggatacca atactgtaca ctttgaagtt    900
gcaaagggaa caagattttt tagcggagaa tttgttgtta tgattttggg attacctgga    960
gctgctcttg ctatgtacca tacatcaaaa cccgaaaata aaaaaaacgt agcttcattg   1020
```

```
ctactatctg ctagctttac atcaatgtta acaggaatta cagaacctct tgaatttgca    1080
ttcctttttg cagcaccagc gctttattac tttatatatg ttcctctttt tggattggcg    1140
tatcttttaa cacaccttttt aaacgtagga gttggactaa cattttctgg aggatttata    1200
```

<br>

```
ctactatctg ctagctttac atcaatgtta acaggaatta cagaacctct tgaatttgca    1080
ttcctttttg cagcaccagc gctttattac tttatatatg ttcctctttt tggattggcg    1140
tatcttttaa cacacctttt aaacgtagga gttggactaa cattttctgg aggatttata    1200
gatatgtttc tatttggaat acttcaagga aatagtaaaa caaattggat agcaattcct    1260
atcttaggaa tcttctactt tattggattc tactttatat ttaaatttgt aatcatgaaa    1320
ttcaatctta aacaatcgg aagagaagat gaagaaatgg aaaagatat aagttcagaa    1380 aaaacaaatt tatcagaaac tgctttaaaa gtattagagg ccttggagg aaaagataat    1440 attacatatc ttgatgcatg tgcatcaaga ttaagagtta atctaaaaca aatagaattc    1500
atcaaatcag atacctattt caaaaatttg ggtgctagtg aatattaaaa aaaaggaaat    1560
agcgtccaaa ttgtatttgg aggattatcc gataacataa aatgaaat cgataagctt    1620 atgtaa                                                               1626

<210> SEQ ID NO 104
<211> LENGTH: 30
<212> TYPE: DNA
<213> ORGANISM: Artificial Sequence
<220> FEATURE:
<223> OTHER INFORMATION: Synthetic Construct

<400> SEQUENCE: 104
gatttgtacc aatcataacc acaataacca                                       30

<210> SEQ ID NO 105
<211> LENGTH: 1197
<212> TYPE: DNA
<213> ORGANISM: Borrelia burgdorferi

<400> SEQUENCE: 105 gtgata

```
ggttcaagaa ttttattaac actttctcgc tctatgaaaa tgaagaataa aacaaaaggg   1140
atagcatctg tttgtattgg tggcggacaa ggaatttcta gttttttgta tagatga      1197
```

<210> SEQ ID NO 106
<211> LENGTH: 33
<212> TYPE: DNA
<213> ORGANISM: Artificial Sequence
<220> FEATURE:
<223> OTHER INFORMATION: Synthetic Construct

<400> SEQUENCE: 106

```
gttttttgata agaagaccaa ctctagcgta act                                33
```

<210> SEQ ID NO 107
<211> LENGTH: 29
<212> TYPE: DNA
<213> ORGANISM: Artificial Sequence
<220> FEATURE:
<223> OTHER INFORMATION: Synthetic Construct

<400> SEQUENCE: 107

```
taatgccttc aatagccata taagctcca                                      29
```

<210> SEQ ID NO 108
<211> LENGTH: 29
<212> TYPE: DNA
<213> ORGANISM: Artificial Sequence
<220> FEATURE:
<223> OTHER INFORMATION: Synthetic Construct

<400> SEQUENCE: 108

```
actttaaata agctagcatc tcttaatcc                                      29
```

<210> SEQ ID NO 109
<211> LENGTH: 28
<212> TYPE: DNA
<213> ORGANISM: Artificial Sequence
<220> FEATURE:
<223> OTHER INFORMATION: Synthetic Construct

<400> SEQUENCE: 109

```
ttagcttata ttggaggatt taaaagcg                                       28
```

<210> SEQ ID NO 110
<211> LENGTH: 1221
<212> TYPE: DNA
<213> ORGANISM: Borrelia garinii

<400> SEQUENCE: 110

```
ttgaaaggca agcttataaa agtttcaaac aaattctcaa tacttgcgct gttactgatt    60
attagctgta atgccaatat gaacacgaat gataaaaaca aagtcttaaa cgaacataac   120
ttaaaaaata tttcagaagt cattaagaat agcttacaaa ttgaatcaga cttaaaaaaa   180
gaacctgaag caaacaaaaa tcaaagtacc ccccctattt tagaaattga aaaaattgaa   240
cctggaacac aagaattttc tttaaaatct gaatctgaaa gctcaatccc tctagaaatc   300
ctagaaggag caaatgtggt caaatcagaa gaagaaattg caaaaataca agaaaaatta   360
ttgttaatcg gagcttctga tgaaagaata gcacaagaat tagaccccaa tattcaaaaa   420
tctttaaatc caactacaat agaattcaaa attctaagca ccgccgacga aaaaacaata   480
cttgatccaa ctgaagaaga aattaatact aatggaaaag acaaaatttt tgatcaaaaa   540
aaagaaaata gcactttaag cgaaactaca aaaactccaa tacaaaatca attccaaaag   600
```

-continued

| | |
|---|---|
| catggcatat ctttaagtaa agatggcaac ttcataacaa agaatatgt agagcaagtt | 660 |
| agagaatctc tagacaaagc gctaaatgca ataaaaagtt tagaaaaatc taaagatctt | 720 |
| ttcaatcttg atgccgaaga aaatttacta aaggatctgg gaaactctca aaacaaaaca | 780 |
| aacagctcaa tctcaataa tattaatgct gagaacatag aaaaaacaaa aaatatattc | 840 |
| cttgaagagc tagaaaaaag tgagcttagt tttgaaaaca ctaaagatcc cttaggaata | 900 |
| agcaccataa aagaagtaat agatgctgcc aacaaatgga agaaaaaga aaactcaagc | 960 |
| caaataaact gggacttagg atcaaagttt catccaaacc cgaagcttta caacgaatca | 1020 |
| gtagctagag agtataaagt tttggctgaa aaatttacca aagtaaaaaa tgaatacaaa | 1080 |
| aacacaaaag aacaactaaa agttcaatct aaattaacag ctaacaacct caacaaaata | 1140 |
| attgacgcaa caaaagagtt tgcaaaccaa gtaagaaatt taatcttatt ggtagaaaac | 1200 |
| aatcaataaa agccctatta a | 1221 |

<210> SEQ ID NO 111
<211> LENGTH: 29
<212> TYPE: DNA
<213> ORGANISM: Artificial Sequence
<220> FEATURE:
<223> OTHER INFORMATION: Synthetic Construct

<400> SEQUENCE: 111
caaattctca atacttgcgc tgttactga                                    29

<210> SEQ ID NO 112
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: n is deoxyinosine

<400> SEQUENCE: 112
tctagnggga ttgagctttc agattca                                      27

<210> SEQ ID NO 113
<211> LENGTH: 31
<212> TYPE: DNA
<213> ORGANISM: Artificial Sequence
<220> FEATURE:
<223> OTHER INFORMATION: Synthetic Construct

<400> SEQUENCE: 113
cttctgattt gaccacattt gcttcttcta g                                 31

<210> SEQ ID NO 114
<211> LENGTH: 33
<212> TYPE: DNA
<213> ORGANISM: Artificial Sequence
<220> FEATURE:
<223> OTHER INFORMATION: Synthetic Construct

<400> SEQUENCE: 114
gcaatttctt cttctgattt gactacattt gct                               33

<210> SEQ ID NO 115
<211> LENGTH: 26
<212> TYPE: DNA

```
<213> ORGANISM: Artificial Sequence
<220> FEATURE:
<223> OTHER INFORMATION: Synthetic Construct

<400> SEQUENCE: 115
agctgtaatg ccaatatgaa cgcgaa                                           26

<210> SEQ ID NO 116
<211> LENGTH: 32
<212> TYPE: DNA
<213> ORGANISM: Artificial Sequence
<220> FEATURE:
<223> OTHER INFORMATION: Synthetic Construct

<400> SEQUENCE: 116
ccctatttta gaaattgaaa aaattgaacc tg                                    32

<210> SEQ ID NO 117
<211> LENGTH: 26
<212> TYPE: DNA
<213> ORGANISM: Artificial Sequence
<220> FEATURE:
<223> OTHER INFORMATION: Synthetic Construct

<400> SEQUENCE: 117
ttcgtgttca tattggcatt acagct                                           26

<210> SEQ ID NO 118
<211> LENGTH: 32
<212> TYPE: DNA
<213> ORGANISM: Artificial Sequence
<220> FEATURE:
<223> OTHER INFORMATION: Synthetic Construct

<400> SEQUENCE: 118
caggttcaat tttttcaatt tctaaaatag gg                                    32

<210> SEQ ID NO 119
<211> LENGTH: 555
<212> TYPE: DNA
<213> ORGANISM: Borrelia garinii

<400> SEQUENCE: 119
atgaaaaaat ttaatttaat aattgtagct ttgtttgttg ctctgctggc agcctgtaat       60
tttggattaa caggagaagt aaaagcaatg cttgaatcgt cttctgataa tgtaaaaaac      120 aaaatttttac aaataaaaga agaagccgct aaaaagggtg taaattttaa agcttttaca     180
ggcaccgcaa ctggttctaa agtgacaaat gggggatcag ccttaagaga agcaaaagta      240
caagccatta atgaagtaga aaagttcctt aagataatag aaaagaagc tttaatactt       300 aaaaaaaatg gaaatagtag tcaattcttg gctatgtttg atttcatgct tgaagttaca      360
ggatcattag atgaaattgg aataaaagga ataaaaagct ccatttcaga ggaagctaaa      420
tctaaccctg taaacacggc tgaaagattg gttgaggtta aggctaaaat agaaaataaa      480
ctagaaggtg tcaagaaaag acaaaaactt gacgatgagg aaaaaaaaat aagtaaaagc      540
aaaaaaaaga aataa                                                      555

<210> SEQ ID NO 120
<211> LENGTH: 28
<212> TYPE: DNA
<213> ORGANISM: Artificial Sequence
<220> FEATURE:
<223> OTHER INFORMATION: Synthetic Construct
```

-continued

<400> SEQUENCE: 120
gctggcagcc tgtaattttg gattaaca                                28

<210> SEQ ID NO 121
<211> LENGTH: 24
<212> TYPE: DNA
<213> ORGANISM: Artificial Sequence
<220> FEATURE:
<223> OTHER INFORMATION: Synthetic Construct

<400> SEQUENCE: 121
ttgtcacttt agaaccagtt gcgg                                    24

<210> SEQ ID NO 122
<211> LENGTH: 27
<212> TYPE: DNA
<213> ORGANISM: Artificial Sequence
<220> FEATURE:
<223> OTHER INFORMATION: Synthetic Construct

<400> SEQUENCE: 122
caatgcttga atcgtcttct gatgatg                                 27

<210> SEQ ID NO 123
<211> LENGTH: 25
<212> TYPE: DNA
<213> ORGANISM: Artificial Sequence
<220> FEATURE:
<223> OTHER INFORMATION: Synthetic Construct

<400> SEQUENCE: 123
aattttaaag cttttacagg caccg                                   25

<210> SEQ ID NO 124
<211> LENGTH: 30
<212> TYPE: DNA
<213> ORGANISM: Artificial Sequence
<220> FEATURE:
<223> OTHER INFORMATION: Synthetic Construct

<400> SEQUENCE: 124
ggctatgttt gatttcatgc ttgaagttac                              30

<210> SEQ ID NO 125
<211> LENGTH: 28
<212> TYPE: DNA
<213> ORGANISM: Artificial Sequence
<220> FEATURE:
<223> OTHER INFORMATION: Synthetic Construct

<400> SEQUENCE: 125
acttattttt ttttcctcat cgtcaagt                                28

<210> SEQ ID NO 126
<211> LENGTH: 28
<212> TYPE: DNA
<213> ORGANISM: Artificial Sequence
<220> FEATURE:
<223> OTHER INFORMATION: Synthetic Construct

<400> SEQUENCE: 126
gtcaagtttt tgtctttttct tgacacct                               28

<210> SEQ ID NO 127

<211> LENGTH: 30
<212> TYPE: DNA
<213> ORGANISM: Artificial Sequence
<220> FEATURE:
<223> OTHER INFORMATION: Synthetic Construct

<400> SEQUENCE: 127
ggatcattag atgagattgg aataaaagga                                    30

<210> SEQ ID NO 128
<211> LENGTH: 28
<212> TYPE: DNA
<213> ORGANISM: Artificial Sequence
<220> FEATURE:
<223> OTHER INFORMATION: Synthetic Construct

<400> SEQUENCE: 128
aggctaaaat agaaaataaa ctagaagg                                      28

<210> SEQ ID NO 129
<211> LENGTH: 756
<212> TYPE: DNA
<213> ORGANISM: Borrelia burgdorferi

<400> SEQUENCE: 129
ttagtaaaag gcaggtttta aagtatcaaa atctttgtaa tatttattaa agtgttctgc    60
cagtattttc tcattatctt gagtattttg attgtaaact ttaagagttt cgtttaaggt   120
tttttaagt ctttgtttta tctctaagtt ggattttatt tgcattagca atgatttaga   180
ttcttcttga cttagatttt ctactccatt ttgtattaat tctaaatttt gctctatttg   240
gaattgaatg ccccatgata tgtgataaat caatcttcca attatattgt aatgttcgga   300
atttttttta agtatttcaa gaatttcttt taattttttct atatttcttt tttataatc   360
taaagatgag taaagcgttc ttttttatttt catttggata tcttcatcaa taagatcgta   420
aggaccaact ttaaaagtgc ttaggaaatc aaattttttcc ttagcaattt tagctatttg   480
tatattttct tcttttttttt gatcttccag ttccttacca attgcttttta gctctgaagc   540
gatagtttcc ataattttttt catcagaagt gctaaggtct ccagatttat cttcaaaatt   600
ttgggtgttt tccccccggat tggtgatttt ttttggctta gtgtttgcat ttgctttagg   660
atcgattttg ctaaaaggtg cgcatgaggt gcaaattaaa gttaatatca ttgcaataat   720
attaatcttg attatattta gtttggcttt tttcaa                             756

<210> SEQ ID NO 130
<211> LENGTH: 33
<212> TYPE: DNA
<213> ORGANISM: Artificial Sequence
<220> FEATURE:
<223> OTHER INFORMATION: Synthetic Construct

<400> SEQUENCE: 130
atttattaaa gtgttctgcc agtattttct cat                                33

<210> SEQ ID NO 131
<211> LENGTH: 33
<212> TYPE: DNA
<213> ORGANISM: Artificial Sequence
<220> FEATURE:
<223> OTHER INFORMATION: Synthetic Construct

<400> SEQUENCE: 131
gcattcaatt ccaaatagag caaaatttag aat                                33

<210> SEQ ID NO 132
<211> LENGTH: 30
<212> TYPE: DNA
<213> ORGANISM: Artificial Sequence
<220> FEATURE:
<223> OTHER INFORMATION: Synthetic Construct

<400> SEQUENCE: 132
cttgagtatt ttgattgtaa actttaagag                                    30

<210> SEQ ID NO 133
<211> LENGTH: 28
<212> TYPE: DNA
<213> ORGANISM: Artificial Sequence
<220> FEATURE:
<223> OTHER INFORMATION: Synthetic Construct

<400> SEQUENCE: 133
tgacttagat tttctactcc attttgta                                      28

<210> SEQ ID NO 134
<211> LENGTH: 31
<212> TYPE: DNA
<213> ORGANISM: Artificial Sequence
<220> FEATURE:
<223> OTHER INFORMATION: Synthetic Construct

<400> SEQUENCE: 134
agtgttctgc cagtattttc tcattatctt g                                  31

<210> SEQ ID NO 135
<211> LENGTH: 32
<212> TYPE: DNA
<213> ORGANISM: Artificial Sequence
<220> FEATURE:
<223> OTHER INFORMATION: Synthetic Construct

<400> SEQUENCE: 135
aaaggcaggt tttaaagtat caaaatcttt gt                                 32

<210> SEQ ID NO 136
<211> LENGTH: 29
<212> TYPE: DNA
<213> ORGANISM: Artificial Sequence
<220> FEATURE:
<223> OTHER INFORMATION: Synthetic Construct

<400> SEQUENCE: 136
gggcattcaa ttccaaatag agcaaaatt                                     29

<210> SEQ ID NO 137
<211> LENGTH: 33
<212> TYPE: DNA
<213> ORGANISM: Artificial Sequence
<220> FEATURE:
<223> OTHER INFORMATION: Synthetic Construct

<400> SEQUENCE: 137
aattccgaac attacaatat aattggaaga ttg                                33

<210> SEQ ID NO 138
<211> LENGTH: 33
<212> TYPE: DNA
<213> ORGANISM: Artificial Sequence
<220> FEATURE:

```
<223> OTHER INFORMATION: Synthetic Construct

<400> SEQUENCE: 138
agcgttcttt ttattttcat ttggatatct tca                              33

<210> SEQ ID NO 139
<211> LENGTH: 29
<212> TYPE: DNA
<213> ORGANISM: Artificial Sequence
<220> FEATURE:
<223> OTHER INFORMATION: Synthetic Construct

<400> SEQUENCE: 139
gcaaacacta agccaaaaaa aatcaccaa                                   29

<210> SEQ ID NO 140
<211> LENGTH: 25
<212> TYPE: DNA
<213> ORGANISM: Artificial Sequence
<220> FEATURE:
<223> OTHER INFORMATION: Synthetic Construct

<400> SEQUENCE: 140
aggtctccag atttatcttc aaaat                                       25

<210> SEQ ID NO 141
<211> LENGTH: 25
<212> TYPE: DNA
<213> ORGANISM: Artificial Sequence
<220> FEATURE:
<223> OTHER INFORMATION: Synthetic Construct

<400> SEQUENCE: 141
caataagatc gtaaggacca acttt                                       25

<210> SEQ ID NO 142
<211> LENGTH: 33
<212> TYPE: DNA
<213> ORGANISM: Artificial Sequence
<220> FEATURE:
<223> OTHER INFORMATION: Synthetic Construct

<400> SEQUENCE: 142
caatcttcca attatattgt aatgttcgga att                              33

<210> SEQ ID NO 143
<211> LENGTH: 33
<212> TYPE: DNA
<213> ORGANISM: Artificial Sequence
<220> FEATURE:
<223> OTHER INFORMATION: Synthetic Construct

<400> SEQUENCE: 143
ctaaagatga gtaaagcgtt ctttttattt tca                              33

<210> SEQ ID NO 144
<211> LENGTH: 29
<212> TYPE: DNA
<213> ORGANISM: Artificial Sequence
<220> FEATURE:
<223> OTHER INFORMATION: Synthetic Construct

<400> SEQUENCE: 144
cctaaagcaa atgcaaacac taagccaaa                                   29
```

```
<210> SEQ ID NO 145
<211> LENGTH: 29
<212> TYPE: DNA
<213> ORGANISM: Artificial Sequence
<220> FEATURE:
<223> OTHER INFORMATION: Synthetic Construct

<400> SEQUENCE: 145
agcaaatgca aacactaagc caaaaaaaa                                          29

<210> SEQ ID NO 146
<211> LENGTH: 32
<212> TYPE: DNA
<213> ORGANISM: Artificial Sequence
<220> FEATURE:
<223> OTHER INFORMATION: Synthetic Construct

<400> SEQUENCE: 146
gcaaatgcaa acactaagcc aaaaaaaatc ac                                      32

<210> SEQ ID NO 147
<211> LENGTH: 30
<212> TYPE: DNA
<213> ORGANISM: Artificial Sequence
<220> FEATURE:
<223> OTHER INFORMATION: Synthetic Construct

<400> SEQUENCE: 147
gccccatgat atgtgataaa tcaatcttcc                                         30

<210> SEQ ID NO 148
<211> LENGTH: 29
<212> TYPE: DNA
<213> ORGANISM: Artificial Sequence
<220> FEATURE:
<223> OTHER INFORMATION: Synthetic Construct

<400> SEQUENCE: 148
ggagacctta gcacttctga tgaaaaaat                                          29

<210> SEQ ID NO 149
<211> LENGTH: 249
<212> TYPE: DNA
<213> ORGANISM: Citrus sinensis

<400> SEQUENCE: 149
ggaaatctaa cgagagagca tgctcctgcg gccccggaga cggtgcgccg cggggtgcgg        60
cgccttcttt cacatgtatc caaaacgtct ctcggcaacg gatatctcgg ctctcgcatc       120
gatgaagaac gtagcgaaat gcgatacttg gtgtgaattg cagaatcccg tgaaccatcg       180
agtctttgaa cgcaagttgc gccccaagcc attaggccga gggcacgtct gcctgggtgt       240
cacgcatcg                                                               249

<210> SEQ ID NO 150
<211> LENGTH: 24
<212> TYPE: DNA
<213> ORGANISM: Artificial Sequence
<220> FEATURE:
<223> OTHER INFORMATION: Synthetic Construct

<400> SEQUENCE: 150
ggaaatctaa cgagagagca tgct                                               24

<210> SEQ ID NO 151
```

<211> LENGTH: 23
<212> TYPE: DNA
<213> ORGANISM: Artificial Sequence
<220> FEATURE:
<223> OTHER INFORMATION: Synthetic Construct

<400> SEQUENCE: 151
ggaaatctaa cgagagagca tgc 23

<210> SEQ ID NO 152
<211> LENGTH: 19
<212> TYPE: DNA
<213> ORGANISM: Artificial Sequence
<220> FEATURE:
<223> OTHER INFORMATION: Synthetic Construct

<400> SEQUENCE: 152
cgatgcgtga cacccaggc 19

<210> SEQ ID NO 153
<211> LENGTH: 18
<212> TYPE: DNA
<213> ORGANISM: Artificial Sequence
<220> FEATURE:
<223> OTHER INFORMATION: Synthetic Construct

<400> SEQUENCE: 153
gatgcgtgac acccaggc 18

<210> SEQ ID NO 154
<211> LENGTH: 30
<212> TYPE: DNA
<213> ORGANISM: Artificial Sequence
<220> FEATURE:
<223> OTHER INFORMATION: Synthetic Construct

<400> SEQUENCE: 154
gagacgtttt ggatacatgt gaaagaaggc 30

<210> SEQ ID NO 155
<211> LENGTH: 26
<212> TYPE: DNA
<213> ORGANISM: Artificial Sequence
<220> FEATURE:
<223> OTHER INFORMATION: Synthetic Construct

<400> SEQUENCE: 155
cgatggttca cgggattctg caattc 26

<210> SEQ ID NO 156
<211> LENGTH: 1236
<212> TYPE: DNA
<213> ORGANISM: Borrelia burgdorferi

<400> SEQUENCE: 156
ttacattata ctaatgtatg cttcaagaac agactggcga gcattttgca tattatctag 60
gtatcttttt ttaatgtact ctgctaagga tttggaatcg cttaaacttg aattagagct 120
agcattagca ataagcccat cagcttgtct tgaccattct tttcttttat ctaatatttg 180
atttagtttt gatttaagct cttttagctt catggtgaaa tcaaaactgt tgattttagc 240
gtttaagtaa tcctggttaa agatttcaat ttttttattt atttcttcta gtgcaagttc 300
gaaagaaatt tgtgttccaa gccctgatat cattaattct cttattaagc tgtgattttg 360
attctcattg taaagagctt ccattattga tccaaattgt tcaattttgt attgatcaaa 420

```
atccataagc gcatagaatt tatttctttc attttctgct tctggtgtgt tagagttaag      480
ctgtggcgcg taacttctgt cataaacttt agcacttgaa ataacatcta gcagttcaaa      540
tgcagaatct ttcattttga attgatcgta agtttctcta aatccaaagt tgttttgtgt      600 tttattttt tcttcagaaa ttgctctaat aagttcgttt tttaatgttt gtaatttact       660
gccagaagat gttgttgttt gtacagcaga gcttgaattt gtttgctgtc ttgttggttg      720
actaaagctg tagtttaagg caaatgttgg cagcccgcta tttctgctgt taaaagttct      780
tgtatttccg ggtacggttg taacggcttg aataggtatt ctttgttttg ttagtgatgc      840
agctcttgct gctgttgttt ttggcagatt tgacagatct gcgctaaaac ttaagctttg      900
caattgtggg cttggtgctg cttgttgatt ttgcgatcct ttatttggtg ttgtttgtgg      960
ttgattttgc gatcctttat ttggcgctgc tgctactgtt tttgccgctt gcgattgttt     1020
ttttagctct gctgctactt tgtcattgtc agcaattggt atatttttg cagcatttga      1080 gtttgtatca gcacttgttg tttcttgatc atctgctgcc ttattaagta ttccttttac    1140
tttgttttta taatcttcgt ttagattggc atcaatcgtg caagaaaata aaaacaatcc    1200
caaaagcttt aattgtatta atggtttgat tttcaa                              1236

<210> SEQ ID NO 157
<211> LENGTH: 25
<212> TYPE: DNA
<213> ORGANISM: Artificial Sequence
<220> FEATURE:
<223> OTHER INFORMATION: Synthetic Construct

<400> SEQUENCE: 157
agctgtagtt taaggcaaat gttgg                                             25

<210> SEQ ID NO 158
<211> LENGTH: 25
<212> TYPE: DNA
<213> ORGANISM: Artificial Sequence
<220> FEATURE:
<223> OTHER INFORMATION: Synthetic Construct

<400> SEQUENCE: 158
ttgtttgctg tcttgttggt tgact                                             25

<210> SEQ ID NO 159
<211> LENGTH: 22
<212> TYPE: DNA
<213> ORGANISM: Artificial Sequence
<220> FEATURE:
<223> OTHER INFORMATION: Synthetic Construct

<400> SEQUENCE: 159
cgcaaaatca acaagcagca cc                                                22

<210> SEQ ID NO 160
<211> LENGTH: 25
<212> TYPE: DNA
<213> ORGANISM: Artificial Sequence
<220> FEATURE:
<223> OTHER INFORMATION: Synthetic Construct

<400> SEQUENCE: 160
aggatcgcaa aatcaaccac aaaca                                             25

<210> SEQ ID NO 161
```

```
<211> LENGTH: 27
<212> TYPE: DNA
<213> ORGANISM: Artificial Sequence
<220> FEATURE:
<223> OTHER INFORMATION: Synthetic Construct

<400> SEQUENCE: 161
gctatttctg ctgttaaaag ttcttgt                                          27

<210> SEQ ID NO 162
<211> LENGTH: 26
<212> TYPE: DNA
<213> ORGANISM: Artificial Sequence
<220> FEATURE:
<223> OTHER INFORMATION: Synthetic Construct

<400> SEQUENCE: 162
ctaaaactta agctttgcaa ttgtgg                                           26

<210> SEQ ID NO 163
<211> LENGTH: 24
<212> TYPE: DNA
<213> ORGANISM: Artificial Sequence
<220> FEATURE:
<223> OTHER INFORMATION: Synthetic Construct

<400> SEQUENCE: 163
tgctgctgtt gttttggca gatt                                              24

<210> SEQ ID NO 164
<211> LENGTH: 25
<212> TYPE: DNA
<213> ORGANISM: Artificial Sequence
<220> FEATURE:
<223> OTHER INFORMATION: Synthetic Construct

<400> SEQUENCE: 164
atgacaaagt agcagcagag ctaaa                                            25

<210> SEQ ID NO 165
<211> LENGTH: 25
<212> TYPE: DNA
<213> ORGANISM: Artificial Sequence
<220> FEATURE:
<223> OTHER INFORMATION: Synthetic Construct

<400> SEQUENCE: 165
cgctaaaact taagctttgc aattg                                            25

<210> SEQ ID NO 166
<211> LENGTH: 25
<212> TYPE: DNA
<213> ORGANISM: Artificial Sequence
<220> FEATURE:
<223> OTHER INFORMATION: Synthetic Construct

<400> SEQUENCE: 166
tgctgctact gttttgctg cttgc                                             25

<210> SEQ ID NO 167
<211> LENGTH: 2421
<212> TYPE: DNA
<213> ORGANISM: Anaplasma phagocytophilum

<400> SEQUENCE: 167
gtggacagta ttatgacaga gcaaaaggca ggttataacc atcaggtcat tgaagagcaa      60
```

```
tgccaagatg catggacaaa atcgaaatcg tatatatgga aaggccgcaa agacgcaagc    120
tttgtcatag acaccccacc accaacagta tcaggaagcc tacacatggg ccacgtattt    180
agttactgcc atgccgactt catagcccgc tacaaacgtc tggccggttt tgacgttcta    240
ttccccatag ggttcgatga taacgggttg cccacagaac gcctcatcga gagggaaaca    300
ggtgtaaaag cctctcaggt cgaccgaggt gagtttataa agacatgtac tgcagtttca    360
aaagaataca ggttaaaata ccgacagtta tttcaaactt tgggaataag tttcgattgg    420
tcccgtgagt accatactgc aagccccact atccaaaagc tttcacaaga gtcgttcata    480
agtttgtata acaaaggtga tgcgtaccgt aaacaacagc cgatattgtg ggacgttgta    540
gatcagacag caatatctaa cgcggagatc aaagacaaaa ttttgccatc tacaatgtat    600
acggttcggt ttcagacaga atgtggtgag agtatactaa tagccacaac ccgtccagaa    660
ctcatgcccg catgtgtagc agtgttctat catccttacg atagccgtta taagcatctt    720
gaaggcaaac atgctatcgt accagtaggc ggaaataacg tcagaattct gccgacgat     780 aaggtagcca tagataaagg aactggcttg gtaatgtgct gcacattcgg cgatgaaact    840
gatgtatatt ggcggcaaaa gcatgcgctt gacaccagaa taattataga taaaaccgga    900
cgccttacag gtctggagaa attggcaaca gagaaatctc tcatctcccc aacacaattc    960
aatggtttaa gaataaaaga ggccaggaaa gccataagcg agaccctggc agcaagcgga   1020
ttgatatcat cccaagcaga tatagttcat agcgtcagat gtgcagagcg ttctggagct   1080
ccaatagaga ttttgccgag tgaacagtgg tttatcaaga ttaaggatca caaagatata   1140
tttaagaacc tagcagaacg tattaagtgg catcctgacc acatgcgaaa acgactatat   1200
acgtggatcg agaacctgaa tagcgattgg tgtatatctc gtcagcgatt ttatggagtc   1260
ccagtcccag tatggtattc aaaacgaaat ggtgaagagg gtagggtgat cttacccaat   1320
gttcaagatt tacctataga tcccattaaa gactttccta ggggctatgg caaagatgaa   1380 gtgataccog atgttgacgt tatggataca tgggcaacga gttcactatc tccaatgtat   1440
cacactatga tgttggaagg tacatgtcat gaaggaaata tacctaccga tcttcgtacc   1500
caaagtcatg agataatacg atcctgggcg ttttacacca tagccatgtc ccaccttcat   1560
cgagcagagc tgccgtggaa aagcataatg ataagcggtt ggtgcgttgc agaagataag   1620
actaaaatga gcaaatctaa aaacaacgcc aaggatccaa gcgaattact aaaaacttac   1680
ggagcagatg cgattagata ctgggcttcc aaagcccgaa acggcgtaga caccgtgttt   1740
tcagaagaag tcattaaaac aggtaagcgt ctagttacaa aattatataa tgcgcataag   1800
tttgtacagc ttgtagccgg taatattaaa ccaagttttg aggctataac aagtcctctc   1860
gaccagtgga tcgtgacacg cttaagtaaa attgtagaaa taagcacaaa agcatatgaa   1920
gaatgtgact ataatacagg actaggtgtt gtcgaggagt ttttcattaa gcagttctgt   1980
gacaactata tagagttatc caaacatcga gcatataacg aggaagactt acagggtcat   2040
aaatctgctc taagtagtct gcaaatcgta ctacaaactg ccatagcact cttctcaccc   2100
atcataccgc acgtaactca ttatataagt agtaatagtg aaacagaaag tccaaagtgg   2160
ccattatacg aagaaatacc acgttatgaa gccatagaac aaatgtgcga ggaagcaatg   2220
agaatagttc acgagattag acgttataag tcagaaaatt gtatcgccat gaaccatccc   2280
cttaatatac tttctatatc tagtagagca gtacaacaag atatgcatcc gcaaatctta   2340
gaggatatta gaaatgcttt gaagatttgc aagataacta gaacaagac gcagggagaa    2400
```

```
gactttatta ttcagcaata a                                              2421

<210> SEQ ID NO 168
<211> LENGTH: 257
<212> TYPE: DNA
<213> ORGANISM: Anaplasma phagocytophilum

<400> SEQUENCE: 168
ctctaagtag tctgcaaatc gtactacaaa ctgccatagc actcttctca cccatcatac      60
cgcacgtaac tcattatata agtagtaata gtgaaacaga aagtccaaag tggccattat     120
acgaagaaat accacgttat gaagccatag aacaaatgtg cgaggaagca atgagaatag     180
ttcacgagat tagacgttat aagtcagaaa attgtatcgc catgaaccat ccccttaata     240
tactttacta tatctag                                                    257
```

NMR METHODS AND SYSTEMS FOR THE RAPID DETECTION OF TICK-BORNE PATHOGENS

FIELD OF THE INVENTION

The invention features methods, panels, and systems for detecting tick-borne pathogens and diagnosing tick-transmitted diseases.

BACKGROUND OF THE INVENTION

A number of diseases are transmitted by ectoparasites such as ticks, including Lyme disease, Rocky Mountain spotted fever, Q-fever, babesiosis, ehrlichiosis, tularemia, and anaplasmosis, which are caused by the tick-borne pathogens *Borrelia burgdorferi* sensu lato (Bbsl; *B. burgdorferi, afzelii*, and *garinii*), *Rickettsia rickettsii, Coxiella burnetii, Babesia microti, Ehrlichia chaffeensis, Francisella tularensis*, and *Anaplasma phagocytophilum*, respectively. Tick-transmitted diseases can be difficult to differentially diagnose, especially in their early phases, in part because these diseases tend to have similar symptoms, which may be variable between patients. However, untreated tick-transmitted diseases can have serious health consequences. As an example, for Lyme disease, following the initial, localized stage (stage 1, acute phase), the Bbsl pathogen can disseminate and cause heart and nervous palsies (stage II). Further complications can arise as the disease progresses, which manifest in nerve damage, brain inflammation, and arthritis (stage III), culminating in chronic Lyme disease with recurring muscle and joint pain, cognitive defects, and chronic fatigue.

Available diagnostic methods for tick-transmitted diseases typically involve detection of the presence of analytes that are associated with the causative pathogen. The difficulty in diagnosing tick-transmitted diseases is compounded by difficulties in detecting the causative pathogens, which may be present in low titer in the infected subject's tissue (e.g, blood, cerebrospinal fluid, urine, and/or synovial fluid, depending on the pathogen and the progression of the disease). Available diagnostic tests for these diseases generally have drawbacks, including being time-consuming and/or having relatively low sensitivity. For example, diagnosis of Lyme disease currently involves a two-tiered serological test, with none of the available nucleic acid-based tests (e.g., polymerase chain reaction (PCR)) being FDA-approved, in part due to sensitivity limitations. Further, current nucleic acid-based tests for these diseases require substantial sample preparation that includes nucleic acid purification to allow for successful amplification. This sample preparation is time consuming, and also can lower the sensitivity of the assay due to loss of analyte. Additionally, current tests are focused on detecting single pathogens, which can further delay diagnosis if the incorrect test is selected.

Thus, there remains a need for rapid and sensitive methods, preferably requiring minimal or no sample preparation, for detecting the presence of tick-borne pathogen-associated analytes for diagnosis of tick-transmitted diseases, including Lyme disease. In particular, there is a need for methods and panels that are able to simultaneously and comprehensively detect multiple tick-borne pathogens in a sample and identify those that are present.

SUMMARY OF THE INVENTION

The invention features methods, panels, and systems for detecting tick-borne pathogens, including *Borrelia* species, and diagnosing and treating tick-transmitted diseases, including Lyme disease.

In one aspect, the invention features a method for detecting the presence of at least two different *Borrelia burgdorferi* sensu lato (Bbsl) species in a biological sample, the method comprising: (a) providing a biological sample and optionally dividing it into portions; (b) amplifying in the biological sample one or more Bbsl target nucleic acids specific to the at least two different Bbsl species; and (c) detecting the amplified nucleic acids to determine whether one or all of the at least two different Bbsl species is present, wherein the method individually detects a concentration of an individual Bbsl species of 10 cells/mL of biological sample or less (e.g., 10, 9, 8, 7, 6, 5, 4, 3, 2, 1 cell/mL of biological sample or less). In some embodiments, the at least two different Bbsl species are selected from *B. burgdorferi, B. afzelii*, and *B. garinii* (e.g., *B. burgdorferi* and *B. afzelii, B. burgdorferi* and *B. garinii*, or *B. afzelii* and *B. garinii*). In some embodiments, the method comprises detecting the presence of *B. burgdorferi, B. afzelii*, and *B. garinii*. In some embodiments, amplifying step (b) further comprises amplifying in the same or different portions of the biological sample a second target nucleic acid specific to a non-Lyme disease pathogen and detecting step (c) further comprises detecting the amplified second target nucleic acid to determine whether the non-Lyme disease pathogen is present. In some embodiments, the method detects a concentration of the non-Lyme disease pathogen of 10 cells/mL of biological sample or less (e.g., 10, 9, 8, 7, 6, 5, 4, 3, 2, 1 cell/mL of biological sample or less).

In another aspect, the invention features a method for detecting the presence of a tick-borne pathogen in a biological sample, the method comprising: (a) providing a biological sample and optionally dividing it into portions; (b) amplifying in the same or different portions of the biological sample a target nucleic acid specific to a Bbsl species and a second target nucleic acid specific to a non-Lyme disease pathogen, wherein the non-Lyme disease pathogen is selected from a *Rickettsia* spp., *Coxiella burnetii*, a *Babesia* spp., *Anaplasma phagocytophilum*, a *Francisella tularensis* subspp., *Streptococcus pneumoniae*, or *Neisseria meningitidis*; and (c) detecting the amplified nucleic acids to determine whether the Bbsl species or the non-Lyme disease pathogen is present in the sample, wherein the method individually detects a concentration of the Bbsl species or the non-Lyme disease pathogen of 10 cells/mL of biological sample or less.

In some embodiments of any of the preceding aspects, amplifying step (b) further comprises amplifying a pan-*Borrelia* target nucleic acid in the presence of a forward primer and a reverse primer, each of which is universal to *Borrelia* species, and detecting step (c) further comprises detecting the amplified pan-*Borrelia* target nucleic acid to determine whether a *Borrelia* species is present.

In some embodiments of any of the preceding aspects, the amplified Bbsl target nucleic acid, non-Lyme disease pathogen target nucleic acid, or pan-*Borrelia* target nucleic acid is detected by optical, fluorescent, mass, density, magnetic, chromatographic, and/or electrochemical measurement. In some embodiments, the amplified Bbsl target nucleic acid, non-Lyme disease pathogen target nucleic acid, or pan-*Borrelia* target nucleic acid is detected by measuring the $T_2$ relaxation response of the biological sample or portion thereof following contacting the biological sample or portion thereof with magnetic particles, wherein the magnetic particles have binding moieties on their surfaces, the binding moieties operative to alter the specific aggregation of the magnetic particles in the presence of the amplified Bbsl target nucleic acid, non-Lyme disease pathogen target nucleic acid, or pan-*Borrelia* target nucleic acid.

In another aspect, the invention features a method for detecting the presence of at least two different *Borrelia burgdorferi* sensu lato (Bbsl) species in a biological sample, the method comprising: (a) providing a biological sample; (b) preparing a first assay sample by contacting a portion of the biological sample with magnetic particles, wherein the magnetic particles have binding moieties on their surfaces, the binding moieties operative to alter the specific aggregation of the magnetic particles in the presence of an analyte associated with a first Bbsl species; (c) preparing a second assay sample by contacting a portion of the biological sample with magnetic particles, wherein the magnetic particles have binding moieties on their surfaces, the binding moieties operative to alter the specific aggregation of the magnetic particles in the presence of an analyte associated with a second Bbsl species; (d) placing each assay sample in a device, the device comprising a support defining a well for holding the assay sample, and having an RF coil configured to detect a signal produced by exposing the assay sample to a bias magnetic field created using one or more magnets and an RF pulse sequence; (e) exposing each assay sample to the bias magnetic field and the RF pulse sequence; (f) following step (e), measuring the signal produced by each assay sample; and (g) using the results of step (f) to determine whether one or all of the at least two different Bbsl species is present in the biological sample. In some embodiments, the at least two different Bbsl species are selected from *B. burgdorferi*, *B. afzelii*, and *B. garinii* (e.g., *B. burgdorferi* and *B. afzelii*, *B. burgdorferi* and *B. garinii*, or *B. afzelii* and *B. garinii*). In some embodiments, the method further comprises preparing a third assay sample by contacting a portion of the biological sample with magnetic particles, wherein the magnetic particles have binding moieties on their surfaces, the binding moieties operative to alter the specific aggregation of the magnetic particles in the presence of an analyte associated with a third Bbsl species. In some embodiments, the method further comprises preparing an additional assay sample by contacting a portion of the biological sample with magnetic particles, wherein the magnetic particles have binding moieties on their surfaces, the binding moieties operative to alter the specific aggregation of the magnetic particles in the presence of an analyte associated with a pathogen selected from an *Ehrlichia* spp., a *Rickettsia* spp., *Coxiella burnetii*, a *Babesia* spp., *Anaplasma phagocytophilum*, a *Francisella tularensis* subspp., *Streptococcus pneumoniae*, or *Neisseria meningitidis*. In some embodiments, an assay sample is contacted with $1\times10^6$ to $1\times10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1\times10^9$ to $1\times10^{12}$ mM$^{-1}$s$^{-1}$. In some embodiments, the magnetic particles are substantially monodisperse.

In another aspect, the invention features a method for detecting the presence of a tick-borne pathogen in a biological sample, the method comprising: (a) providing a biological sample; (b) preparing a first assay sample by contacting a portion of the biological sample with magnetic particles, wherein the magnetic particles have binding moieties on their surfaces, the binding moieties operative to alter the specific aggregation of the magnetic particles in the presence of an analyte associated with a Bbsl species; (c) preparing a second assay sample by contacting a portion of the biological sample with magnetic particles, wherein the magnetic particles have binding moieties on their surfaces, the binding moieties operative to alter the specific aggregation of the magnetic particles in the presence of an analyte associated with a non-Lyme disease pathogen, wherein the non-Lyme disease pathogen is selected from a *Rickettsia* spp., *Coxiella burnetii*, a *Babesia* spp., *Anaplasma phagocytophilum*, a *Francisella tularensis* subspp., *Streptococcus pneumoniae*, or *Neisseria meningitidis*; (d) placing each assay sample in a device, the device comprising a support defining a well for holding the assay sample, and having an RF coil configured to detect a signal produced by exposing the assay sample to a bias magnetic field created using one or more magnets and an RF pulse sequence; (e) exposing each assay sample to the bias magnetic field and the RF pulse sequence; (f) following step (e), measuring the signal produced by each assay sample; and (g) using the results of step (f) to determine whether the Bbsl species or the non-Lyme disease pathogen is present in the biological sample. In some embodiments, the method further comprises preparing a pan-*Borrelia* assay sample by contacting a portion of the biological sample with magnetic particles, wherein the magnetic particles have binding moieties on their surfaces, the binding moieties operative to alter the specific aggregation of the magnetic particles in the presence of a pan-*Borrelia*-associated analyte. In some embodiments, the analyte associated with a Bbsl species, the analyte associated with a non-Lyme disease pathogen, or a pan-*Borrelia*-associated analyte is independently a polypeptide or a nucleic acid. In some embodiments, the nucleic acid is a target nucleic acid that has been amplified in the biological sample or portion thereof. In some embodiments, an assay sample is contacted with $1\times10^6$ to $1\times10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1\times10^9$ to $1\times10^{12}$ mM$^{-1}$s$^{-1}$. In some embodiments, the magnetic particles are substantially monodisperse.

In another aspect, the invention features a method for detecting the presence of at least two different *Borrelia burgdorferi* sensu lato (Bbsl) species in a biological sample, the method comprising: (a) providing a biological sample; (b) lysing the *Borrelia* cells in the biological sample; (c) amplifying one or more Bbsl target nucleic acids in the biological sample to form an amplified biological sample; (d) preparing a first assay sample by contacting a portion of the amplified biological sample with a first population of magnetic particles, wherein the magnetic particles of the first population have binding moieties characteristic of a first Bbsl species on their surface, the binding moieties operative to alter aggregation of the magnetic particles in the presence of the one or more Bbsl target nucleic acids; (e) preparing a second assay sample by contacting a portion of the amplified biological sample with a second population of magnetic particles, wherein the magnetic particles of the second population have binding moieties characteristic of a second Bbsl species on their surface, the binding moieties operative to alter aggregation of the magnetic particles in the presence of the one or more Bbsl target nucleic acids; (f) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence; (g) exposing each assay sample to a bias magnetic field and an RF pulse sequence; (h) following step (g), measuring the signal produced by each assay sample; and (i) on the basis of the result of step (h), determining whether one or all of the at least two different Bbsl species is present in the biological sample. In some embodiments, the at least two different Bbsl species are selected from *B. burgdorferi*, *B. afzelii*, and *B. garinii*. In some embodiments, the method further comprises preparing a third sample assay by contacting a portion of the amplified biological sample with a third population of magnetic particles, wherein the magnetic particles of the third population have binding moieties characteristic of a third Bbsl species on their surface, the binding moieties operative to alter aggregation of the magnetic particles in the presence of the Bbsl target nucleic acid. In some embodiments, the amplifying of step (c) comprises amplifying a Bbsl target nucleic acid to be detected in the presence of a forward primer and a reverse primer, each of which is universal to Bbsl species, thereby forming a pan-Bbsl amplicon. In some embodiments, the magnetic particles of each population comprise two subpopulations, a first subpopulation bearing a first probe on its surface, and a second subpopulation bearing a second probe on its surface. In some embodiments, the amplifying of step (c) comprises amplifying two target nucleic acids characteristic of a single Bbsl species, thereby forming a first amplicon characteristic of a single Bbsl species and a second amplicon characteristic of a single Bbsl species, for at least one of the Bbsl species to be detected. In some embodiments, the amplifying of step (c) comprises amplifying two target nucleic acids characteristic of a single Bbsl species for at least two of the Bbsl species to be detected. In some embodiments, the amplifying of step (c) comprises amplifying two target nucleic acids characteristic of *B. burgdorferi* and two target nucleic acids characteristic of *B. afzelii*. In some embodiments, the magnetic particles of step (d) or (e) comprise a first subpopulation conjugated to a first probe and a second probe, and a second subpopulation conjugated to a third probe and a fourth probe, wherein the first probe and third probe are operative to bind a first segment and a second segment, respectively, of the first amplicon; and the second probe and fourth probe are operative to bind a first segment and a second segment, respectively, of the second amplicon, wherein the magnetic particles form aggregates in the presence of the first amplicon and form aggregates in the presence of the second amplicon. In some embodiments, the method further comprises detecting the presence of a non-Lyme disease pathogen in the biological sample or a portion thereof. In some embodiments, the non-Lyme disease pathogen is detected by: (j) lysing the non-Lyme disease pathogen cells in the biological sample or portion thereof; (k) amplifying a non-Lyme disease pathogen target nucleic acid in the biological sample to form an amplified biological sample; (l) preparing an assay sample by contacting the amplified biological sample with magnetic particles, wherein the magnetic particles have binding moieties on their surface, the binding moieties operative to alter aggregation of the magnetic particles in the presence of the non-Lyme disease pathogen target nucleic acid; (m) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence; (n) exposing the assay sample to a bias magnetic field and an RF pulse sequence; (o) following step (m), measuring the signal; and (p) on the basis of the result of step (o), determining whether the non-Lyme disease pathogen is present in the biological sample. In some embodiments, steps (b) through (i) and (j) through (p) are performed simultaneously. In some embodiments, amplifying step (c) further comprises amplifying a pan-*Borrelia* target nucleic acid in the biological sample. In some embodiments, the method further comprises preparing a pan-*Borrelia* assay sample by contacting a portion of the amplified biological sample with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid, and determining whether a *Borrelia* species is present in the biological sample on the basis of the result of step (h). In some embodiments, step (h) or (o) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1\times10^6$ to $1\times10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1\times10^9$ to $1\times10^{12}$ mM$^{-1}$s$^{-1}$. In some embodiments, the magnetic particles are substantially monodisperse.

In another aspect, the invention features a method for detecting the presence of a *Borrelia burgdorferi* (*B. burgdorferi*) cell in a biological sample, the method comprising: (a) lysing the *B. burgdorferi* cells in the biological sample to form a lysate; (b) amplifying a *B. burgdorferi* target nucleic acid in the lysate in the presence of a first primer pair or a second primer pair to form an amplified lysate comprising a *B. burgdorferi* amplicon, wherein the first primer pair comprises a forward primer comprising the oligonucleotide sequence: 5'-AGA GGA CTT TTA ATA CTG GGC ATT GCT G-3' (SEQ ID NO: 1) and a reverse primer comprising the oligonucleotide sequence: 5'-GGC CAT TAT GTA GGA ATC TCT AAT GGT GC-3' (SEQ ID NO: 2), and the second primer pair comprises a forward primer comprising the oligonucleotide sequence: 5'-ACA TAA TGG CCT TAG AAA ATG AGC TTG ATG-3' (SEQ ID NO: 5) and a reverse primer comprising the oligonucleotide sequence 5'-CCC GCT TGT AAC CAT GTT TTC TGA GC-3' (SEQ ID NO: 6); (c) following step (b), contacting the amplified lysate with magnetic particles to form an assay sample, wherein the magnetic particles comprise binding moieties on their surface, the binding moieties operative to alter aggregation of the magnetic particles in the presence of the *B. burgdorferi* amplicon; (d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence; (e) exposing the assay sample to a bias magnetic field and an RF pulse sequence; (f) following step (e), measuring the signal from the detection tube; and (g) on the basis of the result of step (f), determining whether a *B. burgdorferi* cell was present in the biological sample. In some embodiments, the magnetic particles comprise a first population of magnetic particles conjugated to a first probe, and a second population of magnetic particles conjugated to a second probe, the first probe operative to bind to a first segment of the *B. burgdorferi* amplicon and the second probe operative to bind to a second segment of the *B. burgdorferi* amplicon, wherein the magnetic particles form aggregates in the presence of the *B. burgdorferi* amplicon. In some embodiments, step (b) comprises amplifying a *B. burgdorferi* target nucleic acid in the presence of the first primer pair, and the first probe comprises the oligonucleotide sequence: 5'-CTA AAC CAA AAG ATG ATA TTG TCT TTG GTG-3' (SEQ ID NO: 3), and the second probe comprises the oligonucleotide sequence: 5'-GGA CAT TTC TTA CGA CAA CAC CTG CT-3' (SEQ ID NO: 4). In some embodiments, step (b) comprises amplifying the *B. burgdorferi* target nucleic acid in the presence of the second primer pair, and the first probe comprises the oligonucleotide sequence: 5'-AAC CTA TTA ACA TCA AAG ATA AAA AAT GC-3' (SEQ ID NO: 7), and the second probe comprises the oligonucleotide sequence: 5'-GCT TAC ACA CCC AAT ATT TAT ACC C-3' (SEQ ID NO: 8). In some embodiments, step (b) comprises amplifying the first *B. burgdorferi* target nucleic acid in the presence of the first primer pair to form a first *B. burgdorferi* amplicon and amplifying the second *B. burgdorferi* target nucleic acid in the presence of the second primer pair to form a second *B. burgdorferi* amplicon, and step (g) comprises detecting the first *B. burgdorferi* amplicon and the second *B. burgdorferi* amplicon. In some embodiments, the magnetic particles comprise a first population of magnetic particles conjugated to a first probe and a second probe, and a second population of magnetic particles conjugated to a third probe and a fourth probe, wherein the first probe and third probe are operative to bind a first segment and a second segment, respectively, of the first *B. burgdorferi* amplicon; and the second probe and fourth probe are operative to bind a first segment and a second segment, respectively, of the second *B. burgdorferi* amplicon, wherein the magnetic particles form aggregates in the presence of the first *B. burgdorferi* amplicon and form aggregates in the presence of the second *B. burgdorferi* amplicon. In some embodiments, the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8. In some embodiments, step (b) further comprises amplifying a pan-*Borrelia* target nucleic acid in the biological sample, and wherein the method further comprises preparing a pan-*Borrelia* assay sample by contacting a portion of the amplified lysate with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid; exposing the pan-*Borrelia* assay sample to the bias magnetic field and the RF pulse sequence; and measuring the signal from the detection tube, thereby determining whether a *Borrelia* cell was present in the biological sample. In some embodiments, step (f) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1 \times 10^6$ to $1 \times 10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1 \times 10^9$ to $1 \times 10^{12}$ mM$^{-1}$s$^{-1}$. In some embodiments, the magnetic particles are substantially monodisperse. In some embodiments, the method further comprises detecting the presence of the first *B. afzelii* amplicon and the second *B. afzelii* amplicon. In some embodiments, the method detects *B. burgdorferi* at a concentration of 10 cells/mL of biological sample or less. In some embodiments, the method detects *B. burgdorferi* at a concentration of 1-10 CFU/mL (e.g., 1, 2, 3, 4, 5, 6, 7, 8, 9, or 10 cells/mL). In some embodiments, the method detects *B. burgdorferi* at a concentration of 8 CFU/mL. In some embodiments, the method results in 95% correct detection when the *B. burgdorferi* is present in the biological sample at a frequency of less than or equal to 10 cells/mL (e.g., 1, 2, 3, 4, 5, 6, 7, 8, 9, or 10 cells/mL).

In another aspect, the invention features a method for detecting the presence of a *Borrelia burgdorferi* (*B. burgdorferi*) cell in a biological sample, the method comprising: (a) lysing the *B. burgdorferi* cells in the biological sample to form a lysate; (b) amplifying a *B. burgdorferi* target nucleic acid in the lysate in the presence of a first primer pair or a second primer pair to form an amplified lysate comprising a *B. burgdorferi* amplicon, wherein the first primer pair comprises a forward primer comprising the oligonucleotide sequence: 5'-AGC TGT AGT TTA AGG CAA ATG TTG G-3' (SEQ ID NO: 157) and a reverse primer comprising the oligonucleotide sequence: 5'-AGG ATC GCA AAA TCA ACC ACA AAC A-3' (SEQ ID NO: 160), and the second primer pair comprises a forward primer comprising the oligonucleotide sequence: 5'-TGC TGC TGT TGT TTT TGG CAG ATT-3' (SEQ ID NO:163) and a reverse primer comprising the oligonucleotide sequence 5'-ATG ACA AAG TAG CAG CAG AGC TAA A-3' (SEQ ID NO: 164); (c) following step (b), contacting the amplified lysate with magnetic particles to form an assay sample, wherein the magnetic particles comprise binding moieties on their surface, the binding moieties operative to alter aggregation of the magnetic particles in the presence of the *B. burgdorferi* amplicon; (d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence; (e) exposing the assay sample to a bias magnetic field and an RF pulse sequence; (f) following step (e), measuring the signal from the detection tube; and (g) on the basis of the result of step (f), determining whether a *B. burgdorferi* cell was present in the biological sample. In some embodiments, the magnetic particles comprise a first population of magnetic particles conjugated to a first probe, and a second population of magnetic particles conjugated to a second probe, the first probe operative to bind to a first segment of the *B. burgdorferi* amplicon and the second probe operative to bind to a second segment of the *B. burgdorferi* amplicon, wherein the magnetic particles form aggregates in the presence of the *B. burgdorferi* amplicon. In some embodiments, step (b) comprises amplifying a *B. burgdorferi* target nucleic acid in the presence of the first primer pair, and the first probe comprises the oligonucleotide sequence: 5'-GCT ATT TCT GCT GTT AAA AGT TCT TGT-3' (SEQ ID NO: 161), and the second probe comprises the oligonucleotide sequence: 5'-CTA AAA CTT AAG CTT TGC AAT TGT GG-3' (SEQ ID NO: 162). In some embodiments, step (b) comprises amplifying the *B. burgdorferi* target nucleic acid in the presence of the second primer pair, and the first probe comprises the oligonucleotide sequence 5'-CGC TAA AAC TTA AGC TTT GCA ATT G-3' (SEQ ID NO: 165), and the second probe comprises the oligonucleotide sequence: 5'-TGC TGC TAC TGT TTT TGC TGC TTG C-3' (SEQ ID NO: 166). In some embodiments, step (b) comprises amplifying the first *B. burgdorferi* target nucleic acid in the presence of the first primer pair to form a first *B. burgdorferi* amplicon and amplifying the second *B. burgdorferi* target nucleic acid in the presence of the second primer pair to form a second *B. burgdorferi* amplicon, and step (g) comprises detecting the first *B. burgdorferi* amplicon and the second *B. burgdorferi* amplicon. In some embodiments, the magnetic particles comprise a first population of magnetic particles conjugated to a first probe and a second probe, and a second population of magnetic particles conjugated to a third probe and a fourth probe, wherein the first probe and third probe are operative to bind a first segment and a second segment, respectively, of the first *B. burgdorferi* amplicon; and the second probe and fourth probe are operative to bind a first segment and a second segment, respectively, of the second *B. burgdorferi* amplicon, wherein the magnetic particles form aggregates in the presence of the first *B. burgdorferi* amplicon and form aggregates in the presence of the second *B. burgdorferi* amplicon. In some embodiments, the first probe comprises an oligonucleotide sequence of SEQ ID NO: 161, the second probe comprises an oligonucleotide sequence of SEQ ID NO: 165, the third probe comprises an oligonucleotide sequence of SEQ ID NO: 162, and the fourth probe comprises an oligonucleotide sequence of SEQ ID NO: 166. In some embodiments, step (b) further comprises amplifying a pan-*Borrelia* target nucleic acid in the biological sample, and wherein the method further comprises preparing a pan-*Borrelia* assay sample by contacting a portion of the amplified lysate with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid; exposing the pan-*Borrelia* assay sample to the bias magnetic field and the RF pulse sequence; and measuring the signal from the detection tube, thereby determining whether a *Borrelia* cell was present in the biological sample. In some embodiments, step (f) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1\times10^6$ to $1\times10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1\times10^9$ to $1\times10^{12}$ $mM^{-1}s^{-1}$. In some embodiments, the magnetic particles are substantially monodisperse. In some embodiments, the method further comprises detecting the presence of the first *B. afzelii* amplicon and the second *B. afzelii* amplicon. In some embodiments, the method detects *B. burgdorferi* at a concentration of 10 cells/mL of biological sample or less. In some embodiments, the method detects *B. burgdorferi* at a concentration of 1-10 CFU/mL (e.g., 1, 2, 3, 4, 5, 6, 7, 8, 9, or 10 cells/mL). In some embodiments, the method detects *B. burgdorferi* at a concentration of 8 CFU/mL. In some embodiments, the method results in 95% correct detection when the *B. burgdorferi* is present in the biological sample at a frequency of less than or equal to 10 cells/mL (e.g., 1, 2, 3, 4, 5, 6, 7, 8, 9, or 10 cells/mL).

In another aspect, the invention features a method for detecting the presence of a *Borrelia garinii* (*B. garinii*) cell in a biological sample, the method comprising: (a) lysing the *B. garinii* cells in a biological sample to form a lysate; (b) amplifying a *B. garinii* target nucleic acid in the lysate in the presence of a forward primer comprising the oligonucleotide sequence: 5'-GGA TAT TCA AAT CCT GAG GTT GAC GAA CTA-3' (SEQ ID NO: 9) and a reverse primer comprising the oligonucleotide sequence: 5'-CTG ATA GGG CAA ATC TTT CTG AAG CA-3' (SEQ ID NO: 10) to form an amplified lysate comprising a *B. garinii* amplicon; (c) following step (b), contacting the amplified lysate with magnetic particles to form an assay sample, wherein the magnetic particles comprise binding moieties on their surface, the binding moieties operative to alter aggregation of the magnetic particles in the presence of the *B. garinii* amplicon; (d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence; (e) exposing the assay sample to a bias magnetic field and an RF pulse sequence; (f) following step (e), measuring the signal from the detection tube; and (g) on the basis of the result of step (f), determining whether an *B. garinii* cell was present in the biological sample. In some embodiments, the magnetic particles comprise a first population of magnetic particles conjugated to a first probe, and a second population of magnetic particles conjugated to a second probe, the first probe operative to bind to a first segment of the *B. garinii* amplicon and the second probe operative to bind to a second segment of the *B. garinii* amplicon, wherein the magnetic particles form aggregates in the presence of the *B. garinii* amplicon. In some embodiments, the first probe comprises the oligonucleotide sequence: 5'-CTG AGA TTG AAG TTG ACG AAA AAA TCA G-3' (SEQ ID NO: 11), and the second probe comprises the oligonucleotide sequence: 5'-GAT CAT CCA ATA ATT CCA ATC TAC AGC G-3' (SEQ ID NO: 12). In some embodiments, step (b) further comprises amplifying a pan-*Borrelia* target nucleic acid in the biological sample, and wherein the method further comprises preparing a pan-*Borrelia* assay sample by contacting a portion of the amplified lysate with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid; exposing the pan-*Borrelia* assay sample to the bias magnetic field and the RF pulse sequence; and measuring the signal from the detection tube, thereby determining whether a *Borrelia* cell was present in the biological sample. In some embodiments, step (f) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1 \times 10^6$ to $1 \times 10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1 \times 10^9$ to $1 \times 10^{12}$ mM$^{-1}$s$^{-1}$. In some embodiments, the magnetic particles are substantially monodisperse. In some embodiments, the method detects *B. garinii* at a concentration of 10 cells/mL of biological sample or less. In some embodiments, the method detects *B. garinii* at a concentration of 1-10 CFU/mL (e.g., 1, 2, 3, 4, 5, 6, 7, 8, 9, or 10 cells/mL). In some embodiments, the method detects *B. garinii* at a concentration of 8 CFU/mL. In some embodiments, the method results in 95% correct when the *B. garinii* is present in the biological sample at a frequency of less than or equal to 10 cells/mL.

In another aspect, the invention features a method for detecting the presence of a *Borrelia afzelii* (*B. afzelii*) cell in a biological sample, the method comprising: (a) lysing the *B. afzelii* cells in the biological sample to form a lysate; (b) amplifying a *B. afzelii* target nucleic acid in the lysate in the presence of a first primer pair or a second primer pair to form an amplified lysate comprising a *B. afzelii* amplicon, wherein the first primer pair comprises a forward primer comprising the oligonucleotide sequence: 5'-CCG TGG GCA GAG TCT ATG ACA ATC AG-3' (SEQ ID NO: 13) and a reverse primer comprising the oligonucleotide sequence: 5'-GCC CAA AAA ACC ATC AAC ACT AAT AAG G-3' (SEQ ID NO: 14), and the second primer pair comprises a forward primer comprising the oligonucleotide sequence: 5'-CAA GGT GCA ATG ACT TTG TTT GGG CA-3' (SEQ ID NO: 17) and a reverse primer comprising the oligonucleotide sequence 5'-GCA ACT TCA AAG TGT ACA GTA TTG GTA TCC C-3' (SEQ ID NO: 18); (c) following step (b), contacting the amplified lysate with magnetic particles to form an assay sample, wherein the magnetic particles comprise binding moieties on their surface, the binding moieties operative to alter aggregation of the magnetic particles in the presence of the *B. afzelii* amplicon; (d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence; (e) exposing the assay sample to a bias magnetic field and an RF pulse sequence; (f) following step (e), measuring the signal from the detection tube; and (g) on the basis of the result of step (f), determining whether a *B. afzelii* cell was present in the biological sample. In some embodiments, the magnetic particles comprise a first population of magnetic particles conjugated to a first probe, and a second population of magnetic particles conjugated to a second probe, the first probe operative to bind to a first segment of the *B. afzelii* amplicon and the second probe operative to bind to a second segment of the *B. afzelii* amplicon, wherein the magnetic particles form aggregates in the presence of the *B. afzelii* amplicon. In some embodiments, step (b) comprises amplifying a *B. afzelii* target nucleic acid in the presence of the first primer pair, and the first probe comprises the oligonucleotide sequence: 5'-TAG CAG CTC CTA CTC TTA GCT TGC-3' (SEQ ID NO: 15), and the second probe comprises the oligonucleotide sequence: 5'-AAT ATT GCT TTG TAA GCA TTT TGG TTT-3' (SEQ ID NO: 16). In some embodiments, step (b) comprises amplifying the *B. afzelii* target nucleic acid in the presence of the second primer pair, and the first probe comprises the oligonucleotide sequence: 5'-AAC CTA TTA ACA TCA AAG ATA AAA AAT GC-3' (SEQ ID NO: 7), and the second probe comprises the oligonucleotide sequence: 5'-GCT TAC ACA CCC AAT ATT TAT ACC C-3' (SEQ ID NO: 8). In some embodiments, step (b) comprises amplifying the first *B. afzelii* target nucleic acid in the presence of the first primer pair to form a first *B. afzelii* amplicon and amplifying the second *B. afzelii* target nucleic acid in the presence of the second primer pair to form a second *B. afzelii* amplicon, and step (g) comprises detecting the first *B. afzelii* amplicon and the second *B. afzelii* amplicon. In some embodiments, the magnetic particles comprise a first population of magnetic particles conjugated to a first probe and a second probe, and a second population of magnetic particles conjugated to a third probe and a fourth probe, wherein the first probe and third probe are operative to bind a first segment and a second segment, respectively, of the first *B. afzelii* amplicon; and the second probe and fourth probe are operative to bind a first segment and a second segment, respectively, of the second *B. afzelii* amplicon, wherein the magnetic particles form aggregates in the presence of the first *B. afzelii* amplicon and form aggregates in the presence of the second *B. afzelii* amplicon. In some embodiments, the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8. In some embodiments, step (b) further comprises amplifying a pan-*Borrelia* target nucleic acid in the biological sample, and wherein the method further comprises preparing a pan-*Borrelia* assay sample by contacting a portion of the amplified lysate with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid; exposing the pan-*Borrelia* assay sample to the bias magnetic field and the RF pulse sequence; and measuring the signal from the detection tube, thereby determining whether a *Borrelia* cell was present in the biological sample. In some embodiments, step (f) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1 \times 10^6$ to $1 \times 10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1 \times 10^9$ to $1 \times 10^{12}$ mM$^{-1}$s$^{-1}$. In some embodiments, the magnetic particles are substantially monodisperse. In some embodiments, the method detects *B. afzelii* at a concentration of 10 cells/mL of biological sample or less. In some embodiments, the method detects *B. afzelii* at a concentration of 1-10 CFU/mL (e.g., 1, 2, 3, 4, 5, 6, 7, 8, 9, or 10 cells/mL). In some embodiments, the method detects *B. afzelii* at a concentration of 5 CFU/mL. In some embodiments, the method results in 95% correct when the *B. afzelii* is present in the biological sample at a frequency of less than or equal to 10 cells/mL.

In another aspect, the invention features a method for detecting the presence of a tick-borne pathogen in a biological sample, the method comprising: (a) providing a biological sample; (b) lysing the tick-borne pathogen cells in the biological sample; (c) amplifying a Bbsl target nucleic acid and a non-Lyme disease pathogen target nucleic acid in the biological sample to form an amplified biological sample, wherein the non-Lyme disease pathogen is selected from *Rickettsia* spp., *Coxiella burnetii, Babesia* spp., *Anaplasma phagocytophilum*, a *Francisella tularensis* subspp., *Streptococcus pneumoniae*, or *Neisseria meningitidis*; (d) preparing a first assay sample by contacting a portion of the amplified biological sample with a first population of magnetic particles, wherein the magnetic particles of the first population have binding moieties characteristic of a Bbsl species on their surface, the binding moieties operative to alter aggregation of the magnetic particles in the presence of the Bbsl target nucleic acid; (e) preparing a second assay sample by contacting a portion of the amplified biological sample with a second population of magnetic particles, wherein the magnetic particles of the second population have binding moieties characteristic of the non-Lyme disease pathogen on their surface, the binding moieties operative to alter aggregation of the magnetic particles in the presence of the non-Lyme disease pathogen target nucleic acid; (f) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence; (g) exposing each assay sample to a bias magnetic field and an RF pulse sequence; (h) following step (g), measuring the signal produced by each assay sample; and (i) on the basis of the result of step (h), determining whether a tick-borne pathogen is present in the biological sample. In some embodiments, amplifying step (c) further comprises amplifying a pan-*Borrelia* target nucleic acid in the biological sample. In some embodiments, the method further comprises preparing a pan-*Borrelia* assay sample by contacting a portion of the amplified biological sample with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid, and determining whether a *Borrelia* species is present in the biological sample on the basis of the result of step (h). In some embodiments, step (h) comprises measuring the $T_2$ relaxation response of the assay sample, and wherein increasing agglomeration in the assay sample produces an increase in the observed $T_2$ relaxation time of the assay sample. In some embodiments, an assay sample is contacted with $1\times10^6$ to $1\times10^{13}$ magnetic particles per milliliter of the biological sample. In some embodiments, the magnetic particles have a mean diameter of from 150 nm to 699 nm or from 700 nm to 1200 nm. In some embodiments, the magnetic particles have a mean diameter of from 700 nm to 950 nm. In some embodiments, the magnetic particles have a mean diameter of from 700 nm to 850 nm. In some embodiments, the magnetic particles have a $T_2$ relaxivity per particle of from $1\times10^9$ to $1\times10^{12}$ mM$^{-1}$s$^{-1}$. In some embodiments, the magnetic particles are substantially monodisperse.

In some embodiments, the method detects a concentration of an individual Bbsl species of between 1-10 cells/mL (e.g., 1, 2, 3, 4, 5, 6, 7, 8, 9, or 10 cells/mL) of biological sample. In some embodiments, the method individually detects a concentration of an individual Bbsl species of 8 cells/mL of biological sample. In some embodiments, the method individually detects a concentration of an individual Bbsl species of 5 cells/mL of biological sample. In some embodiments, the method individually detects a concentration of an individual Bbsl species of 3 cells/mL of biological sample. In some embodiments, the method individually detects a concentration of an individual Bbsl species of 1 cells/mL of biological sample. In some embodiments, the method results in 95% correct detection when the individual Bbsl species is present in the biological sample at a frequency of less than or equal to 10 cells/mL (e.g., 1, 2, 3, 4, 5, 6, 7, 8, 9, or 10 cells/mL). In some embodiments, the method results in 95% correct detection when the individual Bbsl species is present in the biological sample at a frequency of less than or equal to 8 cells/mL. In some embodiments, the method results in 95% correct detection when the individual Bbsl species is present in the biological sample at a frequency of less than or equal to 5 cells/mL. In some embodiments, the individual Bbsl species is *B. burgdorferi*, *B. afzelii* cell, or *B. garinii*.

In some embodiments of any of the preceding aspects, the non-Lyme disease pathogen is selected from an *Ehrlichia* spp., a *Rickettsia* spp., *Coxiella burnetii*, a *Babesia* spp., *Anaplasma phagocytophilum*, a *Francisella tularensis* subspp., *Streptococcus pneumoniae*, or *Neisseria meningitidis*. In some embodiments, the *Ehrlichia* spp. is *Ehrlichia chaffeensis*, *Ehrlichia ewingii*, or *Ehrlichia muris*-like; the *Rickettsia* spp. is *Rickettsia rickettsii* or *Rickettsia parkeri*; the *Babesia* spp. is *Babesia microti* or *Babesia divergens*, and the *Francisella tularensis* subspp. is *Francisella tularensis* subspp. *tularensis*, *holarctica*, *mediasiatica*, or *novicida*.

In some embodiments of any of the preceding aspects, the Bbsl target nucleic acid is derived from a single-copy chromosomal locus, a single-copy plasmid, a multi-copy chromosomal locus, or a multi-copy plasmid. In some embodiments, the multi-copy plasmid encodes an outer surface protein opsA and/or opsB.

In some embodiments of any of the preceding aspects, the Bbsl target nucleic acid is a *B. burgdorferi* target nucleic acid, and the *B. burgdorferi* target nucleic acid is derived from the oppA gene encoded on linear plasmid 54 (lp54), an outer membrane protein (OMP) (e.g., *Borrelia burgdorferi* lipoprotein NM71_04585), the crasp1 gene encoded on lp54, the lipoprotein ORF 01110, lipoprotein S2, acetyl CoA acetyltransferase encoded on the chromosome, or lipoprotein encoded on lp54.

In some embodiments of any of the preceding aspects, the Bbsl target nucleic acid is a *B. garinii* target nucleic acid, and the *B. garinii* target nucleic acid is derived from the oppA gene, protein 24 (p24) encoded on lp54, chitibiose transporter protein encoded on lp54, chitibiose transporter protein (chbC) encoded on circular plasmid 26 (cp26), lipoprotein encoded on lp54 (lp54-69226), or dbpB gene encoded on lp54.

In some embodiments of any of the preceding aspects, the Bbsl target nucleic acid is a *B. afzelii* target nucleic acid, and the *B. afzelii* target nucleic acid is derived from conserved hypothetical protein bb0242 encoded on the chromosome, lipoprotein S2. chitibiose transporter protein encoded on lp54, inosine-5'-monophosphate dehydrogenase (guaB) encoded on cp26, or phosphotransferase (PTS) glucose transporter subunit encoded on cp26.

In some embodiments of any of the preceding aspects, the non-Lyme disease pathogen target nucleic acid is derived from an essential housekeeping gene, a virulence factor, or a ribosomal DNA (rDNA) operon. In some embodiments, the non-Lyme disease pathogen target nucleic acid is derived from a single-copy locus.

In some embodiments, amplifying step (c) further comprises amplifying a pan-*Borrelia* target nucleic acid in the biological sample. In some embodiments, the method further comprises preparing a pan-*Borrelia* assay sample by contacting a portion of the amplified biological sample with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid, and determining whether a *Borrelia* species is present in the biological sample on the basis of the result of step (h).

In some embodiments of any of the preceding aspects, the biological sample or portion thereof is between 0.1 and 4 mL. In some embodiments, the biological sample is between 1.25 and 2 mL.

In some embodiments of any of the preceding aspects, the biological sample is blood, cerebrospinal fluid (CSF), urine, or synovial fluid. In some embodiments, the biological sample is blood. In some embodiments, the blood is whole blood or platelet-rich plasma (PRP). In some embodiments, amplifying is in the presence of whole blood proteins and non-target nucleic acids. In some embodiments, the biological sample or portion thereof is a fraction of blood enriched for white blood cells.

In some embodiments of any of the preceding aspects, lysing comprises mechanical lysis or heat lysis. In some embodiments, mechanical lysis is beadbeating or sonicating.

In some embodiments of any of the preceding aspects, the steps of the method are completed within 5 hours. In some embodiments, the steps of the method are completed within 4 hours. In some embodiments, the steps of the method are completed within 3 hours.

In another aspect, the invention features a method for detecting the presence of a tick-borne pathogen in a sample of whole blood, the method comprising: (a) providing an sample produced by lysing the red blood cells in a whole blood sample from a subject, centrifuging the sample to form a supernatant and a pellet, discarding some or all of the supernatant, and optionally washing the pellet; (b) lysing the tick-borne pathogen cells and subject cells in the pellet to form a lysate; (c) amplifying a Bbsl target nucleic acid and a non-Lyme disease pathogen target nucleic acid in the lysate to form an amplified lysate, wherein the non-Lyme disease pathogen is selected from *Rickettsia* spp., *Coxiella burnetii*, *Babesia* spp., *Anaplasma phagocytophilum*, a *Francisella tularensis* subspp., *Streptococcus pneumoniae*, or *Neisseria meningitidis*; (d) following step (c), preparing a first assay sample by adding to a portion of the amplified lysate from $1\times10^6$ to $1\times10^{13}$ magnetic particles per milliliter of the amplified lysate, wherein the magnetic particles have a mean diameter of from 700 nm to 950 nm and binding moieties on their surface, the binding moieties operative to alter aggregation of the magnetic particles in the presence of the Bbsl target nucleic acid, wherein said magnetic particles have a $T_2$ relaxivity per particle of from $1\times10^9$ to $1\times10^{12}$ $mM^{-1}s^{-1}$; (e) following step (c), preparing a second assay sample by adding to a portion of the amplified lysate from $1\times10^6$ to $1\times10^{13}$ magnetic particles per milliliter of the amplified lysate, wherein the magnetic particles have a mean diameter of from 700 nm to 950 nm and binding moieties on their surface, the binding moieties operative to alter aggregation of the magnetic particles in the presence of the non-Lyme disease pathogen target nucleic acid, wherein said magnetic particles have a $T_2$ relaxivity per particle of from $1\times10^9$ to $1\times10^{12}$ $mM^{-1}s^{-1}$ (f) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence; (g) exposing each assay sample to a bias magnetic field and an RF pulse sequence; (h) following step (i), measuring the signal produced by each assay sample; and (i) on the basis of the result of step (h), determining whether a tick-borne pathogen is present in the sample of whole blood. In some embodiments, the non-Lyme disease pathogen is selected from an *Ehrlichia* spp., a *Rickettsia* spp., *Coxiella burnetii*, a *Babesia* spp., *Anaplasma phagocytophilum*, a *Francisella tularensis* subspp., *Streptococcus pneumoniae*, or *Neisseria meningitidis*. In some embodiments, the *Ehrlichia* spp. is *Ehrlichia chaffeensis, Ehrlichia ewingii*, or *Ehrlichia muris*-like; the *Rickettsia* spp. is *Rickettsia rickettsii* or *Rickettsia parkeri*; the *Babesia* spp. is *Babesia microti* or *Babesia divergens*, and the *Francisella tularensis* subspp. is *Francisella tularensis* subspp. *tularensis, holarctica, mediasiatica*, or *novicida*. In some embodiments, amplifying step (c) further comprises amplifying a pan-*Borrelia* target nucleic acid in the lysate. In some embodiments, the method further comprises preparing a pan-*Borrelia* assay sample by contacting a portion of the amplified biological sample with a population of magnetic particles, wherein the magnetic particles have binding moieties characteristic of all *Borrelia* species on their surface, the binding moieties operative to alter aggregation of the magnetic particles in the presence of the pan-*Borrelia* target nucleic acid, and determining whether a *Borrelia* species is present in the biological sample on the basis of the result of step (h). In some embodiments, the whole blood sample is from 0.05 to 4 mL. In some embodiments, the method is capable of detecting a tick-borne pathogen concentration of 10 cells/mL or less (e.g., 10, 9, 8, 7, 6, 5, 4, 3, 2, 1 cell/mL or less) in the whole blood sample. In some embodiments, the method is capable of detecting a tick-borne pathogen concentration of 5 cells/ml in the whole blood sample. In some embodiments, the method is capable of detecting a tick-borne pathogen concentration of 3 cells/ml in the whole blood sample. In some embodiments, the method is capable of detecting a tick-borne pathogen concentration of 1 cells/ml in the whole blood sample. In some embodiments, step (h) comprises measuring the $T_2$ relaxation response of the mixture, and wherein increasing agglomeration in the mixture produces an increase in the observed $T_2$ relaxation time of the mixture. In some embodiments, steps (a) through (i) are completed within 5 hours. In some embodiments, steps (a) through (i) are completed within 3 hours. In some embodiments, the amplified lysate of step (c) comprises whole blood proteins and non-target DNA from subject cells.

In another aspect, the invention features a method for detecting the presence of a *B. burgdorferi* cell in a sample of whole blood, the method comprising: (a) providing an sample produced by lysing the red blood cells in a whole blood sample from a subject, centrifuging the sample to form a supernatant and a pellet, discarding some or all of the supernatant, and optionally washing the pellet; (b) lysing the *B. burgdorferi* cells and subject cells in the pellet to form a lysate; (c) amplifying a *B. burgdorferi* target nucleic acid in the lysate in the presence of a first primer pair or a second primer pair to form an amplified lysate comprising a *B. burgdorferi* amplicon, wherein the first primer pair comprises a forward primer comprising the oligonucleotide sequence: 5'-AGA GGA CTT TTA ATA CTG GGC ATT GCT G-3' (SEQ ID NO: 1) and a reverse primer comprising the oligonucleotide sequence: 5'-GGC CAT TAT GTA GGA ATC TCT AAT GGT GC-3' (SEQ ID NO: 2), and the second primer pair comprises a forward primer comprising the oligonucleotide sequence: 5'-ACA TAA TGG CCT TAG AAA ATG AGC TTG ATG-3' (SEQ ID NO: 5) and a reverse primer comprising the oligonucleotide sequence 5'-CCC GCT TGT AAC CAT GTT TTC TGA GC-3' (SEQ ID NO: 6); (d) following step (c), preparing at least a first assay sample by adding to a portion of the amplified lysate from $1\times10^6$ to $1\times10^{13}$ magnetic particles per milliliter of the amplified lysate, wherein the magnetic particles have a mean diameter of from 700 nm to 950 nm and binding moieties on their surface, the binding moieties operative to alter aggregation of the magnetic particles in the presence of the *B. burgdorferi* target nucleic acid, wherein said magnetic particles have a $T_2$ relaxivity per particle of from $1\times10^9$ to $1\times10^{12}$ $mM^{-1}s^{-1}$; (e) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence; (f) exposing each assay sample to a bias magnetic field and an RF pulse sequence; (g) following step (f), measuring the signal produced by each assay sample; and (h) on the basis of the result of step (g), determining whether a tick-borne pathogen is present in the sample of whole blood. In some embodiments, step (c) comprises amplifying the first *B. burgdorferi* target nucleic acid in the presence of the first primer pair to form a first *B. burgdorferi* amplicon and amplifying the second *B. burgdorferi* target nucleic acid in the presence of the second primer pair to form a second *B. burgdorferi* amplicon, and step (g) comprises detecting the first *B. burgdorferi* amplicon and the second *B. burgdorferi* amplicon. In some embodiments, the magnetic particles comprise a first population of magnetic particles conjugated to a first probe and a second probe, and a second population of magnetic particles conjugated to a third probe and a fourth probe, wherein the first probe and third probe are operative to bind a first segment and a second segment, respectively, of the first *B. burgdorferi* amplicon; and the second probe and fourth probe are operative to bind a first segment and a second segment, respectively, of the second *B. burgdorferi* amplicon, wherein the magnetic particles form aggregates in the presence of the first *B. burgdorferi* amplicon and form aggregates in the presence of the second *B. burgdorferi* amplicon. In some embodiments, the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8. In some embodiments, step (c) further comprises amplifying a *B. garinii* target nucleic acid in the lysate in the presence of a forward primer comprising the oligonucleotide sequence: 5'-GGA TAT TCA AAT CCT GAG GTT GAC GAA CTA-3' (SEQ ID NO: 9) and a reverse primer comprising the oligonucleotide sequence: 5'-CTG ATA GGG CAA ATC TTT CTG AAG CA-3' (SEQ ID NO: 10) to form an amplified lysate comprising a *B. garinii* amplicon. In some embodiments, the method further comprises detecting the presence of the *B. garinii* amplicon. In some embodiments, step (c) further comprises amplifying a *B. afzelii* target nucleic acid in the lysate in the presence of a first primer pair or a second primer pair to form an amplified lysate comprising a *B. afzelii* amplicon, wherein the first primer pair comprises a forward primer comprising the oligonucleotide sequence: 5'-CCG TGG GCA GAG TCT ATG ACA ATC AG-3' (SEQ ID NO: 13) and a reverse primer comprising the oligonucleotide sequence: 5'-GCC CAA AAA ACC ATC AAC ACT AAT AAG G-3' (SEQ ID NO: 14), and the second primer pair comprises a forward primer comprising the oligonucleotide sequence: 5'-CAA GGT GCA ATG ACT TTG TTT GGG CA-3' (SEQ ID NO: 17) and a reverse primer comprising the oligonucleotide sequence 5'-GCA ACT TCA AAG TGT ACA GTA TTG GTA TCC C-3' (SEQ ID NO: 18). In some embodiments, step (c) comprises amplifying the first *B. afzelii* target nucleic acid in the presence of the first primer pair to form a first *B. afzelii* amplicon and amplifying the second *B. afzelii* target nucleic acid in the presence of the second primer pair to form a second *B. afzelii* amplicon, and step (g) comprises detecting the first *B. afzelii* amplicon and the second *B. afzelii* amplicon. In some embodiments, the method further comprises detecting the presence of the first *B. afzelii* amplicon and the second *B. afzelii* amplicon. In some embodiments, the method detects *B. burgdorferi* at a concentration of 10 cells/mL of biological sample or less. In some embodiments, the method detects *B. burgdorferi* at a concentration of 1-10 CFU/mL (e.g., 1, 2, 3, 4, 5, 6, 7, 8, 9, or 10 cells/mL). In some embodiments, the method detects *B. burgdorferi* at a concentration of 8 CFU/mL. In some embodiments, the method results in 95% correct detection when the *B. burgdorferi* is present in the biological sample at a frequency of less than or equal to 10 cells/mL (e.g., 1, 2, 3, 4, 5, 6, 7, 8, 9, or 10 cells/mL). In some embodiments, the method detects *B. garinii* at a concentration of 10 cells/mL of biological sample or less.

In another aspect, the invention features a method for detecting the presence of a *B. burgdorferi* cell in a sample of whole blood, the method comprising: (a) providing an sample produced by lysing the red blood cells in a whole blood sample from a subject, centrifuging the sample to form a supernatant and a pellet, discarding some or all of the supernatant, and optionally washing the pellet; (b) lysing the *B. burgdorferi* cells and subject cells in the pellet to form a lysate; (c) amplifying a *B. burgdorferi* target nucleic acid in the lysate in the presence of a first primer pair or a second primer pair to form an amplified lysate comprising a *B. burgdorferi* amplicon, wherein the first primer pair comprises a forward primer comprising the oligonucleotide sequence: 5'-AGC TGT AGT TTA AGG CAA ATG TTG G-3' (SEQ ID NO: 157) and a reverse primer comprising the oligonucleotide sequence: 5'-AGG ATC GCA AAA TCA ACC ACA AAC A-3' (SEQ ID NO: 160), and the second primer pair comprises a forward primer comprising the oligonucleotide sequence: 5'-TGC TGC TGT TGT TTT TGG CAG ATT-3' (SEQ ID NO:163) and a reverse primer comprising the oligonucleotide sequence 5'-ATG ACA AAG TAG CAG CAG AGC TAA A-3' (SEQ ID NO: 164); (d) following step (c), preparing at least a first assay sample by adding to a portion of the amplified lysate from $1\times10^6$ to $1\times10^{13}$ magnetic particles per milliliter of the amplified lysate, wherein the magnetic particles have a mean diameter of from 700 nm to 950 nm and binding moieties on their surface, the binding moieties operative to alter aggregation of the magnetic particles in the presence of the *B. burgdorferi* target nucleic acid, wherein said magnetic particles have a $T_2$ relaxivity per particle of from $1\times10^9$ to $1\times10^{12}$ mM$^{-1}$s$^{-1}$; (e) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence; (f) exposing each assay sample to a bias magnetic field and an RF pulse sequence; (g) following step (f), measuring the signal produced by each assay sample; and (h) on the basis of the result of step (g), determining whether a tick-borne pathogen is present in the sample of whole blood. In some embodiments, step (c) comprises amplifying the first *B. burgdorferi* target nucleic acid in the presence of the first primer pair to form a first *B. burgdorferi* amplicon and amplifying the second *B. burgdorferi* target nucleic acid in the presence of the second primer pair to form a second *B. burgdorferi* amplicon, and step (g) comprises detecting the first *B. burgdorferi* amplicon and the second *B. burgdorferi* amplicon. In some embodiments, the magnetic particles comprise a first population of magnetic particles conjugated to a first probe and a second probe, and a second population of magnetic particles conjugated to a third probe and a fourth probe, wherein the first probe and third probe are operative to bind a first segment and a second segment, respectively, of the first *B. burgdorferi* amplicon; and the second probe and fourth probe are operative to bind a first segment and a second segment, respectively, of the second *B. burgdorferi* amplicon, wherein the magnetic particles form aggregates in the presence of the first *B. burgdorferi* amplicon and form aggregates in the presence of the second *B. burgdorferi* amplicon. In some embodiments, the first probe comprises an oligonucleotide sequence of SEQ ID NO: 161, the second probe comprises an oligonucleotide sequence of SEQ ID NO: 165, the third probe comprises an oligonucleotide sequence of SEQ ID NO: 162, and the fourth probe comprises an oligonucleotide sequence of SEQ ID NO: 166. In some embodiments, step (c) further comprises amplifying a *B. garinii* target nucleic acid in the lysate in the presence of a forward primer comprising the oligonucleotide sequence: 5'-GGA TAT TCA AAT CCT GAG GTT GAC GAA CTA-3' (SEQ ID NO: 9) and a reverse primer comprising the oligonucleotide sequence: 5'-CTG ATA GGG CAA ATC TTT CTG AAG CA-3' (SEQ ID NO: 10) to form an amplified lysate comprising a *B. garinii* amplicon. In some embodiments, the method further comprises detecting the presence of the *B. garinii* amplicon. In some embodiments, step (c) further comprises amplifying a *B. afzelii* target nucleic acid in the lysate in the presence of a first primer pair or a second primer pair to form an amplified lysate comprising a *B. afzelii* amplicon, wherein the first primer pair comprises a forward primer comprising the oligonucleotide sequence: 5'-CCG TGG GCA GAG TCT ATG ACA ATC AG-3' (SEQ ID NO: 13) and a reverse primer comprising the oligonucleotide sequence: 5'-GCC CAA AAA ACC ATC AAC ACT AAT AAG G-3' (SEQ ID NO: 14), and the second primer pair comprises a forward primer comprising the oligonucleotide sequence: 5'-CAA GGT GCA ATG ACT TTG TTT GGG CA-3' (SEQ ID NO: 17) and a reverse primer comprising the oligonucleotide sequence 5'-GCA ACT TCA AAG TGT ACA GTA TTG GTA TCC C-3' (SEQ ID NO: 18). In some embodiments, step (c) comprises amplifying the first *B. afzelii* target nucleic acid in the presence of the first primer pair to form a first *B. afzelii* amplicon and amplifying the second *B. afzelii* target nucleic acid in the presence of the second primer pair to form a second *B. afzelii* amplicon, and step (g) comprises detecting the first *B. afzelii* amplicon and the second *B. afzelii* amplicon. In some embodiments, the method further comprises detecting the presence of the first *B. afzelii* amplicon and the second *B. afzelii* amplicon. In some embodiments, the method detects *B. burgdorferi* at a concentration of 10 cells/mL of biological sample or less. In some embodiments, the method detects *B. burgdorferi* at a concentration of 1-10 CFU/mL (e.g., 1, 2, 3, 4, 5, 6, 7, 8, 9, or 10 cells/mL). In some embodiments, the method detects *B. burgdorferi* at a concentration of 8 CFU/mL. In some embodiments, the method results in 95% correct detection when the *B. burgdorferi* is present in the biological sample at a frequency of less than or equal to 10 cells/mL (e.g., 1, 2, 3, 4, 5, 6, 7, 8, 9, or 10 cells/mL). In some embodiments, the method detects *B. garinii* at a concentration of 10 cells/mL of biological sample or less.

In another aspect, the invention features a composition comprising: (a) a liquid sample, wherein the liquid sample (i) is suspected of containing at least one *B. burgdorferi* target nucleic acid, or (ii) contains at least one *B. burgdorferi* target nucleic acid amplicon generated from an amplification reaction; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8.

In another aspect, the invention features a composition comprising: (a) a liquid sample, wherein the liquid sample (i) is suspected of containing a *B. garinii* target nucleic acid, or (ii) contains a *B. garinii* amplicon generated by amplifying the *B. garinii* target nucleic acid; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles comprise a first population of magnetic particles conjugated to a first nucleic acid probe comprising the oligonucleotide sequence: 5'-CTG AGA TTG AAG TTG ACG AAA AAA TCA G-3' (SEQ ID NO: 11), and a second population of magnetic particles conjugated to a second nucleic acid probe comprising the oligonucleotide sequence: 5'-GAT CAT CCA ATA ATT CCA ATC TAC AGC G-3' (SEQ ID NO: 12).

In another aspect, the invention features a composition comprising: (a) a liquid sample, wherein the liquid sample (i) is suspected of containing at least one *B. afzelii* target nucleic acid, or (ii) contains at least one *B. afzelii* target nucleic acid amplicon generated from an amplification reaction; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8.

In another aspect, the invention features a removable cartridge comprising a plurality of wells, wherein the removable cartridge comprises one or more of the following: (a) a first well comprising a composition comprising: (a') a liquid sample, wherein the liquid sample (i) is suspected of containing at least one *B. burgdorferi* target nucleic acid, or (ii) contains at least one *B. burgdorferi* target nucleic acid amplicon generated from an amplification reaction; and (b') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8; (b) a second well comprising a composition comprising: (a") a liquid sample, wherein the liquid sample (i) is suspected of containing a *B. garinii* target nucleic acid, or (ii) contains a *B. garinii* amplicon generated by amplifying the *B. garinii* target nucleic acid; and (b") within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles comprise a first population of magnetic particles conjugated to a first nucleic acid probe comprising the oligonucleotide sequence: 5'-CTG AGA TTG AAG TTG ACG AAA AAA TCA G-3' (SEQ ID NO: 11), and a second population of magnetic particles conjugated to a second nucleic acid probe comprising the oligonucleotide sequence: 5'-GAT CAT CCA ATA ATT CCA ATC TAC AGC G-3' (SEQ ID NO: 12); and (c) a third well comprising a composition comprising: (a''') a liquid sample, wherein the liquid sample (i) is suspected of containing at least one *B. afzelii* target nucleic acid, or (ii) contains at least one *B. afzelii* target nucleic acid amplicon generated from an amplification reaction; and (b''') within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8. In some embodiments, the removable cartridge comprises two of (a) through (c) (e.g., (a) and (b), (a) and (c), or (b) and (c)). In some embodiments, the removable cartridge comprises (a) through (c). In some embodiments, the removable cartridge further comprises one or more chambers for holding a plurality of reagent modules for holding one or more assay reagents. In some embodiments, the removable cartridge further comprises a chamber comprising beads for lysing cells. In some embodiments, the removable cartridge further comprises a chamber comprising a polymerase. In some embodiments, the removable cartridge further comprises a chamber comprising one or more primers. In some embodiments, the one or more primers comprise oligonucleotide sequences selected from SEQ ID NOs: 1, 2, 5, 6, 9, 10, 13, 14, 17, and 18.

In another aspect, the invention features a method for diagnosing Lyme disease in a subject, the method comprising: (a) providing a biological sample obtained from the subject; and (b) detecting the presence of at least two different Bbsl species in the biological sample according to any one of the proceeding methods, wherein the presence of a Bbsl species in the biological sample obtained from the subject identifies the subject as one who may have Lyme disease. In some embodiments, the presence of two different Bbsl species selected from *B. burgdorferi*, *B. afzelii*, and *B. garinii* is detected. In some embodiments, the presence of *B. burgdorferi*, *B. afzelii*, and *B. garinii* is detected.

In another aspect, the invention features a method for diagnosing a tick-transmitted disease in a subject, the method comprising: (a) providing a biological sample obtained from the subject; (b) detecting the presence of a tick-borne pathogen according to any one of the proceeding methods, wherein the presence of a tick-borne pathogen identifies the subject as one who may have a tick-transmitted disease.

In another aspect, the invention features a method for diagnosing Lyme disease in a subject, the method comprising: (a) providing a biological sample obtained from the subject; and (b) detecting the presence of a *B. burgdorferi* cell, a *B. afzelii* cell, or a *B. garinii* cell in the sample according to any one of the proceeding methods, wherein the presence of a *B. burgdorferi* cell, a *B. afzelii* cell, or a *B. garinii* cell in the biological sample obtained from the subject identifies the subject as one who may have Lyme disease. In some embodiments, the presence of at least two of a *B. burgdorferi* cell, a *B. afzelii* cell, and a *B. garinii* (e.g., *B. burgdorferi* and *B. afzelii*, *B. burgdorferi* and *B. garinii*, or *B. afzelii* and *B. garinii*) cell is detected. In some embodiments, the presence of a *B. burgdorferi* cell, a *B. afzelii* cell, and a *B. garinii* cell is detected.

In another aspect, the invention features a method for treating Lyme disease in a subject, the method comprising: (a) providing a biological sample obtained from the subject; (b) detecting the presence of at least two different Bbsl species in the biological sample according to any one the proceeding methods, wherein the presence of a Bbsl species in the biological sample obtained from the subject identifies the subject as one who may have Lyme disease, and (c) administering a Lyme disease therapy to the subject identified as one who may have Lyme disease. In some embodiments, the presence of two different Bbsl species selected from *B. burgdorferi*, *B. afzelii*, and *B. garinii* (e.g., *B. burgdorferi* and *B. afzelii*, *B. burgdorferi* and *B. garinii*, or

*B. afzelii* and *B. garinii*) is detected. In some embodiments, the presence of *B. burgdorferi, B. afzelii*, and *B. garinii* is detected.

In another aspect, the invention features a method for treating a tick-transmitted disease in a subject, the method comprising: (a) providing a biological sample obtained from the subject; (b) detecting the presence of a tick-borne pathogen according to any one of the preceding methods, wherein the presence of a tick-borne pathogen identifies the subject as one who may have a tick-transmitted disease; and (c) administering a tick-transmitted disease therapy to the subject identified as one who may have a tick-transmitted disease.

In another aspect, the invention features a method for treating Lyme disease in a subject, the method comprising: (a) providing a biological sample obtained from the subject; and (b) detecting the presence of a *B. burgdorferi* cell, a *B. afzelii* cell, or a *B. garinii* cell in the sample according to the method of any one of the preceding methods, wherein the presence of a *B. burgdorferi* cell, a *B. afzelii* cell, or a *B. garinii* cell in the biological sample obtained from the subject identifies the subject as one who may have Lyme disease; and (c) administering a Lyme disease therapy to the subject identified as one who may have Lyme disease. In some embodiments, the presence of two different Bbsl species selected from *B. burgdorferi, B. afzelii*, and *B. garinii* (e.g., *B. burgdorferi* and *B. afzelii, B. burgdorferi* and *B. garinii*, or *B. afzelii* and *B. garinii*) is detected. In some embodiments, the presence of *B. burgdorferi, B. afzelii*, and *B. garinii* is detected.

In some embodiments, the method detects a concentration of an individual Bbsl species of between 1-10 cells/mL (e.g., 1, 2, 3, 4, 5, 6, 7, 8, 9, or 10 cells/mL) of biological sample. In some embodiments, the method individually detects a concentration of an individual Bbsl species of 8 cells/mL of biological sample. In some embodiments, the method individually detects a concentration of an individual Bbsl species of 5 cells/mL of biological sample. In some embodiments, the method individually detects a concentration of an individual Bbsl species of 3 cells/mL of biological sample. In some embodiments, the method individually detects a concentration of an individual Bbsl species of 1 cells/mL of biological sample. In some embodiments, the method results in 95% correct detection when the individual Bbsl species is present in the biological sample at a frequency of less than or equal to 10 cells/mL (e.g., 1, 2, 3, 4, 5, 6, 7, 8, 9, or 10 cells/mL). In some embodiments, the method results in 95% correct detection when the individual Bbsl species is present in the biological sample at a frequency of less than or equal to 8 cells/mL. In some embodiments, the method results in 95% correct detection when the individual Bbsl species is present in the biological sample at a frequency of less than or equal to 5 cells/mL. In some embodiments, the individual Bbsl species is *B. burgdorferi, B. afzelii* cell, or *B. garinii*.

Other features and advantages of the invention will be apparent from the following detailed description, drawings, and the claims.

BRIEF DESCRIPTION OF THE DRAWINGS

FIG. 1 shows a table describing an exemplary panel of the invention, along with particular tissues that may be tested using the methods and systems of the invention.

FIG. 7 is a table showing $Mg^{2+}$ and dNTP concentration optimization via design of experiments (DOE). 10 copies of genomic DNA of each of the three Bbsl species was tested.

DETAILED DESCRIPTION OF EMBODIMENTS OF THE INVENTION

Figure 2:
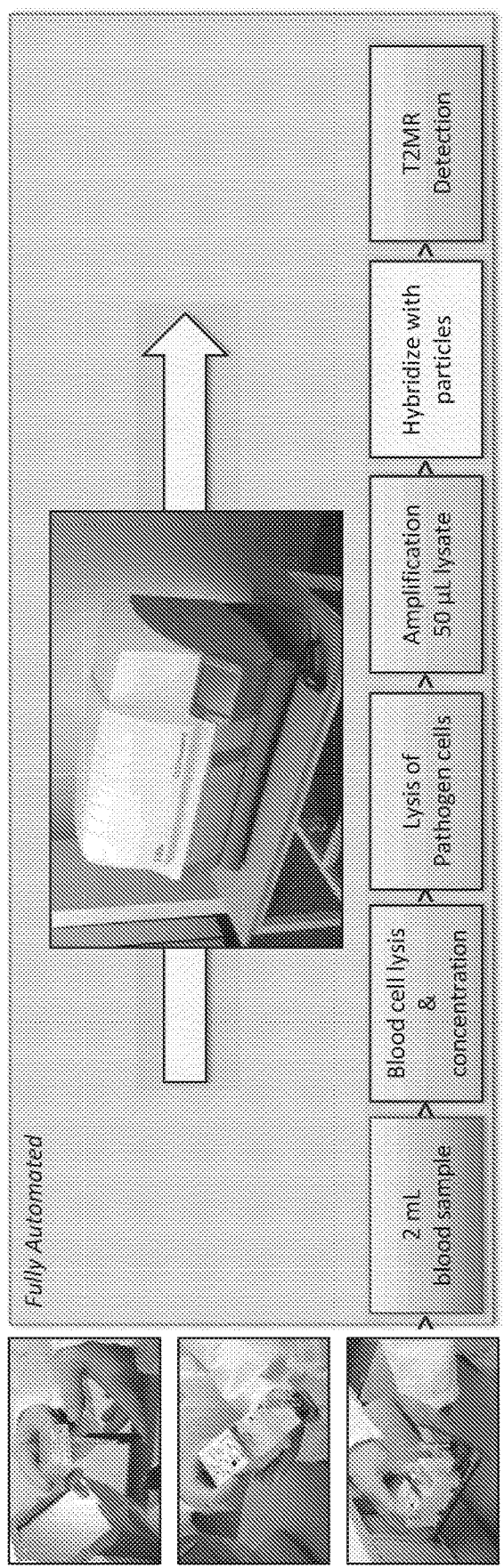
FIG. 2 shows an exemplary workflow for detecting pathogens described herein (including, for example, tick-borne pathogens and others according to the panel shown in FIG. 1) using the T2Dx® instrument.

The invention provides methods, systems, cartridges, and panels for detection of pathogens (including tick-borne pathogens), for example, for detection of pathogens in biological samples. In several embodiments, the analytes are derived from tick-borne pathogens, including *Borrelia* spp. (e.g., *Borrelia burgdorferi* sensu lato spp. that cause Lyme disease, including *Borrelia burgdorferi, Borrelia afzelii*, and *Borrelia garinii*), and non-Lyme disease pathogens that cause Lyme-like diseases, including *Rickettsia* spp. (including *Rickettsia rickettsii* and *Rickettsia parkeri*), *Ehrlichia* spp. (including *Ehrlichia chaffeensis, Ehrlichia ewingii*, and *Ehrlichia muris*-like), *Coxiella* spp. (including *Coxiella burnetii*), *Babesia* spp. (including *Babesia microti* and *Babesia*

*divergens*), *Anaplasma* spp. (including *Anaplasma phagocytophilum*), *Francisella* spp. (including *Francisella tularensis* (including *F. tularensis* subspp. *tularensis*, subspp. *holarctica*, subspp. *mediasiatica*, and subspp. *novicida*), *Streptococcus* spp. (including *Streptococcus pneumonia*), and *Neisseria* spp. (including *Neisseria meningitidis*).

In some embodiments, the methods and systems of the invention employ magnetic particles. In some embodiments, the methods and systems employ an NMR unit, optionally one or more magnetic assisted agglomeration (MAA) units, optionally one or more incubation stations at different temperatures, optionally one or more vortexers, optionally one or more centrifuges, optionally a fluidic manipulation station, optionally a robotic system, and optionally one or more modular cartridges, as described in International Patent Application Publication No. WO 2012/054639, which is incorporated herein by reference in its entirety. The systems, devices, and methods of the invention can be used to assay a biological sample (e.g., whole blood, serum, plasma (e.g., platelet-rich plasma or platelet-poor plasma), cerebrospinal fluid (CSF), urine, synovial fluid, breast milk, sweat, tears, saliva, semen, feces, vaginal fluid or tissue, sputum, nasopharyngeal aspirate or swab, lacrimal fluid, mucous, or epithelial swab (buccal swab), tissues (e.g., tissue homogenates), organs, bones, teeth, among others).

Definitions

The terms "aggregation," "agglomeration," and "clustering" are used interchangeably in the context of the magnetic particles described herein and mean the binding of two or more magnetic particles to one another, for example, via a multivalent analyte, multimeric form of analyte, antibody, nucleic acid molecule, or other binding molecule or entity. In some instances, magnetic particle agglomeration is reversible.

The terms "amplification" or "amplify" or derivatives thereof as used herein mean one or more methods known in the art for copying a target or template nucleic acid, thereby increasing the number of copies of a selected nucleic acid sequence. Amplification may be exponential or linear. A target or template nucleic acid may be either DNA or RNA (e.g., mRNA). The sequences amplified in this manner form an "amplified region" or "amplicon." Primer probes can be readily designed by those skilled in the art to target a specific template nucleic acid sequence.

By "analyte" is meant a substance or a constituent of a sample to be analyzed. Exemplary analytes include one or more species of one or more of the following: a protein, a peptide, a polypeptide, an amino acid, a nucleic acid, an oligonucleotide, RNA (e.g., mRNA), DNA, an antibody, a carbohydrate, a polysaccharide, glucose, a lipid, a gas (e.g., oxygen or carbon dioxide), an electrolyte (e.g., sodium, potassium, chloride, bicarbonate, BUN, magnesium, phosphate, calcium, ammonia, lactate), a lipoprotein, cholesterol, a fatty acid, a glycoprotein, a proteoglycan, a lipopolysaccharide, a cell surface marker (e.g., a cell surface protein of a tick-borne pathogen), a cytoplasmic marker (e.g., CD4/CD8 or CD4/viral load), a therapeutic agent, a metabolite of a therapeutic agent, a marker for the detection of a weapon (e.g., a chemical or biological weapon), an organism, a pathogen, a pathogen byproduct, a parasite (e.g., a protozoan or a helminth), a protist, a fungus (e.g., yeast or mold), a bacterium, an actinomycete, a cell (e.g., a whole cell, a tumor cell, a stem cell, a white blood cell, a T cell (e.g., displaying CD3, CD4, CD8, IL2R, CD35, or other surface markers), or another cell identified with one or more specific markers), a virus, a prion, a plant component, a plant by-product, algae, an algae by-product, plant growth hormone, an insecticide, a man-made toxin, an environmental toxin, an oil component, and components derived therefrom.

A "biological sample" is a sample obtained from a subject including but not limited to whole blood, serum, plasma (e.g., platelet-rich plasma or platelet-poor plasma), cerebrospinal fluid (CSF), urine, synovial fluid, breast milk, sweat, tears, saliva, semen, feces, vaginal fluid or tissue, sputum, nasopharyngeal aspirate or swab, lacrimal fluid, mucous, or epithelial swab (buccal swab), tissues (e.g., tissue homogenates), organs, bones, teeth, among others).

By "*Borrelia burgdorferi* sensu lato" is meant *Borrelia burgdorferi* and the closely-related species *Borrelia afzelii* and *Borrelia garinii*, which are causative pathogens for Lyme disease.

By "Lyme-like disease" is meant a disease caused by a tick-borne pathogen that may manifest similar or overlapping symptoms as compared to Lyme disease. Exemplary Lyme-like diseases include, without limitation, Rocky Mountain spotted fever, Q-fever, babesiosis, ehrlichiosis, and anaplasmosis.

By "non-Lyme disease pathogen" is meant a pathogen that does not cause Lyme disease. Exemplary non-Lyme disease pathogens include, without limitation, *Rickettsia* spp. (including *Rickettsia rickettsii* and *Rickettsia parkeri*), *Ehrlichia* spp. (including *Ehrlichia chaffeensis, Ehrlichia ewingii*, and *Ehrlichia muris*-like), *Coxiella* spp. (including *Coxiella burnetii*), *Babesia* spp. (including *Babesia microti* and *Babesia divergens*), *Anaplasma* spp. (including *Anaplasma phagocytophilum*), *Francisella* spp. (including *F. tularensis*, including *F. tularensis* subspp. *tularensis, holarctica, mediasiatica*, and *novicida*), *Streptococcus* spp. (including *Streptococcus pneumonia*), and *Neisseria* spp. (including *Neisseria meningitidis*).

By "tick-transmitted disease" is meant a disease that can be transmitted to a subject (e.g., a human) by a tick or a related ectoparasite. A tick may be of the genus *Ixodes*, for example, *Ixodes scapularis*. A tick that is a host for a tick-borne pathogen may transmit the tick-borne pathogen to the subject during feeding.

By "tick-borne pathogen" is meant a pathogen for which a tick may be a vector. Exemplary tick-borne pathogens include *Borrelia* spp. (e.g., *Borrelia burgdorferi* sensu lato species, including *Borrelia burgdorferi, Borrelia afzelii*, and *Borrelia garinii*), *Rickettsia* spp. (including *Rickettsia rickettsii* and *Rickettsia parkeri*), *Ehrlichia* spp. (including *Ehrlichia chaffeensis, Ehrlichia ewingii*, and *Ehrlichia muris*-like), *Coxiella* spp. (including *Coxiella burnetii*), *Babesia* spp. (including *Babesia microti* and *Babesia divergens*), *Anaplasma* spp. (including *Anaplasma phagocytophilum*), and *Francisella* spp. (including *F. tularensis*, including *F. tularensis* subspp. *tularensis, holarctica, mediasiatica*, and *novicida*).

As used herein, the term "small molecule" refers to a drug, medication, medicament, or other chemically synthesized compound that is contemplated for human therapeutic use.

As used herein, the term "biologic" refers to a substance derived from a biological source, not synthesized and that is contemplated for human therapeutic use.

A "biomarker" is a biological substance that can be used as an indicator of a particular disease state or particular physiological state of an organism, generally a biomarker is a protein or other native compound measured in bodily fluid whose concentration reflects the presence or severity or staging of a disease state or dysfunction, can be used to monitor therapeutic progress of treatment of a disease or disorder or dysfunction, or can be used as a surrogate measure of clinical outcome or progression.

As used herein, the term "genotyping" refers to the ability to determine genetic differences in specific genes that may or may not affect the phenotype of the specific gene. As used herein, the term "phenotype" refers to the resultant biological expression, (metabolic or physiological) of the protein set by the genotype.

By an "isolated" nucleic acid molecule is meant a nucleic acid molecule that is removed from the environment in which it naturally occurs. For example, a naturally-occurring nucleic acid molecule present in the genome of cell or as part of a gene bank is not isolated, but the same molecule, separated from the remaining part of the genome, as a result of, e.g., a cloning event, amplification, or enrichment, is "isolated." Typically, an isolated nucleic acid molecule is free from nucleic acid regions (e.g., coding regions) with which it is immediately contiguous, at the 5' or 3' ends, in the naturally occurring genome. Such isolated nucleic acid molecules can be part of a vector or a composition and still be isolated, as such a vector or composition is not part of its natural environment.

As used herein, "linked" means attached or bound by covalent bonds, non-covalent bonds, and/or linked via Van der Waals forces, hydrogen bonds, and/or other intermolecular forces.

The term "magnetic particle" refers to particles including materials of high positive magnetic susceptibility such as paramagnetic compounds, superparamagnetic compounds, and magnetite, gamma ferric oxide, or metallic iron.

As used herein, "nonspecific reversibility" refers to the colloidal stability and robustness of magnetic particles against non-specific aggregation in a liquid sample and can be determined by subjecting the particles to the intended assay conditions in the absence of a specific clustering moiety (i.e., an analyte or an agglomerator). For example, nonspecific reversibility can be determined by measuring the $T_2$ values of a solution of magnetic particles before and after incubation in a uniform magnetic field (defined as <5000 ppm) at 0.45 T for 3 minutes at 37° C. Magnetic particles are deemed to have nonspecific reversibility if the difference in $T_2$ values before and after subjecting the magnetic particles to the intended assay conditions vary by less than 10% (e.g., vary by less than 9%, 8%, 6%, 4%, 3%, 2%, or 1%). If the difference is greater than 10%, then the particles exhibit irreversibility in the buffer, diluents, and matrix tested, and manipulation of particle and matrix properties (e.g., coating and buffer formulation) may be required to produce a system in which the particles have nonspecific reversibility. In another example, the test can be applied by measuring the $T_2$ values of a solution of magnetic particles before and after incubation in a gradient magnetic field 1 Gauss/mm-10000 Gauss/mm.

As used herein, the term "NMR relaxation rate" refers to a measuring any of the following in a sample $T_1$, $T_2$, $T_1/T_2$ hybrid, $T_{1rho}$, $T_{2rho}$, and $T_2^*$. The systems and methods of the invention are designed to produce an NMR relaxation rate characteristic of whether an analyte is present in the liquid sample. In some instances the NMR relaxation rate is characteristic of the quantity of analyte present in the liquid sample.

As used herein, the term "$T_1/T_2$ hybrid" refers to any detection method that combines a $T_1$ and a $T_2$ measurement. For example, the value of a $T_1/T_2$ hybrid can be a composite signal obtained through the combination of, ratio, or difference between two or more different $T_1$ and $T_2$ measurements. The $T_1/T_2$ hybrid can be obtained, for example, by using a pulse sequence in which $T_1$ and $T_2$ are alternatively measured or acquired in an interleaved fashion. Additionally, the $T_1/T_2$ hybrid signal can be acquired with a pulse sequence that measures a relaxation rate that is comprised of both $T_1$ and $T_2$ relaxation rates or mechanisms.

A "pathogen" means an agent causing disease or illness to its host, such as an organism or infectious particle, capable of producing a disease in another organism, and includes but is not limited to bacteria, viruses, protozoa, prions, yeast and fungi or pathogen by-products. "Pathogen by-products" are those biological substances arising from the pathogen that can be deleterious to the host or stimulate an excessive host immune response, for example pathogen antigen/s, metabolic substances, enzymes, biological substances, or toxins.

By "pathogen-associated analyte" is meant an analyte characteristic of the presence of a pathogen (e.g., a bacterium, fungus, or virus) in a sample. The pathogen-associated analyte can be a particular substance derived from a pathogen (e.g., a protein, nucleic acid, lipid, polysaccharide, or any other material produced by a pathogen) or a mixture derived from a pathogen (e.g., whole cells, or whole viruses). In certain instances, the pathogen-associated analyte is selected to be characteristic of the genus, species, or specific strain of pathogen being detected. Alternatively, the pathogen-associated analyte is selected to ascertain a property of the pathogen, such as resistance to a particular therapy. In some embodiments, a pathogen-associated analyte may be a target nucleic acid that has been amplified. In other embodiments, a pathogen-associated analyte may be a host antibody or other immune system protein that is expressed in response to an infection by a tick-borne pathogen (e.g., an IgM antibody, an IgA antibody, an IgG antibody, or a major histocompatibility complex (MHC) protein).

By "pulse sequence" or "RF pulse sequence" is meant one or more radio frequency pulses to be applied to a sample and designed to measure, e.g., certain NMR relaxation rates, such as spin echo sequences. A pulse sequence may also include the acquisition of a signal following one or more pulses to minimize noise and improve accuracy in the resulting signal value.

As used herein, the term "signal" refers to an NMR relaxation rate, frequency shift, susceptibility measurement, diffusion measurement, or correlation measurements.

As used herein, reference to the "size" of a magnetic particle refers to the average diameter for a mixture of the magnetic particles as determined by microscopy, light scattering, or other methods.

A "subject" is an animal, preferably a mammal (including, for example, rodents (e.g., mice or rats), farm animals (e.g., cows, sheep, horses, and donkeys), pets (e.g., cats and dogs), or primates (e.g., non-human primates and humans)). In particular embodiments, the subject is a human. A subject may be a patient (e.g., a patient having or suspected of having a disease associated with or caused by a tick-borne pathogen).

As used herein, the term "substantially monodisperse" refers to a mixture of magnetic particles having a polydispersity in size distribution as determined by the shape of the distribution curve of particle size in light scattering measurements. The FWHM (full width half max) of the particle distribution curve less than 25% of the peak position is considered substantially monodisperse. In addition, only one peak should be observed in the light scattering experiments and the peak position should be within one standard deviation of a population of known monodisperse particles.

By "$T_2$ relaxivity per particle" is meant the average $T_2$ relaxivity per particle in a population of magnetic particles.

As used herein, "unfractionated" refers to an assay in which none of the components of the sample being tested are removed following the addition of magnetic particles to the sample and prior to the NMR relaxation measurement.

As used herein, the term "cells/mL" indicates the number of cells per milliliter of a biological sample. The number of cells may be determined using any suitable method, for example, hemocytometer, quantitative PCR, and/or automated cell counting. It is to be understood that in some embodiments, cells/mL may indicate the number of colony-forming units per milliliter of a biological sample.

It is contemplated that units, methods, systems, and processes of the claimed invention encompass variations and adaptations developed using information from the embodiments described herein. Throughout the description, where units and systems are described as having, including, or including specific components, or where processes and methods are described as having, including, or including specific steps, it is contemplated that, additionally, there are units and systems of the present invention that consist essentially of, or consist of, the recited components, and that there are processes and methods according to the present invention that consist essentially of, or consist of, the recited processing steps. It should be understood that the order of steps or order for performing certain actions is immaterial, unless otherwise specified, so long as the invention remains operable. Moreover, in many instances two or more steps or actions may be conducted simultaneously.

Magnetic Particles and NMR-Based Detection

The methods and systems of the invention may involve use of magnetic particles and NMR. The magnetic particles can be coated with a binding moiety (e.g., oligonucleotide, antibody, etc.) such that in the presence of analyte, or multivalent binding agent, aggregates are formed. Aggregation depletes portions of the sample from the microscopic magnetic non-uniformities that disrupt the solvent's $T_2$ signal, leading to an increase in $T_2$ relaxation (see, e.g., FIG. 3 of International Patent Application Publication No. WO 2012/054639, which is incorporated herein by reference in its entirety).

The $T_2$ measurement is a single measure of all spins in the ensemble, measurements lasting typically 1-10 seconds, which allows the solvent to travel hundreds of microns, a long distance relative to the microscopic non-uniformities in the liquid sample. Each solvent molecule samples a volume in the liquid sample and the $T_2$ signal is an average (net total signal) of all (nuclear spins) on solvent molecules in the sample; in other words, the $T_2$ measurement is a net measurement of the entire environment experienced by a solvent molecule, and is an average measurement of all microscopic non-uniformities in the sample.

The observed $T_2$ relaxation rate for the solvent molecules in the liquid sample is dominated by the magnetic particles, which in the presence of a magnetic field form high magnetic dipole moments. In the absence of magnetic particles, the observed $T_2$ relaxation rates for a liquid sample are typically long (i.e., $T_2$ (water)=approximately 2000 ms, $T_2$ (blood)=approximately 1500 ms). As particle concentration increases, the microscopic non-uniformities in the sample increase and the diffusion of solvent through these microscopic non-uniformities leads to an increase in spin decoherence and a decrease in the $T_2$ value. The observed $T_2$ value depends upon the particle concentration in a non-linear fashion, and on the relaxivity per particle parameter.

In the aggregation assays of the invention, the number of magnetic particles, and if present the number of agglomerant particles, remain constant during the assay. The spatial distribution of the particles changes when the particles cluster. Aggregation changes the average "experience" of a solvent molecule because particle localization into clusters is promoted rather than more even particle distributions. At a high degree of aggregation, many solvent molecules do not experience microscopic non-uniformities created by magnetic particles and the $T_2$ approaches that of solvent. As the fraction of aggregated magnetic particles increases in a liquid sample, the observed $T_2$ is the average of the non-uniform suspension of aggregated and single (unaggregated) magnetic particles. The assays of the invention are designed to maximize the change in $T_2$ with aggregation to increase the sensitivity of the assay to the presence of analytes, and to differences in analyte concentration.

In some embodiments, the methods of the invention invole contacting a solution (e.g., a biological sample) with between from $1 \times 10^6$ to $1 \times 10^{13}$ magnetic particles per milliliter of the liquid sample (e.g., from $1 \times 10^6$ to $1 \times 10^8$, $1 \times 10^7$ to $1 \times 10^8$, $1 \times 10^7$ to $1 \times 10^9$, $1 \times 10^8$ to $1 \times 10^{10}$, $1 \times 10^9$ to $1 \times 10^{11}$, or $1 \times 10^{10}$ to $1 \times 10^{13}$ magnetic particles per milliliter).

In some embodiments, the magnetic particles used in the methods and systems of the invention have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm). For example, in some embodiments, the magnetic particles used in the methods of the invention may have a mean diameter of from 150 nm to 699 nm (e.g., from 150 to 250, 200 to 350, 250 to 450, 300 to 500, 450 to 650, or from 500 to 699 nm). In other embodiments, the magnetic particles used in the methods of the invention may have a mean diameter of from 700 nm to 1200 nm (e.g., from 700 to 850, 800 to 950, 900 to 1050, or from 1000 to 1200 nm). In particular embodiments, the magnetic particles may have a mean diameter of from 700 nm to 950 nm (e.g., from 700 to 750, 700 to 800, 700 to 850, or from 700 to 900 nm).

In some embodiments, the magnetic particles used in the methods of the invention may have a $T_2$ relaxivity per particle of from $1 \times 10^8$ to $1 \times 10^{12}$ mM$^{-1}$s$^{-1}$ (e.g., from $1 \times 10^8$ to $1 \times 10^9$, $1 \times 10^8$ to $1 \times 10^{10}$, $1 \times 10^9$ to $1 \times 10^{10}$, $1 \times 10^9$ to $1 \times 10^{11}$, or from $1 \times 10^{10}$ to $1 \times 10^{12}$ mM$^{-1}$s$^{-1}$). In some embodiments, the magnetic particles have a $T_2$ relaxivity per particle of from $1 \times 10^9$ to $1 \times 10^{12}$ mM$^{-1}$s$^{-1}$ (e.g., from $1 \times 10^9$ to $1 \times 10^{10}$, $1 \times 10^9$ to $1 \times 10^{11}$, or from $1 \times 10^{10}$ to $1 \times 10^{12}$ mM$^{-1}$s$^{-1}$).

In some embodiments, the magnetic particles may be substantially monodisperse. In some embodiments, the magnetic particles in a biological sample (e.g., a liquid sample) may exhibit nonspecific reversibility in the absence of the one or more analytes and multivalent binding agent. In some embodiments, the magnetic particles may further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran.

Analytes

Embodiments of the invention include methods and systems for detecting and/or measuring the concentration of one or more analytes in a sample (e.g., a protein, a peptide, an enzyme, a polypeptide, an amino acid, a nucleic acid, an oligonucleotide, a therapeutic agent, a metabolite of a therapeutic agent, RNA (e.g., mRNA), DNA (including, e.g., amplified DNA and circulating DNA (e.g., from a cell, pathogen, or fetus)), an antibody, an organism, a virus, bacteria, a carbohydrate, a polysaccharide, glucose, a lipid, a gas (e.g., oxygen and/or carbon dioxide), an electrolyte (e.g., sodium, potassium, chloride, bicarbonate, BUN, magnesium, phosphate, calcium, ammonia, and/or lactate), general chemistry molecules (creatinine, glucose), a lipoprotein, cholesterol, a fatty acid, a glycoprotein, a proteoglycan, and/or a lipopolysaccharide). The analytes may include identification of cells or specific cell types. The analyte(s) may include one or more biologically active substances and/or metabolite(s), marker(s), and/or other indicator(s) of biologically active substances. A biologically active substance may be described as a single entity or a combination of entities. The term "biologically active substance" includes without limitation, medications; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment; or biologically toxic agents such as those used in biowarfare including organisms Analytes may include or be derived from organisms such as *Borrelia* spp., including *Borrelia burgdorferi* sensu lato (*Borrelia burgdorferi*, *Borrelia afzelii*, and *Borrelia garinii*) species, *Borrelia americana*, *Borrelia andersonii*, *Borrelia bavariensis*, *Borrelia bissettii*, *Borrelia carolinensis*, *Borrelia californiensis*, *Borrelia chilensis*, *Borrelia* genomosp. 1 and 2, *Borrelia japonica*, *Borrelia kurtenbachii*, *Borrelia lusitaniae*, *Borrelia myomatoii*, *Borrelia sinica*, *Borrelia spielmanii*, *Borrelia tanukii*, *Borrelia turdi*, *Borrelia valaisiana* and unclassified *Borrelia* spp. Analytes may also include organisms such as *Rickettsia* spp. (including *Rickettsia rickettsii* and *Rickettsia parkeri*), *Ehrlichia* spp. (including *Ehrlichia chaffeensis*, *Ehrlichia ewingii*, and *Ehrlichia muris*-like), *Coxiella* spp. (including *Coxiella burnetii*), *Babesia* spp. (including *Babesia microti* and *Babesia divergens*), *Anaplasma* spp. (including *Anaplasma phagocytophilum*), *Francisella* spp., (including *Francisella tularensis* (including *Francisella tularensis* subspp. *holarctica*, *mediasiatica*, and *novicida*)), *Streptococcus* spp. (including *Streptococcus pneumonia*), and *Neisseria* spp. (including *Neisseria meningitidis*).

In some embodiments, the analyte may be an excreted or non-excreted (such as a surface antigen) protein expressed by any of the pathogens described above. In other embodiments, the analyte may be an antibody or other immune system protein that was expressed by the host in response to infection by any of the pathogens described above (e.g., an IgM antibody, an IgA antibody, an IgG antibody, or a major histocompatibility complex (MHC) protein).

In some embodiments, the analyte may be a nucleic acid derived from any of the organisms described above. In some embodiments, the nucleic acid is a target nucleic acid derived from the organism that has been amplified. In some embodiments, the target nucleic acid may be a multi-copy locus. Use of a target nucleic acid derived from a multi-copy locus, in particular in methods involving amplification, may lead to an increase in sensitivity in the assay. Exemplary multi-copy loci may include, for example, ribosomal DNA (rDNA) operons, multi-copy plasmids, and the like. In other embodiments, the target nucleic acid may be a single-copy locus. In particular embodiments, the target nucleic acid may be derived from an essential locus, for example, an essential house-keeping gene. In particular embodiments, the target nucleic acid may be derived from a locus that is involved in virulence (e.g., a virulence gene). In any of the above embodiments, a locus may include a gene and/or an intragenic region.

Pan-*Borrelia* Target Nucleic Acids

In some embodiments, a target nucleic acid of the invention may include sequence elements that are common to all known *Borrelia* spp. For example, in some embodiments a target nucleic acid may be amplified in the presence of a forward primer and a reverse primer, each of which is universal to all known *Borrelia* spp. Detection of such a target nucleic acid in a sample typically indicates that a *Borrelia* spp. bacterium was present in the sample. A pan-*Borrelia* target nucleic acid may be derived from a linear chromosome or a linear or circular plasmid (e.g., a single-, low-, or multi-copy plasmid). In particular embodiments, a pan-*Borrelia* target nucleic acid is derived from a linear chromosome of a *Borrelia* spp. In some embodiments, a pan-*Borrelia* target nucleic acid may be derived from a multi-copy locus. In some embodiments, a pan-*Borrelia* target nucleic acid may be derived from an rDNA operon. As a non-limiting example, a pan-*Borrelia* target nucleic acid may be derived from the region of and in between the 5S and 23S region ("5S-ITS-23S") region of a *Borrelia* spp. linear chromosome. All known *Borrelia* spp., and especially Bbsl species, are highly conserved in this region, whereas the closest homology to species beyond the *Borrelia* genus (including other *Spirochaetes* including *Trepanoma*) and other more phylogenetically-distant species is confined to 5S and 23S regions, with homology no higher than about 75%.

*Borrelia burgdorferi* Sensu Lato (Bbsl)-Specific Target Nucleic Acids

Bbsl spp. have a linear chromosome that spans approximately 900-1,000 kb. In addition, all Bbsl spp. carry multiple linear and circular plasmids. In the case of *B. burgdorferi*, 13-21 different extra chromosomal elements are known (see, e.g., Schutzer et al. J. Bacteriology 193(4): 1018-1020, 2011)), some of which harbor essential genes for virulence such as the outer surface protein gene (ops) that is essential for survival of the pathogens in blood. Since the GC content of Bbsl spp. genomes is typically only about 29%, targets may be selected from those that contain suitable islands of 35%+GC to facilitate primer and probe design.

In some embodiments, a target nucleic acid may include sequence elements that are specific for a single Bbsl spp. In other embodiments, a target nucleic acid of the invention may include sequence elements that are common to all Bbsl spp. For example, in some embodiments a Bbsl target nucleic acid may be amplified in the presence of a forward primer and a reverse primer, each of which is universal to all Bbsl spp. Detection of such a target nucleic acid in a sample typically indicates that a Bbsl spp. bacterium was present in the sample. In some embodiments, a Bbsl target nucleic acid may be derived from a linear chromosome or a plasmid (e.g., a multi-copy plasmid). In some embodiments, a Bbsl target nucleic acid may be derived from an essential gene (e.g., an essential housekeeping gene) or a locus involved in virulence (e.g., a gene essential for virulence). In some embodiments, a Bbsl target nucleic acid may be derived from a multi-copy locus. In particular embodiments, a Bbsl target nucleic acid may be derived from a multi-copy plasmid. As a non-limiting example, a Bbsl target nucleic acid may be derived from a plasmid that contains the ospA and ospB genes encoding outer surface proteins (e.g., the plasmid 54 (lp54) in *B. burgdorferi*, for example, strain N40)).

In some embodiments, a Bbsl target nucleic acid is a target that is common in all three Bbsl species that contains sequence elements that can be used for probe-based species detection. In some embodiments, a primer pair (e.g., a forward and a reverse primer) may be used to amplify a Bbsl target nucleic acid, and three pairs of probes (one for each of the three Bbsl species *Borrelia burgdorferi*, *Borrelia afzelii*, and *Borrelia garinii*) are used to detect the presence of the nucleic acid in a sample (e.g., a liquid sample derived from blood, CSF, urine, or synovial fluid), thereby identifying which Bbsl species is present in a sample. In some embodiments, these two approaches are combined.

A Bbsl target nucleic acid may be derived from any Bbsl species. For example, there are presently 27 sequenced *Borrelia burgdorferi* strains (approximately 75% of which are available as contigs/scaffolds) with the following strain designations: B31, 64b, 72a, 94a, 118a, 156a, 29805, Bol26, CA11.2A, JD1, N40, WI91-31, ZS7, CA382, CA8, IPT24, IPT87, IPT23, IPT26, IPT93, IPT61, IPT132, IPT137, IPT51, IPT92, IPT2, and IPT35. As another example, there are presently 22 sequenced *Borrelia garinii* strains (approximately 80% of which are available as contigs/scaffolds) with the following strain designations: IPT96, PBr, IPT124, IPT134, IPT76, IPT120, IPT88, IPT104, IPT105, IPT89, IPT94, IPT75, IPT131, IPT139, IPT130, IPT74, NMJW1, SZ, BgVir, "*Borrelia garinii*," Far04, and IPT108. There are presently 5 sequenced *Borrelia afzelii* strains (of which 4 are finished) with the following strain designations: ACA-1, PKo, HLJ01, Tom3107, IPT138, and PKo.

In some embodiments, the target nucleic acid is derived from the ABC transporter substrate binding domain encoded by the oppA gene on linear plasmid lp54. The oppA gene is annotated in several strains to be coding for a periplasmic oligopeptide ABC transporter (substrate binding protein). In some Bbss strains, e.g., WI91-23 and 72a, this gene is annotated as oppA. This target nucleic acid is present in all sequenced Bbss strains on lp54, as well as in *B. garinii* and *B. afzelii* (all sequenced strains) and in all other sequenced *Borrelia* spp. (albeit in most with significantly lower homology). It has less than 66% homology to another ABC transporter gene that is encoded on circular plasmid cp26 (this homology is annotated in some species as oppA-IV or oppA). The nucleic acid sequence of a *B. burgdorferi* oppA gene is shown in SEQ ID NO: 21. The nucleic acid sequence of a *B. garinii* oppA gene is shown in SEQ ID NO: 22.

In some embodiments, *B. burgdorferi* oppA may be amplified in the presence of a forward primer that includes the oligonucleotide sequence 5'-AGA GGA CTT TTA ATA CTG GGC ATT GCT G-3' (SEQ ID NO: 1) or 5'-ACA TAA TGG CCT TAG AAA ATG AGC TTG ATG-3' (SEQ ID NO: 5) and a reverse primer that includes the oligonucleotide sequence 5'-GGC CAT TAT GTA GGA ATC TCT AAT GGT GC-3' (SEQ ID NO: 2) or 5'-CCC GCT TGT AAC CAT GTT TTC TGA GC-3' (SEQ ID NO: 6).

For example, in some embodiments, *B. burgdorferi* oppA may be amplified in the presence of a forward primer that includes the oligonucleotide sequence 5'-AGA GGA CTT TTA ATA CTG GGC ATT GCT G-3' (SEQ ID NO: 1) and a reverse primer that includes the oligonucleotide sequence 5'-GGC CAT TAT GTA GGA ATC TCT AAT GGT GC-3' (SEQ ID NO: 2). In some embodiments, an amplicon produced using these primers is detected by hybridization using a 5' capture probe that includes the oligonucleotide sequence 5'-CTA AAC CAA AAG ATG ATA TTG TCT TTG GTG-3' (SEQ ID NO: 3) or 5'-TAT TGT CTT TGG TGT TGG AAT TGG A-3' (SEQ ID NO: 23) and a 3' capture probe that includes the oligonucleotide sequence 5'-GGA CAT TTC TTA CGA CAA CAC CTG CT-3' (SEQ ID NO: 4) or 5'-ACC TGC TAT ACA TTC CAT TTA AGA G-3' (SEQ ID NO: 24). In some embodiments, an amplicon produced using these primers is detected by hybridization using a 5' capture probe that includes the oligonucleotide sequence 5'-CTA AAC CAA AAG ATG ATA TTG TCT TTG GTG-3' (SEQ ID NO: 3) and a 3' capture probe that includes the oligonucleotide sequence 5'-GGA CAT TTC TTA CGA CAA CAC CTG CT-3' (SEQ ID NO: 4).

In other embodiments, *B. burgdorferi* oppA may be amplified in the presence of a forward primer that includes the oligonucleotide sequence 5'-ACA TAA TGG CCT TAG AAA ATG AGC TTG ATG-3' (SEQ ID NO: 5) and a reverse primer that includes the oligonucleotide sequence 5'-CCC GCT TGT AAC CAT GTT TTC TGA GC-3' (SEQ ID NO: 6). In some embodiments, an amplicon produced using these primers is detected by hybridization using a 5' capture probe that includes the oligonucleotide sequence 5'-AAC CTA TTA ACA TCA AAG ATA AAA AAT GC-3' (SEQ ID NO: 7) and a 3' capture probe that includes the oligonucleotide sequence 5'-GCT TAC ACA CCC AAT ATT TAT ACC C-3' (SEQ ID NO: 8).

In some embodiments, *B. garinii* oppA may be amplified in the presence of a forward primer that includes the oligonucleotide 5'-GGA TAT TCA AAT CCT GAG GTT GAC GAA CTA-3' (SEQ ID NO: 9), 5'-ATG AAC TTG GAA AGG AAG TTG CCA A-3' (SEQ ID NO: 25), or 5'-CCT AAA TGT TAA ACC CCT TGA CAA CCC A-3' (SEQ ID NO: 26) and a reverse primer that includes the oligonucleotide sequence 5'-CTG ATA GGG CAA ATC TTT CTG AAG CA-3' (SEQ ID NO: 10) or 5'-CTG TCC TTT T/i6diPr/G A/i6diPr/T ATT TGA TAT GTG GCT A-3' (SEQ ID NO: 27), wherein "i6diPr" is 2,6-Diaminopurine. For example, in some embodiments, *B. garinii* oppA may be amplified in the presence of a forward primer that includes the oligonucleotide sequence 5'-GGA TAT TCA AAT CCT GAG GTT GAC GAA CTA-3' (SEQ ID NO: 9) or 5'-ATG AAC TTG GAA AGG AAG TTG CCA A-3' (SEQ ID NO: 25) and a reverse primer that includes the oligonucleotide sequence 5'-CTG ATA GGG CAA ATC TTT CTG AAG CA-3' (SEQ ID NO: 10). In some embodiments, *B. garinii* oppA may be amplified in the presence of a forward primer that includes the oligonucleotide sequence 5'-GGA TAT TCA AAT CCT GAG GTT GAC GAA CTA-3' (SEQ ID NO: 9) and a reverse primer that includes the oligonucleotide sequence 5'-CTG ATA GGG CAA ATC TTT CTG AAG CA-3' (SEQ ID NO: 10). In some embodiments, an amplicon produced using these primers is detected by hybridization using a 5' capture probe that includes the oligonucleotide sequence 5'-CTG AGA TTG AAG TTG ACG AAA AAA TCA G-3' (SEQ ID NO: 11) and a 3' capture probe that includes the oligonucleotide sequence 5'-GAT CAT CCA ATA ATT CCA ATC TAC AGC G-3' (SEQ ID NO: 12) or 5'-TCA GAA ATG ATA AAT GGA CAG GGT GGA AC-3' (SEQ ID NO: 28). In some embodiments, an amplicon produced using these primers is detected by hybridization using a 5' capture probe that includes the oligonucleotide sequence 5'-CTG AGA TTG AAG TTG ACG AAA AAA TCA G-3' (SEQ ID NO: 11) and a 3' capture probe that includes the oligonucleotide sequence 5'-GAT CAT CCA ATA ATT CCA ATC TAC AGC G-3' (SEQ ID NO: 12).

In other embodiments, *B. garinii* oppA may be amplified in the presence of a forward primer that includes the oligonucleotide sequence 5'-CCT AAA TGT TAA ACC CCT TGA CAA CCC A-3' (SEQ ID NO: 26) and a reverse primer that includes the oligonucleotide sequence 5'-CTG TCC TTT T/i6diPr/G A/i6diPr/T ATT TGA TAT GTG GCT A-3' (SEQ ID NO: 27), wherein "i6diPr" is 2,6-Diaminopurine. In some embodiments, an amplicon produced using these primers is detected by hybridization using a 5' capture probe that includes the oligonucleotide sequence 5'-TCT AGC GGT TGA CAG AGA AAC ATT G-3' (SEQ ID NO: 29) and a 3' capture probe that includes the oligonucleotide sequence 5'-AAA AAA TTA AAA CCA TAT AAC CCA CGA A-3' (SEQ ID NO: 30).

In another example, in some embodiments, the target nucleic acid is derived from the conserved lipoprotein (ORF 01110). SEQ ID NO: 31 shows the reverse complement of two adjacent reading frames. Both reading frames overlap partially, which is a common feature of several reading frames on the Bb chromosome. The degree of conservation of the genes in *B. burgdorferi* as well as in *B. garinii* is very high (>99% within each species). This operon is likely an essential lipoprotein of yet unknown function. The degree of divergence between *B. burgdorferi* and *B. garinii* is high enough to allow specific primers and probes for each species. *B. afzelii* lacks homology to ORF 01110 completely and also shows sequence divergence to *B. burgdorferi* and *B. garinii* in its ORF 01115 homolog. There is a homolog of these genes (only 75% sequence identity) to ORFs encoded on lp17 in *B. burgdorferi* and on lp36 in *B. garinii*. However, these plasmid encoded sequences lack about 80 bp of the 5' end of reading frame 01115.

In one example, in some embodiments, *B. burgdorferi* conserved lipoprotein (ORF 01110) may be amplified in the presence of a forward primer that includes the oligonucleotide sequence 5'-GCA GAA AGT TCT GCA TTT CTT ATT GAA CC-3' (SEQ ID NO: 32), 5'-GGA ACC AAA ATG TCT CGT AAA TTC TAA AGC A-3' (SEQ ID NO: 33), or 5'-CTT TAG GAT AAA GCT TTG GGT TGC C-3' (SEQ ID NO: 34) and a reverse primer that includes the oligonucleotide sequence 5'-AGT GAT TCG ATT AAT GAC GGC ATT AAA GC-3' (SEQ ID NO: 35) or 5'-GTG ATT CGA TTA ATG ACG GCA TTA AAG CAA-3' (SEQ ID NO: 36). In some embodiments, an amplicon produced using these primers is detected by hybridization using a 5' capture probe that includes the oligonucleotide sequence 5'-AAT AAT ATC TTA AAT CTC TAT TAC TGC TAA-3' (SEQ ID NO: 37) or 5'-CAG AAA GTT CTG CAT TTC TTA TTG AAC C-3' (SEQ ID NO: 38) and a 3' capture probe that includes the oligonucleotide sequence 5'-ATT GGT AAT TAA AGC AAT ATA CAT ACA TAT-3' (SEQ ID NO: 39) or 5'-GTA TTG GTA ATT AAA GCA ATA TAC ATA CAT AT-3' (SEQ ID NO: 40).

In another example, in some embodiments, the target nucleic acid is derived from a conserved hypothetical protein known as bb0242. This gene is encoded in the glycerol transport and metabolism operon on the chromosome. It is upregulated upon deletion of the diguanylate cyclase gene in *B. burgdorferi* (He et al. 2011. PLoS Pathogens 7(6): e1002133). The degree of conservation within *B. burgdorferi* is >99%. This gene is also present in *B. afzelii* with 95% sequence identity but a large portion is deleted in *B. garinii*. This gene may be used to design *B. afzelii*-specific primers and probes since there are 4 regions with significant differences (nucleotide exchanges, no insertions or deletions (indels)) present between *B. burgdorferi* and *B. afzelii*. The middle portion of the gene is deleted in *B. garinii* (residues 58 to 205, as counted from ATG start are absent). SEQ ID NO: 41 shows the nucleic acid sequence of bb0242 from *B. afzelii*. In some embodiments, bb0242 from *B. afzelii* may be amplified in the presence of a forward primer that includes the oligonucleotide sequence 5'-AAA TTA AAA CAG CAT ATA ATA AAA ATG CAT GG-3' (SEQ ID NO: 42) and a reverse primer that includes the oligonucleotide sequence 5'-TTG GAT ATG CAA TAA CCA ATT TCA TTA GC-3' (SEQ ID NO: 43). In some embodiments, an amplicon produced using these primers is detected by hybridization using a 5' capture probe that includes the oligonucleotide sequence 5'-GCT CTT AAT TAA ATT TTT TCA TCG ATA TCC-3' (SEQ ID NO: 44) and a 3' capture probe that includes the oligonucleotide sequence 5'-GGA TAT AAT TCA TTC GAG AAA TAC ATA AAA ATG-3' (SEQ ID NO: 45).

In yet another example, in some embodiments, the target nucleic acid is derived from lipoprotein S2. Lipoprotein S2 is one of the antigenic determinants of *Borrelia*. This gene varies between the three Bbsl species (*Borrelia burgdorferi*, *Borrelia afzelii*, and *Borrelia garinii*) by a number of insertions about 100 bp after the start codon. It has no major homology in non-Lyme species such as *B. parkeri*, *B. miyamotoi* etc. It is present in Bbsl species as well as *B. valaisiana*, *B. chilensis*, *B. finlandensis* and *B. bissettii*. The nucleic acid sequence of a *Borrelia burgdorferi* lipoprotein S2 gene is shown in SEQ ID NO: 46. The nucleic acid sequence of a *Borrelia afzelii* lipoprotein S2 gene is shown in SEQ ID NO: 52.

For example, in some embodiments, *B. burgdorferi* lipoprotein S2 may be amplified in the presence of a forward primer that includes the oligonucleotide sequence 5'-ACA TTT GGA ACT AAT AAT GCT GCC CAT G-3' (SEQ ID NO: 47) and a reverse primer that includes the oligonucleotide sequence 5'-AGT TGT TTC AAA AAG TAT TAA TAA TGA CGC GT-3' (SEQ ID NO: 48). In some embodiments, an amplicon produced using these primers is detected by hybridization using a 5' capture probe that includes the oligonucleotide sequence 5'-CAT GTT AAT GCT GAG TTG CGC TTT TTT TAA G-3' (SEQ ID NO: 49) and a 3' capture probe that includes the oligonucleotide sequence 5'-CAT GAC GTA ACT TGG ATA AAA ACA AAG GC-3' (SEQ ID NO: 50).

In another example, in some embodiments, *Borrelia afzelii* lipoprotein S2 may be amplified in the presence of a forward primer that includes the oligonucleotide sequence 5'-CCA CAA ACT GCA CAA CAA AAC GGA GC-3' (SEQ ID NO: 52) and a reverse primer that includes the oligonucleotide sequence 5'-CCA ATT TGT TTT TGA TTC TGG TAT TGC TTG-3' (SEQ ID NO: 53) or 5'-TGA ATG ATG AAT ATA GTA GTT ACA CAT CGC T-3' (SEQ ID NO: 54). In some embodiments, an amplicon produced using these primers is detected by hybridization using a 5' capture probe that includes the oligonucleotide sequence 5'-GAA ACC CAA TAA GGG ATG AAT TGC C-3' (SEQ ID NO: 55) or 5'-GGA AAC CCA ATA AG/ideoxyl/GAT GAA TTG CC-3' (SEQ ID NO: 56), wherein /ideoxyl/ is deoxyInosine, and a 3' capture probe that includes the oligonucleotide sequence 5'-GAC GTA ACT TGG ATA AAA ACA AAG GC-3' (SEQ ID NO: 57) or 5'-GAT GGA CAA GCA ATG CCA GAA TTC-3' (SEQ ID NO: 58).

In a still further example, in some embodiments, the target nucleic acid is derived from protein 24 (p24) antigen, which is encoded on lp54. The nucleic acid sequence of a *Borrelia garinii* p24 gene is shown in SEQ ID NO: 59. For example, in some embodiments, *Borrelia garinii* p24 may be amplified in the presence of a forward primer that includes the oligonucleotide sequence 5'-GGT GAT GTT AAA TCG TTA ACA GAA GTT GCT ACT GA-3' (SEQ ID NO: 60), 5'-GGT GAT GTT AAA TCG TTA ACA GAA GTT GCT ACT GAT-3' (SEQ ID NO: 61), or 5'-CTG ATT TTG AGG ATG GCA ATT CTT TTG TTT CTG GG-3' (SEQ ID NO: 62) and a reverse primer that includes the oligonucleotide sequence 5'-TTG TCT GTT AAC ATC CTT AGA AAG CCA ATC-3' (SEQ ID NO: 63), 5'-TTG TCT GTT AMC ATC CTT AGA AAG CCA ATC-3' (SEQ ID NO: 64), wherein M is A or C, or 5'-CTT TTT GTC TGT TA/ideoxyl/CAT CCT TAG AAA GCC AAT C-3' (SEQ ID NO: 65), wherein /ideoxyl/ is deoxylnosine. In some embodiments, an amplicon produced using these primers is detected by hybridization using a 5' capture probe that includes the oligonucleotide sequence 5'-TTG AGG ATG GCA ATT CTT TTG TTT CTG GG-3' (SEQ ID NO: 66) or 5'-AAG GAC CTG TTT TAA CAT CAG AGG AG-3' (SEQ ID NO: 67) and a 3' capture probe that includes the oligonucleotide sequence 5'-AAGCTGAGTATGAGAAATCCTATAAAG-3' (SEQ ID NO: 68).

In a still further example, in some embodiments, the target nucleic acid is derived from chitibiose transporter protein encoded on linear plasmid lp54, also known as the S1 antigen. The nucleic acid sequence of a *Borrelia afzelii* chitibiose transporter protein is shown in SEQ ID NO: 69. The nucleic acid sequence of a *Borrelia garinii* chitibiose transporter protein is shown in SEQ ID NO: 76.

For example, in some embodiments, *Borrelia afzelii* chitibiose transporter protein may be amplified in the presence of a forward primer that includes the oligonucleotide sequence 5'-CAG CAA AGC TTT ACT GTA TCT TGA TTT ACC AAT AC-3' (SEQ ID NO: 70) or 5'-GCT TTA CTG TAT CTT GAT TTA CCA ATA CTG TGC TT-3' (SEQ ID NO: 71) and a reverse primer that includes the oligonucleotide sequence 5'-CAA AAA TTA CCA CTT CTA GCA ATA AAC AAA ACT TAA TCA T-3' (SEQ ID NO: 72) or 5'-TGG GAT CTT TAG GCT TAT TGT TTT TAG AAT CC-3' (SEQ ID NO: 73). In some embodiments, an amplicon produced using these primers is detected by hybridization using a 5' capture probe that includes the oligonucleotide sequence 5'-TTT GCA AAG ACT TAT AAT TAT CTA AAT TAT TGC-3' (SEQ ID NO: 74) and a 3' capture probe that includes the oligonucleotide sequence 5'-CCT TTT AGA ATC TTT AAA TTC TCT TGA GTT TAC-3' (SEQ ID NO: 75).

In another example, *Borrelia garinii* chitibiose transporter protein may be amplified in the presence of a forward primer that includes the oligonucleotide sequence 5'-CAG CAA AGC TTT GCT GTG TTT TGG CTT-3' (SEQ ID NO: 77) or 5'-CTC ATC CTG AGC ATT TTT CAG CAA AGC T-3' (SEQ ID NO: 78) and a reverse primer that includes the oligonucleotide sequence 5'-CCA CTT CCC ATA ATA GAC GAA ATT TAA TCG GC-3' (SEQ ID NO: 79) or 5'-GAA GAA GTT TAA AAC TAC CAC TTC CCA C-3' (SEQ ID NO: 80). In some embodiments, an amplicon produced using these primers is detected by hybridization using a 5' capture probe that includes the oligonucleotide sequence 5'-GTA AAG ATC TAG AAT TAT CTA AAT TAT CCA AAT C-3' (SEQ ID NO: 81) and a 3' capture probe that includes the oligonucleotide sequence 5'-GTT TGT GAA TCC TTT TTA GAA TCT TCC AAC TTA TTC-3' (SEQ ID NO: 82) or 5'-CCA ACT TAT TCT TTT TGG AC/ideoxyl/CCA AAG A-3' (SEQ ID NO: 83), wherein /ideoxyl/ is deoxylnosine.

In a still further example, in some embodiments, the target nucleic acid is derived from chitibiose transporter protein encoded by chbC on circular plasmid cp26 (Tilly et al. Journal of Bacteriology 183(19): 5544-5553, 2001). This protein is a homolog This protein is highly conserved among *Borrelia* spp. but has islands of single nucleotide polymorphisms (SNPs) that can be used to generate species-specific primers to discriminate between species of the *B. burgdorferi* sensu lato group. The nucleic acid sequence of a *Borrelia garinii* chbC is shown in SEQ ID NO: 84.

For example, in some embodiments, *Borrelia garinii* chbC may be amplified in the presence of a forward primer that includes the oligonucleotide sequence 5'-CTT TTA GTT AAT TTA CCC TTT ACA GAT TCT AC-3' (SEQ ID NO: 85) and a reverse primer that includes the oligonucleotide sequence 5'-GTAAGGTATCCAATCTGAT-TGTCCAGCTA-3' (SEQ ID NO: 86) or 5'-CGT AAG GTA TCC AAT CTG ATT GTC CAG CTA-3' (SEQ ID NO: 87). In some embodiments, an amplicon produced using these primers is detected by hybridization using a 5' capture probe that includes the oligonucleotide sequence 5'-CAG CAG TGG TAT GTT GAT TTA ATG GCT-3' (SEQ ID NO: 88) and a 3' capture probe that includes the oligonucleotide sequence 5'-GGA TTC CTG TCT CTT TAT ACA TTT TTA ATT TTA GC-3' (SEQ ID NO: 89).

In another example, in some embodiments, *Borrelia garinii* chbC may be amplified in the presence of a forward primer that includes the oligonucleotide sequence 5'-CAT TAT AAA CTT AGT GGA ATT ACA GGA GGA TTC CT-3' (SEQ ID NO: 90) or 5'-ATA AAC TTA GTG GAA TTA CAG GAG GAT TCC-3' (SEQ ID NO: 91) and a reverse primer that includes the oligonucleotide sequence 5'-AGC AGG CGG AAC AGA CTC TGG A-3' (SEQ ID NO: 92). In some embodiments, an amplicon produced using these primers is detected by hybridization using a 5' capture probe that includes the oligonucleotide sequence 5'-CTC TTT ATA CAT TTT TAA TTT TAG CTG GGC AA-3' (SEQ ID NO: 93) and a 3' capture probe that includes the oligonucleotide sequence 5'-CAA AGA AAT ATG GCA ATT AAA CTT CCA G-3' (SEQ ID NO: 94).

In yet another example, in some embodiments, *Borrelia garinii* chbC may be amplified in the presence of a forward primer that includes the oligonucleotide sequence 5'-GGG CAA TCA GAT TGG ATG CCT TAC GGA GG-3' (SEQ ID NO: 95), 5'-GGG CAA TCA GAT TGG ATG CCT TAC GGA G-3' (SEQ ID NO: 96), or 5'-GCT GGG CAA TCA GAT TGG ATG CCT TAC GGA G-3' (SEQ ID NO: 97) and a reverse primer that includes the oligonucleotide sequence 5'-TAA TTA TTT CGG/ideoxyl/GA AAA GGC TGC CTG CTA-3' (SEQ ID NO: 98) or 5'-CAT AAT TAT TTC GG/ideoxyl/GAA AAG GCT GCC TGC TA-3' (SEQ ID NO: 99), wherein /ideoxyl/ is deoxylnosine. In some embodiments, an amplicon produced using these primers is detected by hybridization using a 5' capture probe that includes the oligonucleotide sequence 5'-GGG ATT CAG CCT AAT/ideoxyl/CA TGG TTT CCT G-3' (SEQ ID NO: 100) and a 3' capture probe that includes the oligonucleotide sequence 5'-GTA CTT TCC ATT GTG GCT CAA GGT G-3' (SEQ ID NO: 101).

In another example, in some embodiments, the target nucleic acid is derived from the guaB gene encoded on circular plasmid cp26, which encodes for inosine-5'-monophosphate dehydrogenase. The nucleic acid sequence of a *Borrelia afzelii* guaB gene is shown in SEQ ID NO: 102. For example, in some embodiments, *Borrelia afzelii* guaB may be amplified in the presence of a forward primer that includes the oligonucleotide sequence 5'-CCG TGG GCA GAG TCT ATG ACA ATC AG-3' (SEQ ID NO: 13) and a reverse primer that includes the oligonucleotide sequence 5'-GCC CAA AAA ACC ATC AAC ACT AAT AAG G-3' (SEQ ID NO: 14). In some embodiments, an amplicon produced using these primers is detected by hybridization using a 5' capture probe that includes the oligonucleotide sequence 5'-TAG CAG CTC CTA CTC TTA GCT TGC-3' (SEQ ID NO: 15) and a 3' capture probe that includes the oligonucleotide 5'-AAT ATT GCT TTG TAA GCA TTT TGG TTT-3' (SEQ ID NO: 16).

In yet another example, in some embodiments, the target nucleic acid is derived from the p26-encoded phosphotransferase system (PTS) (EIIB family protein). This gene codes for a PTS glucose transporter subunit. The nucleic acid sequence of a *Borrelia afzelii* PTS is shown in SEQ ID NO: 104. For example, in some embodiments, *Borrelia afzelii* PTS may be amplified in the presence of a forward primer that includes the oligonucleotide sequence 5'-CAA GGT GCA ATG ACT TTG TTT GGG CA-3' (SEQ ID NO: 17) or 5'-GAT TTG TAC CAA TCA TAA CCA CAA TAA CCA-3' (SEQ ID NO: 104) and a reverse primer that includes the oligonucleotide sequence 5'-GCA ACT TCA AAG TGT ACA GTA TTG GTA TCC C-3' (SEQ ID NO: 18). In some embodiments, *Borrelia afzelii* PTS may be amplified in the presence of a forward primer that includes the oligonucleotide sequence 5'-CAA GGT GCA ATG ACT TTG TTT GGG CA-3' (SEQ ID NO: 17) and a reverse primer that includes the oligonucleotide sequence 5'-GCA ACT TCA AAG TGT ACA GTA TTG GTA TCC C-3' (SEQ ID NO: 18). In some embodiments, an amplicon produced using these primers is detected by hybridization using a 5' capture probe that includes the oligonucleotide sequence 5'-TTG TAG AAC AAT CTG GGC TTT TTG G-3' (SEQ ID NO: 19) and a 3' capture probe that includes the oligonucleotide 5'-GGA GAA CTC ATA TCA GGA GCA CAA-3' (SEQ ID NO: 20).

In a still further another example, in some embodiments, the target nucleic acid is derived from a chromosomally-encoded acetyl CoA acetyltransferase, for example, the ORF NM71_00535 in *B. burgdorferi* B31. This gene encodes an acetyl CoA acetyltransferase and is present in all Borreliaceae. The nucleic acid sequence of a *Borrelia burgdorferi* acetyl CoA acetyltransferase is shown in SEQ ID NO: 105. For example, in some embodiments, *Borrelia burgdorferi* acetyl CoA acetyltransferase may be amplified in the presence of a forward primer that includes the oligonucleotide sequence 5'-GTT TTT GAT AAG AAG ACC AAC TCT AGC GTA ACT-3' (SEQ ID NO: 106) and a reverse primer that includes the oligonucleotide sequence 5'-TAA TGC CTT CAA TAG CCA TAT AAG CTC CA-3' (SEQ ID NO: 107). In some embodiments, an amplicon produced using these primers is detected by hybridization using a 5' capture probe that includes the oligonucleotide sequence 5'-ACT TTA AAT AAG CTA GCA TCT CTT AAT CC-3' (SEQ ID NO: 108) and a 3' capture probe that includes the oligonucleotide 5'-TTAGCTTATATTGGAGGATT-TAAAAGCG-3' (SEQ ID NO: 109).

In another example, in some embodiments, the target nucleic acid is derived from an lp54-encoded lipoprotein, e.g., lp54-69226. This gene is designated as P45-13 in *B. burgdorferi* B31 and encoded on lp54. This gene is specific for the *B. burgdorferi* sensu lato and other Lyme group species. This gene does not appear in Relapsing Fever *Borrelia* species. The nucleic acid sequence of a *Borrelia garinii* lp54-encoded lipoprotein is shown in SEQ ID NO: 110. For example, in some embodiments, *Borrelia garinii* lp54-encoded lipoprotein may be amplified in the presence of a forward primer that includes the oligonucleotide sequence 5'-CAA ATT CTC AAT ACT TGC GCT GTT ACT GA-3' (SEQ ID NO: 111) and a reverse primer that includes the oligonucleotide sequence 5'-TCT AG/ideoxyl/GGG ATT GAG CTT TCA GAT TCA-3' (SEQ ID NO: 112) wherein /ideoxyl/ is deoxylnosine, 5'-CTT CTG ATT TGA CCA CAT TTG CTT CTT CTA G-3' (SEQ ID NO: 113), or 5'-GCA ATT TCT TCT TCT GAT TTG ACT ACA TTT GCT-3' (SEQ ID NO: 114). In some embodiments, an amplicon produced using these primers is detected by hybridization using a 5' capture probe that includes the oligonucleotide sequence 5'-AGC TGT AAT GCC AAT ATG AAC GCG AA-3' (SEQ ID NO: 115) and a 3' capture probe that includes the oligonucleotide 5'-CCC TAT TTT AGA AAT TGA AAA AAT TGA ACC TG-3' (SEQ ID NO: 116). In other embodiments, an amplicon produced using these primers is detected by hybridization using a 5' capture probe that includes the oligonucleotide sequence 5'-TTC GTG TTC ATA TTG GCA TTA CAG CT-3' (SEQ ID NO: 117) and a 3' capture probe that includes the oligonucleotide 5'-CAG GTT CAA TTT TTT CAA TTT CTA AAA TAG GG-3' (SEQ ID NO: 118).

In yet another example, in some embodiments, the target nucleic acid is derived from a decorin binding protein subunit B (dbpB) encoded on linear plasmid lp54. This gene is present in the *B. burgdorferi* sensu lato group. However, *B. burgdorferi* lacks homology at the gene's 5' and 3' ends to *B. garinii* and *B. afzelii*. The gene has no homology in Relapsing Fever group species. The nucleic acid sequence of a *Borrelia garinii* dbpB is shown in SEQ ID NO: 119.

For example, in some embodiments, *Borrelia garinii* dbpB may be amplified in the presence of a forward primer that includes the oligonucleotide sequence 5'-GCT GGC AGC CTG TAA TTT TGG ATT AAC A-3' (SEQ ID NO: 120) and a reverse primer that includes the oligonucleotide sequence 5'-TTG TCA CTT TAG AAC CAG TTG CGG-3' (SEQ ID NO: 121). In some embodiments, an amplicon produced using these primers is detected by hybridization using a 5' capture probe that includes the oligonucleotide sequence 5'-CAA TGC TTG AAT CGT CTT CTG ATG ATG-3' (SEQ ID NO: 122) and a 3' capture probe that includes the oligonucleotide 5'-AAT TTT AAA GCT TTT ACA GGC ACC G-3' (SEQ ID NO: 123).

In other embodiments, *Borrelia garinii* dbpB may be amplified in the presence of a forward primer that includes the oligonucleotide sequence 5'-GGC TAT GTT TGA TTT CAT GCT TGA AGT TAC-3' (SEQ ID NO: 124) and a reverse primer that includes the oligonucleotide sequence 5'-ACT TAT TTT TTT TTC CTC ATC GTC AAG T-3' (SEQ ID NO: 125) or 5'-GTC AAG TTT TTG TCT TTT CTT GAC ACC T-3' (SEQ ID NO: 126). In some embodiments, an amplicon produced using these primers is detected by hybridization using a 5' capture probe that includes the oligonucleotide sequence 5'-GGA TCA TTA GAT GAG ATT GGA ATA AAA GGA-3' (SEQ ID NO: 127) and a 3' capture probe that includes the oligonucleotide 5'-AGG CTA AAA TAG AAA ATA AAC TAG AAG G-3' (SEQ ID NO: 128).

In another example, in some embodiments, the target nucleic acid is derived from a complement regulator-acquiring surface protein 1 (CRASP1) gene, for example, CRASP1 encoded on linear protein lp54. This gene is annotated as an outer surface protein that has affinity to host (e.g., human and the like) cell surface receptors and is most likely needed for translocation and movement into host tissues. This gene has a homolog with ~76% sequence identity that is encoded in the downstream gene (NM_04595). *Borrelia burgdorferi* has at least 5 GRASP proteins according to Hallström et al. *J. Infectious Disease* 202(3):490-498, 2010 that infer different affinities to host cell and matrix proteins. Interestingly, CRASP1 does not have homologs with significant homology on the nucleotide level in *B. afzelii* and *B. garinii*, although genes encoding proteins with predicted similar functions are present in these species. Antibodies against CRASP1 are commercially available. The nucleic acid sequence of a *Borrelia burgdorferi* CRASP1 encoded on lp54 is shown in SEQ ID NO: 129.

In some embodiments, *Borrelia burgdorferi* CRASP1 encoded on lp54 may be amplified in the presence of a forward primer that includes the oligonucleotide sequence 5'-ATT TAT TAA AGT GTT CTG CCA GTA TTT TCT CAT-3' (SEQ ID NO: 130), 5'-AGT GTT CTG CCA GTA TTT TCT CAT TAT CTT G-3' (SEQ ID NO: 134), or 5'-AAA GGC AGG TTT TAA AGT ATC AAA ATC TTT GT-3' (SEQ ID NO: 135), and a reverse primer that includes the oligonucleotide sequence 5'-GCA TTC AAT TCC AAA TAG AGC AAA ATT TAG AAT-3' (SEQ ID NO: 131), 5'-GGG CAT TCA ATT CCA AAT AGA GCA AAA TT-3' (SEQ ID NO: 136), or 5'-AAT TCC GAA CAT TAC AAT ATA ATT GGA AGA TTG-3' (SEQ ID NO: 137). For example, in particular embodiments, *Borrelia burgdorferi* CRASP1 encoded on lp54 may be amplified in the presence of a forward primer that includes the oligonucleotide sequence 5'-ATT TAT TAA AGT GTT CTG CCA GTA TTT TCT CAT-3' (SEQ ID NO: 130) and a reverse primer that includes the oligonucleotide sequence 5'-GCA TTC AAT TCC AAA TAG AGC AAA ATT TAG AAT-3' (SEQ ID NO: 131). In some embodiments, an amplicon produced using these primers is detected by hybridization using a 5' capture probe that includes the oligonucleotide sequence 5'-CTT GAG TAT TTT GAT TGT AAA CTT TAA GAG-3' (SEQ ID NO: 132) and a 3' capture probe that includes the oligonucleotide 5'-TGA CTT AGA TTT TCT ACT CCA TTT TGT A-3' (SEQ ID NO: 133).

In other embodiments, *Borrelia burgdorferi* CRASP1 encoded on lp54 may be amplified in the presence of a forward primer that includes the oligonucleotide sequence 5'-AGC GTT CTT TTT ATT TTC ATT TGG ATA TCT TCA-3' (SEQ ID NO: 138), 5'-CAA TCT TCC AAT TAT ATT GTA ATG TTC GGA ATT-3' (SEQ ID NO: 142), or 5'-CTA AAG ATG AGT AAA GCG TTC TTT TTA TTT TCA-3' (SEQ ID NO: 143), and a reverse primer that includes the oligonucleotide sequence 5'-GCA AAC ACT AAG CCA AAA AAA ATC ACC AA-3' (SEQ ID NO: 139), 5'-CCT AAA GCA AAT GCA AAC ACT AAG CCA AA-3' (SEQ ID NO: 144), 5'-AGC AAA TGC AAA CAC TAA GCC AAA AAA AA-3' (SEQ ID NO: 145), or 5'-GCA AAT GCA AAC ACT AAG CCA AAA AAA ATC AC-3' (SEQ ID NO: 146). In particular embodiments, *Borrelia burgdorferi* CRASP1 encoded on lp54 may be amplified in the presence of a forward primer that includes the oligonucleotide sequence 5'-AGC GTT CTT TTT ATT TTC ATT TGG ATA TCT TCA-3' (SEQ ID NO: 138) and a reverse primer that includes the oligonucleotide sequence 5'-GCA AAC ACT AAG CCA AAA AAA ATC ACC AA-3' (SEQ ID NO: 139). In some embodiments, an amplicon produced using these primers is detected by hybridization using a 5' capture probe that includes the oligonucleotide sequence 5'-AGG TCT CCA GAT TTA TCT TCA AAA T-3' (SEQ ID NO: 140) and a 3' capture probe that includes the oligonucleotide 5'-CAA TAA GAT CGT AAG GAC CAA CTT T-3' (SEQ ID NO: 141).

In some embodiments, *Borrelia burgdorferi* CRASP1 encoded on lp54 may be amplified in the presence of a forward primer that includes the oligonucleotide sequence 5'-GCC CCA TGA TAT GTG ATA AAT CAA TCT TCC-3' (SEQ ID NO: 147) and a reverse primer that includes the oligonucleotide sequence 5'-GCA AAC ACT AAG CCA AAA AAA ATC ACC AA-3' (SEQ ID NO: 139). In some embodiments, an amplicon produced using these primers is detected by hybridization using a 5' capture probe that includes the oligonucleotide sequence 5'-CAA TAA GAT CGT AAG GAC CAA CTT T-3' (SEQ ID NO: 141) and a 3' capture probe that includes the oligonucleotide sequence 5'-AGG TCT CCA GAT TTA TCT TCA AAA T-3' (SEQ ID NO: 140).

In some embodiments, *Borrelia burgdorferi* CRASP1 encoded on lp54 may be amplified in the presence of a forward primer that includes the oligonucleotide sequence 5'-GCC CCA TGA TAT GTG ATA AAT CAA TCT TCC-3' (SEQ ID NO: 147) and a reverse primer that includes the oligonucleotide sequence 5'-GGA GAC CTT AGC ACT TCT GAT GAA AAA AT-3' (SEQ ID NO: 148).

In yet another example, in some embodiments, the target nucleic acid is derived from an outer membrane protein (OMP) gene, for example, an OMP gene encoded on linear protein lp54. In some embodiments, the OMP gene is a lipoprotein (CP009657.1 locus NM_04585 in *B. burgfdorferi* B31) encoded on linear protein lp54. A significant portion in this gene's 5' region is deleted in other *Borrelia* species or lacks significant homology to homologs encoded in the genomes of other *Borrelia* species. The nucleic acid sequence of a *Borrelia burgdorferi* lipoprotein NM71_04585, which maps to lp54 positions 45712-45947, is shown below as SEQ ID NO: 156. An exemplary portion of the gene that may be used for *B. burgdorferi*-specific primer and probe binding is shown in bold and underlined text.

(SEQ ID NO: 156)
TTACATTATACTAATGTATGCTTCAAGAACAGACTGGCGAGCATTTTGCA

TATTATCTAGGTATCTTTTTTTAATGTACTCTGCTAAGGATTTGGAATCG

CTTAAACTTGAATTAGAGCTAGCATTAGCAATAAGCCCATCAGCTTGTCT

TGACCATTCTTTTCTTTTATCTAATATTTGATTTAGTTTTGATTTAAGCT

CTTTTAGCTTCATGGTGAAATCAAAACTGTTGATTTTAGCGTTTAAGTAA

TCCTGGTTAAAGATTTCAATTTTTTTATTTATTTCTTCTAGTGCAAGTTC

GAAAGAAATTTGTGTTCCAAGCCCTGATATCATTAATTCTCTTATTAAGC

TGTGATTTTGATTCTCATTGTAAAGAGCTTCCATTATTGATCCAAATTGT

TCAATTTTGTATTGATCAAAATCCATAAGCGCATAGAATTTATTTCTTTC

ATTTTCTGCTTCTGGTGTGTTAGAGTTAAGCTGTGGCGCGTAACTTCTGT

CATAAACTTTAGCACTTGAAATAACATCTAGCAGTTCAAATGCAGAATCT

TTCATTTTGAATTGATCGTAAGTTTCTCTAAATCCAAAGTTGTTTTGTGT

TTTATTTTTTCTTCAGAAATTGCTCTAATAAGTTCGTTTTTTAATGTTT

GTAATTTACTGCCAGAAGATGTTGTTGTTTGTACAGCAGAGCTTGAATTT

GTTTGCTGTCTTGTTGGTTGACTAAAGCTGTAGTTTAAGGCAAATGTTGG

CAGCCCGCTATTTCTGCTGTTAAAAGTTCTTGTATTTCCGGGTACGGTTG

TAACGGCTTGAATAGGTATTCTTTGTTTTGTTAGTGATGCAGCTCTTGCT

GCTGTTGTTTTTGGCAGATTTGACAGATCTGCGCTAAAACTTAAGCTTTG

CAATTGTGGGCTTGGTGCTGCTTGTTGATTTTGCGATCCTTTATTTGGTG

TTGTTTGTGGTTGATTTTGCGATCCTTTATTTGGCGCTGCTGCTACTGTT

TTTGCCGCTTGCGATTGTTTTTTTAGCTCTGCTGCTACTTTGTCATTGTC

AGCAATTGGTATATTTTTTGCAGCATTTGAGTTTGTATCAGCACTTGTTG

TTTCTTGATCATCTGCTGCCTTATTAAGTATTCCTTTTACTTTGTTTTTA

TAATCTTCGTTTAGATTGGCATCAATCGTGCAAGAAAATAAAAACAATCC

CAAAAGCTTTAATTGTATTAATGGTTTGATTTTCAA

In some embodiments, *Borrelia burgdorferi* lipoprotein NM71_04585 may be amplified in the presence of a forward primer that includes the oligonucleotide sequence 5'-AGC TGT AGT TTA AGG CAA ATG TTG G-3' (SEQ ID NO: 157) or 5'-TTG TTT GCT GTC TTG TTG GTT GAC T-3' (SEQ ID NO: 158) and a reverse primer that includes the oligonucleotide sequence 5'-CGC AAA ATC AAC AAG CAG CAC C-3' (SEQ ID NO: 159) or 5'-AGG ATC GCA AAA TCA ACC ACA AAC A-3' (SEQ ID NO: 160). In particular embodiments, *Borrelia burgdorferi* lipoprotein NM71_04585 may be amplified in the presence of a forward primer that includes the oligonucleotide sequence 5'-AGC TGT AGT TTA AGG CAA ATG TTG G-3' (SEQ ID NO: 157) and a reverse primer that includes the oligonucleotide sequence 5'-AGG ATC GCA AAA TCA ACC ACA AAC A-3' (SEQ ID NO: 160). In some embodiments, an amplicon produced using these primers is detected by hybridization using a 5' capture probe that includes the oligonucleotide sequence 5'-GCT ATT TCT GCT GTT AAA AGT TCT TGT-3' (SEQ ID NO: 161) and a 3' capture probe that includes the oligonucleotide sequence 5'-CTA AAA CTT AAG CTT TGC AAT TGT GG-3' (SEQ ID NO: 162).

In other embodiments, *Borrelia burgdorferi* lipoprotein NM71_04585 may be amplified in the presence of a forward primer that includes the oligonucleotide sequence 5'-TGC TGC TGT TGT TTT TGG CAG ATT-3' (SEQ ID NO: 163) and a reverse primer that includes the oligonucleotide sequence 5-ATG ACA AAG TAG CAG CAG AGC TAA A-3' (SEQ ID NO: 164). In some embodiments, an amplicon produced using these primers is detected by hybridization using a 5' capture probe that includes the oligonucleotide sequence 5'-CGC TAA AAC TTA AGC TTT GCA ATT G-3' (SEQ ID NO: 165) and a 3' capture probe that includes the oligonucleotide sequence 5'-TGC TGC TAC TGT TTT TGC TGC TTG C-3' (SEQ ID NO: 166).

Variant Primers and Probes

In some embodiments, the invention provides a primer that has at least 80% identity (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100%) identity with any of the preceding forward or reverse primers. For example, in some embodiments, the invention provides a forward primer comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 1, 5, 9, 13, 17, 157, 158, or 163. In some embodiments, the invention provides a reverse primer comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 2, 6, 10, 14, 18, 159, 160, or 164. Such primers can be used in any of the methods of the invention described herein.

In some embodiments, the invention provides a probe that has at least 80% identity (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100%) identity with any of the preceding probes. For example, in some embodiments, the invention provides a 5' capture probe comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 3, 7, 11, 15, 19, 161, or 165. In some embodiments, the invention provides a 3' capture probe comprising an oligonucleotide sequence that is at least 80% identical (e.g., at least 80%, 81%, 82%, 83%, 84%, 85%, 86%, 87%, 88%, 89%, 90%, 91%, 92%, 93%, 94%, 95%, 96%, 97%, 98%, 99%, or 100% identical) to any one of SEQ ID NOs: 4, 8, 12, 16, 20, 162, or 166. Such probes can be used in any of the methods of the invention described herein.

In some embodiments, any of the preceding primers or probes may include one or more modified bases, for example, 2,6-Diaminopurine (abbreviated herein as "/i6diPr/"), deoxyinosine (abbreviated herein as "/ideoxyI/"), or other modified bases known in the art.

Rickettsia Target Nucleic Acids

In some embodiments, a target nucleic acid may include sequence elements that are specific for a *Rickettsia* spp., for example, *Rickettsia rickettsii* or *Rickettsia parkeri*. In other embodiments, a target nucleic acid of the invention may include sequence elements that are common to all *Rickettsia* spp. In yet other embodiments, these approaches may be combined. For example, in some embodiments a *Rickettsia* spp. target nucleic acid may be amplified in the presence of a forward primer and a reverse primer, each of which is universal to all *Rickettsia* spp. Detection of such a target nucleic acid in a sample typically would indicate that a *Rickettsia* spp. bacterium was present in the sample.

In some embodiments, a *Rickettsia* spp. target nucleic acid may be derived from a linear chromosome or a linear or circular plasmid (e.g., a single-, low-, or multi-copy plasmid). In some embodiments, a *Rickettsia* spp. target nucleic acid may be derived from an essential locus (e.g., an essential housekeeping gene) or a locus involved in virulence (e.g., a gene essential for virulence). In some embodiments, a *Rickettsia* spp. target nucleic acid may be derived from a multi-copy locus. In particular embodiments, a *Rickettsia* spp. target nucleic acid may be derived from a multi-copy plasmid.

*Rickettsia rickettsii* has a small genome (1.2 Mb single chromosome) with only a single ribosomal rDNA operon encoded. In some embodiments, a *Rickettsia rickettsii* target nucleic acid is a single-copy locus. In some embodiments, the single-copy locus may be an outer membrane protein A (ompA) gene or 17 KD surface protein precursor gene. A *Rickettsia rickettsii* target nucleic acid may be derived from any *Rickettsia rickettsii* strain. For example, there are presently eight whole genome sequences of *Rickettsia rickettsii* available, with the following strain designations: str. Brazil, str. Sheila Smith, str. Colombia, str. Hlp #2, str. Hauke, str. Hino, str. Arizona, and str. Iowa.

Coxiella Target Nucleic Acids

In some embodiments, a target nucleic acid may include sequence elements that are specific for a *Coxiella* spp., for example, *Coxiella burnetii*. In other embodiments, a target nucleic acid of the invention may include sequence elements that are common to all *Coxiella* spp. In other embodiments, a target nucleic acid of the invention may include sequence elements that are common to all *Rickettsia* spp. In yet other embodiments, these approaches may be combined. For example, in some embodiments a *Coxiella* spp. target nucleic acid may be amplified in the presence of a forward primer and a reverse primer, each of which is universal to all *Coxiella* spp. Detection of such a target nucleic acid in a sample typically would indicate that a *Coxiella* spp. bacterium was present in the sample.

In some embodiments, a *Coxiella* spp. target nucleic acid may be derived from a linear chromosome or a linear or circular plasmid (e.g., a single-, low-, or multi-copy plasmid). In some embodiments, a *Coxiella* spp. target nucleic acid may be derived from an essential locus (e.g., an essential housekeeping gene) or a locus involved in virulence (e.g., a gene essential for virulence). In some embodiments, a *Coxiella* spp. target nucleic acid may be derived from a multi-copy locus. In particular embodiments, a *Coxiella* spp. target nucleic acid may be derived from a multi-copy plasmid.

*Coxiella burnetii* has a genome that is relatively large for an intracellular pathogen (2 Mb). In some embodiments, a *Coxiella burnetii* target nucleic acid is a multi-copy locus. For example, a multi-copy locus may be a transposase. In other embodiments, a *Coxiella burnetii* target nucleic acid is a single-copy locus. In some embodiments, a *Coxiella burnetii* target nucleic acid may be derived from an essential locus (e.g., an essential housekeeping gene) or a locus involved in virulence (e.g., a gene essential for virulence). For example, a *Coxiella burnetii* target nucleic acid may be derived from the 5S rDNA gene, which is present as a single copy in the genome and is highly conserved within *C. burnetii* strains. A *Coxiella burnetii* target nucleic acid may be derived from any *Coxiella burnetii* strain. For example, there are presently 19 whole genome sequences of *Coxiella burnetii* available, with the following strain designations: cb109, "*Coxiella burnetii*," RSA 331, RSA 493, CbuG_Q212, RSA 493, CbuK_Q154, MSU Goat Q177, Q321, Dugway 5J108-111, Cb185, Z3055, and Cb175 Guyana.

*Anaplasma* Target Nucleic Acids

In some embodiments, a target nucleic acid may include sequence elements that are specific for an *Anaplasma* spp., for example, *Anaplasma phagocytophilum*. In other embodiments, a target nucleic acid of the invention may include sequence elements that are common to all *Anaplasma* spp. In other embodiments, a target nucleic acid of the invention may include sequence elements that are common to all *Rickettsia* spp. In yet other embodiments, these approaches may be combined. For example, in some embodiments an *Anaplasma* spp. target nucleic acid may be amplified in the presence of a forward primer and a reverse primer, each of which is universal to all *Anaplasma* spp. Detection of such a target nucleic acid in a sample typically would indicate that an *Anaplasma* spp. bacterium was present in the sample.

In some embodiments, an *Anaplasma* spp. target nucleic acid may be derived from a linear chromosome or a linear or circular plasmid (e.g., a single-, low-, or multi-copy plasmid). In some embodiments, an *Anaplasma* spp. target nucleic acid may be derived from an essential locus (e.g., an essential housekeeping gene) or a locus involved in virulence (e.g., a gene essential for virulence). In some embodiments, an *Anaplasma* spp. target nucleic acid may be derived from a multi-copy locus. In particular embodiments, an *Anaplasma* spp. target nucleic acid may be derived from a multi-copy plasmid.

*Anaplasma phagocytophilum* has a relatively small genome (1.4 Mb single chromosome), with only a single ribosomal rDNA operon encoded. In some embodiments, a *Anaplasma phagocytophilum* target nucleic acid is a multi-copy locus. In particular embodiments, an *Anaplasma phagocytophilum* target nucleic acid is a single-copy locus. In some embodiments, an *Anaplasma phagocytophilum* target nucleic acid may be derived from an essential locus (e.g., an essential housekeeping gene) or a locus involved in virulence (e.g., a gene essential for virulence). For example, in some embodiments, the single-copy locus may be derived from an outer membrane protein A (ompA) gene or from another surface protein precursor gene. An *Anaplasma phagocytophilum* target nucleic acid may be derived from any *Anaplasma phagocytophilum* strain. For example, there are presently 9 whole genome sequences of *Anaplasma phagocytophilum* available, with the following strain designations: str. HZ, str. HZ2, str. CRT35, str. CRT38, str. Norway variant2, str. MRK, str. Dog2, str. HGE1, and str. JM.

In some embodiments, an *Anaplasma phagocytophilum* target nucleic acid is derived from the valyl-tRNA synthetase gene (ValRS), a single-copy gene that has a 260 bp repeat duplicated (see bolded and underlined text shown below in SEQ ID NO: 167) about 1 Mbp downstream on the chromosome. The nucleic acid sequence of *A. phagocytophilum* is shown below as SEQ ID NO: 167. The duplicated 260 bp region is located in an apparent non-coding region on the chromosome. This portion of the gene lacks significant homology in species other than *A. phagocytophilum*.

```
                                            (SEQ ID NO: 167)
GTGGACAGTATTATGACAGAGCAAAAGGCAGGTTATAACCATCAGGTCAT

TGAAGAGCAATGCCAAGATGCATGGACAAAATCGAAATCGTATATATGGA

AAGGCCGCAAAGACGCAAGCTTTGTCATAGACACCCCACCACCAACAGTA

TCAGGAAGCCTACACATGGGCCACGTATTTAGTTACTGCCATGCCGACTT

CATAGCCCGCTACAAACGTCTGGCCGGTTTTGACGTTCTATTCCCCATAG

GGTTCGATGATAACGGGTTGCCCACAGAACGCCTCATCGAGAGGGAAACA

GGTGTAAAAGCCTCTCAGGTCGACCGAGGTGAGTTTATAAAGACATGTAC

TGCAGTTTCAAAAGAATACAGGTTAAAATACCGACAGTTATTTCAAACTT

TGGGAATAAGTTTCGATTGGTCCCGTGAGTACCATACTGCAAGCCCCACT

ATCCAAAAGCTTTCACAAGAGTCGTTCATAAGTTTGTATAACAAAGGTGA

TGCGTACCGTAAACAACAGCCGATATTGTGGGACGTTGTAGATCAGACAG

CAATATCTAACGCGGAGATCGAAGACAAAATTTTGCCATCTACAATGTAT

ACGGTTCGGTTTCAGACAGAATGTGGTGAGAGTATACTAATAGCCACAAC

CCGTCCAGAACTCATGCCCGCATGTGTAGCAGTGTTCTATCATCCTTACG

ATAGCCGTTATAAGCATCTTGAAGGCAAACATGCTATCGTACCAGTAGGC

GGAAATAACGTCAGAATTCTGCCGGACGATAAGGTAGCCATAGATAAAGG

AACTGGCTTGGTAATGTGCTGCACATTCGGCGATGAAACTGATGTATATT

GGCGGCAAAAGCATGCGCTTGACACCAGAATAATTATAGATAAAACCGGA

CGCCTTACAGGTCTGGAGAAATTGGCAACAGAGAAATCTCTCATCTCCCC

AACACAATTCAATGGTTTAAGAATAAAAGAGGCCAGGAAAGCCATAAGCG

AGACCCTGGCAGCAAGCGGATTGATATCATCCCAAGCAGATATAGTTCAT

AGCGTCAGATGTGCAGAGCGTTCTGGAGCTCCAATAGAGATTTTGCCGAG

TGAACAGTGGTTTATCAAGATTAAGGATCACAAAGATATATTTAAGAACC

TAGCAGAACGTATTAAGTGGCATCCTGACCACATGCGAAAACGACTATAT

ACGTGGATCGAGAACCTGAATAGCGATTGGTGTATATCTCGTCAGCGATT

TTATGGAGTCCCAGTCCCAGTATGGTATTCAAAACGAAATGGTGAAGAGG

GTAGGGTGATCTTACCCAATGTTCAAGATTTACCTATAGATCCCATTAAA

GACTTTCCTAGGGGCTATGGCAAAGATGAAGTGATACCCGATGTTGACGT

TATGGATACATGGGCAACGAGTTCACTATCTCCAATGTATCACACTATGA

TGTTGGAAGGTACATGTCATGAAGGAAATATACCTACCGATCTTCGTACC

CAAAGTCATGAGATAATACGATCCTGGGCGTTTTACACCATAGCCATGTC
```

-continued
```
CCACCTTCATCGAGCAGAGCTGCCGTGGAAAAGCATAATGATAAGCGGTT

GGTGCGTTGCAGAAGATAAGACTAAAATGAGCAAATCTAAAAACAACGCC

AAGGATCCAAGCGAATTACTAAAAACTTACGGAGCAGATGCGATTAGATA

CTGGGCTTCCAAAGCCCGAAACGGCGTAGACACCGTGTTTTCAGAAGAAG

TCATTAAAACAGGTAAGCGTCTAGTTACAAAATTATATAATGCGCATAAG

TTTGTACAGCTTGTAGCCGGTAATATTAAACCAAGTTTTGAGGCTATAAC

AAGTCCTCTCGACCAGTGGATCGTGACACGCTTAAGTAAAATTGTAGAAA

TAAGCACAAAAGCATATGAAGAATGTGACTATAATACAGGACTAGGTGTT

GTCGAGGAGTTTTTCATTAAGCAGTTCTGTGACAACTATATAGAGTTATC

CAAACATCGAGCATATAACGAGGAAGACTTACAGGGTCATAAATCTGCTC

TAAGTAGTCTGCAAATCGTACTACAAACTGCCATAGCACTCTTCTCACCC

ATCATACCGCACGTAACTCATTATATAAGTAGTAATAGTGAAACAGAAAG

TCCAAAGTGGCCATTATACGAAGAAATACCACGTTATGAAGCCATAGAAC

AAATGTGCGAGGAAGCAATGAGAATAGTTCACGAGATTAGACGTTATAAG

TCAGAAAATTGTATCGCCATGAACCATCCCCTTAATATACTTTCTATATC

TAGTAGAGCAGTACAACAAGATATGCATCCGCAAATCTTAGAGGATATTA

GAAATGCTTTGAAGATTTGCAAGATAACTATAGAACAAGAGCAGGGAGAA

GACTTTATTATTCAGCAATAA.
```

The sequence of the duplicated part of the gene on the chromosome of *A. phagocytophilum* str. JM at positions 248,363 to 248,619 is shown in SEQ ID NO: 168. In some embodiments, use of a target nucleic acid derived from the duplicated part of the ValRS gene may increase the sensitivity of detection due to the duplication on the target. This target nucleic acid may be used for species-specific detection of *A. phagocytophilum* because the low homology to other species (e.g., near neighbor species) is amenable to design of specific primers and probes.

*Babesia* Target Nucleic Acids

In some embodiments, a target nucleic acid may include sequence elements that are specific for a *Babesia* spp., for example, *Babesia microti* or *Babesia divergens*. In other embodiments, a target nucleic acid of the invention may include sequence elements that are common to all *Babesia* spp. In other embodiments, a target nucleic acid of the invention may include sequence elements that are common to all *Rickettsia* spp. In yet other embodiments, these approaches may be combined. For example, in some embodiments a *Babesia* spp. target nucleic acid may be amplified in the presence of a forward primer and a reverse primer, each of which is universal to all *Babesia* spp. Detection of such a target nucleic acid in a sample typically would indicate that a *Babesia* spp. cell was present in the sample.

In some embodiments, a *Babesia* spp. target nucleic acid may be derived from a linear chromosome or a linear or circular plasmid (e.g., a single-, low-, or multi-copy plasmid). In some embodiments, a *Babesia* spp. target nucleic acid may be derived from an essential locus (e.g., an essential housekeeping gene) or a locus involved in virulence (e.g., a gene essential for virulence). In some embodiments, a *Babesia* spp. target nucleic acid may be derived from a multi-copy locus.

*Babesia microti* is a protozoan that has a genome of 6.4 MB on 3 chromosomes, and contains single copies of rDNA genes. In some embodiments, a *Babesia microti* target nucleic acid is a multi-copy locus. In particular embodiments, a *Babesia microti* target nucleic acid is a single-copy locus. In some embodiments, a *Babesia microti* target nucleic acid may be derived from an essential locus (e.g., an essential housekeeping gene) or a locus involved in virulence (e.g., a gene essential for virulence). In some embodiments, a *Babesia microti* target nucleic acid sequence is an intragenic region of an rDNA gene. For example, in some embodiments, a *Babesia microti* target nucleic acid sequence may be derived from the ITS2 intragenic region. A *Babesia microti* target nucleic acid may be derived from any *Babesia microti* strain.

*Ehrlichia* Target Nucleic Acids

In some embodiments, a target nucleic acid may include sequence elements that are specific for an *Ehrlichia* spp., for example, *Ehrlichia chaffeensis*, *Ehrlichia ewingii*, or *Ehrlichia muris*-like. In other embodiments, a target nucleic acid of the invention may include sequence elements that are common to all *Ehrlichia* spp. In other embodiments, a target nucleic acid of the invention may include sequence elements that are common to all *Ehrlichia* spp. In yet other embodiments, these approaches may be combined. For example, in some embodiments an *Ehrlichia* spp. target nucleic acid may be amplified in the presence of a forward primer and a reverse primer, each of which is universal to all *Ehrlichia* spp. Detection of such a target nucleic acid in a sample typically would indicate that an *Ehrlichia* spp. bacterium was present in the sample.

In some embodiments, an *Ehrlichia* spp. target nucleic acid may be derived from a linear chromosome or a plasmid (e.g., a multi-copy plasmid). In some embodiments, an *Ehrlichia* spp. target nucleic acid may be derived from an essential locus (e.g., an essential housekeeping gene) or a locus involved in virulence (e.g., a gene essential for virulence). In some embodiments, an *Ehrlichia* spp. target nucleic acid may be derived from a multi-copy locus. In particular embodiments, an *Ehrlichia* spp. target nucleic acid may be derived from a multi-copy plasmid.

*Ehrlichia chaffeensis* is closest related to the genus *Anaplasma*, which both belong to the phylum Ehrlichiaceae. In some embodiments, an *Ehrlichia chaffeensis* target nucleic acid may be derived from a single-copy locus. In some embodiments, an *Ehrlichia chaffeensis* target nucleic acid may be derived from an essential locus (e.g., an essential housekeeping gene) or a locus involved in virulence (e.g., a gene essential for virulence). An *Ehrlichia chaffeensis* target nucleic acid may be derived from any *Ehrlichia chaffeensis* strain. For example, there are presently eight whole genome sequences of *Ehrlichia chaffeensis* available, with the following strain designations: str. Heartland, str. West Paces, str. Saint Vincent, str. Jax, str. Liberty, str. Arkansas, str. Osceola, and st. Wakulla.

*Francisella* Target Nucleic Acids

In some embodiments, a target nucleic acid may include sequence elements that are specific for a *Francisella* spp., for example, *Francisella tularensis*, *Francisella philomiragia*, or other *Francisella* spp. For example, in some embodiments, a target nucleic acid includes sequence elements that are specific for *Francisella tularensis*. In particular embodiments, a target nucleic acid may include sequence elements that are specific for a *Francisella tularensis* subspp., for example, *F. tularensis* subspp. *tularensis, holarctica, mediasiatica*, and *novicida*. In other embodiments, a target nucleic acid of the invention may include sequence elements that are common to all *Francisella* spp. In particular embodiments, a target nucleic acid may include sequence elements that are common to all *Francisella tularensis* subspp., including *F. tularensis* subspp. *tularensis, holarctica, mediasiatica*, and *novicida*. In yet other embodiments, these approaches may be combined. For example, in some embodiments an *Francisella* spp. target nucleic acid may be amplified in the presence of a forward primer and a reverse primer, each of which is universal to all *Francisella* spp. Detection of such a target nucleic acid in a sample typically would indicate that an *Francisella* spp. bacterium was present in the sample. In another example, in some embodiments a *Francisella tularensis* subspp. target nucleic acid may be amplified in the presence of a forward primer and a reverse primer, each of which is universal to all *Francisella tularensis* subspp., including *F. tularensis* subspp. *tularensis, holarctica, mediasiatica*, and *novicida*.

In some embodiments, a *Francisella tularensis* subspp. target nucleic acid may be derived from a linear chromosome or a linear or circular plasmid (e.g., a single-, low-, or multi-copy plasmid). In some embodiments, a *Francisella tularensis* subspp. target nucleic acid may be derived from an essential locus (e.g., an essential housekeeping gene) or a locus involved in virulence (e.g., a gene essential for virulence). In some embodiments, a *Francisella tularensis* subspp. target nucleic acid may be derived from a multi-copy locus. In particular embodiments, a *Francisella tularensis* subspp. target nucleic acid may be derived from a multi-copy plasmid.

*Francisella tularensis* subspp. have a 1.9 Mb genome harboring many essential genes for virulence and survival in the host's white blood cells. In some embodiments, a *Francisella tularensis* subspp. target nucleic acid may be derived from a virulence gene including acpA, pdpD, and iglC. In other embodiments, a *Francisella tularensis* subspp. target nucleic acid may be derived from a surface antigen including fopA. In yet other embodiments, a *Francisella tularensis* subspp. target nucleic acid may be derived from a housekeeping gene including gyr and speA. In other embodiments, a *Francisella tularensis* subspp. target nucleic acid may be derived from a transcriptional regulator gene including migR. A *Francisella tularensis* subspp. target nucleic acid may be derived from any *Francisella tularensis* subspp. strain.

Medical Conditions

The methods of the invention can also be used to monitor and diagnose an infectious disease. In some embodiments, the methods of the invention may be used to monitor and diagnose infectious disease in a multiplexed, automated, no sample preparation system. Examples of pathogens that may be detected using the methods of the invention include, e.g., *Borrelia* spp., including *Borrelia burgdorferi* sensu lato (*Borrelia burgdorferi, Borrelia afzelii,* and *Borrelia garinii*) species, *Borrelia americana, Borrelia andersonii, Borrelia bavariensis, Borrelia bissettii, Borrelia carolinensis, Borrelia californiensis, Borrelia chilensis, Borrelia* genomosp. 1 and 2, *Borrelia japonica, Borrelia kurtenbachii, Borrelia lusitaniae, Borrelia myomatoii, Borrelia sinica, Borrelia spielmanii, Borrelia tanukii, Borrelia turdi, Borrelia valaisiana* and unclassified *Borrelia* spp; *Rickettsia* spp. (including *Rickettsia rickettsii* and *Rickettsia parkeri*); *Ehrlichia* spp. (including *Ehrlichia chaffeensis, Ehrlichia ewingii,* and *Ehrlichia muris*-like); *Coxiella burnetii; Babesia* spp. (including *Babesia microti* and *Babesia divergens*); *Anaplasma phagocytophilum; Francisella* spp., (including *Francisella tularensis* (including *F. tularensis* subspp. *tularensis, holarctica, novicida,* and *mediasiatica*)); *Streptococcus pneumonia*; and *Neisseria meningitides*.

The methods of the invention can be used to identify and monitor the pathogenesis of disease in a subject, to select therapeutic interventions, and to monitor the effectiveness of the selected treatment. For example, for a patient having or at risk of a tick-borne pathogen infection, the systems and methods of the invention can be used to identify the infectious pathogen, pathogen load, and to monitor white blood cell count and/or biomarkers indicative of the status of the infection. The identity of the pathogen can be used to select an appropriate therapy. In some embodiments, the methods may further include administering a therapeutic agent following monitoring or diagnosing an infectious disease. The therapeutic intervention (e.g., a particular antibiotic agent) can be monitored as well to correlate the treatment regimen to the circulating concentration of antibiotic agent and pathogen load to ensure that the patient is responding to treatment.

The methods and systems may be used to monitor and diagnose diseases caused by or associated with tick-borne pathogens, for example, Lyme disease, and/or diseases that are characterized by similar symptoms to Lyme disease, referred to herein as "Lyme-like diseases." Exemplary diseases and conditions that may be monitor and diagnosed include but are not limited to: Lyme disease, Rocky Mountain spotted fever, anaplasmosis, Q-fever, ehrlichiosis, babesiosis, tularemia, and meningitis.

Lyme Disease

The causative agent for Lyme disease is *Borrelia burgdorferi* senso lato (Bbsl). Bbsl includes *Borrelia burgdorferi* and two near neighbor species, *Borrelia afzelii* and *Borrelia garinii*. Lyme disease is a multisystemic/multistage disease that is considered to be the most prevalent tick-born disease in North America and Europe, accounting for 300,000 and 90,000 cases annually, respectively.

*Borrelia burgdorferi* was isolated from its vector, *Ixodes* (tick) in 1982. The bacterium is a microaerophilic spirochete that typically contains seven periplasmic flagella per cell end. Motility in these spirochetes is by rapid rotation around the long axis, flexation of the cell, and locomotion along a helical path. This corkscrew-like movement along its axis also gives the species its characteristic morphology and facilitates movement in viscous environments such as blood, synovial fluid, and the like, and may be essential for deep tissue invasion and vessel barrier crossing.

Bbsl belongs to the phylum of *Spirochaetes*, order of Spirochaetales, the family of Spirochaetaceae and the genus of *Borrelia*. Apart from the Bbsl species, the *Borrelia* genus includes at least 17 other classified spp. such as *Borrelia americana, Borrelia andersonii, Borrelia bavariensis, Borrelia bissettii, Borrelia carolinensis, Borrelia californiensis, Borrelia chilensis, Borrelia* genomosp. 1 and 2, *Borrelia japonica, Borrelia kurtenbachii, Borrelia lusitaniae, Borrelia myomatoii, Borrelia sinica, Borrelia spielmanii, Borrelia tanukii, Borrelia turdi, Borrelia valaisiana* and numerous unclassified *Borrelia* spp. Among these, *Borrelia myamatoi*, an originally Japanese species, has recently also emerged in North America representing itself with Lyme-like symptoms.

Species of the Bbsl group are endemic in different part of the Northern hemisphere. *Borrelia burgdorferi* sensu stricto (Bbss) is prevalent in the Northeastern and North central United States but also in Western Europe (1-2% of Lyme cases). In contrast, *Borrelia afzelii* is typically only observed in Central and Western Europe, and Russia, and *Borrelia garinii* is typically restricted to Europe, Russia, and northern Asia.

Lyme disease can be difficult to diagnose. At present, the best indication for a 'positive' tick bite is the "bull's eye" rash, or erythema migrans (EM). According to the Centers for Disease Control and Prevention (CDC), EM occurs in approximately 70-80% of infected persons and begins at the site of a tick bite after a delay of 3-30 days, with an average of about 7 days. This rash gradually expands over a period of several days, and can reach up to 12 inches (30 cm) across. As parts of the rash may clear as it grows in size it results in the classical "bull's eye" appearance.

Untreated infections with Bbsl can have serious health consequences. Once the localized stage (stage I, acute phase) has passed (3-30 days after a bite with and infected tick) without targeted treatment, the agent can disseminate and cause heart and nervous system palsies as well as meningitis (stage II). Further complications can arise which manifest in motor and nerve damages, brain inflammation and arthritis (stage III) cumulating in chronic Lyme disease with recurring muscle and joint pain, cognitive defects and chronic fatigue.

Rocky Mountain Spotted Fever

In the U.S., Rocky Mountain spotted fever (RMSF) is the second-most reported disease that is transmitted by ticks after Lyme disease. The disease is endemic in the Central and South Central U.S. and is caused by a non-motile gram-negative highly pleomorphic bacteria, *Rickettsia rickettsii* and by its near neighbor *Rickettsia parkeri* (an emerging RMSF pathogen). These two pathogens are also referred to as RMSF agents.

In the early phase, infections with RMSF agents cause skin lesions, which may or may not include a rash (approximately 20% of patients don't develop a rash), severe headache, high fever, joint and muscle pain, as well as general malaise and gastrointestinal problems. If not treated with antibiotics (e.g., doxycyclin), later complications include signs of cortical blindness, seizures, deafness, ataxia and paralysis, meningoencephalitis and comatose delirium. RSMF has the highest mortality rate (30%) of all tick-borne diseases if left untreated. RMSF is difficult to differentially diagnose and cannot be detected on blood smears, since the RMSF agents are obligative intracellular bacteria.

Anaplasmosis

The causative agent of anaplasosis (also referred to in the art as granulocytic anaplasmosis) is the gram-negative bacterium *Anaplasma phagocytophilum*, a small non-motile obligatory intracellular alpha proteobacterium that infects neutrophils. *Anaplasma phagocytophilum* is transmitted by ticks.

Symptoms of anaplasmosis include fever, headache, muscle pain, malaise, chills, nausea, abdominal pain, cough, confusion, and (rarely) rash. Anaplasmosis can be fatal if not treated correctly, even in previously healthy people. More severe symptoms during later stages of infection include difficulty breathing, hemorrhaging, renal failure, and/or neurological problems. The estimated fatality rate is less than 1%. Patients generally recover quickly with treatment, but more severe cases may require intravenous antibiotics, prolonged hospitalization, or intensive care.

Differential diagnosis of anaplasmosis can be difficult, as symptoms vary and can appear similar to other tick-borne diseases. Treatment is most effective if started early. Timely diagnosis is prudent since antibiotic treatment (doxycycline) is most effective at an early (less than 5 days after tick bite) stage of infection. *A. phagocytophilum* can be transmitted through blood transfusions as it can survive for more than a week in refrigerated blood.

Q-Fever

Q-fever is caused by the obligate intracellular bacteria *Coxiella burnetii*. This bacteria belongs to the class of Legionenales and is a small (0.2-0.4 µm wide, 0.4-1 µm long) gram-negative bacterium.

Since domestic animals (cattle, sheep, goats) are the dominant reservoir for *Coxiella burnetii* most human infections occur in farmers, veterinarians, and workers that are exposed to dairy products and animal waste. *Coxiella burnetii* can sporulate, and spores are very resistant to desiccation, low or high pH, ammonium chloride, 0.5% sodium hypochlorite, and UV radiation and thus are stable in the environment for a prolonged time. Exposure to formalin (≥about 5%) for 24-48 hours can kill spores. Typically, transmission of *Coxiella burnetii* is via inhalation of tainted dust. Transmission through ticks is rare but possible. As transient bacteremia occurs in animals after infection, the pathogen can be passed to feeding ticks and transmitted to other animals including humans.

Acute symptoms develop within 2 to 3 weeks of infection, but many infected individuals remain unsymptomatic. General symptoms include high fever, headaches, myalgia, chills, sweats, non-productive cough, nausea, vomiting, diarrhea, abdominal pain, and chest pain. Most people recover after the acute phase, but some experience complications including pneumonia, granulomatous hepatitis, myocarditis, and central nervous system complications. The fatality rate is <2% of hospitalized patients.

Chronic Q fever occurs in <5% of acutely infected patients. It may manifest in as little as 6 weeks or years later. Endocarditis occurs in 60-70% of chronic cases, with a 25-60% fatality rate in untreated patients. Aortic aneurysms and infections in the bone, liver, or reproductive organs can also occur with chronic Q-fever. Because the organism can persist for a long time in the host, 10-25% of acute patients can develop post-Q fever fatigue syndrome, which is characterized by fatigue, night sweats, headaches, photophobia, muscle pain, mood changes, and insomnia.

Diagnosis of Q-fever can be difficult. However, treatment is most effective if started when symptoms occur. Serological detection tests (IgG against *C. burnetii* antigen) can take longer than 7 to 10 days to become positive.

Ehrlichiosis

Ehrlichiosis is a general name that describes several bacterial diseases that affect humans and animals. Human ehrlichiosis is caused mainly by 2 species, *Ehrlichia chaffeensis* and *Ehrlichia ewingii*, with a third species possibly emerging, called *Erlichia muris*-like (provisional name). All three species are transmitted by ticks. *Ehrlichia chaffensis* and *Ehrlichia ewingii* are endemic southeastern and south central U.S., while *Erlichia muris*-like has so far only been detected in a small number of human cases in Minnesota and Wisconsin.

*Ehrlichia* species are related to *Rickettsia* spp. and are, like other bacteria in this class, obligatory intracellular pathogens. Their target cells are monocytes and granulocytes, in which they manifest as so-called morulae, which are bacterial microcolonies. *Ehrlichia* spp., like *Anaplasma*, can be transmitted through blood transfusions, as they can survive more than a week in refrigerated blood.

Ehrlichiosis symptoms typically develop 1 to 2 weeks after an infected tick bite. Symptoms of ehrlichiosis include fever, headache, chills, malaise, muscle pain, nausea, vomiting, diarrhea, confusion, conjunctival injection, and rash. Ehrlichiosis can be fatal, even in previously healthy people, if not treated correctly. Severe symptoms may include difficulty breathing or bleeding disorders. The estimated fatality rate is 1.8%. Patients treated early with doxycyclin recover quickly, but those with a more severe case may need intravenous antibiotics, prolonged hospitalization or intensive care. In addition, headache, weakness, and malaise can continue for weeks even after treatment. Since the symptoms vary, differential diagnosis of ehrlichiosis can be very difficult.

Babesiosis

Babesiosis is caused by intraerythrocytic protozoan parasites of the genus *Babesia*. *Babesia* spp. typically require vertebrate and nonvertebrate hosts to complete their life cycle, and all known organisms of this genus are found to be transmitted by ticks. *Babesia microti* is a rodent-borne parasite that is the most common cause of babesiosis in North America. In contrast, in Europe, babesiosis is typically caused by the bovine pathogen *Babesia divergens*, which causes a more severe disease.

*Babesia* species are often confused with *Plasmodium*, which represents a problem since treatment with anti-malaria therapy can be fatal for infected people. However, differential diagnosis of babesiosis is typically difficult, in part due to the similar symptoms as compared with other diseases caused by tick-borne pathogens. In most *Babesia*-infected people, there are no symptoms. However, if not treated, *B. microti* and other can cause flu-like symptoms including fever, chills, sweats, headache, body aches, loss of appetite, nausea, or fatigue and at a later stage also hemolytic anemia, which can lead to jaundice, proteinuria, and/or hemoglobinuria.

Tularemia

Tularemia is a disease of animals and humans caused by the bacterium *Francisella tularensis*. Rabbits, hares, and rodents are especially susceptible and often die in large numbers during outbreaks. Humans can become infected through several routes, including tick and deer fly bites, but also through skin contact with infected animals as well as inhalation of infected dust. *F. tularensis* is a select agent due to its postential use in bioterrorism. The genus *Francisella* is subdivided into at least three species including *F. tularensis, F. philomiragia*, and other *Francisella* spp. Three of the four recognized *Francisella tularensis* subspecies, subspp. *tularensis* (also known as nearctica, biovar A), *holarctica* (palearctica, biovar B), and *mediasiatica* are human pathogens whereas subspp. *novicida* is typically non-pathogenic to healthy individuals (Sjostedt A (2003) Family XVII, Francisellaceae. Genus I, *Francisella*. Bergey's Manual of Systematic Bacteriology. New York, N.Y.: Springer-Verlag. 111-113).

*Francisella tularensis* subspp. *tularensis*, which is typically found in North America, causes Type A Tularemia, which has a high mortality rate (Cross J, Penn R (2000) *Francisella tularensis* (tularemia). Principles and Practice of Infectious Diseases Philadelphia, Pa.: Churchill Livingstone. 2393-2402). In contrast, *Francisella tularensis* subspp. *holarctica* and *mediasiatica* are found primarily outside of North America and cause the milder Type B Tularemia. *Francisella philomiragia* and the other *Francisella* spp. are presently not known to be human pathogens.

Tularemia is a rare disease (203 cases were reported in the U.S. in 2013). As with all other Lyme-like diseases described herein, differential diagnosis can be difficult. Blood tests and cultures can help confirm the diagnosis but may be cumbersome and do not presently identify the subspecies. Treatment for tularemia typically includes antibiotics such as streptomycin, gentamicin, doxycycline, and ciprofloxacin. When treated, symptoms may last for several weeks, but most patients completely recover.

The signs and symptoms of tularemia vary depending on how the *Francisella tularensis* bacteria enter the body. Illness ranges from mild to life-threatening. All forms are typically accompanied by fever, which can be as high as 104° F. The tick-transmitted forms of the disease include ulcerglandular and glandular forms. Ulcerglandular is the most common form of tularemia. A skin ulcer appears at the site where the organism entered the body. The ulcer is accompanied by swelling of regional lymph glands, usually in the armpit or groin. Glandular tularemia typically has all the symptoms of the above but without an ulcer.

Meningitis

The pathogens *Streptococcus pneumoniae* and *Neisseria meningitides*, which are causative agents for meningitis, can cause similar symptoms as compared to tick-borne pathogens. *Streptococcus pneumonia* is a gram positive, alpha-hemotytic, facultative anaerobe. *Neisseria meningitides* is a gram negative bacterium that belongs to the class Betaproteobacteria. Exemplary symptoms of meningitis include headache, neck stiffness, fever, confusion or altered consciousness, vomiting, photophobia, and phonophobia.

Treatment

In some embodiments, the methods further include administering a therapeutic agent to a subject following a diagnosis. Typically, the identification of a particular pathogen will guide the selection of the appropriate therapeutic agent. For example, if Lyme disease is diagnosed, the method may involve the step of administering a Lyme disease therapy. If Rocky Mountain spotted fever is diagnosed, the method may involve the step of administering a Rocky Mountain spotted fever disease therapy. If Rocky Mountain spotted fever is diagnosed, the method may involve the step of administering a Rocky Mountain spotted fever disease therapy. If ehrlichiosis is diagnosed, the method may involve the step of administering an ehrlichiosis therapy. If Q-fever is diagnosed, the method may involve the step of administering a Q-fever therapy. If babesiosis is diagnosed, the method may involve the step of administering a babesiosis therapy. If meningitis is diagnosed, the method may involve the step of administering a meningitis therapy.

For example, for a bacterial infection (e.g., Lyme disease, Rocky Mountain spotted fever, ehrlichiosis, Q-fever, tularemia, and bacterial meningitis), a therapy may include an antibiotic. In some instances, an antibiotic may be administered orally. In other instances, the antibiotic may be administered intravenously. Exemplary non-limiting antibiotics that may be used in the methods of the invention include but are not limited to: acrosoxacin, amifloxacin, amikacin, amoxycillin, ampicillin, aspoxicillin, azidocillin, azithromycin, aztreonam, balofloxacin, benzylpenicillin, biapenem, brodimoprim, cefaclor, cefadroxil, cefatrizine, cefcapene, cefdinir, cefetamet, ceftmetazole, cefoxitin, cefprozil, cefroxadine, ceftarolin, ceftazidime, ceftibuten, ceftobiprole, cefuroxime, cephalexin, cephalonium, cephaloridine, cephamandole, cephazolin, cephradine, chlorquinaldol, chlortetracycline, ciclacillin, cinoxacin, ciprofloxacin, clarithromycin, clavulanic acid, clindamycin, clofazimine, cloxacillin, colistin, danofloxacin, dapsone, daptomycin, demeclocycline, dicloxacillin, difloxacin, doripenem, doxycycline, enoxacin, enrofloxacin, erythromycin, fleroxacin, flomoxef, flucloxacillin, flumequine, fosfomycin, gentamycin, isoniazid, imipenem, kanamycin, levofloxacin, linezolid, mandelic acid, mecillinam, meropenem, metronidazole, minocycline, moxalactam, mupirocin, nadifloxacin, nafcillin, nalidixic acid, netilmycin, netromycin, nifuirtoinol, nitrofurantoin, nitroxoline, norfloxacin, ofloxacin, oxacillin, oxytetracycline, panipenem, pefloxacin, phenoxymethylpenicillin, pipemidic acid, piromidic acid, pivampicillin, pivmecillinam, polymixin-b, prulifloxacin, rufloxacin, sparfloxacin, sulbactam, sulfabenzamide, sulfacytine, sulfametopyrazine, sulphacetamide, sulphadiazine, sulphadimidine, sulphamethizole, sulphamethoxazole, sulphanilamide, sulphasomidine, sulphathiazole, teicoplanin, temafioxacin, tetracycline, tetroxoprim, tigecycline, tinidazole, tobramycin, tosufloxacin, trimethoprim, vancomycin, and pharmaceutically acceptable salts or esters thereof. An exemplary treatment for babesiosis may include administration of atovaquone and azithromycin or clindamycin and quinine.

In some embodiments, a sample is obtained from a subject (e.g., a patient) prior to administration of any therapy, e.g., administration of an antibiotic. In other embodiments, a sample is obtained from a patient during administration of a therapy, e.g., an antibiotic. In yet other embodiments, a sample is obtained from a patient after the conclusion of administration of a therapy, e.g., an antibiotic.

Assay Reagents

The assays described herein may include any suitable reagents, for example, surfactants, buffer components, additives, chelating agents, and the like. The surfactant may be selected from a wide variety of soluble non-ionic surface active agents including surfactants that are generally commercially available under the IGEPAL trade name from GAF Company. The IGEPAL liquid non-ionic surfactants are polyethylene glycol p-isooctylphenyl ether compounds and are available in various molecular weight designations, for example, IGEPAL CA720, IGEPAL CA630, and IGEPAL CA890. Other suitable non-ionic surfactants include those available under the trade name TETRONIC 909 from BASF Wyandotte Corporation. This material is a tetra-functional block copolymer surfactant terminating in primary hydroxyl groups. Suitable non-ionic surfactants are also available under the VISTA ALPHONIC trade name from Vista Chemical Company and such materials are ethoxylates that are non-ionic biodegradables derived from linear primary alcohol blends of various molecular weights. The surfactant may also be selected from poloxamers, such as polyoxyethylene-polyoxypropylene block copolymers, such as those available under the trade names Synperonic PE series (ICI), PLURONIC® series (BASF), Supronic, Monolan, Pluracare, and Plurodac, polysorbate surfactants, such as TWEEN® 20 (PEG-20 sorbitan monolaurate), and glycols such as ethylene glycol and propylene glycol.

Such non-ionic surfactants may be selected to provide an appropriate amount of detergency for an assay without having a deleterious effect on assay reactions. In particular, surfactants may be included in a reaction mixture for the purpose of suppressing non-specific interactions among various ingredients of the aggregation assays of the invention. The non-ionic surfactants are typically added to the liquid sample prior in an amount from 0.01% (w/w) to 5% (w/w).

The non-ionic surfactants may be used in combination with one or more proteins (e.g., albumin, fish skin gelatin, lysozyme, or transferrin) also added to the liquid sample prior in an amount from 0.01% (w/w) to 5% (w/w).

Furthermore, the assays, methods, and cartridge units of the invention can include additional suitable buffer components (e.g., Tris base, selected to provide a pH of about 7.8 to 8.2 in the reaction milieu); and chelating agents to scavenge cations (e.g., ethylene diamine tetraacetic acid (EDTA), EDTA disodium, citric acid, tartaric acid, glucuronic acid, saccharic acid or suitable salts thereof).

Sample Preparation and Cell Lysis

The methods and systems of the invention may involve sample preparation and/or cell lysis. For example, a pathogen present in a biological sample may be lysed prior to amplification of a target nucleic acid. Suitable lysis methods for lysing pathogen cells in a biological sample (e.g., whole blood, cerebrospinal fluid (CSF), urine, and synovial fluid) include, for example, mechanical lysis (e.g., beadbeating and sonication), heat lysis, and alkaline lysis. In some embodiments, beadbeating may be performed by adding glass beads (e.g., 0.5 mm glass beads) to a biological sample to form a mixture and agitating the mixture. As an example, the sample preparation and cell lysis (e.g., beadbeating) may be performed using any of the approaches and methods described in WO 2012/054639.

In some embodiments, the methods of the invention involve detection of one or more pathogen-associated analytes in a whole blood sample. In some embodiments, the methods may involve disruption of red blood cells (erythrocytes). In some embodiments, the disruption of the red blood cells can be carried out using an erythrocyte lysis agent (i.e., a lysis buffer, an isotonic lysis agent, or a nonionic detergent). Erythrocyte lysis buffers which can be used in the methods of the invention include, without limitation, isotonic solutions of ammonium chloride (optionally including carbonate buffer and/or EDTA), and hypotonic solutions. The basic mechanism of hemolysis using isotonic ammonium chloride is by diffusion of ammonia across red blood cell membranes. This influx of ammonium increases the intracellular concentration of hydroxyl ions, which in turn reacts with $CO_2$ to form hydrogen carbonate. Erythrocytes exchange excess hydrogen carbonate with chloride which is present in blood plasma via anion channels and subsequently increase in intracellular ammonium chloride concentrations. The resulting swelling of the cells eventually causes loss of membrane integrity.

Alternatively, the erythrocyte lysis agent can be an aqueous solution of nonionic detergents (e.g., nonyl phenoxypolyethoxylethanol (NP-40), 4-octylphenol polyethoxylate (Triton-X100), Brij-58, or related nonionic surfactants, and mixtures thereof). The erythrocyte lysis agent disrupts at least some of the red blood cells, allowing a large fraction of certain components of whole blood (e.g., certain whole blood proteins) to be separated (e.g., as supernatant following centrifugation) from the white blood cells or other cells (e.g., bacterial cells and protozoan cells) present in the whole blood sample. Following erythrocyte lysis and centrifugation, the resulting pellet may be reconstituted to form an extract.

In some embodiments, the methods of the invention may involve providing a sample of whole blood (e.g., a sample of about 0.05 to 10 mL of whole blood). In some embodiments, this sample may be split into a first 1 mL to 8 mL (e.g., 1 mL, 2 mL, 3 mL, 4 mL, 5 mL, 6 mL, 7 mL, or 8 mL) aliquot for detection of a *Borrelia burgorferi* sensu lato species, which is subjected to little or no sample preparation, and a second 0.05 to 2 mL (e.g., 0.05 mL, 0.1 mL, 0.2 mL, 0.3 mL, 0.4 mL, 0.5 mL, 0.6 mL, 0.7 mL, 0.8 mL, 0.9 mL, 1 mL, 1.1 mL, 1.2 mL, 1.3 mL, 1.4 mL, or 1.5 mL) aliquot for detection of a Lyme-like disease pathogen, which may be subjected to white blood cell or red blood cell concentration (e.g., by centrifugation) followed by red blood cell lysis (e.g., as described above) to enrich and purify the white blood cells, or by separation of red blood cells, followed by mechanical (e.g., beadbeating or sonication) or heat lysis to release nucleic acids from intracellular pathogens that may be present in the white blood cells or red blood cells. Such a method may be used during detection of intracellular pathogens, including *Rickettsia* spp. (including *Rickettsia rickettsii* and *Rickettsia parkeri*), *Ehrlichia* spp. (including *Ehrlichia chaffeensis*, *Ehrlichia ewingii*, and *Ehrlichia muris*-like), *Coxiella* spp., (including *Coxiella burnetii*), *Babesia* spp. (including *Babesia microti* and *Babesia divergens*), *Francisella* spp. (including *Francisella tularensis* subsp. (including *Francisella tularensis* subsp. *tularensis, holarctica, novicida,* and *mediasiatica*)) and *Anaplasma* spp., (including *Anaplasma phagocytophilum*).

In some embodiments, the methods of the invention may include (a) providing a whole blood sample from a subject; (b) mixing the whole blood sample with an erythrocyte lysis agent solution to produce disrupted red blood cells; (c) following step (b), centrifuging the sample to form a supernatant and a pellet, discarding some or all of the supernatant, and resuspending the pellet to form an extract, (d) lysing cells of the extract (which may include white blood cells and/or pathogen cells) to form a lysate. In some embodiments, the method further comprises amplifying one or more target nucleic acids (e.g., a Bbsl species target nucleic acid, a non-Lyme disease pathogen target nucleic acid, or both) in the lysate. In some embodiments, the method may include washing the pellet (e.g., with a buffer such as TE buffer) prior to resuspending the pellet and optionally repeating step (c). In some embodiments, the method may include 1, 2, 3, 4, 5, or more wash steps. In other embodiments, the method is performed without performing any wash step. In some embodiments, the amplifying is in the presence of whole blood proteins, non-target nucleic acids, or both. In some embodiments, the amplifying may be in the presence of from 0.5 µg to 60 µg (e.g., 0.5 µg, 1 µg, 5 µg, 10 µg, 15 µg, 20 µg, 25 µg, 30 µg, 35 µg, 40 µg, 45 µg, 50 µg, 55 µg, or 60 µg) of subject DNA. In some embodiments, the subject DNA is from white blood cells of the subject.

Amplification and Detection of Nucleic Acids from Complex Samples

In some embodiments, methods and systems of the invention can include amplification-based nucleic acid detection assays conducted starting with complex samples (e.g., for diagnostic, forensic, and environmental analyses).

In several embodiments, the methods of the invention involve amplification of one or more nucleic acids. Amplification may be exponential or linear. A target or template nucleic acid may be either DNA or RNA. The sequences amplified in this manner form an "amplified region" or "amplicon." Primer probes can be readily designed by those skilled in the art to target a specific template nucleic acid sequence. In certain preferred embodiments, resulting amplicons are short to allow for rapid cycling and generation of copies. The size of the amplicon can vary as needed to provide the ability to discriminate target nucleic acids from non-target nucleic acids. For example, amplicons can be less than about 1,000 nucleotides in length. Desirably the amplicons are from 100 to 500 nucleotides in length (e.g., 100 to 200, 150 to 250, 300 to 400, 350 to 450, or 400 to 500 nucleotides in length). In some embodiments, more than one (e.g., 1, 2, 3, 4, 5, 6, 7, 8, 9, 10, or more than 10) target nucleic acids may be amplified in one reaction. In other embodiments, a single target nucleic acid may be amplified in one reaction.

Sample preparation typically involves removing or providing resistance for common PCR inhibitors found in complex samples (e.g., body fluids, tissue homogenates). Common inhibitors are listed in Table 1 (see also, Wilson, Appl. Environ. Microbiol., 63:3741 (1997)). Inhibitors typically act by either prevention of cell lysis, degradation or sequestering a target nucleic acid, and/or inhibition of a polymerase activity. The "facilitators" in Table 1 indicate methodologies or compositions that may be used to reduce or overcome inhibition. The most commonly employed polymerase, Taq, is inhibited by the presence of 0.1% blood in a reaction. Mutant Taq polymerases have been engineered that are resistant to common inhibitors (e.g., hemoglobin and/or humic acid) found in blood (Kermekchiev et al., Nucl. Acid. Res., 37(5): e40, (2009)). Manufacturer recommendations indicate these mutations enable direct amplification from up to 20% blood. Despite resistance afforded by the mutations, accurate real time PCR detection is complicated due to fluorescence quenching observed in the presence of blood sample (Kermekchiev et al., Nucl. Acid. Res., 37:e40 (2009)).

TABLE 1

PCR inhibitors and facilitators/methods for overcoming inhibition.

| Substrate | Target | Inhibitor | Facilitator |
|---|---|---|---|
| feces | *Escherichia coli* | >$10^3$ bacterial cells | ion-exchange column |
| CSF | *Treponema pallidum* | Cellular debris causing nonspecific amplification | nested primers |
| whole blood | mammalian tissue | >4 µl of blood/100-ml reaction mix (hemoglobin) | 1-2% blood per reaction |
| feces | Rotatvirus | unknown dilution | cellulose fiber |
| clinical specimens | Cytomegalovirus | unidentified components | glass bead extraction |
| human blood and tissue | human genes | DNA binding proteins | thermophilic protease from Thermus strain rt44A |
| mammalian tissue | Mammalian tissue genetics | thermal cycler variations | formamide |
| mammalian tissue | Mammalian tissue genetics | thermal cycler variations | DMSO, glycerol, PEG, organic solvents |
| clinical specimens | *Treponema pallidum* | unknown factors | Various substrate-specific physicochemical methods |
| forensic semen samples | Sperm | Genotyping errors; selective/total PCR inhibition by vaginal microorganisms | |
| feces | *Salmonella enterica* | various body fluids | immunomagnetic separation |
| feces | Various enteric viruses | unknown | size exclusion chromatography, physicochemical extraction |

TABLE 1-continued

PCR inhibitors and facilitators/methods for overcoming inhibition.

| Substrate | Target | Inhibitor | Facilitator |
|---|---|---|---|
| clinical specimens | Herpes simplex virus | endogenous inhibitors, random effects | repurification, coamplified positive control |
| feces | Escherichia coli | nonspecific inhibitors, urea, hemoglobin, heparin, phenol, SDS | additional primers and reaction cyclers, booster PCR |
| tissue culture | Cytomegalovirus HIV | glove powder | |
| suspensions, skin biopsies | Mycobacterium leprae | mercury-based fixatives, neutral buffered formaline | reduced fixation times, ethanol fixation |
| clinical specimens | Mycobacterium tuberculosis | unknown inhibitors in pus, tissue biopsies, sputum, pleural fluid | physicochemical extraction |
| mammalian tissue | mammalian tissue genetics | unknown contaminant of reverse transcriptase | additional DNA |
| formalin-fixed paraffin tissue | Hepatitus C virus | ribonucleotide vanadyl complexes | phenol/chloroform extraction |
| nasopharyngeal aspirates and swabs | Bordetella pertussis | unknown inhibitors | phenol/chloroform extraction |
| human mononuclear blood cells | HIV type I | detergents | mineral oil |
| bloodstain | human mitochondrial DNA | unidentified heme compound, hemin | BSA |
| blood | various | heparin | alternative polymerases and buffers, chelex, spermine, [Mg2+], glycerol, BSA, heparinase |
| sputa | Mycoplasma pneumonia | N-acetyl-L-cysteine, dithiothreitol, mucolytic agents | |
| human tissue | HLA-DRB1 genotyping | pollen, glove powder, impure DNA, heparin, hemoglobin | |
| clinical specimens | Mycobacterium tuberculosis | unknown | competitive internal control |
| dental plaque | many | unknown | diatomaceous earth, guanidium isothiocyante, ethanol, acetone |
| ancient mammalian tissues | Cytochrome b gene | unknown | ammonium acetate, ethidium bromide |

Polymerase chain reaction amplification of DNA or cDNA is a tried and trusted methodology; however, as discussed above, polymerases are inhibited by agents contained in crude samples, including but not limited to commonly used anticoagulants and hemoglobin. Recently mutant Taq polymerases have been engineered to harbor resistance to common inhibitors found in blood and soil. Currently available polymerases, e.g., HemoKlenTaq™ (New England BioLabs, Inc., Ipswich, Mass.) as well as OmniTaq™ and OmniKlenTaq™ (DNA Polymerase Technology, Inc., St. Louis, Mo.) are mutant (e.g., N-terminal truncation and/or point mutations) Taq polymerase that render them capable of amplifying DNA in the presence of up to 10%, 20% or 25% whole blood, depending on the product and reaction conditions (See, e.g., Kermekchiev et al. Nucl. Acids Res. 31:6139 (2003); and Kermekchiev et al., Nucl. Acid. Res., 37:e40 (2009); and see U.S. Pat. No. 7,462,475). Additionally, PHUSION® Blood Direct PCR Kits (Finnzymes Oy, Espoo, Finland), include a unique fusion DNA polymerase enzyme engineered to incorporate a double-stranded DNA binding domain, which allows amplification under conditions which are typically inhibitory to conventional polymerases such as Taq or Pfu, and allow for amplification of DNA in the presence of up to about 40% whole blood under certain reaction conditions. See Wang et al., Nuc. Acids Res. 32:1197 (2004); and see U.S. Pat. Nos. 5,352,778 and 5,500,363. Furthermore, Kapa Blood PCR Mixes (Kapa Biosystems, Woburn, Mass.), provide a genetically engineered DNA polymerase enzyme which allows for direct amplification of whole blood at up to about 20% of the reaction volume under certain reaction conditions. Despite these breakthroughs, direct optical detection of generated amplicons is not possible with existing methods since fluorescence, absorbance, and other light based methods yield signals that are quenched by the presence of blood. See Kermekchiev et al., Nucl. Acid. Res., 37:e40 (2009).

A variety of impurities and components of whole blood can be inhibitory to the polymerase and primer annealing. These inhibitors can lead to generation of false positives and low sensitivities. To reduce the generation of false positives and low sensitivities when amplifying and detecting nucleic acids in complex samples, it is desirable to utilize a thermal stable polymerase not inhibited by whole blood samples, for example as described above, and include one or more internal PCR assay controls (see Rosenstraus et al. J. Clin Microbiol. 36:191 (1998) and Hoofar et al., J. Clin. Microbiol. 42:1863 (2004)). For example, the assay can include an internal control nucleic acid that contains primer binding regions identical to those of the target sequence to assure that clinical specimens are successfully amplified and detected. In some embodiments, the target nucleic acid and internal control can be selected such that each has a unique probe binding region that differentiates the internal control from the target nucleic acid. The internal control is, optionally, employed in combination with a processing positive control, a processing negative control, and a reagent control for the safe and accurate determination and identification of an infecting organism in, e.g., a whole blood clinical sample. The internal control can be an inhibition control that is designed to co-amplify with the nucleic acid target being detected. Failure of the internal inhibition control to be amplified is evidence of a reagent failure or process error. Universal primers can be designed such that the target sequence and the internal control sequence are amplified in the same reaction tube. Thus, using this format, if the target DNA is amplified but the internal control is not it is then assumed that the target DNA is present in a proportionally greater amount than the internal control and the positive result is valid as the internal control amplification is unnecessary. If, on the other hand, neither the internal control nor the target is amplified it is then assumed that inhibition of the PCR reaction has occurred and the test for that particular sample is not valid. Exemplary non-limiting internal control nucleic acids that may be used in the methods of the invention include internal control sequences derived from *Citrus sinensis*.

For example, the *Citrus sinensis* (orange) internal control nucleic acid, which includes the nucleic acid sequence of SEQ ID NO: 149 cloned into plasmid pBR322, may be amplified in the presence of a forward primer comprising the nucleic acid sequence 5'-GGA AAT CTA ACG AGA GAG CAT GCT-3' (SEQ ID NO: 150) or 5'-GGA AAT CTA ACG AGA GAG CAT GC-3' (SEQ ID NO: 151) and a reverse primer comprising the nucleic acid sequence 5'-CGA TGC GTG ACA CCC AGG C-3' (SEQ ID NO: 152) or 5'-GAT GCG TGA CAC CCA GGC-3' (SEQ ID NO: 153). In some embodiments, an amplicon produced using these primers is detected by hybridization using a 5' capture probe that includes the oligonucleotide sequence 5'-GAG ACG TTT TGG ATA CAT GTG AAA GAA GGC-3' (SEQ ID NO: 154) and/or a 3' capture probe that includes the oligonucleotide sequence 5' CGA TGG TTC ACG GGA TTC TGC AAT TC-3' (SEQ ID NO: 155) to detect the presence of the *Citrus sinensis* internal control nucleic acid in a biological sample. In some embodiments, the 5' capture probe and/or the 3' capture probe is conjugated to a magnetic nanoparticle.

The assays of the invention can include one or more positive processing controls in which one or more target nucleic acids is included in the assay (e.g., each included with one or more cartridges) at 3× to 5× the limit of detection. The measured $T_2$ for each of the positive processing controls must be above the pre-determined threshold indicating the presence of the target nucleic acid. The positive processing controls can detect all reagent failures in each step of the process (e.g., lysis, PCR, and $T_2$ detection), and can be used for quality control of the system. The assays of the invention can include one or more negative processing controls consisting of a solution free of target nucleic acid (e.g., buffer alone). The $T_2$ measurements for the negative processing control should be below the threshold indicating a negative result while the $T_2$ measured for the internal control is above the decision threshold indicating an internal control positive result. The purpose of the negative control is to detect carry-over contamination and/or reagent contamination. The assays of the invention can include one or more reagent controls. The reagent control will detect reagent failures in the PCR stage of the reaction (i.e. incomplete transfer of master mix to the PCR tubes). The reagent controls can also detect gross failures in reagent transfer prior to $T_2$ detection.

In some embodiments, complex biological samples, which may be a liquid sample (including whole blood, cerebrospinal fluid, urine, synovial fluid, and tissue biopsy homogenates (e.g., skin biopsies) can be directly amplified using about 5%, about 10%, about 20%, about 25%, about 30%, about 25%, about 40%, and about 45% or more complex liquid sample in amplification reactions, and that the resulting amplicons can be directly detected from amplification reaction using magnetic resonance (MR) relaxation measurements upon the addition of conjugated magnetic particles bound to oligonucleotides complementary to the target nucleic acid sequence. Alternatively, the magnetic particles can be added to the sample prior to amplification. Thus, provided are methods for the use of nucleic acid amplification in a complex dirty sample, hybridization of the resulting amplicon to paramagnetic particles, followed by direct detection of hybridized magnetic particle conjugate and target amplicons using magnetic particle based detection systems. In particular embodiments, direct detection of hybridized magnetic particle conjugates and amplicons is via MR relaxation measurements (e.g., $T_2$, $T_1$, $T_1/T_2$ hybrid, $T_2^*$, etc). Further provided are methods which are kinetic, in order to quantify the original nucleic acid copy number within the sample (e.g., sampling and nucleic acid detection at pre-defined cycle numbers, comparison of endogenous internal control nucleic acid, use of exogenous spiked homologous competitive control nucleic acid).

While the exemplary methods described hereinafter relate to amplification using polymerase chain reaction ("PCR"), numerous other methods are known in the art for amplification of nucleic acids (e.g., isothermal methods, rolling circle methods, etc.). Those skilled in the art will understand that these other methods may be used either in place of, or together with, PCR methods. See, e.g., Saiki, "Amplification of Genomic DNA" in PCR Protocols, Innis et al., Eds., Academic Press, San Diego, Calif., pp 13-20 (1990); Wharam et al., Nucleic Acids Res. 29:E54 (2001); Hafner et al., Biotechniques, 30:852 (2001). Further amplification methods suitable for use with the present methods include, for example, polymerase chain reaction (PCR) method, reverse transcription PCR (RT-PCR), ligase chain reaction (LCR), transcription based amplification system (TAS), transcription mediated amplification (TMA), nucleic acid sequence based amplification (NASBA) method, the strand displacement amplification (SDA) method, the loop mediated isothermal amplification (LAMP) method, the isothermal and chimeric primer-initiated amplification of nucleic acid (ICAN) method, and the smart amplification system (SMAP) method. These methods, as well as others are well known in the art and can be adapted for use in conjunction with provided methods of detection of amplified nucleic acid.

The PCR method is a technique for making many copies of a specific template DNA sequence. The PCR process is disclosed in U.S. Pat. Nos. 4,683,195; 4,683,202; and 4,965,188, each of which is incorporated herein by reference. One set of primers complementary to a template DNA are designed, and a region flanked by the primers is amplified by DNA polymerase in a reaction including multiple amplification cycles. Each amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33:556 (1995). Various modified PCR methods are available and well known in the art.

Various modifications such as the "RT-PCR" method, in which DNA is synthesized from RNA using a reverse transcriptase before performing PCR; and the "TaqMan PCR" method, in which only a specific allele is amplified and detected using a fluorescently labeled TaqMan probe, and Taq DNA polymerase, are known to those skilled in the art. RT-PCR and variations thereof have been described, for example, in U.S. Pat. Nos. 5,804,383; 5,407,800; 5,322,770; and 5,310,652, and references described therein, which are hereby incorporated by reference; and TaqMan PCR and related reagents for use in the method have been described, for example, in U.S. Pat. Nos. 5,210,015; 5,876,930; 5,538,848; 6,030,787; and 6,258,569, which are hereby incorporated by reference.

LCR is a method of DNA amplification similar to PCR, except that it uses four primers instead of two and uses the enzyme ligase to ligate or join two segments of DNA. Amplification can be performed in a thermal cycler (e.g., LCx of Abbott Labs, North Chicago, Ill.). LCR can be performed for example, as according to Moore et al., Journal of Clinical Microbiology 36:1028 (1998). LCR methods and variations have been described, for example, in European Patent Application Publication No. EP0320308, and U.S. Pat. No. 5,427,930, each of which is incorporated herein by reference.

The TAS method is a method for specifically amplifying a target RNA in which a transcript is obtained from a template RNA by a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS 86:1173 (1989). The TAS method has been described, for example, in International Patent Application Publication No. WO1988/010315, which is incorporated herein by reference.

Transcription mediated amplification (TMA) is a transcription-based isothermal amplification reaction that uses RNA transcription by RNA polymerase and DNA transcription by reverse transcriptase to produce an RNA amplicon from target nucleic acid. TMA methods are advantageous in that they can produce 100 to 1000 copies of amplicon per amplification cycle, as opposed to PCR or LCR methods that produce only 2 copies per cycle. TMA has been described, for example, in U.S. Pat. No. 5,399,491 which is incorporated herein by reference. NASBA is a transcription-based method which for specifically amplifying a target RNA from either an RNA or DNA template. NASBA is a method used for the continuous amplification of nucleic acids in a single mixture at one temperature. A transcript is obtained from a template RNA by a DNA-dependent RNA polymerase using a forward primer having a sequence identical to a target RNA and a reverse primer having a sequence complementary to the target RNA a on the 3' side and a promoter sequence that recognizes T7 RNA polymerase on the 5' side. A transcript is further synthesized using the obtained transcript as template. This method can be performed as according to Heim, et al., Nucleic Acids Res., 26:2250 (1998). The NASBA method has been described in U.S. Pat. No. 5,130,238, which is incorporated herein by reference.

The SDA method is an isothermal nucleic acid amplification method in which target DNA is amplified using a DNA strand substituted with a strand synthesized by a strand substitution type DNA polymerase lacking 5'→3' exonuclease activity by a single stranded nick generated by a restriction enzyme as a template of the next replication. A primer containing a restriction site is annealed to template, and then amplification primers are annealed to 5' adjacent sequences (forming a nick). Amplification is initiated at a fixed temperature. Newly synthesized DNA strands are nicked by a restriction enzyme and the polymerase amplification begins again, displacing the newly synthesized strands. SDA can be performed according to Walker, et al., PNAS, 89:392 (1992). SDA methods have been described in U.S. Pat. Nos. 5,455,166 and 5,457,027, each of which are incorporated by reference.

The LAMP method is an isothermal amplification method in which a loop is always formed at the 3' end of a synthesized DNA, primers are annealed within the loop, and specific amplification of the target DNA is performed isothermally. LAMP can be performed according to Nagamine et al., *Clinical Chemistry.* 47:1742 (2001). LAMP methods have been described in U.S. Pat. Nos. 6,410,278; 6,974,670; and 7,175,985, each of which are incorporated by reference.

The ICAN method is anisothermal amplification method in which specific amplification of a target DNA is performed isothermally by a strand substitution reaction, a template exchange reaction, and a nick introduction reaction, using a chimeric primer including RNA-DNA and DNA polymerase having a strand substitution activity and RNase H. ICAN can be performed according to Mukai et al., J. Biochem. 142: 273 (2007). The ICAN method has been described in U.S. Pat. No. 6,951,722, which is incorporated herein by reference.

The SMAP (MITANI) method is a method in which a target nucleic acid is continuously synthesized under isothermal conditions using a primer set including two kinds of primers and DNA or RNA as a template. The first primer included in the primer set includes, in the 3' end region thereof, a sequence (Ac') hybridizable with a sequence (A) in the 3' end region of a target nucleic acid sequence as well as, on the 5' side of the above-mentioned sequence (Ac'), a sequence (B') hybridizable with a sequence (Bc) complementary to a sequence (B) existing on the 5' side of the above-mentioned sequence (A) in the above-mentioned target nucleic acid sequence. The second primer includes, in the 3' end region thereof, a sequence (Cc') hybridizable with a sequence (C) in the 3' end region of a sequence complementary to the above-mentioned target nucleic acid sequence as well as a loopback sequence (D-Dc') including two nucleic acid sequences hybridizable with each other on an identical strand on the 5' side of the above-mentioned sequence (Cc'). SMAP can be performed according to Mitani et al., Nat. Methods, 4(3): 257 (2007). SMAP methods have been described in U.S. Patent Application Publication Nos. 2006/0160084, 2007/0190531 and 2009/0042197, each of which is incorporated herein by reference.

The amplification reaction can be designed to produce a specific type of amplified product, such as nucleic acids that are double stranded; single stranded; double stranded with 3' or 5' overhangs; or double stranded with chemical ligands on the 5' and 3' ends. The amplified PCR product can be detected by: (i) hybridization of the amplified product to magnetic particle bound complementary oligonucleotides, where two different oligonucleotides are used that hybridize to the amplified product such that the nucleic acid serves as an interparticle tether promoting particle agglomeration; (ii)

hybridization mediated detection where the DNA of the amplified product must first be denatured; (iii) hybridization mediated detection where the particles hybridize to 5' and 3' overhangs of the amplified product; (iv) binding of the particles to the chemical or biochemical ligandson the termini of the amplified product, such as streptavidin functionalized particles binding to biotin functionalized amplified product.

The systems and methods of the invention can be used to perform real time PCR and provide quantitative information about the amount of target nucleic acid present in a sample (see, e.g., FIG. 52 and Example 18 of WO 2012/054639). Methods for conducting quantitative real time PCR are provided in the literature (see for example: RT-PCR Protocols. Methods in Molecular Biology, Vol. 193. Joe O'Connell, ed. Totowa, N.J.: Humana Press, 2002, 378 pp. ISBN 0-89603-875-0.). Example 18 describes use of the methods of the invention for real time PCR analysis of a whole blood sample.

The systems and methods of the invention can be used to perform real time PCR directly in opaque samples, such as whole blood, using magnetic nanoparticles modified with capture probes and magnetic separation. Using real-time PCR allows for the quantification of a target nucleic acid without opening the reaction tube after the PCR reaction has commenced.

In one approach, biotin or avidin labeled primers can be used to perform real-time PCR. These labels would have corresponding binding moieties on the magnetic particles that could have very fast binding times. This allows for a double stranded product to be generated and allows for much faster particle binding times, decreasing the overall turnaround time. The binding chemistry would be reversible, preventing the primers from remaining particle bound. In order to reverse the binding, the sample can be heated or the pH adjusted.

In another approach, the real-time PCR can be accomplished through the generation of duplex DNA with overhangs that can hybridize to the superparamagnetic particles. Additionally, LNA and/or fluorinated capture probes may speed up the hybridization times.

In still another approach, the particles are designed to have a hairpin that buries the capture probe binding site to the amplicon. Heating the particles to a higher melt temperature would expose the binding site of the hairpin of the capture probes on the particles to allow binding to the target.

In another approach, a probe that hybridizes to an amplicon is tethering two (or more) particles. The reaction would be conducted in the presence of a polymerase with 5' exonuclease activity, resulting in the cleavage of the inter-particle tether and a subsequent change in $T_2$. The polymerase is selected to have exonuclease activity and compatibility with the matrix of choice (e.g. blood). In this approach, smaller particles (e.g., 30 nm CLIO) can be used to reduce steric hindrance of the hybridization to target or subsequent enzymatic digestion during polymerization (see, e.g., Heid et al Genome Research 1996 6: 986-994).

In another approach, two particle populations can be synthesized to bear complementary capture probes. In the absence of amplicon, the capture probes hybridize promoting particle clustering. Upon generation of amplicon, the amplicon can compete, hybridize, and displace the capture probes leading to particle declustering. The method can be conducted in the presence or absence of nanoparticles. The particles free in solution will cluster and decluster due to the thermocycling (because, e.g., the Tm can be below 95° C.). The Tm of the amplicon binding to one of the particle-immobilized capture probes can be designed such that that binding interaction is more favorable than the particle-to-particle binding interaction (by, e.g., engineering point mutations within the capture probes to thermodynamically destabilize the duplexes). In this embodiment, the particle concentration can be kept at, e.g., low or high levels.

Previous work showed that in some cases the presence of particles in the PCR reaction could inhibit PCR. For these inhibitory particles, it is envisioned that the particles could be pulled to the side of the tube (or other location within the container) to keep them out of solution during the PCR reaction. Methods can be used to release the particles back into suspension to allow them to hybridize to the PCR product and then pull them back out of solution. Other previous work has shown that specific formulations of particles are not inhibitory to the PCR reaction and can remain in solution during amplification.

In certain embodiments, the invention features the use of enzymes compatible with whole blood, including but not limited to NEB HemoKlenTaq™, DNAP OmniKlenTaq™, Kapa Biosystems whole blood enzyme, and Thermo-Fisher Finnzymes Phusion® enzyme.

The invention also features quantitative asymmetric PCR. In any of the real-time PCR methods of the invention, the method can involve the following steps:
1. aliquoting whole blood into a prepared PCR mastermix containing superparamagnetic particles;
2. prior to the first PCR cycle, closing the tube until PCR cycling is completed;
3. loading the tube onto thermal cycler;
4. running "n" cycles of standard PCR thermal cycling;
5. conducting a T2 detection (the exact time duration and steps for this vary depending on the biochemical and particle design approach described below); and
6. repeating steps 4 and 5 until enough T2 readings have been taken for an accurate quantification of initial target concentration.

The above methods can be used with any of the following categories of detection of aggregation or disaggregation described herein, including those described in Table 2.

TABLE 2

Categories of Detection of Aggregation or Disaggregation

| Name | Description |
|---|---|
| Clustering-based detection and magnetic separation | Particles > 100 nm or magnetic-separation compatible. Particles removed from solution during PCR $T_2$ goes up with amplicon generation Agitation during step 5 |
| Clustering-based detection with particles >100 nm | Particles > 100 nm Particles do not inhibit PCR $T_2$ goes up with amplicon generation Agitation during step 5 |
| De-clustering-based detection and magnetic separation | Particles > 100 nm Particles on the side of the tube during PCR $T_2$ goes down with amplicon generation Agitation during step 5 |
| De-clustering-based detection with particles >100 nm | Particles > 100 nm Particles do not inhibit PCR $T_2$ goes down with amplicon generation Agitation during step 5 |
| Clustering-based detection with particles <100 nm | Particles < 100 nm (e.g., 30 nm particles) $T_2$ goes down with amplicon appearance (at least for initial cycles, T2 may subsequently increase as cluster size increases) Has potential for much more rapid hybridization times No agitation required to keep particles suspended Particle concentration in nM range |

TABLE 2-continued

Categories of Detection of Aggregation or Disaggregation

| Name | Description |
|---|---|
| De-clustering-based detection with particles <100 nm | Particles < 100 nm (e.g., 30 nm particles)<br>$T_2$ goes up with amplicon appearance<br>$T_2$ could decrease as the cluster size increase above 100 nm<br>No agitation required to keep particles suspended<br>Has potential for most rapid detection times<br>Particle concentration in nM range |

Contamination Control

One potential problem in the use of PCR as an analytical tool is the risk of having new reactions contaminated with old, amplified products. Potential sources of contamination include a) large numbers of target organisms in clinical specimens that may result in cross-contamination, b) plasmid clones derived from organisms that have been previously analyzed and that may be present in larger numbers in the laboratory environment, and c) repeated amplification of the same target sequence leading to accumulation of amplification products in the laboratory environment. A common source of the accumulation of the PCR amplicon is aerosolization of the product. Typically, if uncontrolled aerosolization occurs, the amplicon will contaminate laboratory reagents, equipment, and ventilation systems. When this happens, all reactions will be positive, and it is not possible to distinguish between amplified products from the contamination or a true, positive sample. In addition to taking precautions to avoid or control this carry-over of old products, preferred embodiments include a blank reference reaction in every PCR experiment to check for carry-over. For example, carry-over contamination will be visible on the agarose gel as faint bands or fluorescent signal when TaqMan probes, MolBeacons, or intercalating dyes, among others, are employed as detection mechanisms. Furthermore, it is preferred to include a positive sample. As an example, in some embodiments, contamination control is performed using any of the approaches and methods described in WO 2012/054639.

Typically, the instrumentation and processing areas for samples that undergo amplification are split into pre- and post-amplification zones. This minimizes the chances of contamination of samples with amplicon prior to amplification. For example, the T2Dx® instrument design is such that the pre- and post-amplification instrumentation and processing areas are integrated into a single instrument. This is made possible as described in the sections below.

Systems

The invention provides systems for carrying out the methods of the invention, which may include one or more NMR units, MAA units, cartridge units, and agitation units, as described in WO 2012/054639. Such systems may further include other components for carrying out an automated assay of the invention, such as a thermocycling unit for the amplification of oligonucleotides; a centrifuge, a robotic arm for delivery an liquid sample from unit to unit within the system; one or more incubation units; a fluid transfer unit (i.e., pipetting device) for combining assay reagents and a biological sample to form the liquid sample; a computer with a programmable processor for storing data, processing data, and for controlling the activation and deactivation of the various units according to a one or more preset protocols; and a cartridge insertion system for delivering pre-filled cartridges to the system, optionally with instructions to the computer identifying the reagents and protocol to be used in conjunction with the cartridge. FIG. 42 of WO 2012/054639 depicts an exemplary system of the invention.

The systems of the invention can provide an effective means for high throughput and real-time detection of analytes present in a bodily fluid from a subject. The detection methods may be used in a wide variety of circumstances including, without limitation, identification and/or quantification of analytes that are associated with specific biological processes, physiological conditions, disorders or stages of disorders. As such, the systems have a broad spectrum of utility in, for example, disease diagnosis, parental and forensic identification, disease onset and recurrence, individual response to treatment versus population bases, and monitoring of therapy. The devices and systems can provide a flexible system for personalized medicine. The system of the invention can be changed or interchanged along with a protocol or instructions to a programmable processor of the system to perform a wide variety of assays as described herein. The systems of the invention offer many advantages of a laboratory setting contained in a desk-top or smaller size automated instrument.

The systems of the invention can be used to simultaneously assay analytes that are present in the same liquid sample over a wide concentration range, and can be used to monitor the rate of change of an analyte concentration and/or or concentration of PD or PK markers over a period of time in a single subject, or used for performing trend analysis on the concentration, or markers of PD, or PK, whether they are concentrations of drugs or their metabolites. Thus, the data generated with the use of the subject fluidic devices and systems can be utilized for performing a trend analysis on the concentration of an analyte in a subject.

For example, a subject (e.g., a patient having or suspected of having a disease caused by or associated with a tick-borne pathogen) may be provided with a plurality of cartridge units to be used for detecting a variety of analytes, such as analytes sampled from different tissues, and at predetermined times. A subject may, for example, use different cartridge units on different days of the week. In some embodiments the software on the system is designed to recognize an identifier on the cartridge instructing the system computer to run a particular protocol for running the assay and/or processing the data. The protocols on the system can be updated through an external interface, such as an USB drive or an Ethernet connection, or in some embodiments the entire protocol can be recorded in the barcode attached to the cartridge. The protocol can be optimized as needed by prompting the user for various inputs (i.e., for changing the dilution of the sample, the amount of reagent provided to the liquid sample, altering an incubation time or MAA time, or altering the NMR relaxation collection parameters).

A multiplexed assay can be performed using a variety of system designs. For example, a multiplexed assay can performed using any of the following configurations: (i) a spatially-based detection array can be used to direct magnetic particles to a particular region of a tube (i.e., without aggregation) and immobilize the particles in different locations according to the particular analyte being detected. The immobilized particles are detected by monitoring their local effect on the relaxation effect at the site of immobilization. The particles can be spatially separated by gravimetric separation in flow (i.e., larger particles settling faster along with a slow flow perpendicular to gravity to provide spatial separation based on particle size with different magnetic particle size populations being labeled with different targets). Alternatively, of capture probes can be used to locate magnetic particles in a particular region of a tube (i.e., without aggregation) and immobilize the particles in different locations (i.e., on a functionalized surface, foam, or gel). Optionally, the array is flow through system with multiple coils and magnets, each coil being a separate detector that has the appropriate particles immobilized within it, and the presence of the analyte detected with signal changes arising from clustering in the presence of the analyte. Optionally, once the particles are spatially separated, each individual analyte in the multiplexed assay can be detected by sliding a coil across the sample to read out the now spatially separated particles. (ii) A microfluidic tube where the sample is physically split amongst many branches and a separate signal is detected in each branch, each branch configured for detection of a separate analyte in the multiplexed assay. (iii) An array of 96 wells (or less or more) where each well has its own coil and magnet, and each well is configured for detection of a separate analyte in the multiplexed assay. (iv) A sipper or flow through device with multiple independently addressable coils inside one magnet or inside multiple mini magnets that can be used for sequential readings, each reading being a separate reaction for detection of a separate analyte in the multiplexed assay. (v) A sipper or flow through device with multiple independently addressable wells on a plate inside one magnet or inside multiple mini magnets that can be used for sequential readings using a single sided coil that can be traversed along the plate, each reading being a separate reaction for detection of a separate analyte in the multiplexed assay. (vi) A tube containing two compartments read simultaneously, resulting in one relaxation curve which is then fit using bi-exponential fitting to produce the separate readings for the multiplexed array. (vii) A microfluidics system where each droplet of liquid is moved around individually, to produce readings for the multiplexed array. (viii) Sequential measurements using magnetic separation and resuspension requires novel binding probes or the ability to turn them on and off. This method would be used for nucleic acid analytes in which turn on/off mechanism is based mostly on melting temperature (at higher temperatures hairpin loops relax, denaturation of double strand binding), and hybridization will occur at different temperatures. (ix) Individual capillaries, each equipped with dried particles within them, allow for small volume rapid multiplexing of one small aliquot. The dried particles are spatially separated, and this spatial separation permits the MR Reader to read each capillary tube independently. (x) Binding moieties conjugated to nanoparticles are placed in a gel or other viscous material forming a region and analyte specific viscous solution. The gel or viscous solution enhances spatial separation of more than one analyte in the starting sample because after the sample is allowed to interact with the gel, the target analyte can readily diffuse through the gel and specifically bind to a conjugated moiety on the gel or viscous solution held nanoparticle. The clustering or aggregation of the specific analyte, optionally enhanced via one of the described magnetic assisted agglomeration methods, and detection of analyte specific clusters can be performed by using a specific location NMR reader. In this way a spatial array of nanoparticles, and can be designed, for example, as a 2d array. (xi) Magnetic particles can be spotted and dried into multiple locations in a tube and then each location measured separately. For example, one type of particle can be bound to a surface and a second particle suspended in solution, both of which hybridize to the analyte to be detected. Clusters can be formed at the surface where hybridization reactions occur, each surface being separately detectable. (xii) A spotted array of nucleic acids can be created within a sample tube, each configured to hybridize to a first portion of an array of target nucleic acids. Magnetic particles can be designed with probes to hybridize to a second portion of the target nucleic acid. Each location can be measured separately. Alternatively, any generic beacon or detection method could be used to produce output from the nucleic acid array. (xiii) An array of magnetic particles for detecting an array of targets can be included in a single sample, each configured (e.g., by size, or relaxation properties) to provide a distinct NMR relaxation signature with aggregate formation. For example, each of the particles can be selected to produce distinct $T_2$ relaxation times (e.g., one set of particles covers 10-200 ms, a second set from 250-500 a third set from 550-1100, and so on). Each can be measured as a separate band of relaxation rates. (xiv) For detection of analytes of various size or magnetic particles, or aggregates of various size, a single sample with multiple analytes and magnetic particles can undergo separation in the presence of a magnetic or electric field (i.e., electrophoretic separation of magnetic particles coated with analytes), the separate magnetic particles and/or aggregates reaching the site of a detector at different times, accordingly. (xv) The detection tube could be separated into two (or more) chambers that each contain a different nanoparticle for detection. The tube could be read using the reader and through fitting a multiple exponential curve such as $A*\exp(T2\_1)+B*\exp(T2\_2)$, the response of each analyte could be determined by looking at the relative size of the constants A and B and $T2\_1$ and $T2\_2$. (xvi) Gradient magnetic fields can be shimmed to form narrow fields. Shim pulses or other RF based Shimming within a specific field can be performed to pulse and receive signals within a specific region. In this way one could envision a stratification of the RF pulse within a shim and specific resonance signals could be received from the specific shim. While this method relies on shimming the gradient magnetic field, multiplexing would include then, to rely on one of the other methods described to get different nanoparticles and the clusters to reside in these different shims. Thus there would be two dimensions, one provided by magnetic field shims and a second dimension provided by varying nanoparticle binding to more than one analyte. Nanoparticles having two distinct NMR relaxation signals upon clustering with an analyte may be employed in a multiplexed assay. In this method, the observation that small particles (30-200 nm) cause a decrease in $T_2$ with clustering whereas large particles (>800 nm) cause an increase with clustering. The reaction assay is designed as a competitive reaction, so that with the addition of the target it changes the equilibrium relaxation signal. For example, if the $T_2$ relaxation time is shorter, clusters forming of analyte with small particles are forming. If on the other hand, the $T_2$ relaxation becomes longer, clusters of analyte with larger particles are forming. It's probably useful to change the density/viscosity of the solution with additives such as trehalose or glucose or glycerol to make sure the big particles stay in solution. One nanoparticle having binding moieties to a specific analyte for whose $T_2$ signal is decreased on clustering may be combined with a second nanoparticle having a second binding moiety to a second analyte for whose $T_2$ signal is increased on clustering. In the case for which the sample is suspected to have both analytes and the clustering reaction may cancel each other out (the increased clustering cancels the decreased clustering), one could envision an ordering of the analysis, i.e. addition of competitive binding agents to detect a competitive binding and thus $T_2$ signal that would be related to the presence/absence of the analyte of interest in the sample. Alternatively, if the increased clustering cancels the decreased clustering in this multiplexing format, one could envision use of different relaxation pulse sequences or relaxation determinants to identify the presence/absence or concentration of analyte in the sample. (xvii) Precipitation measurement of particles. In this method, multiple types of particles designed to capture different target sequences of nucleic acid are designed So that the particle size is small enough that the particles bound with analyte remain suspended in solution. Sequential addition of an "initiator" sequence that is complementary to a nucleic acid sequence conjugated to a second set of particles (a larger particle, not necessarily having magnetic properties) and contains a complementary sequence to the captured target DNA sequence. After hybridization, clusters will form if the target DNA sequence is present, e.g. the magnetic nanoparticle conjugated with probe anneals to one specific sequence on the target analyte and the other particle binds to another sequence on the target nucleic acid sequence. These clusters will be big enough to precipitate (this step may require a centrifugation step). In the same reaction, and simultaneously, one could design an additional magnetic particle, second particle set to anneal with a second nucleic acid sequence for which formation of the magnetic nanoparticle-analyte-second particle clusters do not precipitate. In this way sequential addition of particles can result in differential signaling. (xvii) One possible different detection technique includes phase separated signals, which would stem from differing RF coil pulse sequences that are optimized for the conjugated nanoparticle-analyte interaction. Optimally, this could be achieved with multiple coils in an array that would optimize the ability of the different RF pulses and relaxation signal detection to be mapped and differentiated to ascertain the presence/absence of more than one analyte. Multiplexing may also employ the unique characteristic of the nanoparticle-analyte clustering reaction and subsequent detection of water solvent in the sample, the ability of the clusters to form various "pockets" and these coordinated clusters to have varying porosity. For example, linkers having varying length or conformational structures can be employed to conjugate the binding moiety to the magnetic nanoparticle. In this way, more than one type of cluster formed in the presence of an analyte could be designed having the ability of differing solvent water flow, and thus relaxation signal differences, through the aggregated nanoparticle-analyte-nanoparticle formation. In this way, two or more linker/binding moiety designs would then allow for detection of more than one analyte in the same sample. (xviii) The methods of the invention can include a fluorinated oil/aqueous mixture for capturing particles in an emulsion. In this design one hydrophobic capture particle set and an aqueous capture set are used, the hydrophobic capture particle set is designed to bind and aggregate more readily in an hydrophobic environment, whereas the aqueous capture particle set is designed to bind and aggregate in an aqueous environment. Introduction of an analyte containing sample having specific analytes that will bind to either the hydrophobic or aqueous particle, and subsequent mixing in the detection tube having both hydrophobic and aqueous solvents, binding and clustering would then result in a physical separation of analytes to either the aqueous or hydrophobic phase. The relaxation signal could be detected in either solution phase. In the event that the analytes and nanoparticles designed in this manner are physically found in an emulsion created by the mixing of the hydrophobic/aqueous phases, relaxation curves would be distinguishable in the emulsion phase. The detection tube may have a capsular design to enhance the ability to move the capsules through an MR detector to read out the signal. Further, additional use of a fluorescent tag to read out probe identity may be employed, i.e. in the case of two different analytes in the same aqueous or hydrophobic phase, the addition of a fluorescent tag can assist determination of the identity of the analyte. This method is amenable in samples for which limited isolation or purification of the target analyte away from the other material in the sample because the described resonance signals are independent of sample quality. Further, the addition of the fluorescent tag can be added in much higher concentrations that usually added in typical fluorescent studies because these tags will never interfere with the relaxation measurements. In this method, oligonucleotide capture probes that are conjugated to the magnetic nanoparticles are designed so that specific restriction endonuclease sites are located within the annealed section. After hybridization with the sample forming nanoparticle-analyte clusters, a relaxation measurement then provides a base signal. Introduction of a specific restriction endonuclease to the detection tube and incubation will result in a specific reduction of the nanoparticle/analyte cluster after restriction digestion has occurred. After a subsequent relaxation measurement, the pattern of signal and restriction enzyme digestion, one can deduce the target. (xix) In a combined method, a magnetic nanoparticle is conjugated with two separate and distinct binding moieties, i.e. an oligonucleotide and an antibody. This nanoparticle when incubated with a sample having both types of analytes in the sample will form nanoparticle-analyte complexes, and a baseline $T_2$ relaxation signal will be detectable. Subsequent addition of a known concentration of one of the analytes can be added to reduce the clustering formed by that specific analyte from the sample. After known analyte addition a subsequent $T_2$ relaxation signal is detected and the presence/absence of the sample analyte can be surmised. Further, a second analyte can be added to compete with the analyte in the sample to form clusters. Again, after a subsequent $T_2$ relaxation signal detection the presence/absence of the second sample analyte can be surmised. This can be repeated.

Broadly a multiplexed assay employing the methods of this invention can be designed so that the use of one non-superparamagnetic nanoparticle to generate clusters with analyte from a sample, will reduce the overall $Fe^{2+}$ in assay detection vessel and will extend the dynamic range so that multiple reactions can be measured in the same detection vessel.

Multiplexing nucleic acid detection can make use of differing hybridization qualities of the conjugated magnetic nanoparticle and the target nucleic acid analyte. For example, capture probes conjugated to magnetic nanoparticles can be designed so that annealing the magnetic nanoparticle to the target nucleic acid sequence is different for more than one nucleic acid target sequence. Factors for the design of these different probe-target sequences include G-C content (time to form hybrids), varying salt concentration, hybridization temperatures, and/or combinations of these factors. This method then would entail allowing various nucleic acid conjugated magnetic nanoparticles to interact with a sample suspected of having more than one target nucleic acid analyte. Relaxation times detected after various treatments, i.e. heating, addition of salt, hybridization timing, would allow for the ability to surmise which suspected nucleic acid sequence is present or absent in the sample.

Use complimentary amplicons to block one reaction and allow serial hybridizations. In this method, universal amplification primers are used to amplify more than one specific nucleic acid sequence in the starting sample, forming an amplicon pool. Specific oligonucleotide conjugated to magnetic nanoparticles are added to the sample and a relaxation measurement is taken. The sample is then exposed to a temperature to melt the oligonucleotide-analyte interaction and addition of a oligonucleotide that is not attached to a magnetic nanoparticle is added to compete away any analyte binding to the magnetic nanoparticle. A second magnetic nanoparticle having a second oligonucleotide conjugated to it is then added to form clusters with a second specific target nucleic acid analyte. Alternatively, the method could have a step prior to the addition of the second magnetic nanoparticle that would effectively sequester the first magnetic nanoparticle from the reaction vessel, i.e. exposing the reaction vessel to a magnetic field to move the particles to an area that would not be available to the second, or subsequent reaction.

Each of the multiplexing methods above can employ a step of freezing the sample to slow diffusion and clustering time and thus alter the measurement of the relaxation time. Slowing the diffusion and clustering of the method may enhance the ability to separate and detect more than one relaxation time. Each of the multiplexing methods above can make use of sequential addition of conjugated nanoparticles followed by relaxation detection after each addition. After each sequential addition, the subsequent relaxation baseline becomes the new baseline from the last addition and can be used to assist in correlating the relaxation time with presence/absence of the analyte or analyte concentration in the sample.

In some embodiments, the method of multiplexing may involve hidden capture probes. In this method of multiplexing, oligonucleotides conjugated to the magnetic nanoparticles are designed so that secondary structure or a complementary probe on the surface of the particle hides or covers the sequence for hybridization initially in the reaction vessel. These hidden hybridization sequences are then exposed or revealed in the sample vessel spatially or temporally during the assay. For example, as mentioned above, hybridization can be affected by salt, temperature and time to hybridize. Thus, in one form of this method, secondary or complementary structures on the oligonucleotide probe conjugated to the magnetic nanoparticle can be reduced or relaxed to then expose or reveal the sequence to hybridize to the target nucleic acid sample. Further, secondary structures could be reduced or relaxed using a chemical compound, e.g., DMSO. Another method to selectively reveal or expose a sequence for hybridization of the oligonucleotide conjugated nanoparticle with the target analyte is to design stem-loop structures having a site for a restriction endonuclease; subsequent digestion with a restriction endonuclease would relax the stem-loop structure and allow for hybridization to occur. Alternatively, a chemical cut of the stem-loop structure, releasing one end could make the sequence free to then hybridize to the target nucleic acid sequence.

Where the multiplexed array is configured to detect a target nucleic acid, the assay can include a multiplexed PCR to generate different amplicons and then serially detect the different reactions.

The multiplexed assay optionally includes a logical array in which the targets are set up by binary search to reduce the number of assays required (e.g., gram positive or negative leads to different species based tests that only would be conducted for one group or the other).

The systems of the invention can run a variety of assays, regardless of the analyte being detected from a bodily fluid sample. A protocol dependent on the identity of the cartridge unit being used can be stored on the system computer. In some embodiments, the cartridge unit has an identifier (ID) that is detected or read by the system computer, or a bar code (1 D or 2D) on a card that then supplies assay specific or patient or subject specific information needed to be tracked or accessed with the analysis information (e.g., calibration curves, protocols, previous analyte concentrations or levels). Where desired, the cartridge unit identifier is used to select a protocol stored on the system computer, or to identify the location of various assay reagents in the cartridge unit. The protocol to be run on the system may include instructions to the controller of the system to perform the protocol, including but not limited to a particular assay to be run and a detection method to be performed. Once the assay is performed by the system, data indicative of an analyte in the biological sample is generated and communicated to a communications assembly, where it can either be transmitted to the external device for processing, including without limitation, calculation of the analyte concentration in the sample, or processed by the system computer and the result presented on a display readout.

For example, the identifier may be a bar code identifier with a series of black and white lines, which can be read by a bar code reader (or another type of detector) upon insertion of the cartridge unit. Other identifiers could be used, such as a series of alphanumerical values, colors, raised bumps, RFID, or any other identifier which can be located on a cartridge unit and be detected or read by the system computer. The detector may also be an LED that emits light which can interact with an identifier which reflects light and is measured by the system computer to determine the identity of a particular cartridge unit. In some embodiments, the system includes a storage or memory device with the cartridge unit or the detector for transmitting information to the system computer.

Thus, the systems of the invention can include an operating program to carry out different assays, and cartridges encoded to: (i) report to the operating program which pre-programmed assay was being employed; (ii) report to the operating program the configuration of the cartridges; (iii) inform the operating system the order of steps for carrying out the assay; (iv) inform the system which pre-programmed routine to employ; (v) prompt input from the user with respect to certain assay variables; (vi) record a patient identification number (the patient identification number can also be included on the vacutainer holding the blood sample); (vii) record certain cartridge information (e.g., lot number, calibration data, assays on the cartridge, analytic data range, expiration date, storage requirements, acceptable sample specifics); or (viii) report to the operating program assay upgrades or revisions (i.e., so that newer versions of the assay would occur on cartridge upgrades only and not to the larger, more costly system).

The systems of the invention can include one or more fluid transfer units configured to adhere to a robotic arm (see, e.g., FIGS. 43A-43C of WO 2012/054639). The fluid transfer unit can be a pipette, such as an air-displacement, liquid backed, or syringe pipette. For example, a fluid transfer unit can further include a motor in communication with a programmable processor of the system computer and the motor can move the plurality of heads based on a protocol from the programmable processor. Thus, the programmable processor of a system can include instructions or commands and can operate a fluid transfer unit according to the instructions to transfer liquid samples by either withdrawing (for drawing liquid in) or extending (for expelling liquid) a piston into a closed air space. Both the volume of air moved and the speed of movement can be precisely controlled, for example, by the programmable processor. Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion.

A system can include one or more incubation units for heating the liquid sample and/or for control of the assay temperature. Heat can be used in the incubation step of an assay reaction to promote the reaction and shorten the duration necessary for the incubation step. A system can include a heating block configured to receive a liquid sample for a predetermined time at a predetermined temperature. The heating block can be configured to receive a plurality of samples.

The system temperature can be carefully regulated. For example, the system includes a casing kept at a predetermined temperature (i.e., 37° C.) using stirred temperature controlled air. Waste heat from each of the units will exceed what can be passively dissipated by simple enclosure by conduction and convection to air. To eliminate waste heat, the system can include two compartments separated by an insulated floor. The upper compartment includes those portions of the components needed for the manipulation and measurement of the liquid samples, while the lower compartment includes the heat generating elements of the individual units (e.g., the motor for the centrifuge, the motors for the agitation units, the electronics for each of the separate units, and the heating blocks for the incubation units). The lower floor is then vented and forced air cooling is used to carry heat away from the system. See, e.g., FIGS. 44A and 44B of WO 2012/054639.

The MR unit may require more closely controlled temperature (e.g., ±0.1° C.), and so may optionally include a separate casing into which air heated at a predetermined temperature is blown. The casing can include an opening through which the liquid sample is inserted and removed, and out of which the heated air is allowed to escape. See, e.g., FIGS. 45A and 45B of WO 2012/054639. Other temperature control approaches may also be utilized.

Cartridge Units

The invention provides methods and systems that may involve one or more cartridge units to provide a convenient method for placing all of the assay reagents and consumables onto the system. For example, the system may be customized to perform a specific function, or adapted to perform more than one function, e.g., via changeable cartridge units containing arrays of micro wells with customized magnetic particles contained therein. The system can include a replaceable and/or interchangeable cartridge containing an array of wells pre-loaded with magnetic particles, and designed for detection and/or concentration measurement of a particular analyte. Alternatively, the system may be usable with different cartridges, each designed for detection and/or concentration measurements of different analytes, or configured with separate cartridge modules for reagent and detection for a given assay. The cartridge may be sized to facilitate insertion into and ejection from a housing for the preparation of a liquid sample which is transferred to other units in the system (e.g., a magnetic assisted agglomeration unit, or an NMR unit). The cartridge unit itself could potentially interface directly with manipulation stations as well as with the MR reader(s). The cartridge unit can be a modular cartridge having an inlet module that can be sterilized independent of the reagent module.

For handling biological samples, such as blood samples, there are numerous competing requirements for the cartridge design, including the need for sterility for the inlet module to prevent cross contamination and false positive test results, and the need to include reagents in the package which cannot be easily sterilized using standard terminal sterilization techniques like irradiation. An inlet module for sample aliquoting can be designed to interface with uncapped vacutainer tubes, and to aliquot two a sample volume that can be used to perform, for example, an assay to detect a tick-borne pathogen (see FIGS. 7D-7F of WO 2012/054639). The vacutainer permits a partial or full fill. The inlet module has two hard plastic parts, that get ultrasonically welded together and foil sealed to form a network of channels to allow a flow path to form into the first well overflow to the second sample well. A soft vacutainer seal part is used to for a seal with the vacutainer, and includes a port for sample flow, and a venting port. To overcome the flow resistance once the vacutainer is loaded and inverted, some hydrostatic pressure is needed. Every time sample is removed from a sample well, the well will get replenished by flow from the vacutainer.

A modular cartridge can provide a simple means for cross contamination control during certain assays, including but not limited to distribution of amplification (e.g., PCR products) into multiple detection aliquots. In addition, a modular cartridge can be compatible with automated fluid dispensing, and provides a way to hold reagents at very small volumes for long periods of time (in excess of a year). Finally, pre-dispensing these reagents allows concentration and volumetric accuracy to be set by the manufacturing process and provides for a point of care use instrument that is more convenient as it can require much less precise pipetting.

Figure 6:
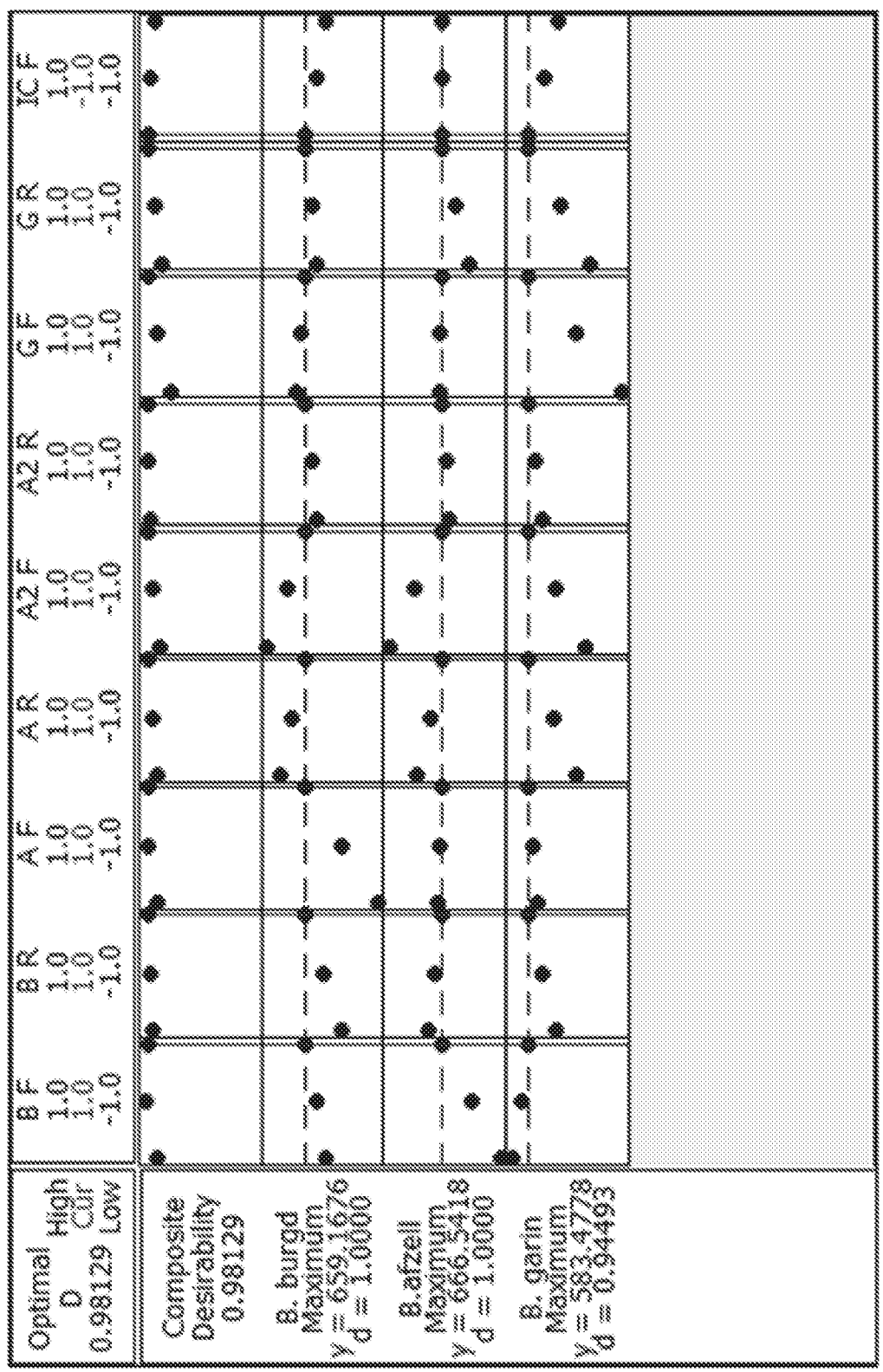
FIG. 6 is a graph showing a response optimization plot generated from a primer ratio factorial. 10 copies of genomic DNA of each of the three Bbsl species in whole blood lysate was tested. Primers are abbreviated according to species: BF and BR=*B. burgdorferi* oppA forward (F) and reverse (R) primers; AF, AR, AF2, AR2=*B. afzelii* S2 and PTS F/R primers; GF and GR=*B. garinii* p24 F/R primers; ICF=internal control F primer (R primer was 300 nM and was not varied). The three conditions for F primers were 74 nM, 112.5 nM, and 150 nM and the three conditions for R primers were 300 nM, 400 nM, and 500 nM. The dashed line depicts the maximum T2 signal achievable in milliseconds with the experimental parameters explored in this factorial.

The modular cartridge of the invention is a cartridge that is separated into modules that can be packaged and if necessary sterilized separately. They can also be handled and stored separately, if for example the reagent module requires refrigeration but the detection module does not. FIG. 6 of WO 2012/054639 shows a representative cartridge with an inlet module, a reagent module and a detection module that are snapped together. In this embodiment, the inlet module would be packaged separately in a sterile package and the reagent and detection modules would be pre-assembled and packaged together.

Figure 8:
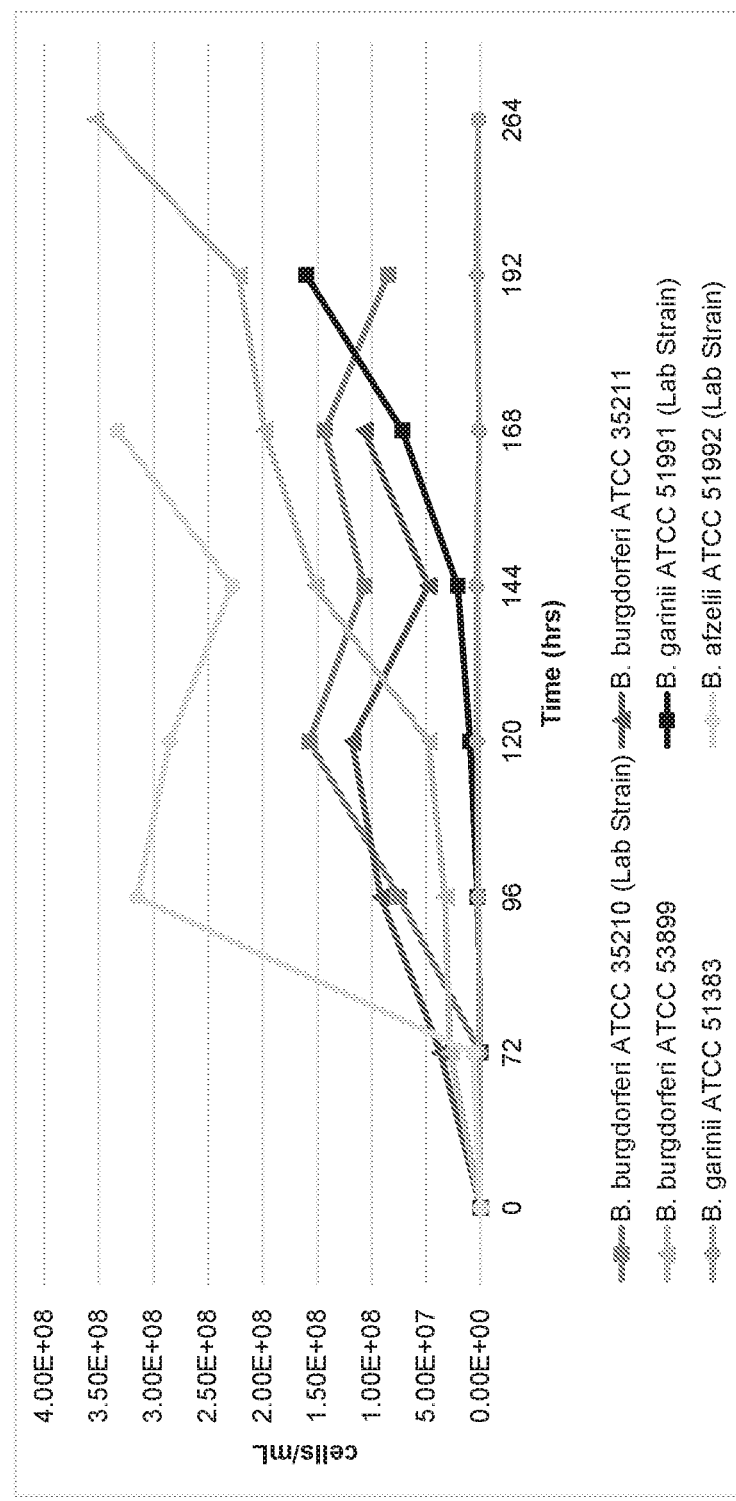
FIG. 8 is a graph showing growth curves of *Borrelia burgdorferi* sensu lato strains. The number of cells per mL (cells/mL) is plotted on the y-axis, and the growth time (min) is plotted on the x-axis.

During storage, the reagent module could be stored in a refrigerator while the inlet module could be stored in dry storage. This provides the additional advantage that only a very small amount of refrigerator or freezer space is required to store many assays. At time of use, the operator would retrieve a detection module and open the package, potentially using sterile technique to prevent contamination with skin flora if required by the assay. The Vacutainer tube is then decapped and the inverted inlet module is placed onto the tube as shown in FIG. 7A of WO 2012/054639. This module has been designed to be easily moldable using single draw tooling as shown in FIGS. 7B and 7C of WO 2012/054639 and the top and bottom of the cartridge are sealed with foil to prevent contamination and also to close the channels. Once the tube has been re-sealed using the inlet module, the assembly is turned right side up and snapped onto the remainder of the cartridge. The inlet section includes a well with an overflow that allows sample tubes with between 2 and 6 ml of blood to be used and still provide a constant depth interface to the system automation. It accomplishes this by means of the overflow shown in FIG. 8 of WO 2012/054639, where blood that overflows the sampling well simply falls into the cartridge body, preventing contamination.

Figure 9:
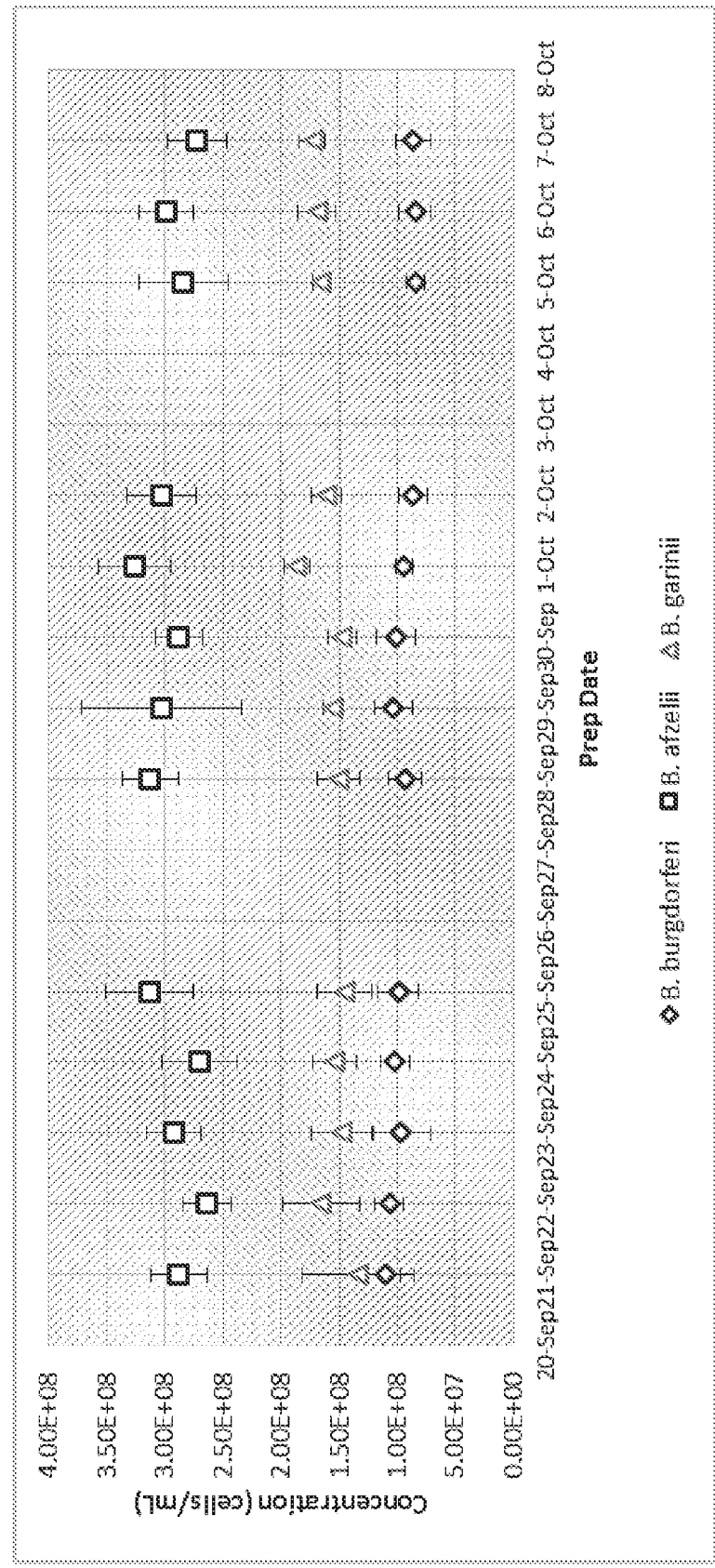
FIG. 9 is a graph showing aliquot and day-to-day reproducibility of the automated cell counting method for Bbsl species described in Example 4.
Figure 10:
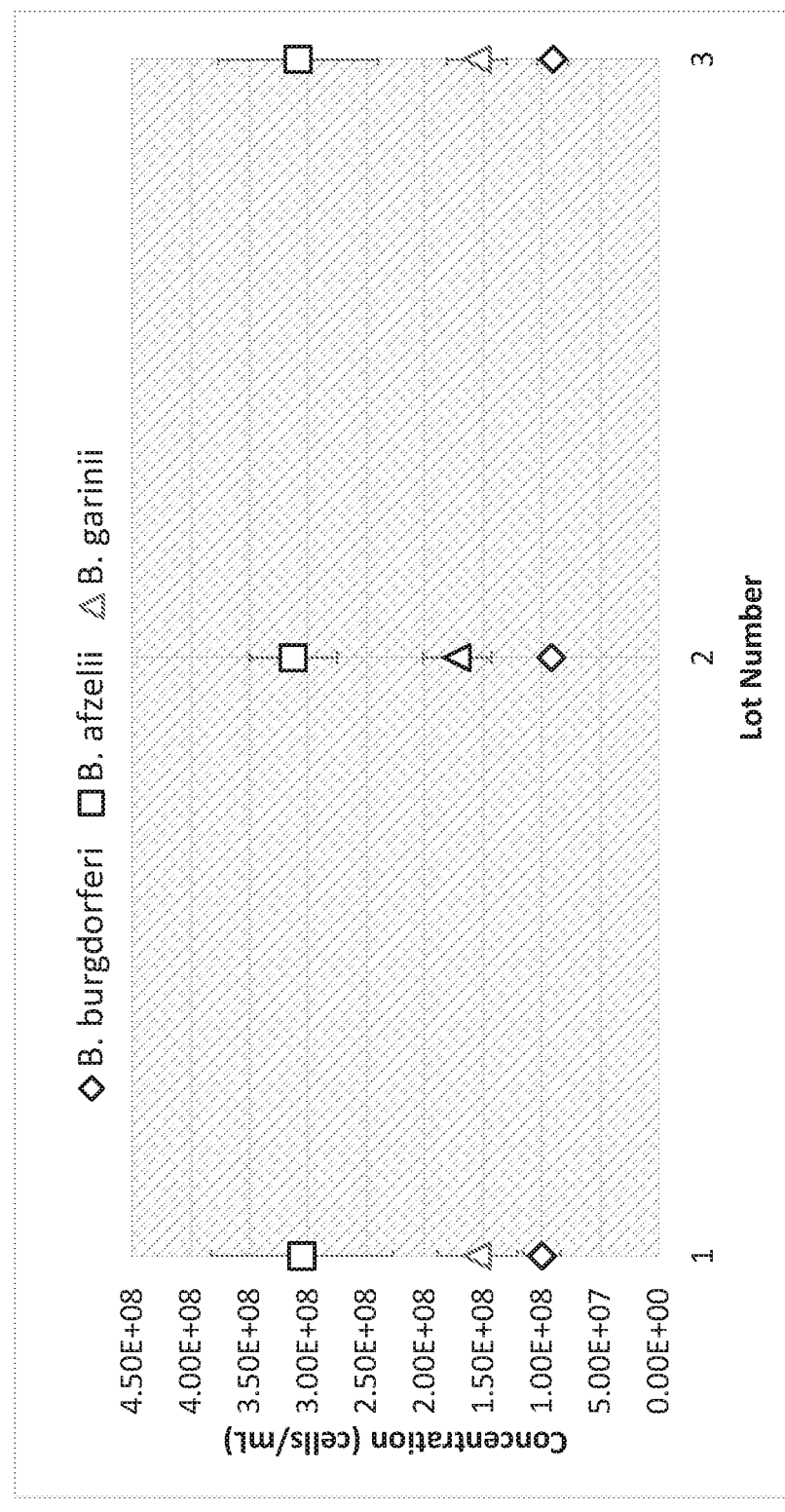
FIG. 10 is a graph showing reproducible growth of all three Bbsl species across three lots.

FIGS. 9A-9C of WO 2012/054639 show the means of storing precisely pipetted small volume reagents. The reagents are kept in pipette tips that are shown in FIG. 9C of WO 2012/054639. These are filled by manufacturing automation and then are placed into the cartridge to seal their tips in tight fitting wells which are shown in a cutaway view FIG. 9B of WO 2012/054639. Finally, foil seals are placed on the back of the tips to provide a complete water vapor proof seal. It is also possible to seal the whole module with a seal that will be removed by the operator, either in place of or in addition to the aforementioned foils. This module also provides storage for empty reaction vessels and pipette tips for use by the instrument while the detection module provides storage for capped 200 μl PCR vials used by the instrument to make final measurements from.

FIGS. 10-13C of WO 2012/054639 show an alternative embodiment of the detection module of the cartridge which is design to provide for contamination control during, for example, pipetting of post-amplification (e.g., PCR) products. This is required because the billion fold amplification produced by DNA amplification (e.g., PCR) presents a great risk of cross contamination and false positives. However, it is desirable to be able to aliquot this mixture safely, because low frequency analytes will have been amplified up and can be distributed for separate detection or identification. There are three ways in which this portion of the cartridge aids in contamination control during this aliquoting operation.

Figure 11:
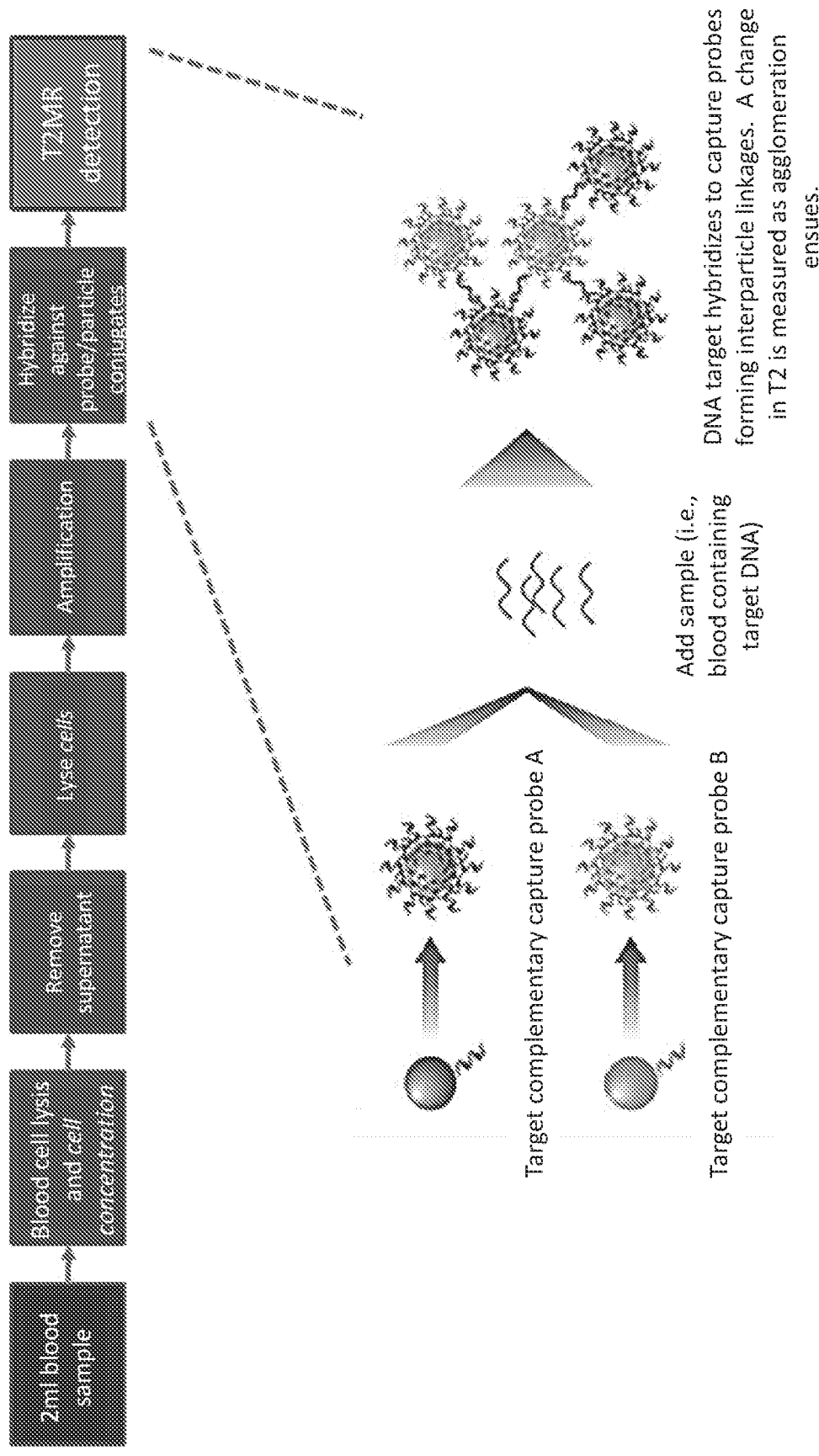
FIG. 11 is a schematic depiction of an exemplary workflow for multiplexed T2MR-based Lyme panel assays starting from whole blood. The workflow is similar to that described in Neely et al. *Sci Transl. Med.* 5(182):182ra54, 2013, except for slight variations in amplification conditions.

First, the cartridge contains a recessed well to perform the transfer operations in as shown in FIGS. 10A and 10B of WO 2012/054639. Second, the machine provides airflow through this well and down into the cartridge through holes in the bottom of the well, as shown in FIG. 11 of WO 2012/054639. The depth of the well is such that a pipette tip will remain in the airflow and prevent any aerosol from escaping. FIG. 12 of WO 2012/054639 depicts a bottom view of the detection module, showing the bottom of the detection tubes and the two holes used to ensure airflow. An optional filter can be inserted here to capture any liquid aerosol and prevent it from entering the machine. This filter could also be a sheet of a hydrophobic material like GORE-TEX® that will allow air but not liquids to escape. Finally, there is a special seal cap on each 200 ul tube to provide a make then break seal for each pipette tip as it enters the vessel, as shown in FIGS. 13A-13C of WO 2012/054639. It is contemplated that the pipette tip used for aliquoting be stored in this well at all, thus making it possible for the tip never to leave the controlled air flow region.

Alternatively, the modular cartridge is designed for a multiplexed assay. The challenge in multiplexing assays is combining multiple assays which have incompatible assay requirements (i.e., different incubation times and/or temperatures) on one cartridge. The cartridge format depicted in FIGS. 14A-14C of WO 2012/054639 allows for the combination of different assays with dramatically different assay requirements. The cartridge features two main components: (i) a reagent module (i.e., the reagent strip portion) that contains all of the individual reagents required for the full assay panel (for example, a panel as described below), and (ii) the detection module. In some embodiments, a cartridge may be configured to detect from 2 to 24 or more pathogens (e.g., 2, 3, 4, 5, 6, 7, 8, 9, 10, 11, 12, 13, 14, 15, 16, 17, 18, 19, 20, 21, 22, 23, 24, or more pathogens). The detection modules contain only the parts of the cartridge that carry through the incubation, and can carry single assays or several assays, as needed. The detection module depicted in FIG. 14B of WO 2012/054639 includes two detection chambers for a single assay, the first detection chamber as the control and the second detection chamber for the sample. This cartridge format is expandable in that additional assays can be added by including reagents and an additional detection module.

The operation of the module begins when the user inserts the entire or a portion of the cartridge into the instrument. The instruments performs the assay actuation, aliquoting the assays into the separate detection chambers. These individual detection chambers are then disconnected from the reagent strip and from each other, and progress through the system separately. Because the reagent module is separated and discarded, the smallest possible sample unit travels through the instrument, conserving internal instrument space. By splitting up each assay into its own unit, different incubation times and temperatures are possible as each multiplexed assay is physically removed from the others and each sample is individually manipulated.

The cartridge units of the invention can include one or more populations of magnetic particles, either as a liquid suspension or dried magnetic particles which are reconstituted prior to use. For example, the cartridge units of the invention can include a compartment including from $1 \times 10^6$ to $1 \times 10^{13}$ magnetic particles (e.g., from $1 \times 10^6$ to $1 \times 10^8$, $1 \times 10^7$ to $1 \times 10^9$, $1 \times 10^8$ to $1 \times 10^{10}$, $1 \times 10^9$ to $1 \times 10^{11}$, $1 \times 10^{10}$ to $1 \times 10^{12}$, $1 \times 10^{11}$ to $1 \times 10^{13}$, or from $1 \times 10^7$ to $5 \times 10^8$ magnetic particles) for assaying a single liquid sample.

Panels

The methods, systems, and cartridges of the invention can be configured to detect a predetermined panel of pathogen-associated analytes. For example, the panel can be a Lyme disease pathogen panel configured to individually detect one, two, or three *Borrelia burgdorferi* sensu lato (*Borrelia burgdorferi, Borrelia afzelii,* and *Borrelia garinii*) species. These species may be detected using individual target nucleic acids or using target nucleic acids that are universal to all three species, for example, target nucleic acids amplified using universal primers. In some embodiments, the panel is configured to detect *Borrelia burgdorferi.* In some embodiments, the panel is configured to detect *Borrelia afzelii.* In some embodiments, the panel is configured to detect *Borrelia garinii.* In some embodiments, the panel is configured to detect *Borrelia burgdorferi* and *Borrelia afzelii.* In some embodiments, the panel is configured to detect *Borrelia burgdorferi* and *Borrelia garinii.* In some embodiments, the panel is configured to detect *Borrelia afzelii* and *Borrelia garinii.* In some embodiments, the panel is configured to detect *Borrelia burgdorferi, Borrelia afzelii* and *Borrelia garinii.*

In some embodiments, the panel can be a Lyme disease-like pathogen panel configured to individually detect between 1 and 18 (e.g., 1, 2, 3, 4, 5, 6, 7, 8, 9, 10, 11, 12, 13, 14, 15, 16, 17, or 18) pathogens selected from the following: a *Rickettsia* spp. (including *Rickettsia rickettsii* and *Rickettsia parkeri*), a *Ehrlichia* spp. (including *Ehrlichia chaffeensis, Ehrlichia ewingii,* and *Ehrlichia muris*-like); a *Coxiella* spp. (including *Coxiella burnetii*), a *Babesia* spp. (including *Babesia microti* and *Babesia divergens*), a *Francisella* spp. (including *Francisella tularensis* (including *F. tularensis* subspp. *tularensis, holarctica, mediasiatica,* and *novicida*), and an *Anaplasma* spp. (including *Anaplasma phagocytophilum*). In cases where multiple species of a genus are detected, the species may be detected using individual target nucleic acids or using target nucleic acids that are universal to all of the species, for example, target nucleic acids amplified using universal primers. For example, in some embodiments, the panel may be configured to individually detect one or more (e.g., 1, 2, 3, 4, 5, or 6) of *Rickettsia rickettsii, Coxiella burnettii, Ehrlichia chaffeensis, Babesia microti, Francisella tularensis*, and *Anaplasma phagocytophilum*. In some embodiments, the panel may be configured to individually detect *Rickettsia rickettsii, Coxiella burnettii, Ehrlichia chaffeensis, Babesia microti, Francisella tularensis*, and *Anaplasma phagocytophilum*. In some embodiments, a Lyme-like disease pathogen panel may be used to detect and/or identify pathogen species that may be present in blood, cerebrospinal fluid (CSF), or synovial fluid.

In some embodiments, any of the panels described herein may be configured to additionally individually detect a meningitis pathogen analyte. For example, a panel may be configured to individually detect *Streptococcus pneumonia, Neisseria meningitides*, or both. In some embodiments, such a panel may be used to detect and/or identify meningitis pathogen species that may be present in blood, cerebrospinal fluid (CSF), or synovial fluid. In particular embodiments, such a panel may be used to detect and/or identify mengingitis pathogen species in CSF.

In some embodiments, a panel is configured to detect the presence of a *Borrelia* spp., for example, *Borrelia americana, Borrelia andersonii, Borrelia bavariensis, Borrelia bissettii, Borrelia carolinensis, Borrelia californiensis, Borrelia chilensis, Borrelia* genomosp. 1 and 2, *Borrelia japonica, Borrelia kurtenbachii, Borrelia lusitaniae, Borrelia myomatoii, Borrelia sinica, Borrelia spielmanii, Borrelia tanukii, Borrelia turdi, Borrelia valaisiana* and/or unclassified *Borrelia* spp. In some embodiments, a Lyme disease pathogen panel may be used to detect and/or identify *Borrelia* species that may be present in blood, cerebrospinal fluid (CSF), urine, or synovial fluid. These species may be detected using individual target nucleic acids or using target nucleic acids that are universal to all *Borrelia* species, for example, target nucleic acids amplified using universal primers.

In some embodiments, a panel may be configured to individually detect one or more (e.g., 1, 2, 3, 4, 5, 6, 7, 8, 9, 10 or 11) of the following: *Borrelia burgdorferi, Borrelia afzelii, Borrelia garinii, Rickettsia rickettsii, Coxiella burnettii, Ehrlichia chaffeensis, Babesia microti, Francisella tularensis, Anaplasma phagocytophilum, Streptococcus pneumonia*, and *Neisseria meningitides*. For example, in some embodiments, a panel may be configured to individually detect *Borrelia burgdorferi, Borrelia afzelii, Borrelia garinii, Rickettsia rickettsii, Coxiella burnettii, Ehrlichia chaffeensis, Babesia microti, Anaplasma phagocytophilum, Francisella tularensis, Streptococcus pneumonia*, and *Neisseria meningitides*. In some embodiments, the panel may be further configured to detect the presence of a *Borrelia* spp., for example, for example, *Borrelia americana, Borrelia andersonii, Borrelia bavariensis, Borrelia bissettii, Borrelia carolinensis, Borrelia californiensis, Borrelia chilensis, Borrelia* genomosp. 1 and 2, *Borrelia japonica, Borrelia kurtenbachii, Borrelia lusitaniae, Borrelia myomatoii, Borrelia sinica, Borrelia spielmanii, Borrelia tanukii, Borrelia turdi, Borrelia valaisiana* and unclassified *Borrelia* spp. In some embodiments, detection of a *Borrelia* spp. may involve detection of a pan-*Borrelia* target nucleic acid sequence.

In any of the above panels, the analyte may be a nucleic acid (e.g., an amplified target nucleic acid, as described above), or a polypeptide (e.g., a polypeptide derived from the pathogen or a pathogen-specific antibody produced by a host subject, for example, an IgM or IgG antibody).

Amplifying Multiple Amplicons Characteristic of a Species for Improved Sensitivity and/or Specificity In some embodiments, the methods of the invention may involve amplification and detection of more than one amplicon characteristic of a species. In some embodiments, amplification of more than one target nucleic acid characteristic of a species increases the total amount of amplicons characteristic of the species in an assay (in other words, the amount of analyte is increased in the assay). This increase may allow, for example, an increase in sensitivity and/or specificity of detection of the species compared to a method that involves amplification and detection of a single amplicon characteristic of a species. In some embodiments, the methods of the invention may involve amplifying 2, 3, 4, 5, 6, 7, 8, 9, or 10 amplicons characteristic of a species. In some embodiments, the species is selected from *Borrelia burgdorferi, Borrelia afzelii, Borrelia garinii, Rickettsia rickettsii, Coxiella burnettii, Ehrlichia chaffeensis, Babesia microti, Francisella tularensis, Anaplasma phagocytophilum, Streptococcus pneumonia*, and *Neisseria meningitides*.

In some embodiments, multiple (e.g., 2, 3, 4, 5, 6, 7, 8, 9, or 10) single-copy loci from a species are amplified and detected. In some embodiments, 2 single-copy loci from a species are amplified and detected. In some embodiments, amplification and detection of multiple single-copy loci from a species may allow for a sensitivity of detection comparable with methods that involve detecting an amplicon that is derived from a multi-copy locus. In some embodiments, methods involving detection of multiple single-copy loci amplified from a microbial species can detect from about 1-10 cells/mL (e.g., 1, 2, 3, 4, 5, 6, 7, 8, 9 or 10 cells/mL) of the microbial species in a liquid sample. In some embodiments, methods involving detection of multiple single-copy loci amplified from a microbial species have at least 95% correct detection when the microbial species is present in the liquid sample at a frequency of less than or equal to 5 cells/mL (e.g., 1, 2, 3, 4, or 5 cells/mL) of liquid sample.

The invention also provides embodiments in which at least three amplicons are produced by amplification of two target nucleic acids, each of which is characteristic of a species. For example, in some embodiments, a first target nucleic acid and a second target nucleic acid to be amplified may be separated (for example, on a chromosome or on a plasmid) by a distance ranging from about 50 base pairs to about 1000 1500 base pairs (bp), e.g., about 50, 100, 150, 200, 250, 300, 400, 500, 600, 700, 800, 900, or 1000, 1100, 1200, 1300, 1400, or 1500 bp base pairs. In some embodiments, a first target nucleic acid and a second target nucleic acid to be amplified may be separated (for example, on a chromosome or on a plasmid) by a distance ranging from about 50 bp to about 1000 bp (e.g., about 50, 100, 150, 200, 250, 300, 400, 500, 600, 700, 800, 900, or 1000 bp). In some embodiments the first target nucleic acid and the second target nucleic acid to be amplified may be separated by a distance ranging from about 50 bp to about 1500 bp, from about 50 bp to about 1400 bp, from about 50 bp to about 1300 bp, from about 50 bp to about 1200 bp, from about 50 bp to about 1100 bp, from about 50 bp to about 1000 bp, from about 50 bp to about 950 bp, from about 50 bp to about 900 bp, from about 50 bp to about 850 bp, from about 50 bp to about 800 bp, from about 50 bp to about 800 bp, from about 50 bp to about 750 bp, from about 50 bp to about 700 bp, from about 50 bp to about 650 bp, from about 50 bp to about 600 bp, from about 50 bp to about 550 bp, from about 50 bp to about 500 bp, from about 50 bp to about 500 bp, from about 50 bp to about 450 bp, from about 50 bp to about 400 bp, from about 50 bp to about 350 bp, from about 50 bp to about 300 bp, from about 50 bp to about 250 bp, from about 50 bp to about 200 bp, from about 50 bp to about 150 bp, or from about 50 bp to about 100 bp. In some embodiments, amplification of the first and second target nucleic acids using individual primer pairs (each having a forward and a reverse primer) may lead to amplification of an amplicon that includes the first target nucleic acid, an amplicon that includes the second target nucleic acid, and an amplicon that contains both the first and the second target nucleic acid. This may result in an increase in sensitivity of detection of the species compared to samples in which the third amplicon is not present. In any of the preceding embodiments, amplification may be by asymmetric PCR.

The invention provides magnetic particles decorated with nucleic acid probes to detect two or more amplicons characteristic of a species. For example, in some embodiments, the magnetic particles include two populations, wherein each population is conjugated to probes such that the magnetic particle that can operably bind each of the two or more amplicons. For instance, in embodiments where two target nucleic acids have been amplified to form a first amplicon and a second amplicon, a pair of particles each of which have a mix of capture probes on their surface may be used. In some embodiments, the first population of magnetic particles may be conjugated to a nucleic acid probe that operably binds a first segment of the first amplicon and a nucleic acid probe that operably binds a first segment of the second amplicon, and the second population of magnetic particles may be conjugated to a nucleic acid probe that operably binds a second segment of the first amplicon and a nucleic acid probe that operably binds a second segment of the second amplicon. For instance, one particle population may be conjugated with a 5' capture probe specific to the first amplicon and a 5' capture probe specific to second amplicon, and the other particle population may be conjugated with a 3' capture probe specific to the first amplicon and a 3' capture probe specific to the second amplicon.

In such embodiments, the magnetic particles may aggregate in the presence of the first amplicon and aggregate in the presence of the second amplicon. Aggregation may occur to a greater extent when both amplicons are present.

In some embodiments, a magnetic particle may be conjugated to two, three, four, five, six, seven, eight, nine, or ten nucleic acid probes, each of which operably binds a segment of a distinct target nucleic acid. In some embodiments, a magnetic particle may be conjugated to a first nucleic acid probe and a second nucleic acid probe, wherein the first nucleic acid probe operably binds to a first target nucleic acid, and the second nucleic acid probe operably binds to a second target nucleic acid. In other embodiments, a magnetic particle may be conjugated to a first nucleic acid probe that operably binds a first target nucleic acid, a second nucleic acid probe that operably binds a second target nucleic acid, and a third nucleic acid that operably binds a third target nucleic acid. In yet other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, and a fourth nucleic acid probe that operably binds a fourth target nucleic acid. In still other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, a fourth nucleic acid probe that operably binds a fourth target nucleic acid, and a fifth nucleic acid probe that operably binds a fifth target nucleic acid. In some embodiments, one population of magnetic particles includes the 5' capture probe for each amplicon to be detected, and the other population of magnetic particles includes the 3' capture probe for each amplicon to be detected.

EXAMPLES

The following examples are put forth so as to provide those of ordinary skill in the art with a complete disclosure and description of how the devices, systems, and methods described herein are performed, made, and evaluated, and are intended to be purely exemplary of the invention and are not intended to limit the scope of what the inventors regard as their invention.

Example 1: Combination Blood Assay

One assay of the present invention is a combination assay that detects *Borrelia burgdorferi* sensu lato (Bbsl)-specific antibodies (IgM and IgG) and Bbsl-specific nucleic acid targets in whole blood specimens. To test a blood sample for the presence of a Bbsl species, for example during diagnosis of Lyme disease, a single blood sample drawn from the subject may be subjected to simple fractionation by high speed centrifugation. Antibodies expressed by a subject in response to Bbsl infection may be present in serum, which is the supernatant produced by the high-speed centrifugation. These antibodies can be detected by a serological test, including those known in the art, or using methods of the invention as described herein. In contrast, pathogen-specific nucleic acids, if present, will be concentrated in the pellet, which may be lysed to form a lysate for detection. The detection may involve an amplification step, such as PCR.

Example 2: Panel for Comprehensive Detection of Tick-Borne Pathogens

This example describes an exemplary panel of the invention. Detection of this panel enables rapid and accurate differential diagnosis of tick-transmitted diseases, which often manifest with similar symptoms. A patient presenting with symptoms consistent with a tick-transmitted disease may be tested for the panel, which may be performed in a multiplexed assay.

The panel includes two sub-panels (see FIG. 1). The first sub-panel, termed "Lyme panel," targets Bbsl and pan-*Borrelia* species, which are extracellular bacteria that are viable in blood and that can also disseminate into and establish themselves in non-blood tissues, including cerebrospinal fluid, urine, and synovial fluid. Titer levels in the different tissues, including blood, vary depending on the stage of the disease. Using the methods of the invention, this panel can be used to rapidly and sensitively diagnose Lyme disease in both the acute (stage I) and later stages. The methods used to detect the Bbsl and pan-*Borrelia* species are as described herein or in WO 2012/054639, for example, Example 22 of WO 2012/054639. Testing for the presence of a pan-*Borrelia* analyte (e.g., a pan-*Borrelia* target nucleic acid that is amplified using primers that are universal to known *Borrelia* species) can enable detection of emerging *Borrelia* species that can cause Lyme disease or very similar diseases, such as *Borrelia myamatoi*, or presently-unclassified *Borrelia* species, especially if the patient tests negative for other pathogens of the panel.

The second subpanel, termed "Lyme-like", includes bacteria that are obligatory intracellular pathogens that infect white blood cells (WBC) such as neutrophils and macropages and the intracellular protozoan *Babesia microti*, which is an intracellular protozoan parasite specific to red blood cells (RBC). These species replicate within blood cells, and also depend on blood cells to disseminate into other tissues. Since these species are present within WBC or RBC, isolation of buffy coat or RBC cells after sedimentation will concentrate these species. Alternatively, *Babesia* may be released from RBC by hypotonic lysis of erythrocytes, followed by sedimentation with the WBC fraction and extracellular pathogens (Bbsl fraction) by centrifugation prior to mechanical or heat lysis and amplification.

The panel also detects two pathogens, *S. pneumoniae* and *N. meningitis*, that can cause meningitis and neurological disease, which can have similar symptoms as tick-transmitted diseases.

One way to use this panel is as follows. When starting from blood, the sample is split into about 2-8 mL of whole blood (for the Lyme panel) and a smaller volume of about 0.1-2 mL (non-Lyme panel) whole blood. The fraction for the Lyme panel is subjected to minimal sample preparation (for example, sample preparation may be performed as described in Example 22 of WO 2012/054639 or as described below in Example 3) to avoid loss of analyte. In contrast, the fraction for the non-Lyme panel may subjected to WBC concentration followed by hypotonic RBC lysis, to enrich and purify the WBC before mechanical or simple heat lysis to release the DNA from the intracellular pathogens. This may be followed by amplifying and detecting species-specific target nucleic acids.

Example 3: Workflow for Detecting Tick-Borne or Other Pathogens Using the T2Dx® Instrument The methods described herein may be performed using a T2Dx® instrument (T2 Biosystems, Lexington, Mass.). A sample obtained from a subject (e.g., a 1.7-2 mL whole blood sample from a human suspected of being infected with a tick-borne pathogen) is inserted into the device, for example, as described in WO 2012/054639. If the sample is a whole blood sample, the next step typically includes blood cell lysis and concentration, for instance, by (a) by mixing the whole blood sample with an erythrocyte lysis agent solution to produce disrupted red blood cells, (b) centrifuging the sample to form a supernatant and a pellet, discarding some or all of the supernatant, and optionally washing the pellet (for example, by resuspending the pellet in volume of a buffer, and centrifuging the pellet), and (c) lysing cells in the pellet (which may include white blood cells and/or pathogen cells) to form a lysate. The lysis may involve mechanical lysis, such as beadbeating or sonication. Next, one or more target nucleic acid(s) is amplified in the lysate, for instance, using PCR. Typically, the lysate volume used for amplification is approximately 50 μL. As an example, target nucleic acids for the members of the panel described in Example 2 may be amplified in the lysate. Typically, the target nucleic acid(s) are amplified without performing any wash steps or other purification steps, such that amplification occurs in the presence of whole blood proteins and non-target nucleic acids (e.g., subject DNA from white blood cells). Next, each target nucleic acid is hybridized with magnetic particles coated with specific probes that specifically hybridize to the target nucleic acid, leading to changes in the specific aggregation of the magnetic particles in the presence of the amplified target nucleic acid. Finally, the device measures the $T_2$ relaxation response in the sample to determine the presence or absence of the pathogen. This exemplary workflow is also shown in FIG. 2.

This approach has a number of advantages. Using small sample volumes of whole blood (e.g., between 1.7-8 mL of whole blood), this workflow allows for detection of pathogens at very low titer (as low as 1 colony-forming unit (CFU)/mL) in the blood. Further, the entire workflow can be performed very rapidly, allowing for detection of the pathogen(s) present in the sample within 3 h. The workflow allows for accurate and specific detection of pathogens (at least 95% correct detection when the pathogen is present in the blood at a frequency of less than or equal to 10, 5, or 1 CFU/mL of blood). Further, the target nucleic acid can be detected in complex samples with minimal or no sample preparation. For instance, the target nucleic acid(s) may be amplified in the presence of from 0.5 μg to 60 μg of subject DNA (e.g., DNA from white blood cells). This workflow enables rapid and comprehensive detection of pathogens that cause Lyme disease and Lyme-like diseases in complex biological samples, allowing for accurate diagnosis of tick-transmitted diseases.

Example 4: Development of a Multiplexed Lyme Panel Assay for Detection of *Borrelia* Species This example describes the development of a Lyme panel assay that allows rapid (within 3-5 hours), highly sensitive, and accurate detection of *Borrelia* species (including *B. burgdorferi*, *B. garinii*, and *B. afzelii*) with a limit of detection of less than 10 cells/mL of biological sample. This panel may be used for the presumptive diagnosis of Lyme disease (also known as borreliosis or Lyme borreliosis), and is typically performed independent of blood culture or other pre-culture such as skin culture.

A. Target Selection

T2MR nucleic acid panels utilize a pair of primers to amplify a target locus and a pair of capture probes that are conjugated to superparamagnetic particles and are used to detect the amplified product. Specificity is made possible by either or both of primers and probes. Typically, the amplified product is between about 100 and about 450 bp long and the probes are spaced about 50-200 nucleotides (nt) apart.

All *B. burgdorferi* B31 chromosomally- and essential plasmid-encoded annotated open reading frames (ORFs) were compared against the other two Bbsl species (*Borrelia afzelii* and *Borrelia garinii*) as well as near-neighbor species (e.g., *Borrelia chilensis, valaisiana, finlandensis*, and *bissettii*) and those ORFs that displayed sequence diversities between species or were species-specific were selected for further examination. In total 796 annotated ORFs encoded on the chromosome, 54 on essential plasmid lp54, and 26 on essential plasmid cp26 were subjected to blastn against the other two Bbsl species (*B. afzelii* pKo and *B. garinii* SZ) and exclusive near-neighbors *B. valaisiana* Tom4006, *B. chilensis* VA1, *B. bissettii* DN127. Selected targets are described above in the Detailed Description of the Invention under the heading "Analytes."

B. Primer and Probe Design

All primers and probes were designed by using VisualOMP (DNA Software, Ann Arbor, Mich.). Parameters including di- and monovalent cation concentrations, glycerol content, and the like, were adjusted to closely reflect T2MR panel amplification (for primers) and hybridization (for probes) conditions as described in Neely et al. Science Translational Medicine 5(182): 182ra54, which is incorporated herein by reference in its entirety. $T_m$ for primers were targeted to be 65° C. (±1.5° C.) and for probes to be 68° C.

Primers with potential to form homodimers, heterodimers or secondary structures that could lead to internal 3' extensions were excluded. All primers and probes were screened for potential mispriming against GenBank_nr database (excluding non-cultured organisms). In certain cases, base modifications such as diaminopurine were substituted for adenine in the primer sequence to achieve the desired $T_m$ of 65° C. Adenine to diaminopurine substitutions can increase basepair stability depending on sequence context (Bailly et al. *Nucl. Acids Res.* 26:4309-4314).

C. Magnetic Particles

Magnetic particles similar to those described in WO 2012/054639 were used in this Example. Briefly, the magnetic particles are carboxylate-modified superparamagnetic particles that were functionalized with species-specific aminated oligonucleotide capture probes. The carboxylate modified particles are uniform, colloidally stable, non-porous spheres. The carboxylate-modified particle was made by free-radical emulsion polymerization of styrene and acrylic acid. The superparamagnetic property of these particles is made possible by magnetite ($Fe_3O_4$) that is coated onto this core particle and then encapsulated with polymers. These particles have a nominal diameter of 0.8 micrometers (800 nm) and have strong physical integrity and have stability of 5 years.

The capture probe that hybridizes to the 5' end of the amplicon was 3'-aminated, whereas the capture probe that hybridizes to the 3' end of the amplicon was 5'-aminated. The aminated DNA capture probes were covalently attached to the carboxylated particles via 1-Ethyl-3-(3-dimethylaminopropyl)carbodiimide (EDC, a water soluble carbodiimide) bioconjugation chemistry. Subsequent washes removed any unbound DNA. Functional performance of the capture-probe conjugated particles was evaluated by measuring the T2MR signal produced in a titration series using a synthetic oligonucleotide that has a sequence identical to the target sequence.

D. Exemplary T2MR Assay Conditions

To perform the assays, 1.75 mL of spiked whole blood was added to a lysis tube, mixed with lysis detergent by pipetting, and incubated for about 5 minutes. The tubes were centrifuged for 10 min at 11,700 g, and the supernatant was removed. 150 µL of Internal Control was added and mixed. The tubes were centrifuged for 10 min at 11,700 g, and the supernatant was removed. 50 µL of Internal Control was added, and the samples were bead beat for 5 min at 3200 rpm using 700-850 µm zirconium oxide beads. The tubes were then centrifuged for 2 min at 6000 g. The lysate was mixed and 50 µL was added to 30 µL of a reagent mix containing deoxynucleotides and PCR primers as described above, denatured at 95° C. for 5 min, centrifuged at 8,000 g, followed by addition of a whole blood compatible thermophilic DNA polymerase and PCR amplification as described below. Another possible workflow is as follows: 50 µL of washed and bead-beat lysate is transferred to a tube. 30 µL of a mixture including PCR buffer and primers is added to the tube, followed by denaturation at 95° C. for 5 min. The tube is centrifuged at 6000 g for 5 min, and 20 µL of Formulated Enzyme (a hot-start thermophilic DNA polymerase and dNTPs) is added, followed by PCR amplification.

Thermocycling was conducted using the following cycle parameters: initial denaturation at 95° C., 46 cycles consisting of a 20 sec denaturation step at 95° C., a 30 sec annealing step at 58° C., a 30 sec extension step at 68° C., followed by a final extension of 3-10 min at 68° C. Each magnetic particle hybridization mix was vortexed prior to aspirating and dispensing. 15 µL of the magnetic particle hybridization mixes were added to each designated detection tube. 15 µL of diluted amplicon supernatants are added to the tubes containing the magnetic particle hybridization mixes, and the samples are hybridized for 30 min at 62° C. T2MR detection was performed as described in Example 3 and in International Patent Application Publication No. WO 2012/054639.

E. Multiplexed Lyme Panel Assay Development

Following primer and probe design, the following testing strategy was used to screen and select suitable candidates for a multiplexed Lyme panel assay.

Figure 3:
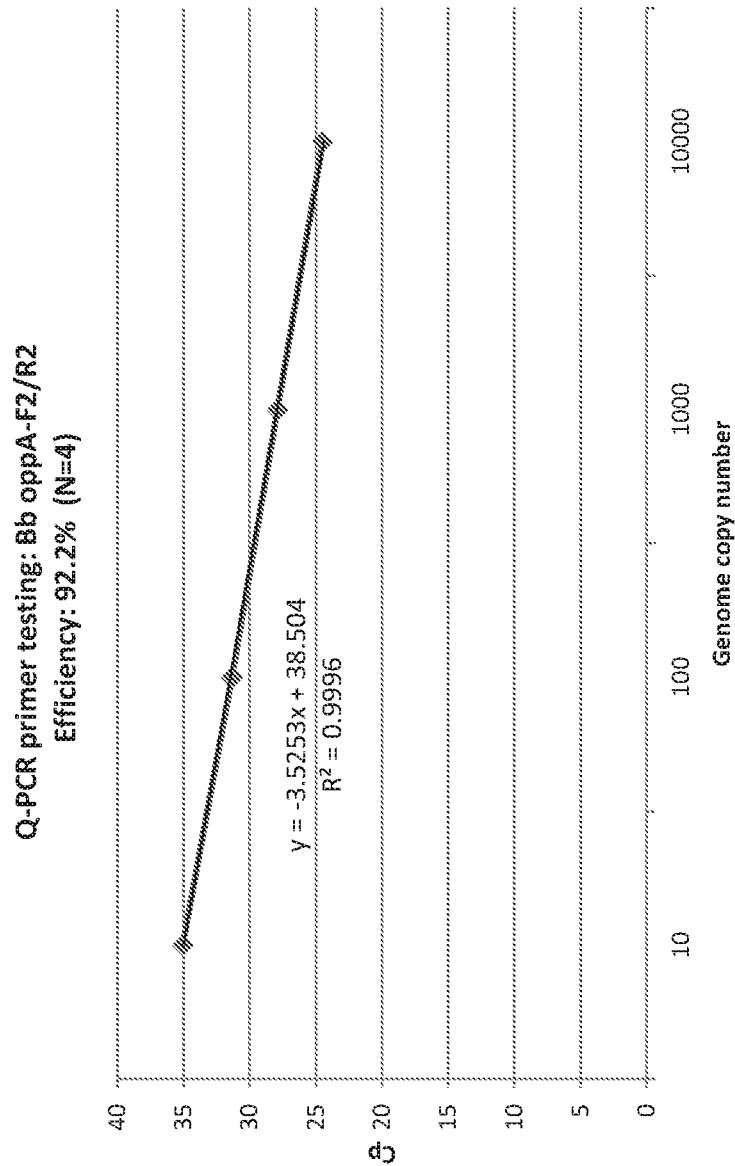
FIG. 3 is a graph showing quantitative polymerase chain reaction (Q-PCR) tests of primer pair F2/R2 (SEQ ID NO: 5 and 6, respectively) specific for *Borrelia burgdorferi* (Bb) oppA (lp54 encoded). The assay was performed in buffer with purified genomic DNA isolated from Bb strain B31. All concentrations were tested in quadruplicate and detection was by SYBR® Green.

First, primer pairs were screened in quantitative PCR (Q-PCR) assays on a Roche LC480 LIGHTCYCLER® instrument. For most targets, multiple primer pairs were tested at 200 nM primer concentration using T2MR panel conditions for amplification efficiency. Detection was by SYBR® Green. FIG. 3 shows an example of a primer pair that was selected for subsequent multiplexed assay development.

Figure 4:
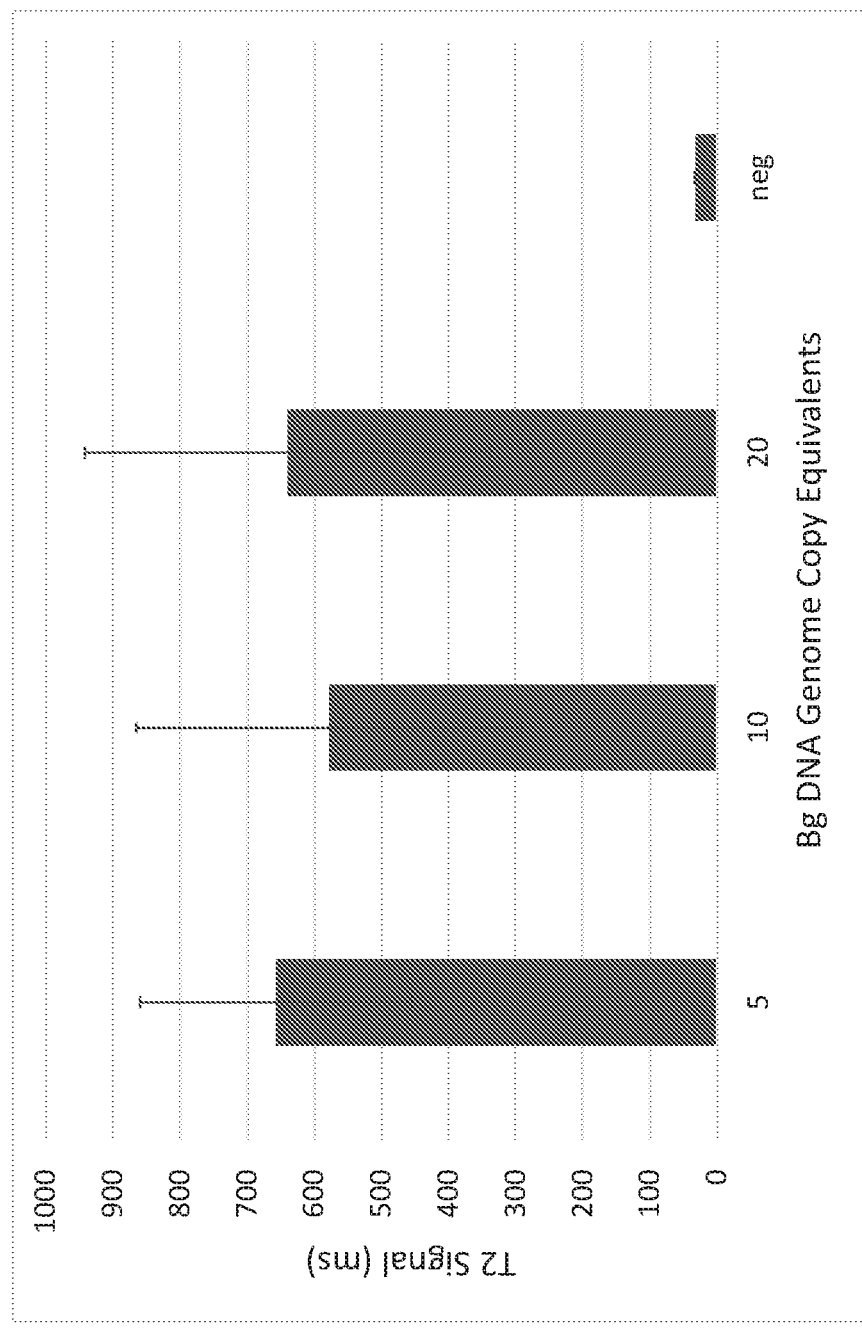
FIG. 4 is a graph showing an exemplary single-plex T2MR-based Lyme panel assay using primers and probes specific for a *Borrelia garinii* oppA target (Forward primer; SEQ ID NO: 9; reverse primer: SEQ ID NO: 10; 5' capture probe: SEQ ID NO: 11; 3' capture probe: SEQ ID NO: 12).

Second, the primer pairs and probes were tested in single-plex T2MR assays. Whole blood lysate was prepared according to the exemplary T2MR assay conditions described above. Blood lysate was spiked with isolated DNA from Bbsl species at different concentrations. Each assay contained 50 µl of concentrated blood lysate that corresponds to lysate that would be obtained from 2 mL of blood. Products were detected by hybridization using a pair of capture probe-decorated magnetic particles. These particles were prepared by conjugation of oligonucleotide capture probes to superparamagnetic particles prior to hybridization as described above. Hybridization results in a T2MR signal increase (measured in milliseconds or ms) as compared to a baseline value that occurs when particles are not clustered in absence of amplification product. FIG. 4 shows an example of a primer and probe combination that resulted in detection of 5 genome copy number equivalents of *Borrelia garinii* (Bg) DNA spiked into 50 µl of blood lysate. Table 3 shows targets, primers, and probes that were tested in single-plex T2MR assays.

TABLE 3

Primer and Probe Combinations Tested in Single Plex Assays

| Target | | Primers (F = Forward; R = reverse) | Probes (Probes are shown without linkers and spacers) | Single Plex Sensitivity (gDNA in Blood Lysate) |
|---|---|---|---|---|
| *B. burgdorferi* | oppA encoded on lp54: periplasmic oligopeptide ABC transporter substrate binding subunit | F: AGAGGACTTTTAATACTGGGCATTGCTG (SEQ ID NO: 1); R: GGCCATTATGTAGGAATCTCTAATGGTGC (SEQ ID NO: 2) | 5' Capture: CTAAACCAAAGATGATATATTGTCTTTGGTG (SEQ ID NO: 3) 3' Capture: GGACATTCTTACGACAACACCTGCT (SEQ ID NO: 4) | 5 copies (100%; N = 4) 10 copies (100%; N = 4) |
| | | F2: ACATAATGGCCTTAGAAATGAGCTTGATG (SEQ ID NO: 5) R2: CCCGCTTGTAACCATGTTTTCTGAGC (SEQ ID NO: 6) | 5' Capture: AACCTATTAACATCAAAGATAAAAATGC (SEQ ID NO: 7) 3' Capture: GCTTACACACCCATATTTATACCC (SEQ ID NO: 8) | 5 copies (100%; N = 4) 10 copies (100%; N = 4) |
| | craspl encoded on lp54: outer surface protein, complement regulator-acquiring surface protein (translocation into tissue) | F: ATTTATTAAAGTGTTCTGCCAGTATTTTCTCAT (SEQ ID NO: 130) R: GCATTCAATTCCAAATAGAGCAAATTTAGAAT (SEQ ID NO: 131) | 5' Capture: CTTGAGTATTTTGATTGTAAACTTTAAGAG (SEQ ID NO: 132) 3' Capture: TGACTTAGATTTTCTACTCCATTTTGTA (SEQ ID NO: 133) | 5 copies (75%; N = 4) 10 copies (100%; N = 4) |
| | | F2: GCCCCATGATATGTGATAAATCAATCTTCC (SEQ ID NO: 147) R2: GCAAACACTAAGCCAAAAAAAAATCACCAA (SEQ ID NO: 139) | 5' Capture: CAATAAGATCGTAAGGACCAACTTT (SEQ ID NO: 141) 3' Capture: AGGTCTCCAGATTTATCTTCAAAAT (SEQ ID NO: 140) | 5 copies (50%; N = 4) 10 copies (100%; N = 4) |
| | | F3: AGCGTTCTTTTTATTTTCATTTGGATATCTTCA (SEQ ID NO: 138) R3: GCAAACACTAAGCCAAAAAAAATCACCAA (SEQ ID NO: 139) | 5' Capture: AGGTCTCCAGATTTATCTTCAAAAT (SEQ ID NO: 140) 3' Capture: CAATAAGATCGTAAGGACCAACTTT (SEQ ID NO: 141) | 5 copies (100%; N = 4) 10 copies (100%; N = 4) |
| *B. garinii* | p24: surface protein p24 | F: GGTGATGTTAAATCGTTAACAGAAGTTGCTACT GA (SEQ ID NO: 60) R: TTGTCTGTTAACATCCTTAGAAAGCCAATC (SEQ ID NO: 63) (contains diaminopurine) | 5' Capture: TTGAGGATGGCAATTCTTTTGTTCTGGG (SEQ ID NO: 66) 3' Capture: AAGCTGAGTATGAGAAATCCTATAAAG (SEQ ID NO: 68) | 5 copies (67%; N = 6) 10 copies (67%; N = 6) |
| | oppA encoded on lp54: periplasmic oligopeptide ABC transporter substrate binding subunit | F: CCTAAATGTTAAACCCCTTGACAACCCA (SEQ ID NO: 26) R: CTGTCCTTTT/i6diPr/GA/i6diPr/ TATTTGATATGTGGCTA (SEQ ID NO: 27) F2: | 5' Capture: TCTAGCGGTTGACAGAGAAACATTG (SEQ ID NO: 29) 3' Capture: AAAAATTAAAACCATATAACCCACGAA (SEQ ID NO: 30) 5' Capture: | 5 copies (50%; N = 4) 10 copies (100%; N = 4) 5 copies |

TABLE 3-continued

Primer and Probe Combinations Tested in Single Plex Assays

| Target | | Primers (F = Forward; R = reverse) | Probes (Probes are shown without linkers and spacers) | Single Plex Sensitivity (gDNA in Blood Lysate) |
|---|---|---|---|---|
| | dbpB encoded on Ip24: decorin binding protein B | F: GGATATTCAAATCCTGAGGTTGACGAACTA (SEQ ID NO: 9) R2: CTGATAGGGCAAATCTTTCTGAAGCA (SEQ ID NO: 10) | 5' Capture: CTGAGATTGAAGTTGACGAAAAATCAG (SEQ ID NO: 11) 3' Capture: GATCATCCAATAATTCCAATCTACAGCG (SEQ ID NO: 12) | 5 copies (100%; N = 4) 10 copies (100%; N = 4) |
| | | F: GCTGGCAGCCTGTAATTTTGGATTAACA (SEQ ID NO: 120) R: TTGTCACTTTAGAACCAGTTGCGG (SEQ ID NO: 121) | 5' Capture: CAATGCTTGAATCGTCTTCTGATGATG (SEQ ID NO: 122) 3' Capture: AATTTTAAAGCTTTTACAGGCACCG (SEQ ID NO: 123) | 5 copies (50%; N = 4) 10 copies (100%; N = 4) |
| | ORF 69226: Ip54 encoded conserved lipoprotein | F: GGCTATGTTTGATTTCATGCTTGAAGTTAC (SEQ ID NO: 124) R: ACTTATTTTTTTTCCTCATCGTCAAGT (SEQ ID NO: 125) | 5' Capture: GGATCATTAGATGAGATTGGAATAAAGGA (SEQ ID NO: 127) 3' Capture: AGGCTAAAATAGAAAATAAACTAGAAGG (SEQ ID NO: 128) | 5 copies (50%; N = 4) 10 copies (100%; N = 4) |
| | | F: CAAATTCTCAATACTTGCGCTGTTACTGA (SEQ ID NO: 111) R: TCTAGIGGGATTGAGCTTTCAGATTCA (SEQ ID NO: 112) | 5' Capture: CAGGTTCAATTTTTCAATTTCTAAAATAGG (SEQ ID NO: 118) 3' Capture: TTCGTGTTCATATTGGCATTACAGCT (SEQ ID NO: 117) | 5 copies (75%; N = 4) 10 copies (100%; N = 4) |
| | chbC: cp26 encoded chitibiose transporter protein | F: GCTGGGCAATCAGATTGGATGCCTTACGGAG (SEQ ID NO: 97) R: CATAATTATTTCGIGAAAAGGCTGCCTGCTA (SEQ ID NO: 98) | 5' Capture: GGGATTCAGCCTAATICATGGTTTTCCTG (SEQ ID NO: 100) 3' Capture: GTACTTTCCATTGTGGCTCAAGGTG (SEQ ID NO: 101) | 5 copies (100%; N = 4) 10 copies (100%; N = 4) |
| B. afzelii | gua B encoded on cp26: Inosine-5'-monophosphate dehydrogenase | F: CCGTGGGCAGAGTCTATGACAATCAG (SEQ ID NO: 13) R: GCCCAAAAAACCATCAACACTAATAAGG (SEQ ID NO: 14) | 5' Capture: TAGCAGCTCCTACTCCTTAGCTTGC (SEQ ID NO: 15) 3' Capture: AATATTGCTTTGTAAGCATTTTGGTTT (SEQ ID NO: 16) | 5 copies (25%; N = 4) 10 copies (75%; N = 4) |
| | PTS encoded on cp26: glucose transporter subunit | F: CAAGGTGCAATGACTTTGTTTGGGCA (SEQ ID NO: 17) R: GCAACTTCAAAGTGTACAGTATTGGTATCCC (SEQ ID NO: 18) | 5' Capture: TTGTAGAACAATCTGGGCTTTTGG (SEQ ID NO: 19) 3' Capture: GGAGAACTCATATCAGGAGGACACAA (SEQ ID NO: 20) | 5 copies (50%; N = 4) 10 copies (75%; N = 4) |
| | Lipoprotein S2 encoded on the chromosome: antigenic | F: CCACAAACTGCACAACAAAACGGAGC (SEQ ID NO: 52) R: | 5' Capture: GGAAACCCAATAAGIGATGAATTGCC (SEQ ID NO: 56) 3' Capture: | 5 copies (25%; N = 4) 10 copies (83%; N = 4) |

TABLE 3-continued

Primer and Probe Combinations Tested in Single Plex Assays

| Target | Primers (F = Forward; R = reverse) | Probes (Probes are shown without linkers and spacers) | Single Plex Sensitivity (gDNA in Blood Lysate) |
|---|---|---|---|
| determinant (surface protein) S2 | CCAAATTTGTTTTGAATTCTGGTATTGCTTG (SEQ ID NO: 53) (contains diaminopurine) | GATGGACAAGCAATGCCAGAATTC (SEQ ID NO: 58) | |

Figure 5:
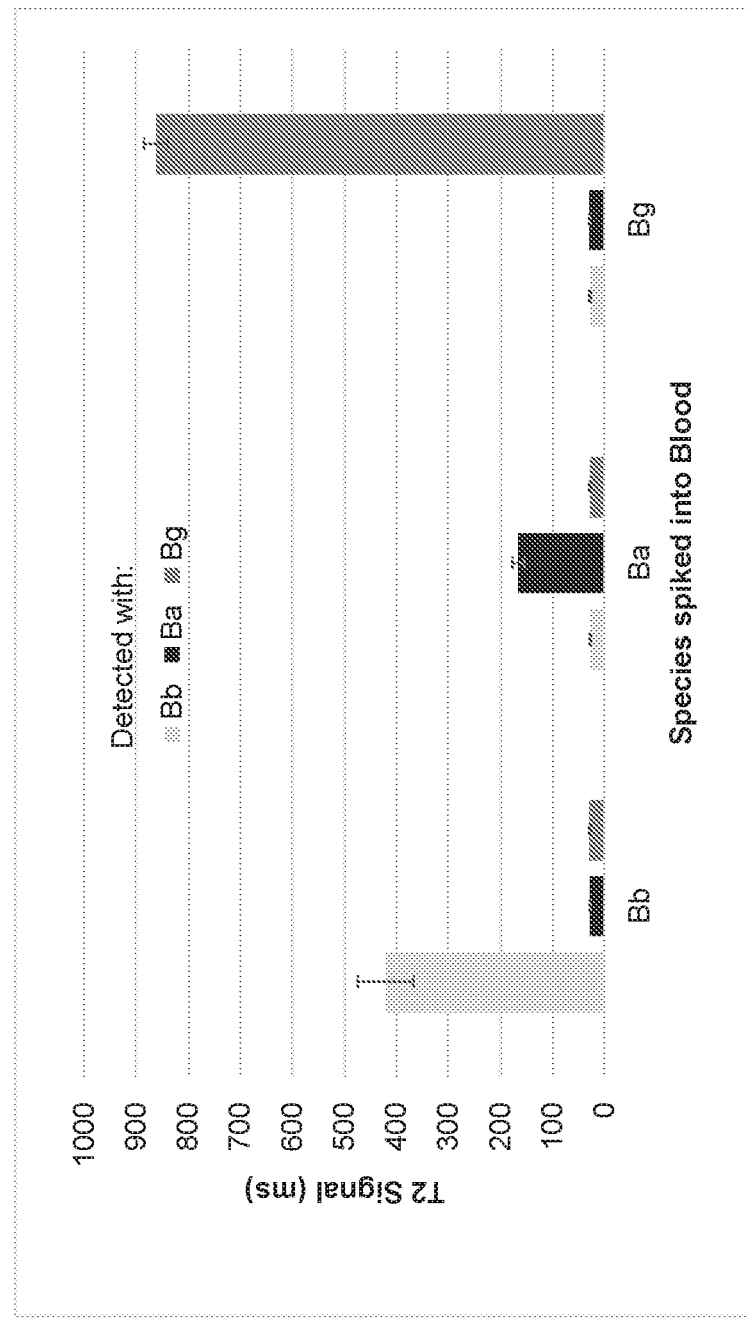
FIG. 5 is a graph showing a cross-reactivity test of primers and probes in a multiplex assay containing primers specific for all three *Borrelia burgdorferi* sensu lato (Bbsl) target species (i.e., *Borrelia burgdorferi* (Bb), *Borrelia afzelii* (Ba), and *Borrelia garinii* (Bg)) and 100,000 Bb, Ba, or Bg cells in buffer. Detection was performed using Bb-, Ba-, or Bg-specific probes as indicated.

Third, the preliminary specificity of the primers and probes was evaluated against cells spiked directly into amplification reactions. FIG. 5 shows an example of a T2MR assay performed with a multiplex mix containing primers for all three Bbs/targets in buffer with approximately 100,000 cells Ba, Bg or Bb per reaction. No cross-reactivity was seen even at these high cell concentrations.

Fourth, multiplex testing of primer pairs and subsequent detection was performed. Primers and probes that showed promising sensitivity and specificity were then tested in multiplex panels. Multiplex panel testing also included the addition of a primer pair for an internal control (IC). The internal control was a plant (Citrus sinensis) gene fragment cloned into a plasmid that was added in linearized form to the blood lysate during the lysate preparation. The Citrus sinensis IC is detected by its own specific pair of capture probes. Preliminary limits of detection (LoD) experiments were performed by spiking Borrelia cells into whole blood samples using the workflow shown in FIG. 11.

F. Exemplary Optimization of a Multiplexed Lyme Panel Assay

In this example, the primers and probes shown in Table 4 were used in a multiplexed Lyme panel assay.

primer ratio factorial (Plackett-Burman design) was performed. FIG. 6 shows the optimization plot generated from the factorial data examining three concentrations of primer for each target species. The optimization plot illustrates how the different experimental variables affected the predicted response in the factorial design. This was utilized to determine the concentration of primers (the variables) that together yielded increased response (in this case, longer measured T2 signal in ms) across all three Borrelia species. The factorial was executed using ten genomic equivalents of DNA from each of the three Bbsl species spiked into human whole blood lysate using three conditions for forward primers and reverse primers (74, 112.5, and 150 nM for forward primers and 300, 400, and 500 nM for reverse primers) (FIG. 6). Results indicated that in this example, optimized concentrations were 150 nM for the forward primers for all targets except for the internal control, which was 75 nM. The optimized reverse primer concentration in this example was 500 mM for all species.

Optimization of divalent cation and dNTP concentration: assay conditions such as divalent cation and dNTP concentration and amplification conditions (annealing temperature ($T_{anneal}$), extension times, etc.) were optimized using spiked

TABLE 4

Primers and Probes of a Multiplexed Lyme Panel Assay

| Species | Primers | Probes (P1 = 5' capture; P2 = 3' capture) |
|---|---|---|
| B. burgdorferi | oppA Forward Primer 1:<br>5'-AGA GGA CTT TTA ATA CTG GGC ATT GCT G-3' (SEQ ID NO: 1)<br>oppA Reverse Primer 1:<br>5'-GGC CAT TAT GTA GGA ATC TCT AAT GGT GC-3' (SEQ ID NO: 2)<br>oppA Forward Primer 2:<br>5'-ACA TAA TGG CCT TAG AAA ATG AGC TTG ATG-3' (SEQ ID NO: 5)<br>oppA Reverse Primer 2:<br>5'-CCC GCT TGT AAC CAT GTT TTC TGA GC-3' (SEQ ID NO: 6) | P1:<br>5'-CTA AAC CAA AAG ATG ATA TTG TCT TTG GTG-3' (SEQ ID NO: 3)<br>P2:<br>5'-GGA CAT TTC TTA CGA CAA CAC CTG CT-3' (SEQ ID NO: 4)<br>P1:<br>5'-AAC CTA TTA ACA TCA AAG ATA AAA AAT GC-3' (SEQ ID NO: 7)<br>P2:<br>5'-GCT TAC ACA CCC AAT ATT TAT ACC C-3' (SEQ ID NO: 8) |
| B. garinii | oppA Forward Primer:<br>5'-GGA TAT TCA AAT CCT GAG GTT GAC GAA CTA-3' (SEQ ID NO: 9)<br>oppA Reverse Primer:<br>5'-CTG ATA GGG CAA ATC TTT CTG AAG CA-3' (SEQ ID NO: 10) | P1:<br>5'-CTG AGA TTG AAG TTG ACG AAA AAA TCA G-3' (SEQ ID NO: 11)<br>P2:<br>5'-GAT CAT CCA ATA ATT CCA ATC TAC AGC G-3' (SEQ ID NO: 12) |
| B. afzelii | guaB Forward Primer:<br>5'-CCG TGG GCA GAG TCT ATG ACA ATC AG-3' (SEQ ID NO: 13)<br>guaB Reverse Primer:<br>5'-GCC CAA AAA ACC ATC AAC ACT AAT AAG G-3' (SEQ ID NO: 14)<br>PTS Forward Primer:<br>5'-CAA GGT GCA ATG ACT TTG TTT GGG CA-3' (SEQ ID NO: 17)<br>PTS Reverse Primer:<br>5'-GCA ACT TCA AAG TGT ACA GTA TTG GTA TCC C-3' (SEQ ID NO: 18) | P1:<br>5'-TAG CAG CTC CTA CTC TTA GCT TGC-3' (SEQ ID NO: 15)<br>P2:<br>5'-AAT ATT GCT TTG TAA GCA TTT TGG TTT-3' (SEQ ID NO: 16)<br>P1:<br>5'-TTG TAG AAC AAT CTG GGC TTT TTG G-3' (SEQ ID NO: 19)<br>P2:<br>5'-GGA GAA CTC ATA TCA GGA GCA CAA-3' (SEQ ID NO: 20) |

Optimization of Primer Ratios: Amplification of the Lyme panel members as described in this Example is performed under asymmetric amplifications with one primer in excess over the other. Asymmetric amplification ensures that single stranded product is synthesized, thereby facilitating more efficient hybridization against complementary, particle-conjugated capture probes. In addition, interactions between primers specific for different targets may require adjustments of individual primer concentrations. The ratios of forward and reverse primers can be optimized as follows. A DNA into whole blood lysate. Multiplexed primer configurations that included sets for all three Bbsl species were tested with the optimized primer concentrations identified above. FIG. 7 shows the results of a factorial conducted to determine optimized magnesium chloride (tested at 4, 4.5, and 5 mM) and dNTP (tested at 200, 300, 400, and 500 μM) concentration. Optimized concentrations based on T2MR signal and hit rate (N=8) were established as 4.5 mM $Mg^{2+}$ and 300-400 μM dNTP.

G. Growth and Quantification of *Borrelia* Cells for Cell Spiking Experiments Growth Curves The growth properties of *Borrelia* strains were examined to establish conditions for cell growth and quantification for cell spiking experiments. Table 5 lists the strains examined.

TABLE 5

*Borrelia* Species and Strains Tested for Cell Spiking Experiments

| Species and Strain | ATCC # |
| --- | --- |
| *B. burgdorferi* B31 | 35210 (lab strain) |
| *B. burgdorferi* 297 | 53899 |
| *B. burgdorferi* IRS | 35211 |
| *B. afzelii* BO23 | 51992 (lab strain) |
| *B. garinii* Fuji P1 | 51991 (lab strain) |
| *B.garinii* CIP 103362 | 51383 |

Lab strains were identified based on growth during reconstitution according to ATCC recommendations. The fastest growing isolates that yielded final counts near $1\times10^8$ cells/mL for each species were selected as lab strains, based on hemocytometer counts.

Growth curves were generated by testing four conditions based on supplier and advisor recommendations for optimal growth conditions. An inoculation volume of 1.3 mL into 13 mL of media grown at 34° C. was identified as an optimized growth condition across all lab strain species. Cultivation time differed across species with optimized harvest time of 3-4 days for *B. burgdorferi* ATCC 35210, 6-7 days for *B. garinii* ATCC 51991, and 2-3 days for *B. afzelli* ATCC 51992.

The optimized growth temperature and inoculation volume was utilized to generate growth curves for the other available ATCC stocks. Results indicated similar growth with *B. burgdorferi* ATCC 35211 (B31 lab strain) and a longer lag phase for strain ATCC 53899 compared to the lab strain. For *B. garinii*, ATCC 51383 does not enter log phase even after 11 days of incubation. A summary of results is found in Figure.

Quantification Methods

A variety of quantification methods can be used to quantify *Borrelia* cells, including hemocytometer, quantitative PCR, and automated cell counting instruments. For example, the Nexcelcom CELLOMETER® X2 counting system was evaluated relative to hemocytometer counting results. A factorial design was used to optimize conditions related to cell concentration, SYBR® green stain volume, and slide type available from the manufacturer (thick versus thin). Results indicated a robust system with a detection range of $5\times10^6$-$5\times10^8$ cells/mL with 5-15 μL of SYBR® green diluted 100× and added to 1 mL of sample. Table 6 compares automated cell counting results established with the optimized condition (1:10-1:20 cell stock dilution, 10 μL 100×SYBR green:1 mL sample, thick slide) to hemocytometer counting. Automated cell counting resulted in improved precision but comparable accuracy to hemocytometer counts. Aliquots within a single lot were value-assigned by automated cell counting for 13 days of sample prep. Results show reproducible value assignment across aliquots indicated limited counting method and aliquot variability within a lot of cell bullets (FIG. 9).

TABLE 6

Comparison of Automated Cell Counting and Hemocytometer Counting

| | Automated Cell Counting | | | Hemocytometer Counting | | | |
|---|---|---|---|---|---|---|---|
| | N | cells/mL | % CV | N | cells/mL | % CV | % Difference |
| *B. burgdorferi* | 24 | 9.78E+07 | 4% | 9 | 9.89E+07 | 19% | −1% |
| *B. afzelii* | 12 | 2.78E+08 | 3% | 9 | 2.09E+08 | 39% | 33% |
| *B. garinii* | 12 | 1.46E+08 | 5% | 20 | 1.57E+08 | 45% | −7% |

Cell bullets were created for each of the 3 lab strains indicated in Table 5 and value-assigned using the automated cell counting system. Reproducible growth for all 3 species across 3 lots was observed (FIG. 10). Statistical analysis via one-way analysis of variance (ANOVA) indicated p values of 0.117, 0.020, 0.264 for *B. burgdorferi, B. afzelii*, and *B. garinii*, respectively. In conclusion, these data demonstrate that *Borrelia* species can be accurately counted for use in cell spiking experiments to determine the limit of detection of multiplex Lyme panel assays.

H. Limit of Detection Determination

The limit of detection (LoD) was established for each species using the optimized assay conditions described above in a duplex or triplex reaction. The panel included the primers and probes shown in Table 4. The *B. burgdorferi* (Bb)-specific assay contained 3 primer pairs: two for the oppA target and one for the internal control, resulting in the amplification of at least two oppA amplicons. The *B. afzelii* (Ba)-specific assay also contained 3 primer pairs, two of which are specific for the guaB and PTS targets, respectively, and one of which is for the internal control. The *B. garinii* (Bg)-specific assay was a duplex assay that tested for the oppA target and the internal control. The Bb and Ba targets were detected with a mixed probe particle pair, i.e., magnetic particle pairs in which each member of the pair bears probes for binding to the two species-specific amplicons. The 5' capture probes for each amplicon are conjugated to one population of the pair of magnetic particles, while the 3' capture probes for each amplicon are conjugated to the other population of the pair of magnetic particles.

Spiked blood for the LoD panel was prepared from bulk volumes of $K_2$EDTA whole blood obtained from healthy volunteers that was spiked with cells from a frozen cell stock. Cells were quantified at time of use using the automated cell counter as described above and diluted to targeted test concentrations for spiking into the blood. Each day of preparation involved a new blood donor and quantified cell spike preparation.

The assay was carried out using the workflow outlined in FIG. 11. Briefly, 2 mL of the spiked blood was transferred to a tube containing red blood cell (RBC) lysis solution and high density yttrium zirconia beads. After mixing, the sample was centrifuged, the internal control (IC) was added, and the sample was subjected to a mechanical bead beating step. The resulting lysate was directly transferred to the amplification reaction tube containing the amplification reagents. After thermocycling, the amplified products were mixed with target-specific probe-particle conjugates and hybridized prior to T2MR detection. The results from limit of detection testing are shown in Table 7. Starting from an initial spike titer of 20 cells/mL, the concentration of each species was reduced stepwise until the lower limit of 95% hit rate in 20 replicas (1 false negative per 20) was reached. At this target concentration which was <10 cells/mL for all species, 60 replicates were performed in sets of 20 (three independent spiked blood bulks) across three separate days (20 replicates per day). A limit of detection of 8 cells/mL for *B. burgdorferi* and *B. garinii* and 5 cells/mL for *B. afzelii* was determined (Table 7). These values are considered to be, at minimum, equivalent to 8 colony-forming units/mL and 5 colony-forming units/cell, respectively, and are most likely more sensitive, as it is well known that a colony can form from 1 or more cells, but a colony cannot be formed without a single cell. For example, it is documented that for many organisms 1 CFU>10 cells.

TABLE 7

Assay Performance Data for Limit of Detection Data

| Target | Cells/mL | Hit Rate | #Positive/Total | Average T2 | Standard Deviation T2 | % CV T2 |
|---|---|---|---|---|---|---|
| B. burgdorferi | 10 | 97% | 68/70 | 417 | 135 | 32% |
|  | 8 | 95% | 57/60 | 439 | 179 | 41% |
| B. afzelii | 10 | 100% | 60/60 | 485 | 86 | 17.7 |
|  | 5 | 97% | 58/60 | 379 | 55 | 14% |
| B. garinii | 10 | 97% | 58/60 | 689 | 129 | 18.7% |
|  | 8 | 97% | 58/60 | 538 | 148 | 27% |
| Negatives | 0 | N/A | N/A | 29 | 2 | 8% |

Note:
"% CV T2" indicates the coefficient of variance of the average T2 signal

In conclusion, the methods described in this example allow detection of *Borrelia* species including *Borrelia burgdorferi*, *Borrelia garinii*, and *Borrelia afzelii* at 1-10 cells/mL in biological samples such as blood with ≥95% sensitivity for each of these target species.

Example 5: Detection of *Borrelia* Species in Platelet-Rich Plasma Using a T2MR-Based Detection There is evidence that *Borrelia burgdorferi* attaches to platelets via integrin alpha IIB. Platelet-rich plasma (PRP) can be prepared by conducting a slow speed centrifugation (e.g., in a swinging bucket centrifuge) and collecting the platelet-rich plasma fraction, which is within the buffy coat. For traditional PCR, the PRP fraction would be problematic since it contains approximately 60 µg of human DNA. This amount of DNA would inhibit a traditional PCR reaction and require a large dilution to obtain more tolerated levels of background DNA. However, the T2MR reactions as described herein are compatible with a range of matrix types. Further, using PRP represents an attractive enrichment strategy since for every 10 mL of human whole blood, the PRP fraction is approximately 1-2 mL.

To determine whether the PRP fraction was compatible with T2MR-based detection of *Borrelia* cells, experiments were conducted to determine whether *Borrelia* cells could be detected by T2MR in plasma prepared from whole blood specimens spiked in vitro, *B. burgdorferi*, *B. afzelii*, or *B. garinii* cells were spiked at a titer of 10 cells/mL into 4 mL of whole blood. A slow speed centrifugation was performed to isolate PRP. PRP was transferred to lysis tubes and the T2MR assay was performed essentially as described above in Example 4. The preliminary results indicated that *B. burgdorferi*, *B. afzelii*, and *B. garinii* cells could be detected at 10 cell/mL with a hit rate of from 98% to 100%, as shown in Table 8.

TABLE 8

T2MR Results from Platelet-Rich Plasma Prepared from Spiked Blood

| Target | Cells/mL | Hit Rate | #Positive/Total | Average T2 (ms) | Standard Deviation T2 | % CV T2 |
|---|---|---|---|---|---|---|
| B. burgdorferi | 10 | 98% | 59/60 | 362 | 111 | 31% |
| B. afzelii | 10 | 100% | 20/20 | 360 | 34 | 9% |
| B. garinii | 10 | 98% | 59/60 | 764 | 139 | 18% |

TABLE 8-continued

T2MR Results from Platelet-Rich Plasma Prepared from Spiked Blood

| Target | Cells/mL | Hit Rate | #Positive/Total | Average T2 (ms) | Standard Deviation T2 | % CV T2 |
|---|---|---|---|---|---|---|
| Negative controls | 0 | N/A | N/A | 29 | 1.5 | 5% |

Therefore, platelet-rich plasma represents an alternative sample type to be used in T2MR-based methods of detection of spirochetes such as *Borrelia* and is compatible with sensitive and accurate detection.

An alternative approach to prepare PRP from whole blood for use in T2MR-based detection of *Borrelia* cells is as follows. 4-10 mL of whole blood can be centrifuged at 200 g to 1,000 g for 5 to 15 minutes to initially collect plasma. This plasma can be used directly in the assay, or a secondary centrifugation step can be performed at 6,000 g to 14,000 g for 10 minutes to further concentrate the PRP. At this point, the upper ⅔ of the plasma sample is removed and the lower ⅓ of the sample comprises the PRP fraction. This final PRP fraction can then be processed using the method described above in Example 4 for T2MR-based detection of *Borrelia* cells including *B. burgdorferi*, *B. afzelii*, or *B. garinii*.

Example 6: Multiplexed Lyme Panel Assay Detects *Borrelia* Cells in Clinical Samples Preliminary studies were performed to determine whether the multiplexed Lyme panel assay as described in Example 4 could detect *Borrelia* cells in clinical samples. First, a limit of blank testing was performed. Blood specimens were obtained from 40 healthy donors, and the *B. burgdorferi* T2MR assay was conducted as described in Example 4, Section F was performed to calculate a provisional clinical threshold. In this experiment, the provisional cutoff was 45 ms, which was 10 standard deviations above the signal measured from 40 negative controls (Table 9).

TABLE 9

Limit of Blank Testing from 40 Healthy Donors

| Donor | B. burgdorferi T2 signal (ms) | IC T2 Signal (ms) |
|---|---|---|
| 1 | 28.48 | 455.44 |
| 2 | 28.69 | 474.33 |
| 3 | 28.08 | 314.79 |
| 4 | 27.97 | 465.50 |
| 5 | 28.55 | 354.87 |
| 6 | 28.63 | 385.06 |
| 7 | 28.75 | 423.68 |
| 8 | 27.97 | 476.97 |
| 9 | 28.13 | 476.79 |
| 10 | 24.37 | 399.38 |
| 11 | 26.70 | 499.59 |
| 12 | 28.70 | 325.61 |
| 13 | 27.57 | 489.47 |
| 14 | 28.37 | 469.44 |
| 15 | 27.44 | 445.53 |
| 16 | 29.04 | 271.59 |
| 17 | 27.70 | 412.63 |
| 18 | 28.03 | 467.24 |
| 19 | 29.02 | 415.52 |
| 20 | 29.37 | 501.30 |
| 21 | 30.09 | 494.00 |
| 22 | 30.22 | 452.34 |
| 23 | 29.71 | 452.11 |
| 24 | 30.04 | 488.11 |
| 25 | 30.13 | 414.83 |
| 26 | 30.07 | 368.48 |
| 27 | 32.27 | 338.01 |
| 28 | 29.10 | 495.94 |
| 29 | 29.97 | 430.57 |
| 30 | 30.86 | 419.55 |
| 31 | 31.82 | 519.81 |
| 32 | 30.04 | 481.45 |
| 33 | 33.35 | 523.12 |
| 34 | 29.74 | 462.72 |
| 35 | 28.93 | 495.56 |
| 36 | 29.74 | 625.09 |
| 37 | 30.44 | 671.30 |
| 38 | 29.42 | 474.01 |
| 39 | 29.72 | 629.04 |
| 40 | 30.50 | 572.23 |
| Average T2 | 29.19 | 458.33 |
| St Dev T2 | 1.55 | 81.56 |
| % CV | 5.3% | 17.8% |
| Provisional cut-off | 45 ms | |

This clinical threshold was applied in the analysis of clinical samples from 3 patients diagnosed with Lyme disease. Each patient had experienced a tick bite, and none of the patients had antibiotic treatment prior to the blood draw. The multiplexed Lyme panel assay was performed on ~2 mL blood samples as described in Example 4, Section F. 100% of the patient samples (n=3/3) were positive for *B. burgdorferi* by T2MR, confirming that the multiplexed Lyme panel assay could detect *Borrelia* cells in clinical samples from patients suspected to be suffering from Lyme disease (Table 10).

TABLE 10

Detection of *Borrelia* cells in clinical samples using a multiplexed Lyme panel assay

| Patient ID | # days since tick bite | T2MR Result |
|---|---|---|
| MFLD-04 | 6 | POS |
| MFLD-11 | 21 | POS |
| MFLD-20 | Multiple tick bites | POS |

In conclusion, multiplexed Lyme panel assays as described herein are useful for rapid (3-5 hr), sensitive, and accurate detection of *Borrelia* cells in clinical samples, allowing for diagnosis of Lyme disease as well as guidance of proper therapy for those infected and removing unnecessary therapy for those who are not infected.

Example 7: An Alternate Multiplexed Lyme Panel that Includes *B. burgdorferi*-Specific Primers and Probes for Amplification and Detection of Outer Membrane Proteins An alternate panel configuration for use in multiplexed Lyme panel assays is shown in Table 11. This panel is similar to that described in Table 4, except that the *B. burgdorferi* primers and probes are replaced with primers and probes for amplification and detection of the outer membrane protein (OMP) lipoprotein NM71_04585. The panel shown in Table 11 can be used following the methodology described in Example 4 to detect *B. burgdorferi*, *B. afzelii*, and *B. garinii* in biological samples including whole blood and plasma (e.g., PRP). The Bb and Ba targets are detected with a mixed probe particle pair, i.e., magnetic particle pairs in which each member of the pair bears probes for binding to the two species-specific amplicons. The 5' capture probes for each amplicon are conjugated to one population of the pair of magnetic particles, while the 3' capture probes for each amplicon are conjugated to the other population of the pair of magnetic particles.

TABLE 11

Primers and Probes of an Alternate Multiplexed Lyme Panel Assay

| Species | Primers | Probes (P1 = 5' capture; P2 = 3' capture) |
|---|---|---|
| B. burgdorferi | OMP-1F Forward Primer:<br>5'-AGC TGT AGT TTA AGG CAA ATG TTG G-3' (SEQ ID NO: 157)<br>OMP-1R Reverse Primer:<br>5'-AGG ATC GCA AAA TCA ACC ACA AAC A-3' (SEQ ID NO: 160)<br>OMP-2F Forward Primer:<br>5'-TGC TGC TGT TGT TTT TGG CAG ATT-3' (SEQ ID NO:163)<br>OMP-2R Reverse Primer:<br>5'-ATG ACA AAG TAG CAG CAG AGC TAA A-3' (SEQ ID NO: 164) | P1:<br>5'-GCT ATT TCT GCT GTT AAA AGT TCT TGT-3' (SEQ ID NO: 161)<br>P2:<br>5'-CTA AAA CTT AAG CTT TGC AAT TGT GG-3' (SEQ ID NO: 162)<br>P1:<br>5'-CGC TAA AAC TTA AGC TTT GCA ATT G-3' (SEQ ID NO: 165)<br>P2:<br>5'-TGC TGC TAC TGT TTT TGC TGC TTG C-3' (SEQ ID NO: 166) |
| B. garinii | oppA Forward Primer:<br>5'-GGA TAT TCA AAT CCT GAG GTT | P1:<br>5'-CTG AGA TTG AAG TTG ACG AAA |

TABLE 11-continued

Primers and Probes of an Alternate Multiplexed Lyme Panel Assay

| Species | Primers | Probes (P1 = 5' capture; P2 = 3' capture) |
|---|---|---|
| | GAC GAA CTA-3' (SEQ ID NO: 9)<br>oppA Reverse Primer:<br>5'-CTG ATA GGG CAA ATC TTT CTG AAG CA-3' (SEQ ID NO: 10) | AAA TCA G-3' (SEQ ID NO: 11)<br>P2:<br>5'-GAT CAT CCA ATA ATT CCA ATC TAC AGC G-3' (SEQ ID NO: 12) |
| B. afzelii | guaB Forward Primer:<br>5'-CCG TGG GCA GAG TCT ATG ACA ATC AG-3' (SEQ ID NO: 13)<br>guaB Reverse Primer:<br>5'-GCC CAA AAA ACC ATC AAC ACT AAT AAG G-3' (SEQ ID NO: 14)<br>PTS Forward Primer:<br>5'-CAA GGT GCA ATG ACT TTG TTT GGG CA-3' (SEQ ID NO: 17)<br>PTS Reverse Primer:<br>5'-GCA ACT TCA AAG TGT ACA GTA TTG GTA TCC C-3' (SEQ ID NO: 18) | P1:<br>5'-TAG CAG CTC CTA CTC TTA GCT TGC-3' (SEQ ID NO: 15)<br>P2:<br>5'-AAT ATT GCT TTG TAA GCA TTT TGG TTT-3' (SEQ ID NO: 16)<br>P1:<br>5'-TTG TAG AAC AAT CTG GGC TTT TTG G-3' (SEQ ID NO: 19)<br>P2:<br>5'-GGA GAA CTC ATA TCA GGA GCA CAA-3' (SEQ ID NO: 20) |

SEQUENCE LISTING

The following sequences are used throughout the application.

| SEQ ID NO: | Sequence |
|---|---|
| 1 | AGAGGACTTTTAATACTGGGCATTGCTG |
| 2 | GGCCATTATGTAGGAATCTCTAATGGTGC |
| 3 | CTAAACCAAAAGATGATATTGTCTTTGGTG |
| 4 | GGACATTTCTTACGACAACACCTGCT |
| 5 | ACATAATGGCCTTAGAAAATGAGCTTGATG |
| 6 | CCCGCTTGTAACCATGTTTTCTGAGC |
| 7 | AACCTATTAACATCAAAGATAAAAAATGC |
| 8 | GCTTACACACCCAATATTTATACCC |
| 9 | GGATATTCAAATCCTGAGGTTGACGAACTA |
| 10 | CTGATAGGGCAAATCTTTCTGAAGCA |
| 11 | CTGAGATTGAAGTTGACGAAAAAATCAG |
| 12 | GATCATCCAATAATTCCAATCTACAGCG |
| 13 | CCGTGGGCAGAGTCTATGACAATCAG |
| 14 | GCCCAAAAAACCATCAACACTAATAAGG |
| 15 | TAGCAGCTCCTACTCTTAGCTTGC |
| 16 | AATATTGCTTTGTAAGCATTTTGGTTT |
| 17 | CAAGGTGCAATGACTTTGTTTGGGCA |
| 18 | GCAACTTCAAAGTGTACAGTATTGGTATCCC |
| 19 | TTGTAGAACAATCTGGGCTTTTTGG |
| 20 | GGAGAACTCATATCAGGAGCACAA |
| 21 | ATGATAATAAAAAAAGAGGACTTTTAATACTGGGCATTGCTACTGTAATCTCGTGCTCAGCA<br>ATGTCTAAACCAAAAGATGATATTGTCTTTGGTGTTGGAATTGGAAACGAACCAACATCGCTT<br>GATCCACAATTTTGCAGCGATAGGCTAGGTAATTTAATTATAAACGAACTATTTGTAGGGCTT<br>TTAAGGGGTGACCCCAAAACGGTGGATACAGGCCAGGACTTGCAAAAAATTGGGACATTT<br>CTTACGACAACACCTGCTATACATTCCATTTAAGAGACGACATTTATTGGAGTGACGGCATTA |

| SEQ ID NO: | Sequence |
|---|---|
| | AAATAACAGCAAGCACCATTAGAGATTCCTACATAATGGCCTTAGAAAATGAGCTTGATGTG<br>CCACATATTAACCTATTAACATCAAAGATAAAAAATGCACAAGAATTTTACGAAACAAAATTAA<br>ATGCAGATGAAGTTGGAGTAAAGGTAATCAATGAGCAAACTTTAGAAATAACTCTCTCTCGC<br>CCAGCAAGATATTTTCTTGACATGCTTACACACCCAATATTTATACCCATTCCTACGCACATT<br>GTTAAAAAGTTTGGAAACAAATGGACAAGCTCAGAAAACATGGTTACAAGCGGGCCTTTCAA<br>GCTAAAAAGAAGGATCTTAAACGAAGAAATATCTCTTGAAAAAAATGAAAAATTCTATGATGC<br>TAAAAACGTTGCTATTAATGAGCTCATATTTGTTACTATAAACGACACCCGCAGAATTTACAG<br>TATGTACGAGCACAACGAAATAGATGCTATTTTTAATAACATCCCCTTAAGCCTTATTAATGA<br>GCTTATCTTAAGAGAAGATTTTTATTCAGCTGACATTAATCAAATTGGGTTTTTTTCACTAAAC<br>ACAAATGTTAAACCTCTTAACAATGTAAAAGTAAGAGAAGCATTGGCTCTTGCGGTTGACAG<br>AGAAACTCTAACTTACAGAGTTCTTGACAACAACTTTAAAGCAACAAGAAAAATAAGCCCTAA<br>TATTAACAACTATAATTATGGGAAAAAGCTTAAGCCATACAACCCGCGAAAAGCAGAAAAGC<br>TCTTAGCCGAAGCTGGATATCCAGATGGTAAAAATTTTCCAACTCTTACAATAAAATACAATA<br>AAAATGACCTTGAAAAAGAAGTTGCTAGTTTTATTCAAAGCCAATGGAAAAAAGTTTTAAATA<br>TTGATGTAGAAATTGAGCCTGAAACATGGGTCAACCACATATCAAATATTTTAAAAGGTCAAT<br>ATGAGATCTCAGTAAGGTCCTGGCAAGGAGATTATTTAGATCCCATGGCATTCTTTAATATAT<br>TTGAAACTAAAAACTCACATTTTGCATCTTACGGATATTCAAATCCTGAACTTGATGAGCTTAT<br>AATAAAATCCGATCTTGAAGAGGATGAAAAACTAAGATTAGAAATATTAAAAAAGATAGAAGA<br>AATAATTATTGAAAATGATTATCCAATAATTCCAATATACAGTGTTGCGGGAAACTATCTTTTT<br>AAAAACGACAAATGGCTAGGGTGGAATACAAACAATTCAGAAAGATTTGCCCTATCAGAAAT<br>AAAACCTATAGAAGAATAA |
| 22 | ATGATAAGAAAAAAAATATTACTTTTAACACTACTCATTACAGCTGCAAGCTCATGCACAATTT<br>CTAAAACAAAAGAGGATCTTGTCTTTGGAGTTGGAATCGGAAACGAACCAACATCACTTGAT<br>CCACAGTTTTGCAGCGATAAATCGGGTAACTTAATTATAAACGAGCTATTTATAGGGCTTTTA<br>CGAGGGGATCCAAAAACAGGTGGTTATAGGCCAGGACTTGCAAAAAATTGGGAAATTTCTC<br>AAGACAACACCTCCTATACATTCCACTTAAGAGACGACATTTATTGGAGTGACGGCGTTAAA<br>ATAACAGCAGACACTATTAGAGGCTCATACATAATGGCCTTAGAAACTGAGGAGAATCTCCC<br>ACATATTAACCTTTTAACATCAAAATAAAAATGCAAAAGAATTTCACACAACAAAATTAAAT<br>TCAGATGAAGTTGGAATAAAGGTAATTGATGAAAAAACTTTGGAAATAACTCTTGAACAACCA<br>ACAGCATATTTCCTTGATATGATTACACATCCAATATTTATACCTATTCCTACTCACGTTGTTA<br>AAAAGTTTGGAAATAAATGGACAAACCCAGAAAACATGGTTACAAGCGGGCCTTTCAAACTA<br>AAAAGAAGAATATTAAACGAAGAAATTTCTCTTGAAAAAAATAAAAAATTTTATGATGCTAAAA<br>ATGTTGATATTAATGAGCTTACATTTGTTACTATAAACGATGCCCGCAGAATTTACAGCATGT<br>ATGAACACAACGAAATAGATGCTATTTTTAACAACATTCCGTTAAATCTTATTAATGAGCTTAT<br>TTTAAGAGAAGATTTTTATTCATCTGACATTAACCAAATTGGTTTTCTTTCATTAAACCTAAAT<br>GTTAAACCCCTTGACAACCCAAAAGTAAGAGAAGCATTATCTCTAGCGGTTGACAGAGAAAC<br>ATTGGCCTACAGAGTGCTTGATAACAACTTTAAAGCAACAAGAAAGGTAAGCCCTAATATTAA<br>TAATTATAATTATGGAAAAAAATTAAAACCATATAACCCACGAAAAGCAGAAAAACTTTTAGC<br>CGAAGCTGGATATCCTGATGGGAAAAAATTTCCAACTATTACAATAAAATATGATAAAAATGA<br>ACTTGGAAAGGAAGTTGCCAATTTTATTCAAAGCCAATGGAAAAAAGTTTTAAATATTAATGT<br>AGAAGTCGAGACTGAAACACGAGGTAGCCACATATCAAATATTCTAAAGGACAGTATGAGA<br>TCTCAGTAAGATCCTGGCAAGGAGATTATTTAGATCCCATGACATTCTTTAATATATTTGAAA<br>CTAAAAACTCACATCTTTCAGCTTACGGATATTCAAATCCTGAGGTTGACGAACTATTAAATA<br>AATCTGAGATTGAAGTTGACGAAAAAATCAGATTAGAACTATTTAAAAAGATTGAAGAAATAA<br>TTATTGAAAATGATCATCCAATAATTCCAATCTACAGCGTTGCGGGGAACTATCTTTTCAAAA<br>ATGATAAATGGACAGGGTGGAACACAAATGCTTCAGAAAGATTTGCCCTATCAGAAATTAAA<br>CCTTTGGAAGAATAA |
| 23 | TATTGTCTTTGGTGTTGGAATTGGA |
| 24 | ACCTGCTATACATTCCATTTAAGAG |
| 25 | ATGAACTTGGAAAGGAAGTTGCCAA |
| 26 | CCTAAATGTTAAACCCCTTGACAACCCA |
| 27 | CTGTCCTTTT/i6diPr/GA/i6diPr/TATTTGATATGTGGCTA wherein /i6diPr/ is 2,6-Diaminopurine |
| 28 | TCAGAAATGATAAATGGACAGGGTGGAAC |
| 29 | TCTAGCGGTTGACAGAGAAACATTG |
| 30 | AAAAAATTAAAACCATATAACCCACGAA |
| 31 | TTAATCTAAATAATAATAAATAGTTGAAGCAATCCTTAATATTTCTTTAGGATAAAGCTTTGGG<br>TTGCCAAAGATTATATCAACTAGAAAAAATTTAAAGTATTCTTGATTTGCATTTTTAATTTTATC<br>TAATTTGGAACCAAAATGTCTCGTAAATTCTAAAGCAGAAAGTTCTGCATTTCTTATTGAACC<br>TGCTAGAATTTGAAAATTTGTATCATTAATTCTATTTAAATAATATCTTAAATCTCTATTACTGC<br>TAATTGGCAAGCCTTGATTATAAAACTCAATAATATTTTTTCTACTGTTTTCATTTTTTCAATA<br>TCAATTGTATTGGTAATTAAAGCAATATACATACATATTTAATAAAAAGCTTTAATCTTAGATA<br>AATTTAAATTATTTGCTTTAATGCCGTCATTAATCGAATCACTATTCAAGTCATAATGCAAATT<br>ACAACTTACAGATGCCAAAGGATTTCTTTTTCGCTTATGCCCTTAGCCTTAATACAATTGCC<br>ATTTTTAATGACAATTCCTTTTACTCTGCAAGAAATTATAATTGAAATGACAGAAAAGTATT<br>AAAAAAAATAAATCCTTTCTTCCAGGCATATAACAATTCCTCCTAAAAAAGAATAAATAATTGT<br>TAAATCAGCTCGTTTATTCTAACATATTATATAATGTTAATGAATCGAAAAAT |

| SEQ ID NO: | Sequence |
|---|---|
| 32 | GCAGAAAGTTCTGCATTTCTTATTGAACC |
| 33 | GGAACCAAAATGTCTCGTAAATTCTAAAGCA |
| 34 | CTTTAGGATAAAGCTTTGGGTTGCC |
| 35 | AGTGATTCGATTAATGACGGCATTAAAGC |
| 36 | GTGATTCGATTAATGACGGCATTAAAGCAA |
| 37 | AATAATATCTTAAATCTCTATTACTGCTAA |
| 38 | CAGAAAGTTCTGCATTTCTTATTGAACC |
| 39 | ATTGGTAATTAAAGCAATATACATACATAT |
| 40 | GTATTGGTAATTAAAGCAATATACATACATAT |
| 41 | ATGCACAATTTATTTGATTTTTTAAAATTAAAACAGCATATAATAAAAATGCATGGCAAGCAAATAAATCAATTATACAAAAAGCTCTTAATTAAATTTTTTCATCGTATCCATTAATATTACAAATGGATTCAAGAAATAAACTATCTACACCTTACAAAAAAGGATATAATTCATTCGAGAAATACATAAAAATGTTTAATAACATAGTAAACGAAAGAAAAATCACAAAAAATTGAAAAATTTGCTAATGAAATTGGTTTATTGCATTATCCAATAA |
| 42 | AAATTAAAACAGCATATAATAAAAATGCATGG |
| 43 | TTGGATATGCAATAACCAATTTCATTAGC |
| 44 | GCTCTTAATTAAATTTTTTCATCGATATCC |
| 45 | GGATATAATTCATTCGAGAAATACATAAAAATG |
| 46 | ATGGTATTTAGAACATATAAACATTTGGAACTAATAATGCTGCCCATGTTAATGCTGAGTTGCGCTTTTTTTAAGAAACCACAATCTGTACATCAAGACAGCAATACTGGCAAACCAATAAGCGATGAAAAATTACATTTAATATCAGGCAAAATTTCAAATAAAAAATTGCCAATCATAAATAGTAATCATGACGTAACTTGGATAAAAACAAAGGCAATGACAATCTTAGGCGAAGATGGAAAAGAAATACCAGAATTTAAAAACAAATTTGGATATTCTTATATAATATCCTGTAAAAATGGATGGAAAATATAGTTATTACGCGTCATTATTAATACTTTTTGAAACAACTAAAAATGGAGATGATGAATATGAAATTGAAGATGTTAAATTTGTAACAGCTGGTTCCACCCTAGAACTTAAAAATTCTCTTTTAGCTGTTGAAAATTCACAAGAAGAAGGATATGTTACTGCATACCCATTTGGAATATTGATGAGTGACGAGATTAAAAATGCTTTTAAATTAACATATAAAAATGGTCATTGGAATTATATGCTTGCAGATTTAACTGTCAAAATAAACTTACTCAAGAAACTAAAATTTATAAAATTTCTCTTAATTCAAAATTAATTATTGAATTTTTAAAAGAAGTGCTAAAAGAAAATTCTATATTAAAAGACATAGCTGGAGATTTATTTGAAGATATATAA |
| 47 | ACATTTGGAACTAATAATGCTGCCCATG |
| 48 | AGTTGTTTCAAAAAGTATTAATAATGACGCGT |
| 49 | CATGTTAATGCTGAGTTGCGCTTTTTTTAAG |
| 50 | CATGACGTAACTTGGATAAAAACAAAGGC |
| 51 | ATGATATTTAGAACATATAAGCATTTAAAATTAATAGCAATACTTATGTTAATGTTGAGTTGCGCTTTTTTTAAAAAGCCACAAACTGCACAACAAAACGGAGCTATTGGAAACCCAATAAGGGATGAATTGCCTTTAAACGATGGAAAATTACATTTAATATCAGGAAAATTTTGAATAAAAAATTGCCAGTCGTAAATGAAAATCATGACGTAACTTGGATAAAAACAAAGGCAATGGCAATCTTAGATAAAGATGGACAAGCAATGCCAGAATTCAAAAACAAATTTGGATATTCTTATATACTATCCCCTATAAAAATGAATGATGAATATAGTAGTTACACATCGCTATTAATACTTTTTGAAACAACTGAAAATGGAGATAAAGAATATGAAATTGAAGATATTTAAACTTATAACAGCTGGTTCCAACCTAGAACTTAAACATTCTCTTCTAATTGCTGAAAAATCACAAGAAGAAGGATATGTTACTGCATACCCATTTGGAATCTTGATGGACGAAGAACTTAGAAAAGCTTTTCAATTAACATATCAAAATGGTCATTGGAATTATATGCTTGCAAATTTAACCGTTAAAAACAAGATTACTCAAAAAACTGAAATTTATACAATTTCTCTTAATTCAAAATTAATTATTGACTTTGTAAAAGAAGTATTAAAAGAAAATCCCATCTTAAAAGAGACAAATGGAGATCTATTTGAAGATATATAA |
| 52 | CCACAAACTGCACAACAAAACGGAGC |
| 53 | CCAATTTGTTTTTGATTCTGGTATTGCTTG |
| 54 | TGAATGATGAATATAGTAGTTACACATCGCT |
| 55 | GAAACCCAATAAGGGATGAATTGCC |
| 56 | GGAAACCCAATAAG/ideoxyl/GATGAATTGCC wherein /ideoxyl/ is deoxyInosine |

| SEQ ID NO: | Sequence |
|---|---|
| 57 | GACGTAACTTGGATAAAAACAAAGGC |
| 58 | GATGGACAAGCAATGCCAGAATTC |
| 59 | ATGAAAAGAATAAGTATTTTATCAATACTACTGTTATTATTGTTGTTTTCTTGTAAACAGTATG<br>GTGATGTTAAATCATTAACAGAAGTTGCTACTGATCTTGAGGATGACAATTCTTTTGCTTCTG<br>GGAGTGTAGAGTCTAAAGATCAAATTATCGAAAAAGGACCCGTTTTAACATCAGAGGAGTTT<br>GAAAGGTTAGAGGCTTTAAAAACCTTTTTAAAAGACGCAATGGGTGTTAATGGTAGAGAAGG<br>CGATACAAAAGCTGAGTATGAGAAATCCTATAAAGAATTTTTTGATTGGCTTTCTAAGGATGT<br>TAACAGACAGAAAGAGTTTGTAAGTTTTTTTAACAATATTTGTGGCATTATTACTAAAGCAGT<br>GGATGCAAGCAAAAAAAGGTATAATAGTAATCCAAATCCTTAGGTTTTAATGAATATGTTTG<br>TTATGATATTAAAACCAGGACTGGGGATGATTTAAGTTTATTTTTCCAAAAAGTAGCTGATGC<br>ATTTGGCACTCAAGAGTACAAAAATAAAGATGAGGATGATGAGAACAATCAAAAGCCTGAAA<br>AATGCAATGAAGAGATTTTTAAAGTAATTAAAAGAGTGTTTACTGAAAGCGAGAATAATAACG<br>AATTGGCAAATTTAAAAAATT |
| 60 | GGTGATGTTAAATCGTTAACAGAAGTTGCTACTGA |
| 61 | GGTGATGTTAAATCGTTAACAGAAGTTGCTACTGAT |
| 62 | CTGATTTTGAGGATGGCAATTCTTTTGTTTCTGGG |
| 63 | TTGTCTGTTAACATCCTTAGAAAGCCAATC |
| 64 | TTGTCTGTTAMCATCCTTAGAAAGCCAATC wherein M is A or C |
| 65 | CTTTTTGTCTGTTA/ideoxyl/CATCCTTAGAAAGCCAATC wherein /ideoxyl/ is deoxylnosine |
| 66 | TTGAGGATGGCAATTCTTTTGTTTCTGGG |
| 67 | AAGGACCTGTTTTAACATCAGAGGAG |
| 68 | AAGCTGAGTATGAGAAATCCTATAAAG |
| 69 | TTAACGTCTACTAATTTCTTTTATCAAACCGTTTAAAATGCGATTTATATAATCATAAAGTTTTT<br>TATTTTTGCCAATATTTTTATAATAAAGTTTAAAAATTTCTAAAAGGGTATTTCTAACTTTAAGA<br>ATTACTATTCTTTTGTTTTATTCTCAACAGACCCTAATGCCTGTTTGAAAGATTTGGTTGATT<br>TCTCCATTTCTTTTAAAAATCTATTAACATTATAATTTAGCGTTATTTCTTCTAGCTTTCTCAAT<br>ATCAACCTAGAATATTCTTTTCCAAGTCTTTTAAATAAATCATCAAGATTCTCAGAATCTAATT<br>CTCCGTCTAATAAAACCCTACAAAATTGTAACGTCTCGTCTTCTTCGTCTGTTAAATTCCGCT<br>TCCAATTTAAATACCAATCAAGCTCTGACTTTGTAGTAAGAGAAAAATTTTTTAATTCAAGAG<br>CTCTTTGCTAACGCTACTAATTTGTTGATCAACTGTTTTTTCAAGAGCAACAAGAATGTCTGT<br>GTTTGAACCACTAGCATTAATTTTGGTTAAGTAAAATTGTTGACACAAATTCATATCTAAGAGA<br>GAAATTTCATCTTCTCTATCACTTTTATCGGAATAGTTTTCAATCAATCCCACTAAAATACTTA<br>TTTTAGAAGACAAATCTCCCCAACGCTTTTTGCCTATATCAATCAAGAACTGATTAACATCTTT<br>TTCGCTGTACTTATACTTTACTAACACCTCATCATTGTTTAAAAGCCATCCACCAAGAGCATA<br>TCTATTCTCATCATTTTGCAAAGATTTCTTGAAAAACTCAAAATTTTTATCCTCTTCCAAGTTTA<br>AATGGGGAATCAAACTATCATCATGAGAATTTTTCAGCAAAGCTTTACTGTATCTTGATTTAC<br>CAATACTGTGCTTTGAAGAAGTTTTTTGCAAAGACTTATAATTATCTAAATTATTGCTAGCCTG<br>ATCTAAGTTTTGCGACATTGAATTTTTAGAATTTCTTAAAGTTTGTAAATCCCTTTTAGAATCTT<br>TAAATTCTCTTGAGTTTACTTGGCTATTTTTTTTGCTTTTAAAATTACTTAAATTGGGATCTTTA<br>GGCTTATTGTTTTAGAATCCAAAGATTTTTTTTCATTAATGATTAAGTTTTGTTTATTGCTAGA<br>AGTGGTAATTTTTGAATCTTCTTCTAAAGATTTGCTACTGCAATTAATAAACAATAGAAAACTA<br>ATAATAAATGAAATTCCTATTTTATTCAT |
| 70 | CAGCAAAGCTTTACTGTATCTTGATTTACCAATAC |
| 71 | GCTTTACTGTATCTTGATTTACCAATACTGTGCTT |
| 72 | CAAAAATTACCACTTCTAGCAATAAACAAAACTTAATCAT |
| 73 | TGGGATCTTTAGGCTTATTGTTTTAGAATCC |
| 74 | TTTGCAAAGACTTATAATTATCTAAATTATTGC |
| 75 | CCTTTTAGAATCTTTAAATTCTCTTGAGTTTAC |
| 76 | TTAACGTCTACTAATCTCTTTTATTAAGCTGTTTAAAATACGATTTATATAATCATAAAGTTTTT<br>TATTCTTGCCAATATTTTTGTAATAAAGTTTAAAAATTTCCAAAAGAGTATTTCTAACCTTAGAA<br>ATCAACCCTTTTCTGTTTTTATTTCTAATAGAGACTAATGCTTGTTTGAAAGATTTGCGTGATT<br>TTTCCATTTCCTTTAAAAAACTATTAACATCATAATTTAATATGATTTCCTCTAGCTTTCTCAAT<br>ATCAACCTAGAATATTCCTTTCCAAGCCTTTTAAACAAATCATCAAGATTCTCAAATCTAATT<br>CCCCATCTACCAAAACCCTGCACAATTGTAGTGTTTCGTCTTCTTCGTCTGTTAAATTGCGCT<br>TCCAATTTAAATGCCAATCAAGCTCTGACTTTGTAGTAAGGGAAAAATTTTTTAATTCAAGAA<br>GCTCTTTGCTAACACTGCTAATTTGTTGATCGATTGTTTTTTCAAGAGCAACAAAAATGTCTG |

| SEQ ID NO: | Sequence |
|---|---|
| | CATTTGAACCATTGGCATTAATCTTGGTTAAATAAAATTGTTGACACAAATTCATATCTAAAAG<br>AGACATTTCATCTTCTCTATCACTTTTATCGGAATAATTTTCAATCAATCGCACTAAAATGCTC<br>ATTTTAGCAGACAACTCTCCCCATCGCTTTTTCCCTATATCAATCAAAAACTGATTAACATCTT<br>TTTCGCTGTACCTATACTTTACCAACACTTCATCATTGTTTAAAAGCCATCCACCAAGAGCAT<br>ATCTATTCTCATCGTTTTGCAAAGATTTCTTGAAAAACTCAAAATTTTTATCCTCTTCTGAGTT<br>TAAATGGGGAATCAAAATCTCATCCTGAGCATTTTTCAGCAAAGCTTTGCTGTGTTTTGGCTT<br>ATTAATATTGTGCTTTGAAGAAGTTTTTTGTAAAGATCTAGAATTATCTAAATTATCCAAATCA<br>TTGCTGGTCTGATTCGGGTCTATTAACATTAATTTTTAGAATTTTTTAAAGTTTGTGAATCCT<br>TTTTAGAATCTTCCAACTTATTCTTTTTAGACGCCAAAGATTTTTTTCATTGCCGATTAAATTT<br>CGTCTATTGTGGGAAGTGGTGGTTTTTAAATCTTCTTCTAAAGATTTACTATTACAATTAACAA<br>AAAACAGAAAGCTAATACTAAATGCAATTCCTATTTTATTCAT |
| 77 | CAGCAAAGCTTTGCTGTGTTTTGGCTT |
| 78 | CTCATCCTGAGCATTTTTCAGCAAAGCT |
| 79 | CCACTTCCCATAATAGACGAAATTTAATCGGC |
| 80 | GAAGAAGTTTAAAACTACCACTTCCCAC |
| 81 | GTAAAGATCTAGAATTATCTAAATTATCCAAATC |
| 82 | GTTTGTGAATCCTTTTTAGAATCTTCCAACTTATTC |
| 83 | CCAACTTATTCTTTTTGGACICCAAAGA |
| 84 | ATGAATTTTCAAAATTTTATTGAAACTACTTTAGTTCCTATTGCTAGTAAAATTGGTTCAAATA<br>GATATTTAATTGCTTTAAGAGATGGTTTTACTTTTTCTATGCCCTTTTTGATAGTTGGTCTTTT<br>ATTTTACTTTTAGTTAATTTACCCTTTACAGATTCTACAACATTATTATATCAACAGTGGTATGT<br>TGATTTAATGGCTAAATATAAAGGAAATATTGTTCAGCCATTTTATGTAAGTATGGGGATTAT<br>GTCCATATTTGTTGTTTTGGTATTGGTTATAACTTATCTAATCATTATAAACTTAGTGGAATT<br>ACAGGAGGATTCCTGTCTCTTTATACATTTTTAATTTTAGCTGGACAATCAGATTGGATACCT<br>TACGGAGGAGATGCTGCTAAATGGGGAATTCAGCCTAATTCATGGTTTCCTGTAATTGATGC<br>AAGATATTTTAGTGCTCAAGGAGTATTTACAGCTATTATTTCTGCTATTTTTGCTGTTGAAGTT<br>TATAAATTTTTAGTTCAAAGAAATATGGCAATTAAACTTCCAGAGTCTGTTCCGCCTGCTGTT<br>TTAAAATCTTTTGAAGCTTTAGTTCCTGTTGTTGTACTTTCCATTGTGGCTCAAAGTGTTAATA<br>TTGCTATTCAAAGTTTAGCAGGCAGCCTTTTCCCCGAAATAATTATGAGTATGTTTAGGCCTG<br>TTTTACAAATTAGCGATACTTTAGTTGGGACTTTAATGATTTCTTTTATCGTTCATATACTATG<br>GTTTTGTGGCCTTCATGGTACCAATGTTATTGTTGCCTTGCTTAATCCCATAATTCTGACAAA<br>TCTTGATTCTAATATTAGGGCTCTTTCTGACAATCTTCCACTTCCTCATATTTTAGCGGGTGG<br>ATTTCTTGATTCATTTGTATATATTGGTGGTGCTGGTTCAACTTTAGGCCTTGTTATTGCCAT<br>GATGCTTAGTAAATCTCAACATCTAAAGGCCATAGGTAAACTTTCATTTGCTCCTGGTCTTTT<br>TAATATTAATGAGCCTATTATGTTTGGGGCACCAATAGTTTTAAATCCTATACTAGGTATTCCT<br>TTTTTACTTATTCCTATGTTTAATATAATTGTCGCATATACTCTTACTAATTTTGGAATTATTGA<br>AAGAGTTAGAACCTTAACTCCATGGACAACCCCTGCTCCTATTGCCGCTTTTTTGTCTACAG<br>GGCTTGATATTAAATCTTTTGTTCTGGTTTTATTATTATTGATTATTTCGGTATTTATGTATTTA<br>CCCTTTATAAAAGCATATGATAAGGTTCTGCTTTTGCAGGAAAAAGAATAG |
| 85 | CTTTTAGTTAATTTACCCTTTACAGATTCTAC |
| 86 | GTAAGGTATCCAATCTGATTGTCCAGCTA |
| 87 | CGTAAGGTATCCAATCTGATTGTCCAGCTA |
| 88 | CAGCAGTGGTATGTTGATTTAATGGCT |
| 89 | GGATTCCTGTCTCTTTATACATTTTTAATTTTAGC |
| 90 | CATTATAAACTTAGTGGAATTACAGGAGGATTCCT |
| 91 | ATAAACTTAGTGGAATTACAGGAGGATTCC |
| 92 | AGCAGGCGGAACAGACTCTGGA |
| 93 | CTCTTTATACATTTTTAATTTTAGCTGGGCAA |
| 94 | CAAAGAAATATGGCAATTAAACTTCCAG |
| 95 | GGGCAATCAGATTGGATGCCTTACGGAGG |
| 96 | GGGCAATCAGATTGGATGCCTTACGGAG |
| 97 | GCTGGGCAATCAGATTGGATGCCTTACGGAG |
| 98 | TAATTATTTCGG/ideoxyl/GAAAAGGCTGCCTGCTA wherein /ideoxyl/ is deoxyInosine |

| SEQ ID NO: | Sequence |
|---|---|
| 99 | CATAATTATTTCGG/ideoxyl/GAAAAGGCTGCCTGCTA wherein /ideoxyl/ is deoxylnosine |
| 100 | GGGATTCAGCCTAAT/ideoxyl/CATGGTTTCCTG wherein /ideoxyl/ is deoxylnosine |
| 101 | GTACTTTCCATTGTGGCTCAAGGTG |
| 102 | TTACGGCATTTTAAAAACATCGTGTGGATGCGATTCTTTTAATGAAGAATGGCTTATTTTTAC<br>AAACTTAGAATTTATTTTTAAATCAGATATTGTGATTGCTCCTAAATAACCCATTCCAGACATT<br>AATCCACCTTTTAGTTGGTTCAAAATATCTTTTAATTCTCCAGAATACGGTACCATACCTTCAA<br>TTCCTTCAGGGACTAATTTTTTAGGCTCGTTGTTCTCGAGTTGAAAATATCTTGATTTAGAGC<br>CCCTTTTCATAGCGGAAATAGAACCCATTCCAACGTAAGATTTGAATTTCTTTCCATTGTAAA<br>TTATTTCCTCTGAAGGAGATTCTTTCGCGCCTGCAAAGAGATTTCCTATCATTACGCTATCAG<br>CTCCTGCTGCAATGGCTTTAACTACATCTCCTGAAAACCGGATTCCACCGTCTGCTATAATG<br>CAAATATTTGTGTTTTTGCAAACTTCATAAACGTCGCAGATTGCTGTTATTTGGGGAACGCCA<br>ACTCCTGCAACGATTCTTGTTGTGCATATACTACCTGGACCTATTCCTACTTTTAAACAGTCT<br>GCTCCTGCATTGATTAAATCTAATGCGGCTTCTTTAGTTACTATATTGCCAGCAATAAGGTCT<br>AAATTTGGATACTTGTTTTTAATTGTTTTTACAAGTTCTATTATTCTTGTAGAATGCCCGTGGG<br>CAGAGTCTATGACAATCAGATCTACATGTGCTTTTACAAGTTCTTCAACTCGTTCTATGGTAT<br>CAATATCAATAGAAATAGCAGCTCCTACTCTTAGCTTGCTATTTAAATCTTTACATGCATTAGA<br>AAAATCTTCTTTGTGTTCTGTATTTTTATGTATTTCGGGTTCTTCTAAATATTGCTTTGTAAGC<br>ATTTTGGTTTCTTGTTCGTTGTAACCTTATTAGTGTTGATGGTTTTTTGGGCTTTATATGTTT<br>TTACTTTCTCAATTTCTTTTTTTGAGCCTCTATTGACATATTTTTATGTATAATCCCTATTCCG<br>CCTTCTTTAGCAATAGCTATTGCCATTTGGCTTTCTGTAACAGTATCCATGGCTGAGCTTAAA<br>AATGGTATATTTAAGGATATGTTTTTTGTCAACTGTGTTTTTAAGCTAACCTCACTAGGTAATA<br>TAGAGGATTTTCTTGGAATTAAAGACACATCATCAAAAGTTAAAGCTTCTTTTATTATCTTGTT<br>TGTCAT |
| 103 | ATGTCAACATCATCCGCATCTATATCTATATTTACAATATTACAAAAAGTAGGAAAAGCTTTCA<br>TGCTTCCTATAGCACTTTTACCAGCAGCTGGAATTTTATTGGGAATCGGAGGAGCATTTACC<br>AACGAAACAATGATTCAGGCTTATGGATTAGAAGGAATACTTGGAAAAGGAACTGTAGCAAG<br>CTCAATACTTTACCTTATGAAATATACAGGAGAAGTAATTTTTGCTAACTTACCTTTAATGTTT<br>GCAGCAGCAATTCCAATAGGACTTGCTAAAGTAGAAAAAGGAACAGCTGCTTTAGCAGGAG<br>TAGTTGGTTTTTTAGTTATGCACCAAACTATAAATGGAATCTTATATATACAAGGAATCACACC<br>AGAAAGCGCAAGCTTAAAAGCACTATTAGAATTAGGAATGCCTGAAACAGCTGCAACTGCAA<br>AAAGTCAGGAATATACAAATGTACTTGGAATATTCTCTCTTCAAATGAGCGTAATGGGGGGA<br>CTAGTAGCAGGATTGTTGCTGTTTTTCTTCATAACAGATTCTATAATATTCAATTACCCACAT<br>TTTTAGCATTTTTGGAGGCACAAGATTTGTACCAATCATAACCACAATAACCATGTTTGTAG<br>TAGGGATATTTTAACATTTATTTGGCCTTTCATTCAAGGTGCAATGACTTCGTTTGGGCAAA<br>TTGTAGAACAATCTGGGCTTTTTGGAACATTTGCATATGGAGCAATAAAAAGATCCTTAATTC<br>CATTTGGACTTCACCATATATTTTACTTACCATTTTGGCAAACAGCTGTTGGTGGAACATTAG<br>AAATAAATGGAGAACTCATATCAGGAGCACAAAATATATTCTTCAAGCAACTTGGGGATACC<br>AATACTGTACACTTTGAAGTTGCAAAGGGAACAAGATTTTTTAGCGGAGAATTTGTTGTTATG<br>ATTTTTGGATTACCTGGAGCTGCTCTTGCTATGTACCATACATCAAAACCCGAAAATAAAAAA<br>AACGTAGCTTCATTGCTACTATCTGCTAGCTTTACATCAATGTTAACAGGAATTACAGAACCT<br>CTTGAATTTGCATTCCTTTTTGCAGCACCAGCGCTTTATTACTTTATATATGTTCCTCTTTTTG<br>GATTGGCGTATCTTTTAACACACCTTTTAAACGTAGGAGTTGGACTAACATTTTCTGGAGGAT<br>TTATAGATATGTTTCTATTTGGAATACTTCAAGGAAATAGTAAAACAAATTGGATAGCAATTCC<br>TATCTTAGGAATCTTCTACTTTATTGGATTCTACTTTATATTTAAATTTGTAATCATGAAATTCA<br>ATCTTAAAACAATCGGAAGAGAAGATGAAGAAATGGAAAAAGATATAAGTTCAGAAAAAACA<br>AATTTATCAGAAACTGCTTTAAAAGTATTAGAGGGCCTTGGAGGAAAAGATAATATTACATAT<br>CTTGATGCATGTGCATCAAGATTAAGAGTTAATCTAAAACAAATAGAATTCATCAAATCAGAT<br>ACCTATTTCAAAAATTTGGGTGCTAGTGGAATATTAAAAAAAGGAAATAGCGTCCAAATTGTA<br>TTTGGAGGATTATCCGATAACATAAGAATGGAAATCGATAAGCTTATGTAA |
| 104 | GATTTGTACCAATCATAACCACAATAACCA |
| 105 | GTGATAAAAAAGGTAGCTATTATTGATGGACTTAGAACACCCAATTTCAAGTTTGGAGGTTCT<br>TTTAAGGGTTTAAATATTATTGATGAATCTTCAAAAGTTGTTAAAGCTTTGCTTGAAAGAAATA<br>AGTTATACAAAGTGGATGAGGTTATTATTGGTAATGTAATATCTGCGGGACTTGGTCAAAATA<br>TTGCAAGACAAATTGCTTTAAAGTCTGACTTAGGCGATACTGTGCCTGCATTTAGCGTTAATA<br>AAGTTTGTGGTTCTGGGCTTAAGGCCTTGGAGCTTGCATTTAATTCTATTGCCCTTGGAGAC<br>AATGATATTGTTTTAGCTGGAGGAGTTGAAGATTTAACCAATTCTCCTTATTTATTACCTAGAA<br>AGATTAGATTTGACGGTCTTAAATTTGGTAATTTTGGAATTGAAGATTCAATCCAAAAGACG<br>CCCTTAATAGATTCTCTGAATTTTATTTCTATGGGGCTTACGGCTGAAAATCTTTCAGAAAAATA<br>TAGAATAACAAGAGAAATGCAAGATGAATTTGCTATATAATTCTCATGTAAAGGCATTAAAGGC<br>AAGAGAGCTTGGATATTTTGAGGATGAAATTTATCCCCTGACTGTTTTTGATAAGAAGACCAA<br>CTCTAGCGTAACTATCTCAAGTGATGAGGAAATAAGAGATAATTTAACTTTAAATAAGCTAGC<br>ATCTCTTAATCCTGTTTTTAAAGAATCAGGCACAGTAACTGCCGGAAATTCTTCAAGTTTAAA<br>TGATGGTGCTTGTTTTTAATTTTAGCAAGTGAGGAAAGAGTAAAAGCTTGGGGTTAAGTC<br>CATTAGCTTATATTGGAGGATTTAAAAGCGTGGGGCTTGATCCACTTTATATGGGTTTTGGA<br>GCTTATATGGCTATTGAAGGCATTATTAGTAAATTAAGTTTAAATCCTAGCGAAATAGATTTG<br>ATTGAGGTAAATGAGGCATTTGCAGCTCAAGCATTAAGCATTGAAAAGGCCTTGTTTAAAAA<br>ATACAATATAACTAGCGATATTATTAATGTAAATGGTGGTGCTATTGCTTTGGGGCATCCATT<br>TGCCGTTAGCGGTTCAAGAATTTTTATTAACACTTTCTCGCTCTATGAAAATGAAGAATAAAAC<br>AAAAGGGATAGCATCTGTTTGTATTGGTGGCGGACAAGGAATTTCTAGTTTTTTGTATAGATG<br>A |

| SEQ ID NO: | Sequence |
|---|---|
| 106 | GTTTTTGATAAGAAGACCAACTCTAGCGTAACT |
| 107 | TAATGCCTTCAATAGCCATATAAGCTCCA |
| 108 | ACTTTAAATAAGCTAGCATCTCTTAATCC |
| 109 | TTAGCTTATATTGGAGGATTTAAAAGCG |
| 110 | TTGAAAGGCAAGCTTATAAAAGTTTCAAACAAATTCTCAATACTTGCGCTGTTACTGATT<br>ATTAGCTGTAATGCCAATATGAACACGAATGATAAAAACAAAGTCTTAAACGAACATAAC<br>TTAAAAAATATTTCAGAAGTCATTAAGAATAGCTTACAAATTGAATCAGACTTAAAAAAA<br>GAACCTGAAGCAAACAAAAATCAAAGTACCCCCCCTATTTTAGAAATTGAAAAAATTGAA<br>CCTGGAACACAAGAATTTTCTTTAAAATCTGAATCTGAAAGCTCAATCCCTCTAGAAATC<br>CTAGAAGGAGCAAATGTGGTCAAATCAGAAGAAGAAATTGCAAAAATACAAGAAAAATTA<br>TTGTTAATCGGAGCTTCTGATGAAAGAATAGCACAAGAATTAGACCCCAATATTCAAAAA<br>TCTTTAAATCCAACTACAATAGAATTCAAAATTCTAAGCACCGCCGACGAAAAACAATA<br>CTTGATCCAACTGAAGAAGAAATTAATACTAATGGAAAAGACAAAATTTTTGATCAAAAA<br>AAAGAAAATAGCACTTTAAGCGAAACTACAAAAACTCCAATACAAAATCAATTCCAAAAG<br>CATGGCATATCTTTAAGTAAAGATGGCAACTTCATAACAAAAGAATATGTAGAGCAAGTT<br>AGAGAATCTCTAGACAAAGCGCTAAATGCAATAAAAAGTTTAGAAAAATCTAAAGATCTT<br>TTCAATCTTGATGCCGAAGAAAATTTACTAAAGGATCTGGGAAACTCTCAAAACAAAACA<br>AACAGCTCAATCTCAAATAATATTAATGCTGAGAACATAGAAAAACAAAAAATATATTC<br>CTTGAAGAGCTAGAAAAAAGTGAGCTTAGTTTTGAAAACACTAAAGATCCCTTAGGAATA<br>AGCACCATAAAAGAAGTAATAGATGCTGCCAACAAATGGAAAGAAAAAGAAAACTCAAGC<br>CAAATAAACTGGGACTTAGGATCAAAGTTTCATCCAAACCCGAAGCTTTACAACGAATCA<br>GTAGCTAGAGAGTATAAAGTTTTGGCTGAAAAATTTACCAAAGTAAAAAATGAATACAAA<br>AACACAAAAGAACAACTAAAAGTTCAATCTAAATTAACAGCTAACAACCTCAACAAAATA<br>ATTGACGCAACAAAAGAGTTTGCAAACCAAGTAAGAAATTTAATCTTATTGGTAGAAAAC<br>AATCAATAAAAGCCCTATTAA |
| 111 | CAAATTCTCAATACTTGCGCTGTTACTGA |
| 112 | TCTAG/ideoxyI/GGGATTGAGCTTTCAGATTCA wherein /ideoxyI/ is deoxyInosine |
| 113 | CTTCTGATTTGACCACATTTGCTTCTTCTAG |
| 114 | GCAATTTCTTCTTCTGATTTGACTACATTTGCT |
| 115 | AGCTGTAATGCCAATATGAACGCGAA |
| 116 | CCCTATTTTAGAAATTGAAAAAATTGAACCTG |
| 117 | TTCGTGTTCATATTGGCATTACAGCT |
| 118 | CAGGTTCAATTTTTTCAATTTCTAAAATAGGG |
| 119 | ATGAAAAAATTTAATTTAATAATTGTAGCTTTGTTTGTTGCTCTGCTGGCAGCCTGTAATTTTG<br>GATTAACAGGAGAAGTAAAAGCAATGCTTGAATCGTCTTCTGATAATGTAAAAAACAAAATTT<br>TACAAATAAAAGAAGAAGCCGCTAAAAAGGGTGTAAATTTTAAAGCTTTTACAGGCACCGCA<br>ACTGGTTCTAAAGTGACAAATGGGGGATCAGCCTTAAGAGAAGCAAAAGTACAAGCCATTAA<br>TGAAGTAGAAAAGTTCCTTAAGATAATAGAAAAAGAAGCTTTAATACTTAAAAAAAATGGAAA<br>TAGTAGTCAATTCTTGGCTATGTTTGATTTCATGCTTGAAGTTACAGGATCATTAGATGAAAT<br>TGGAATAAAAGGAATAAAAAGCTCCATTTCAGAGGAAGCTAAATCTAACCCTGTAAACACGG<br>CTGAAAGATTGGTTGAGGTTAAGGCTAAAATAGAAATAAACTAGAAGGTGTCAAGAAAAGA<br>CAAAAACTTGACGATGAGGAAAAAAAAATAAGTAAAAGCAAAAAAAGAAATAA |
| 120 | GCTGGCAGCCTGTAATTTTGGATTAACA |
| 121 | TTGTCACTTTAGAACCAGTTGCGG |
| 122 | CAATGCTTGAATCGTCTTCTGATGATG |
| 123 | AATTTTAAAGCTTTTACAGGCACCG |
| 124 | GGCTATGTTTGATTTCATGCTTGAAGTTAC |
| 125 | ACTTATTTTTTTTCCTCATCGTCAAGT |
| 126 | GTCAAGTTTTTGTCTTTTCTTGACACCT |
| 127 | GGATCATTAGATGAGATTGGAATAAAAGGA |
| 128 | AGGCTAAAATAGAAAATAAACTAGAAGG |
| 129 | TTAGTAAAAGGCAGGTTTTAAAGTATCAAAATCTTTGTAATATTTATTAAAGTGTTCTGCCAGT<br>ATTTTCTCATTATCTTGAGTATTTTGATTGTAAACTTTAAGAGTTTCGTTTAAGGTTTTTTTAAG |

| SEQ ID NO: | Sequence |
|---|---|
| | TCTTTGTTTTATCTCTAAGTTGGATTTTATTTGCATTAGCAATGATTTAGATTCTTCTTGACTTA<br>GATTTTCTACTCCATTTTGTATTAATTCTAAATTTTGCTCTATTTGGAATTGAATGCCCCATGA<br>TATGTGATAAATCAATCTTCCAATTATATTGTAATGTTCGGAATTTTTTTAAGTATTTCAAGAA<br>TTTCTTTTAATTTTTCTATATTTTCTTTTTTATAATCTAAAGATGAGTAAAGCGTTCTTTTTATTT<br>TCATTTGGATATCTTCATCAATAAGATCGTAAGGACCAACTTTAAAAGTGCTTAGGAAATCAA<br>ATTTTTCCTTAGCAATTTTAGCTATTTGTATATTTTCTTCTTTTTTTTGATCTTCCAGTTCCTTA<br>CCAATTGCTTTTAGCTCTGAAGCGATAGTTTCCATAATTTTTTCATCAGAAGTGCTAAGGTCT<br>CCAGATTTATCTTCAAAATTTTGGGTGTTTTCCCCCGGATTGGTGATTTTTTTTGGCTTAGTG<br>TTTGCATTTGCTTTAGGATCGATTTTGCTAAAAGGTGCGCATGAGGTGCAAATTAAAGTTAAT<br>ATCATTGCAATAATATTAATCTTGATTATATTTAGTTTGGCTTTTTTCAA |
| 130 | ATTTATTAAAGTGTTCTGCCAGTATTTTCTCAT |
| 131 | GCATTCAATTCCAAATAGAGCAAAATTTAGAAT |
| 132 | CTTGAGTATTTTGATTGTAAACTTTAAGAG |
| 133 | TGACTTAGATTTTCTACTCCATTTTGTA |
| 134 | AGTGTTCTGCCAGTATTTTCTCATTATCTTG |
| 135 | AAAGGCAGGTTTTAAAGTATCAAAATCTTTGT |
| 136 | GGGCATTCAATTCCAAATAGAGCAAAATT |
| 137 | AATTCCGAACATTACAATATAATTGGAAGATTG |
| 138 | AGCGTTCTTTTTATTTTCATTTGGATATCTTCA |
| 139 | GCAAACACTAAGCCAAAAAAATCACCAA |
| 140 | AGGTCTCCAGATTTATCTTCAAAAT |
| 141 | CAATAAGATCGTAAGGACCAACTTT |
| 142 | CAATCTTCCAATTATATTGTAATGTTCGGAATT |
| 143 | CTAAAGATGAGTAAAGCGTTCTTTTTATTTTCA |
| 144 | CCTAAAGCAAATGCAAACACTAAGCCAAA |
| 145 | AGCAAATGCAAACACTAAGCCAAAAAAA |
| 146 | GCAAATGCAAACACTAAGCCAAAAAAAATCAC |
| 147 | GCCCCATGATATGTGATAAATCAATCTTCC |
| 148 | GGAGACCTTAGCACTTCTGATGAAAAAAT |
| 149 | GGAAATCTAACGAGAGAGCATGCTCCTGCGGCCCCGGAGACGGTGCGCCGCGGGGTGCG<br>GCGCCTTCTTTCACATGTATCCAAAACGTCTCTCGGCAACGGATATCTCGGCTCTCGCATCG<br>ATGAAGAACGTAGCGAAATGCGATACTTGGTGTGAATTGCAGAATCCCGTGAACCATCGAG<br>TCTTTGAACGCAAGTTGCGCCCCAAGCCATTAGGCCGAGGGCACGTCTGCCTGGGTGTCAC<br>GCATCG |
| 150 | GGA AAT CTA ACG AGA GAG CAT GCT |
| 151 | GGA AAT CTA ACG AGA GAG CAT GC |
| 152 | CGA TGC GTG ACA CCC AGG C |
| 153 | GAT GCG TGA CAC CCA GGC |
| 154 | GAG ACG TTT GGA TAC ATG TGA AAA GAA GGC |
| 155 | CGA TGG TTC ACG GGA TTC TGC AAT TC |
| 156 | TTACATTATACTAATGTATGCTTCAAGAACAGACTGGCGAGCATTTTGCATATTATCTAGGTA<br>TCTTTTTTTAATGTACTCTGCTAAGGATTTGGAATCGCTTAAACTTGAATTAGAGCTAGCATTA<br>GCAATAAGCCCATCAGCTTGTCTTGACCATTCTTTTCTTTTATCTAATATTTGATTTAGTTTTG<br>ATTTAAGCTCTTTTAGCTTCATGGTGAAATCAAAACTGTTGATTTTAGCGTTTAAGTAATCCTG<br>GTTAAAGATTTCAATTTTTTTATTTATTTCTTCTAGTGCAAGTTCGAAAGAAATTTGTGTTCCA<br>AGCCCTGATATCATTAATTCTCTTATTAAGCTGTGATTTTGATTCTCATTGTAAAGAGCTTCCA<br>TTATTGATCCAAATTGTTCAATTTTGTATTGATCAAAATCCATAAGCGCATAGAATTTATTTCT<br>TTCATTTTCTGCTTCTGGTGTGTTAGAGTTAAGCTGTGGCGCGTAACTTCTGTCATAAACTTT<br>AGCACTTGAAATAACATCTAGCAGTTCAAATGCAGAATCTTTCATTTTGAATTGATCGTAAGT |

| SEQ ID NO: | Sequence |
|---|---|
| | TTCTCTAAATCCAAAGTTGTTTTGTGTTTTATTTTTTCTTCAGAAATTGCTCTAATAAGTTCGT<br>TTTTAATGTTTGTAATTTACTGCCAGAAGATGTTGTTGTTTGTACAGCAGAGCTTGAATTTGT<br>TTGCTGTCTTGTTGGTGACTAAAGCTGTAGTTTAAGGCAAATGTTGGCAGCCCGCTATTTC<br>TGCTGTTAAAAGTTCTTGTATTTCCGGGTACGGTTGTAACGGCTTGAATAGGTATTCTTTGTT<br>TTGTTAGTGATGCAGCTCTTGCTGCTGTTGTTTTGGCAGATTTGACAGATCTGCGCTAAAA<br>CTTAAGCTTTGCAATTGTGGGCTTGGTGCTGCTTGTTGATTTTGCGATCCTTTATTTGGTGTT<br>GTTTGTGGTTGATTTTGCGATCCTTTATTTGGCGCTGCTGCTACTGTTTTTGCCGCTTGCGAT<br>TGTTTTTTTAGCTCTGCTGCTACTTTGTCATTGTCAGCAATTGGTATATTTTTGCAGCATTTG<br>AGTTTGTATCAGCACTTGTTGTTTCTTGATCATCTGCTGCCTTATTAAGTATTCCTTTTACTTT<br>GTTTTTATAATCTTCGTTTAGATTGGCATCAATCGTGCAAGAAAATAAAAACAATCCCAAAAG<br>CTTTAATTGTATTAATGGTTTGATTTTCAA |
| 157 | AGCTGTAGTTTAAGGCAAATGTTGG |
| 158 | TTGTTTGCTGTCTTGTTGGTTGACT |
| 159 | CGCAAAATCAACAAGCAGCACC |
| 160 | AGGATCGCAAAATCAACCACAAACA |
| 161 | GCTATTTCTGCTGTTAAAAGTTCTTGT |
| 162 | CTAAAACTTAAGCTTTGCAATTGTGG |
| 163 | TGCTGCTGTTGTTTTTGGCAGATT |
| 164 | ATGACAAAGTAGCAGCAGAGCTAAA |
| 165 | CGCTAAAACTTAAGCTTTGCAATTG |
| 166 | TGCTGCTACTGTTTTTGCTGCTTGC |
| 167 | GTGGACAGTATTATGACAGAGCAAAAGGCAGGTTATAACCATCAGGTCATTGAAGAGCAATG<br>CCAAGATGCATGGACAAAATCGAAATCGTATATATGGAAAGGCCGCAAAGACGCAAGCTTT<br>GTCATAGACACCCCACCACCAACAGTATCAGGAAGCCTACACATGGGCCACGTATTTAGTTA<br>CTGCCATGCCGACTTCATAGCCCGCTACAAACGTCTGGCCGGTTTTGACGTTCTATTCCCCA<br>TAGGGTTCGATGATAACGGGTTGCCCACAGAACGCCTCATCGAGAGGGAAACAGGTGTAAA<br>AGCCTCTCAGGTCGACCGAGGTGAGTTTATAAAGACATGTACTGCAGTTTCAAAAGAATACA<br>GGTTAAAATACCGACAGTTATTTCAAACTTTGGGAATAAGTTTTCGATTGGTCCCGTGAGTAC<br>CATACTGCAAGCCCCACTATCCAAAAGCTTTCACAAGAGTCGTTCATAAGTTTGTATAACAAA<br>GGTGATGCGTACCGTAAACAACAGCCGATATTGTGGGACGTTGTAGATCAGACAGCAATAT<br>CTAACGCGGAGATCGAAGCAAAATTTTGCCATCTACAATGTATACGGTTCGGTTTCAGACA<br>GAATGTGGTGAGAGTATACTAATAGCCACAACCCGTCCAGAACTCATGCCCGCATGTGTAG<br>CAGTGTTCTATCATCCTTACGATAGCCGTTATAAGCATCTTGAAGGCAAACATGCTATCGTAC<br>CAGTAGGCGGAAATAACGTCAGAATTCTGCCGGACGATAAGGTAGCCATAGATAAAGGAAC<br>TGGCTTGGTAATGTGCTGCACATTCGGCGATGAAACTGATGTATATTGGCGGCAAAAGCAT<br>GCGCTTGACACCAGAATAATTATAGATAAAACCGGACGCCTTACAGGTCTGGAGAAATTGGC<br>AACAGAGAAATCTCTCATCTCCCCAACACAATTCAATGGTTTAAGAATAAAAGAGGCOAGGA<br>AAGCCATAAGCGAGACCCTGGCAGCAAGCGGATTGATATCATCCCAAGCAGATATAGTTCA<br>TAGCGTCAGATGTGCAGAGCGTTCTGGAGCTCCAATAGAGATTTTGCCGAGTGAACAGTGG<br>TTTATCAAGATTAAGGATCACAAAGATATATTTAAGAACCTAGCAGAACGTATTAAGTGGCAT<br>CCTGACCACATGCGAAAACGACTATATACGTGGATCGAGAACCTGAATAGCGATTGGTGTAT<br>ATCTCGTCAGCGATTTTATGGAGTCCCAGTCCCAGTATGGTATTCAAAACGAAATGGTGAAG<br>AGGGTAGGGTGATCTTACCCAATGTTCAAGATTTACCTATAGATCCCATTAAAGACTTTCCTA<br>GGGGCTATGGCAAAGATGAAGTGATACCCGATGTTGACGTTATGGATACATGGGCAACGAG<br>TTCACTATCTCCAATGTATCACACTATGATGTTGGAAGGTACATGTCATGAAGGAAATATACC<br>TACCGATCTTCGTACCCAAAGTCATGAGATAATACGATCCTGGGCGTTTTACACCATAGCCA<br>TGTCCCACCTTCATCGAGCAGAGCTGCCGTGGAAAAGCATAATGATAAGCGGTTGGTGCGT<br>TGCAGAAGATAAGACTAAAATGAGCAAATCTAAAAACAACGCCAAGGATCCAAGCGAATTAC<br>TAAAAACTTACGGAGCAGATGCGATTAGATACTGGGCTTCCAAAGCCCGAAACGGCGTAGA<br>CACCGTGTTTTCAGAAGAAGTCATTAAAACAGGTAAGCGTCTAGTTACAAAATTATATAATGC<br>GCATAAGTTTGTACAGCTTGTAGCCGGTAATATTAAACCAAGTTTTGAGGCTATAACAAGTCC<br>TCTCGACCAGTGGATCGTGACACGCTTAAGTAAAATTGTAGAAATAAGCACAAAAGCATATG<br>AAGAATGTGACTATAATACAGGACTAGGTGTTGTCGAGGAGTTTTTCATTAAGCAGTTCTGT<br>GACAACTATATAGAGTTATCCAAACATCGAGCATATAACGAGAAGACTTACAGGGTCATAA<br>ATCTGCTCTAAGTAGTCTGCAAATCGTACTACAAACTGCCATAGCACTCTTCTCACCCATCAT<br>ACCGCACGTAACTCATTATATAAGTAGTAATAGTGAAACAGAAAGTCCAAAGTGGCCATTATA<br>CGAAGAAATACCACGTTATGAAGCCATAGAACAAATGTGCGAGGAAGCAATGAGAATAGTTC<br>ACGAGATTAGACGTTATAAGTCAGAAAATTGTATCGCCATGAACCATCCCCTTAATATACTTT<br>CTATATCTAGTAGAGCAGTACAACAAGATATGCATCCGCAAATCTTAGAGGATATTAGAAATG<br>CTTTGAAGATTTGCAAGATAACTATAGAACAAGAGCAGGGAGAAGACTTTATTATTCAGCAAT<br>AA |
| 168 | CTCTAAGTAGTCTGCAAATCGTACTACAAACTGCCATAGCACTCTTCTCACCCATCATACCG<br>CACGTAACTCATTATATAAGTAGTAATAGTGAAACAGAAAGTCCAAAGTGGCCATTATACGAA<br>GAAATACCACGTTATGAAGCCATAGAACAAATGTGCGAGGAAGCAATGAGAATAGTTCACGA |

| SEQ ID NO: | Sequence |
|---|---|
| | GATTAGACGTTATAAGTCAGAAAATTGTATCGCCATGAACCATCCCCTTAATATACTTTACTA<br>TATCTAG |

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for detecting the presence of a *Borrelia burgdorferi* (*B. burgdorferi*) cell in a biological sample, the method comprising:
   (a) lysing the *B. burgdorferi* cells in the biological sample to form a lysate;
   (b) amplifying a *B. burgdorferi* target nucleic acid in the lysate in the presence of a first primer pair or a second primer pair to form an amplified lysate comprising a *B. burgdorferi* amplicon, wherein the first primer pair comprises a forward primer comprising the oligonucleotide sequence: 5'-AGA GGA CTT TTA ATA CTG GGC ATT GCT G-3' (SEQ ID NO: 1) and a reverse primer comprising the oligonucleotide sequence: 5'-GGC CAT TAT GTA GGA ATC TCT AAT GGT GC-3' (SEQ ID NO: 2), and the second primer pair comprises a forward primer comprising the oligonucleotide sequence: 5'-ACA TAA TGG CCT TAG AAA ATG AGC TTG ATG-3' (SEQ ID NO: 5) and a reverse primer comprising the oligonucleotide sequence 5'-CCC GCT TGT AAC CAT GTT TTC TGA GC-3' (SEQ ID NO: 6);
   (c) following step (b), contacting the amplified lysate with magnetic particles to form an assay sample, wherein the magnetic particles comprise binding moieties on their surface, the binding moieties operative to alter aggregation of the magnetic particles in the presence of the *B. burgdorferi* amplicon;
   (d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence;
   (e) exposing the assay sample to a bias magnetic field and an RF pulse sequence;
   (f) following step (e), measuring the signal from the detection tube; and
   (g) on the basis of the result of step (f), determining whether a *B. burgdorferi* cell was present in the biological sample.

2. The method of claim 1, wherein the magnetic particles of step (c) comprise a first population of magnetic particles conjugated to a first probe, and a second population of magnetic particles conjugated to a second probe, the first probe operative to bind to a first segment of the *B. burgdorferi* amplicon and the second probe operative to bind to a second segment of the *B. burgdorferi* amplicon, wherein the magnetic particles form aggregates in the presence of the *B. burgdorferi* amplicon.

3. The method of claim 2, wherein:
   step (b) comprises amplifying a *B. burgdorferi* target nucleic acid in the presence of the first primer pair, and the first probe comprises the oligonucleotide sequence: 5'-CTA AAC CAA AAG ATG ATA TTG TCT TTG GTG-3' (SEQ ID NO: 3), and the second probe comprises the oligonucleotide sequence: 5'-GGA CAT TTC TTA CGA CAA CAC CTG CT-3' (SEQ ID NO: 4); or
   step (b) comprises amplifying the *B. burgdorferi* target nucleic acid in the presence of the second primer pair, and the first probe comprises the oligonucleotide sequence: 5'-AAC CTA TTA ACA TCA AAG ATA AAA AAT GC-3' (SEQ ID NO: 7), and the second probe comprises the oligonucleotide sequence: 5'-GCT TAC ACA CCC AAT ATT TAT ACC C-3' (SEQ ID NO: 8).

4. The method of claim 1, wherein step (b) comprises amplifying the first *B. burgdorferi* target nucleic acid in the presence of the first primer pair to form a first *B. burgdorferi* amplicon and amplifying the second *B. burgdorferi* target nucleic acid in the presence of the second primer pair to form a second *B. burgdorferi* amplicon, and step (g) comprises detecting the first *B. burgdorferi* amplicon and the second *B. burgdorferi* amplicon, and wherein the magnetic particles of step (c) comprise a first population of magnetic particles conjugated to a first probe and a second probe, and a second population of magnetic particles conjugated to a third probe and a fourth probe, wherein
   the first probe and third probe are operative to bind a first segment and a second segment, respectively, of the first *B. burgdorferi* amplicon; and
   the second probe and fourth probe are operative to bind a first segment and a second segment, respectively, of the second *B. burgdorferi* amplicon,
   wherein the magnetic particles form aggregates in the presence of the first *B. burgdorferi* amplicon and form aggregates in the presence of the second *B. burgdorferi* amplicon.

5. The method of claim 4, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8.

6. The method of claim 1, wherein step (b) further comprises amplifying a pan-*Borrelia* target nucleic acid in the biological sample, and wherein the method further comprises preparing a pan-*Borrelia* assay sample by contacting a portion of the amplified lysate with a population of magnetic particles, wherein the magnetic particles have binding moieties operative to bind the pan-*Borrelia* target nucleic acid on their surface, the binding moieties operative to alter aggregation of the magnetic particles in the presence of the pan-*Borrelia* target nucleic acid; exposing the pan-*Borrelia* assay sample to the bias magnetic field and the RF pulse sequence; and measuring the signal from the detection tube, thereby determining whether a *Borrelia* cell was present in the biological sample.

7. The method of claim 1 wherein the biological sample or portion thereof is between 0.1 and 4 mL.

8. The method of claim 1, wherein the biological sample is blood, cerebrospinal fluid (CSF), urine, or synovial fluid.

9. The method of claim 1, wherein lysing comprises mechanical lysis or heat lysis.

10. The method of claim 1, wherein the steps of the method are completed within 5 hours, within 4 hours, or within 3 hours.

11. The method of claim 1, wherein an assay sample is contacted with $1\times10^6$ to $1\times10^{13}$ magnetic particles per milliliter of the biological sample.

12. The method of claim 1, wherein step (f) comprises measuring the $T_2$ relaxation response of the assay sample, and wherein increasing agglomeration in the assay sample produces an increase in the observed $T_2$ relaxation time of the assay sample.

13. The method of claim 1, wherein the magnetic particles have a mean diameter of from 150 nm to 699 nm or from 700 nm to 1200 nm, have a T2 relaxivity per particle of from $1\times10^9$ to $1\times10^{12}$ $mM^{-1}s^{-1}$, and/or are substantially monodisperse.

14. A method for detecting the presence of a *Borrelia garinii* (*B. garinii*) cell in a biological sample, the method comprising:
(a) lysing the *B. garinii* cells in a biological sample to form a lysate;
(b) amplifying a *B. garinii* target nucleic acid in the lysate in the presence of a forward primer comprising the oligonucleotide sequence: 5'-GGA TAT TCA AAT CCT GAG GTT GAC GAA CTA-3' (SEQ ID NO: 9) and a reverse primer comprising the oligonucleotide sequence: 5'-CTG ATA GGG CAA ATC TTT CTG AAG CA-3' (SEQ ID NO: 10) to form an amplified lysate comprising a *B. garinii* amplicon;
(c) following step (b), contacting the amplified lysate with magnetic particles to form an assay sample, wherein the magnetic particles comprise binding moieties on their surface, the binding moieties operative to alter aggregation of the magnetic particles in the presence of the *B. garinii* amplicon;
(d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence;
(e) exposing the assay sample to a bias magnetic field and an RF pulse sequence;
(f) following step (e), measuring the signal from the detection tube; and
(g) on the basis of the result of step (f), determining whether an *B. garinii* cell was present in the biological sample.

15. The method of claim 14, wherein the magnetic particles comprise a first population of magnetic particles conjugated to a first probe, and a second population of magnetic particles conjugated to a second probe, the first probe operative to bind to a first segment of the *B. garinii* amplicon and the second probe operative to bind to a second segment of the *B. garinii* amplicon, wherein the magnetic particles form aggregates in the presence of the *B. garinii* amplicon.

16. The method of claim 15, wherein the first probe comprises the oligonucleotide sequence: 5'-CTG AGA TTG AAG TTG ACG AAA AAA TCA G-3' (SEQ ID NO: 11), and the second probe comprises the oligonucleotide sequence: 5'-GAT CAT CCA ATA ATT CCA ATC TAC AGC G-3' (SEQ ID NO: 12).

17. A method for detecting the presence of a *Borrelia afzelii* (*B. afzelii*) cell in a biological sample, the method comprising:
(a) lysing the *B. afzelii* cells in the biological sample to form a lysate;
(b) amplifying a *B. afzelii* target nucleic acid in the lysate in the presence of a first primer pair or a second primer pair to form an amplified lysate comprising a *B. afzelii* amplicon, wherein the first primer pair comprises a forward primer comprising the oligonucleotide sequence: 5'-CCG TGG GCA GAG TCT ATG ACA ATC AG-3' (SEQ ID NO: 13) and a reverse primer comprising the oligonucleotide sequence: 5'-GCC CAA AAA ACC ATC AAC ACT AAT AAG G-3' (SEQ ID NO: 14), and the second primer pair comprises a forward primer comprising the oligonucleotide sequence: 5'-CAA GGT GCA ATG ACT TTG TTT GGG CA-3' (SEQ ID NO: 17) and a reverse primer comprising the oligonucleotide sequence 5'-GCA ACT TCA AAG TGT ACA GTA TTG GTA TCC C-3' (SEQ ID NO: 18);
(c) following step (b), contacting the amplified lysate with magnetic particles to form an assay sample, wherein the magnetic particles comprise binding moieties on their surface, the binding moieties operative to alter aggregation of the magnetic particles in the presence of the *B. afzelii* amplicon;
(d) providing the assay sample in a detection tube within a device, the device comprising a support defining a well for holding the detection tube comprising the assay sample, and having an RF coil configured to detect a signal produced by exposing the assay sample to a bias magnetic field created using one or more magnets and an RF pulse sequence;
(e) exposing the assay sample to a bias magnetic field and an RF pulse sequence;
(f) following step (e), measuring the signal from the detection tube; and
(g) on the basis of the result of step (f), determining whether a *B. afzelii* cell was present in the biological sample.

18. The method of claim 17, wherein the magnetic particles of step (c) comprise a first population of magnetic particles conjugated to a first probe, and a second population of magnetic particles conjugated to a second probe, the first probe operative to bind to a first segment of the *B. afzelii* amplicon and the second probe operative to bind to a second segment of the B. afzelii amplicon, wherein the magnetic particles form aggregates in the presence of the B. afzelii amplicon.

19. The method of claim 18, wherein:
   step (b) comprises amplifying a B. afzelii target nucleic acid in the presence of the first primer pair, and the first probe comprises the oligonucleotide sequence: 5'-TAG CAG CTC CTA CTC TTA GCT TGC-3' (SEQ ID NO: 15), and the second probe comprises the oligonucleotide sequence: 5'-AAT ATT GCT TTG TAA GCA TTT TGG TTT-3' (SEQ ID NO: 16); or
   step (b) comprises amplifying the B. afzelii target nucleic acid in the presence of the second primer pair, and the first probe comprises the oligonucleotide sequence: 5'-TTG TAG AAC AAT CTG GGC TTT TTG G-3' (SEQ ID NO: 19), and the second probe comprises the oligonucleotide sequence: 5'-GGA GAA CTC ATA TCA GGA GCA CAA-3' (SEQ ID NO: 20).

20. The method of claim 17, wherein step (b) comprises amplifying the first B. afzelii target nucleic acid in the presence of the first primer pair to form a first B. afzelii amplicon and amplifying the second B. afzelii target nucleic acid in the presence of the second primer pair to form a second B. afzelii amplicon, and step (g) comprises detecting the first B. afzelii amplicon and the second B. afzelii amplicon, and wherein the magnetic particles of step (c) comprise a first population of magnetic particles conjugated to a first probe and a second probe, and a second population of magnetic particles conjugated to a third probe and a fourth probe, wherein
   the first probe and third probe are operative to bind a first segment and a second segment, respectively, of the first B. afzelii amplicon; and
   the second probe and fourth probe are operative to bind a first segment and a second segment, respectively, of the second B. afzelii amplicon,
   wherein the magnetic particles form aggregates in the presence of the first B. afzelii amplicon and form aggregates in the presence of the second B. afzelii amplicon.

21. The method of claim 20, wherein the first probe comprises an oligonucleotide sequence of SEQ ID NO: 3, the second probe comprises an oligonucleotide sequence of SEQ ID NO: 19, the third probe comprises an oligonucleotide sequence of SEQ ID NO: 4, and the fourth probe comprises an oligonucleotide sequence of SEQ ID NO: 20.

22. A method for detecting the presence of a B. burgdorferi cell in a sample of whole blood, the method comprising:
   (a) providing an sample produced by lysing the red blood cells in a whole blood sample from a subject, centrifuging the sample to form a supernatant and a pellet, discarding some or all of the supernatant, and optionally washing the pellet;
   (b) lysing the B. burgdorferi cells and subject cells in the pellet to form a lysate;
   (c) amplifying a B. burgdorferi target nucleic acid in the lysate in the presence of a first primer pair or a second primer pair to form an amplified lysate comprising a B. burgdorferi amplicon, wherein the first primer pair comprises a forward primer comprising the oligonucleotide sequence: 5'-AGA GGA CTT TTA ATA CTG GGC ATT GCT G-3' (SEQ ID NO: 1) and a reverse primer comprising the oligonucleotide sequence: 5'-GGC CAT TAT GTA GGA ATC TCT AAT GGT GC-3' (SEQ ID NO: 2), and the second primer pair comprises a forward primer comprising the oligonucleotide sequence: 5'-ACA TAA TGG CCT TAG AAA ATG AGC TTG ATG-3' (SEQ ID NO: 5) and a reverse primer comprising the oligonucleotide sequence 5'-CCC GCT TGT AAC CAT GTT TTC TGA GC-3' (SEQ ID NO: 6);
   (d) following step (c), preparing at least a first assay sample by adding to a portion of the amplified lysate from 1×10$^6$ to 1×10$^{13}$ magnetic particles per milliliter of the amplified lysate, wherein the magnetic particles have a mean diameter of from 700 nm to 950 nm and binding moieties on their surface, the binding moieties operative to alter aggregation of the magnetic particles in the presence of the B. burgdorferi target nucleic acid, wherein said magnetic particles have a T$_2$ relaxivity per particle of from 1×10$^9$ to 1×10$^{12}$ mM$^{-1}$s$^{-1}$;
   (e) providing each assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence;
   (f) exposing each assay sample to a bias magnetic field and an RF pulse sequence;
   (g) following step (f), measuring the signal produced by each assay sample; and
   (h) on the basis of the result of step (g), determining whether a tick-borne pathogen is present in the sample of whole blood.

23. The method of claim 22, wherein step (c) further comprises amplifying a B. garinii target nucleic acid in the lysate in the presence of an additional forward primer comprising the oligonucleotide sequence: 5'-GGA TAT TCA AAT CCT GAG GTT GAC GAA CTA-3' (SEQ ID NO: 9) and an additional reverse primer comprising the oligonucleotide sequence: 5"-CTG ATA GGG CAA ATC TTT CTG AAG CA-3' (SEQ ID NO: 10) to form an amplified lysate comprising a B. garinii amplicon.

24. The method of claim 22, wherein step (c) further comprises amplifying a B. afzelii target nucleic acid in the lysate in the presence of one or more additional primer pairs to form an amplified lysate comprising a B. afzelii amplicon, wherein the first additional primer pair comprises a forward primer comprising the oligonucleotide sequence: 5"-CCG TGG GCA GAG TCT ATG ACA ATC AG-3' (SEQ ID NO: 13) and a reverse primer comprising the oligonucleotide sequence: 5"-GCC CAA AAA ACC ATC AAC ACT AAT AAG G-3' (SEQ ID NO: 14), and the second additional primer pair comprises a forward primer comprising the oligonucleotide sequence: 5'-CAA GGT GCA ATG ACT TTG TTT GGG CA-3' (SEQ ID NO: 17) and a reverse primer comprising the oligonucleotide sequence 5"-GCA ACT TCA AAG TGT ACA GTA TTG GTA TCC C-3' (SEQ ID NO: 18).

25. The method of claim 24, wherein step (c) comprises amplifying the first B. afzelii target nucleic acid in the presence of the first additional primer pair to form a first B. afzelii amplicon and amplifying the second B. afzelii target nucleic acid in the presence of the second additional primer pair to form a second B. afzelii amplicon, and step (g) comprises detecting the first B. afzelii amplicon and the second B. afzelii amplicon.

26. A composition comprising:
   (a) a liquid sample, wherein the liquid sample
      (i) is suspected of containing at least one B. burgdorferi target nucleic acid, or (ii) contains at least one *B. burgdorferi* target nucleic acid amplicon generated from an amplification reaction; and (b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8.

27. A removable cartridge comprising a plurality of wells, wherein the removable cartridge comprises a first well comprising the composition of claim 26.

28. A composition comprising:
(a) a liquid sample, wherein the liquid sample
    (i) is suspected of containing a *B. garinii* target nucleic acid, or
    (ii) contains a *B. garinii* amplicon generated by amplifying the *B. garinii* target nucleic acid; and
(b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, wherein the magnetic particles comprise a first population of magnetic particles conjugated to a first nucleic acid probe comprising the oligonucleotide sequence: 5'-CTG AGA TTG AAG TTG ACG AAA AAA TCA G-3' (SEQ ID NO: 11), and a second population of magnetic particles conjugated to a second nucleic acid probe comprising the oligonucleotide sequence: 5'-GAT CAT CCA ATA ATT CCA ATC TAC AGC G-3' (SEQ ID NO: 12).

29. A composition comprising:
(a) a liquid sample, wherein the liquid sample
    (i) is suspected of containing at least one *B. afzelii* target nucleic acid, or
    (ii) contains at least one *B. afzelii* target nucleic acid amplicon generated from an amplification reaction; and
(b) within the liquid sample, from $1\times10^6$ to $1\times10^{13}$ magnetic particles per milliliter of the liquid sample, the magnetic particles having a mean diameter of from 700 nm to 950 nm, a $T_2$ relaxivity per particle of from $1\times10^4$ to $1\times10^{12}$ mM$^{-1}$s$^{-1}$, the magnetic particles comprising a first population and a second population, the first population having a first nucleic acid probe and a second nucleic acid probe conjugated to their surface and the second population having a third nucleic acid probe and a fourth nucleic acid probe conjugated to their surface, wherein the first probe comprises an oligonucleotide sequence of SEQ ID NO: 3, the second probe comprises an oligonucleotide sequence of SEQ ID NO: 7, the third probe comprises an oligonucleotide sequence of SEQ ID NO: 4, and the fourth probe comprises an oligonucleotide sequence of SEQ ID NO: 8.

\* \* \* \* \*

UNITED STATES PATENT AND TRADEMARK OFFICE
CERTIFICATE OF CORRECTION

PATENT NO. : 11,326,213 B2
APPLICATION NO. : 15/545663
DATED : May 10, 2022
INVENTOR(S) : Ulrich Hans Thomann et al.

It is certified that error appears in the above-identified patent and that said Letters Patent is hereby corrected as shown below:

In the Claims

Column 192, Line 37, replace "5'"" with --5'--;
    Line 45, replace "5'"" with --5'--;
    Line 48, replace "5'"" with --5'--;
    Line 53, replace "5'"" with --5'--.

Signed and Sealed this
Twentieth Day of December, 2022

Katherine Kelly Vidal
*Director of the United States Patent and Trademark Office*